US012539510B2

(12) United States Patent
Lai et al.

(10) Patent No.: US 12,539,510 B2
(45) **Date of Patent: *Feb. 3, 2026**

(54) INTEGRATED PURIFICATION AND MEASUREMENT OF DNA METHYLATION AND CO-MEASUREMENT OF MUTATIONS AND/OR MRNA EXPRESSION LEVELS IN AN AUTOMATED REACTION CARTRIDGE

(71) Applicant: Cepheid, Sunnyvale, CA (US)

(72) Inventors: Edwin Wei-Lung Lai, Santa Clara, CA (US); Andrew Kohlway, Santa Clara, CA (US); Reuel Van Atta, Sunnyvale, CA (US); Russell Higuchi, Alameda, CA (US); Alexander A. Gall, Woodinville, WA (US); Kriszten Kocmond, Los Altos, CA (US)

(73) Assignee: Cepheid, Sunnyvale, CA (US)

( * ) Notice: Subject to any disclaimer, the term of this patent is extended or adjusted under 35 U.S.C. 154(b) by 832 days.

This patent is subject to a terminal disclaimer.

(21) Appl. No.: 17/586,645

(22) Filed: Jan. 27, 2022

(65) Prior Publication Data

US 2022/0226809 A1 Jul. 21, 2022

Related U.S. Application Data

(63) Continuation of application No. 15/839,731, filed on Dec. 12, 2017, now Pat. No. 11,260,387.

(60) Provisional application No. 62/433,165, filed on Dec. 12, 2016.

(51) Int. Cl.

| | |
|---|---|
| ***B01L 3/00*** | (2006.01) |
| ***B01L 7/00*** | (2006.01) |
| ***C12N 15/10*** | (2006.01) |
| ***C12Q 1/6827*** | (2018.01) |
| ***C12Q 1/6853*** | (2018.01) |
| ***C12Q 1/686*** | (2018.01) |

(52) U.S. Cl.

CPC ................. *B01L 3/502* (2013.01); *B01L 7/52* (2013.01); *C12N 15/1006* (2013.01); *C12Q 1/6827* (2013.01); *C12Q 1/6853* (2013.01); *C12Q 1/686* (2013.01); *B01L 3/5027* (2013.01); *B01L 2200/16* (2013.01); *B01L 2300/0816* (2013.01); *B01L 2300/0861* (2013.01); *B01L 2300/0864* (2013.01); *B01L 2300/087* (2013.01); *B01L 2300/1805* (2013.01); *B01L 2400/0478* (2013.01); *B01L 2400/0644* (2013.01); *C12Q 2537/143* (2013.01); *C12Q 2537/149* (2013.01); *C12Q 2537/164* (2013.01)

(58) Field of Classification Search

CPC .......... B01L 3/502; B01L 7/52; B01L 3/5027; B01L 2200/16; B01L 2300/0816; B01L 2300/0861; B01L 2300/0864; B01L 2300/087; B01L 2300/1805; B01L 2400/0478; B01L 2400/0644; B01L 2200/0652; B01L 2200/0663; C12N 15/1006; C12Q 1/6827; C12Q 1/6853; C12Q 1/686; C12Q 2537/143; C12Q 2537/149; C12Q 2537/164; C12Q 2523/125; C12Q 2531/113; C12Q 2535/122; G01N 35/00

See application file for complete search history.

(56) References Cited

U.S. PATENT DOCUMENTS

| | | | |
|---|---|---|---|
| 5,958,349 | A | 9/1999 | Petersen et al. |
| 6,403,037 | B1 | 6/2002 | Chang et al. |
| 6,440,725 | B1 | 8/2002 | Pourahmadi et al. |
| 6,783,736 | B1 | 8/2004 | Taylor et al. |
| 6,818,185 | B1 | 11/2004 | Petersen et al. |
| 8,062,849 | B2 | 11/2011 | Sukumar et al. |
| 10,450,609 | B2 | 10/2019 | Sukumar et al. |
| 10,533,210 | B2 | 1/2020 | Nauwelaers et al. |
| 11,260,387 | B2 | 3/2022 | Lai et al. |
| 2003/0082600 | A1 | 5/2003 | Olek et al. |

(Continued)

FOREIGN PATENT DOCUMENTS

| | | | |
|---|---|---|---|
| CN | 101285096 | A | 10/2008 |
| CN | 101984069 | A | 3/2011 |

(Continued)

OTHER PUBLICATIONS

Analytic Jena AG., (2014) "innuCONVERT Bisulfite All-in-One Kit", AJ Innuscreen Gmbh, 4 pages, Retrieved from the Internet: URL: http://journals.plos.org/plosone/article?id=10.1371/journal.pone.0093933 [Retrieved on Nov. 11, 2015].

(Continued)

*Primary Examiner* — Narayan K Bhat

(74) *Attorney, Agent, or Firm* — McAndrews, Held & Malloy, Ltd.

(57) ABSTRACT

Methods of determining methylation of DNA are provided that include filtering a biological sample comprising a nucleic acid with a first matrix material to purify the DNA; eluting and denaturing the DNA to produce eluted denatured DNA; heating the DNA in the presence of bisulfite ions to produce deaminated nucleic acid; optionally contacting said deaminated nucleic acid with a second matrix material; desulphonating and eluting the bound deaminated nucleic acid; and performing methylation specific PCR, nucleic acid sequencing, and/or high resolution melting analysis (HRM) on said bisulfite-converted nucleic acid to determine the methylation of said nucleic acid, wherein multiple steps may be performed in a single reaction cartridge.

20 Claims, 41 Drawing Sheets

Specification includes a Sequence Listing.

(56) References Cited

U.S. PATENT DOCUMENTS

| | | | |
|---|---|---|---|
| 2006/0068399 A1 | 3/2006 | McMillan et al. |
| 2006/0134643 A1 | 6/2006 | Berlin et al. |
| 2006/0286577 A1 | 12/2006 | Jia |
| 2007/0098600 A1 | 5/2007 | Kayyem |
| 2008/0014576 A1 | 1/2008 | Jovanovich et al. |
| 2009/0036665 A1 | 2/2009 | Domingo et al. |
| 2009/0253181 A1 | 10/2009 | Vangbo et al. |
| 2010/0041024 A1 | 2/2010 | Fuhrmann et al. |
| 2010/0330580 A1 | 12/2010 | Gimenez et al. |
| 2012/0088249 A1 | 4/2012 | Jovanovich et al. |
| 2012/0252015 A1 | 10/2012 | Hindson et al. |
| 2014/0098252 A1 | 4/2014 | Chang et al. |
| 2014/0272967 A1 | 9/2014 | Gundling et al. |
| 2014/0272997 A1 | 9/2014 | Ivie et al. |
| 2014/0274735 A1 | 9/2014 | Granados |
| 2015/0099670 A1 | 4/2015 | Li et al. |
| 2015/0119268 A1 | 4/2015 | Bishop |
| 2015/0204813 A1 | 7/2015 | Toumazou et al. |
| 2016/0223442 A1 | 8/2016 | Guldberg et al. |
| 2017/0137871 A1 | 5/2017 | Lai et al. |
| 2018/0214864 A1 | 8/2018 | Lai et al. |

FOREIGN PATENT DOCUMENTS

| | | | | |
|---|---|---|---|---|
| CN | 104321442 A | 1/2015 | |
| CN | 105378108 A | 3/2016 | |
| CN | 107922941 A | 4/2018 | |
| EP | 1394173 A1 | 3/2004 | |
| EP | 2218793 A1 | 8/2010 | |
| JP | 2009519023 A | 5/2009 | |
| JP | 2009236933 A | 10/2009 | |
| RU | 2332462 C2 | 8/2008 | |
| WO | WO-9856952 A1 | 12/1998 | |
| WO | WO-9920396 A1 * | 4/1999 | ............ B01L 3/5025 |
| WO | WO-9933559 A1 | 7/1999 | |
| WO | WO-0073412 A2 | 12/2000 | |
| WO | WO-2004096825 A1 | 11/2004 | |
| WO | WO-2006136990 A2 | 12/2006 | |
| WO | WO-2007004103 A1 | 1/2007 | |
| WO | WO-2007068437 A1 | 6/2007 | |
| WO | WO-2009024019 A1 | 2/2009 | |
| WO | WO-2014052551 A1 | 4/2014 | |
| WO | WO-2016205233 A2 | 12/2016 | |
| WO | WO-2018111935 A1 | 6/2018 | |

OTHER PUBLICATIONS

Athamanolap et al. (2014) "Droplet Array Platform for High-Resolution Melt Analysis of DNA Methylation Density" Journal of Laboratory Automation 19(3): 304-312.
AU First Office Action dated Aug. 26, 2021 issued in AU 2016277943.
AU Office Action dated Feb. 1, 2022 in Application No. AU2017376118.
Bailey et al. (2010) "Single-Tube Analysis of DNA Methylation with Silica Superparamagnetic Beads" Clinical Chemistry, 56(6): 1022-1025.
Bianco et al. (1999) "Methylation-sensitive, single-strand conformation analysis (Ms-Ssca): A rapid method to screen for and analyze methylation" Hum. Mutat. 14(4): 289-293.
BR Office Action dated Aug. 3, 2021 issued in BR 112019011670-2.
Butkus, Ben (2015) "Hopkins Lab, Cepheid Developing Methylated DNA Panel for Breast Cancer Dx, Monitoring GenomeWeb" Genomeweb Retrieved from the Internet: URL:https://www.genomeweb.com/molecular-diagnostics/hopkins-lab-cepheid-developing-methylated-dna-panel-breast-cancer-dx#.Wq97n2fderg [retrieved on Mar. 19, 2018] 3 pages.
Clark, S. et al., "High Sensitivity mapping of methylated cytosines" Nucleic Acid Research, 1994, vol. 22, No. 15, pp. 2990-2997.
CN First Office Action with Search Report dated Jan. 14, 2021 issued in CN 201680048155.X.
CN First Office Action with Search Report dated Mar. 12, 2021 issued in CN 201780085871.X.
CN Office Action dated Feb. 8, 2022, in Application No. CN201780085871.X with English translation.
CN Office Action dated Nov. 26, 2021, in Application No. CN201680048155.X with English translation.
Colella et al. (2003) "Sensitive and quantitative universal Pyrosequencing methylation analysis of CpG sites." BioTechniques 35(1): 146-150.
Eads et al. (1999) "CpG Island Hypermethylation in Human Colorectal Tumors Is Not Associated with DNA Methyltransferase Overexpression" Cancer Res., 59: 2302-2306.
Eads et al. (2000) "MethyLight: a high-throughput assay to measure DNA methylation" Nucleic Acids Research, 28(8): e32 (9 pages).
Ehrich et al. (2005) "Quantitative high-throughput analysis of DNA methylation patterns by base-specific cleavage and mass spectrometry." Proc. Natl. Acad. Sci. USA, 102 (44): 15785-15790.
EP Extended Search Report dated May 27, 2021 issued in EP 20202659.7.
EP Office Action dated May 21, 2019 issued in EP 16732159.5.
EP Office Action dated Nov. 5, 2020 issued in EP 17822953.0.
Esteller et al. (1999) "Detection of Aberrant Promoter Hypermethylation of Tumor Suppressor Genes in Serum DNA from Non-Small Cell Lung Cancer Patients" Cancer Research, 59: 67-70.
Fink et al. (1998) "Real-time quantitative RT-PCR after laser-assisted cell picking." Nat. Med., 4(11): 1329-1333.
Frommer et al. (1992) "A genomic sequencing protocol that yields a positive display of 5-methylcytosine residues in individual DNA strands." Proc. Natl. Acad. Sci. USA, 89 (5): 1827-1831.
Herman et al. (1996) "Methylation-specific PCR: a novel PCR assay for methylation status of CpG islands." Proc. Natl. Acad. Sci. USA, 93: 9821-9826.
Holmes, E.E. et al., "Performance Evaluation of Kits for Bisulfite-Conversion of DNA from Tissues, Cell Lines, FFPE Tissues, Aspirates, Lavages, Effusions, Plasma, Serum, and Urine", 2014, PLOS One, 9(4): e93933 (14 pages).
IN Office Action dated Dec. 10, 2021, in Application No. IN201817001016.
JP Final Office Action dated Jun. 21, 2021 issued in JP 2017-564901.
JP Office Action dated Dec. 6, 2021, in Application No. JP2019-531197 with English translation.
JP Office Action dated Jul. 13, 2020 issued in JP 2017-564901.
Lee et al. (1993) "Allelic discrimination by nick-translation PCR with fluorogenic probes." Nucleic Acids Res., 21(16): 3761-3766.
Livak et al. (1995) "Oligonucleotides With Fluorescent Dyes at Opposite Ends Provide a Quenched Probe System Useful for Detecting PCR Product and Nucleic Acid Hybridization" Genome Res. PCR Meth. Appl., 4: 357-362.
Meissner, A. et al., "Reduced Representation Bisulfite Sequencing for Comparative High-resolution DNA Methylation Analysis", Nucleic Acid Research, 2005, vol. 33, No. 18, pp. 5868-5877.
Notice of Allowance dated Oct. 29, 2021 in U.S. Appl. No. 15/839,731.
PCT International Preliminary Report on Patentability dated Dec. 19, 2017 issued in PCT/US2016/037422.
PCT International Preliminary Report on Patentability dated Jun. 18, 2019 issued in PCT/US2017/065905.
PCT International Search Report and Written Opinion dated Apr. 3, 2018 issued in PCT/US2017/065905.
PCT International Search Report and Written Opinion dated Dec. 6, 2016 issued in PCT/US2016/037422.
PCT Invitation to pay additional fees dated Oct. 4, 2016 issued in PCT/US2016/037422.
Qian and Brent (1997) "Methylation Hot Spots in the 5' Flanking Region Denote Silencing of the O6-Methylguanine-DNA Methyltransferase Gene" Cancer Research, 57: 3672-3677.
Rand et al. (2002) "Conversion-specific detection of DNA methylation using real-time polymerase chain reaction (ConLight-MSP) to avoid false positives" Methods 27(2): 114-120.
Roche Diagnostics K.K, (Jan. 2005) "High Pure PCR Product Purification Kit," 3 pages.
RU Office Action dated Dec. 8, 2021, in Application No. RU20190119086 with English Translation.

(56) References Cited

OTHER PUBLICATIONS

RU Office Action dated May 7, 2021, in Application No. RU20190119086 with English Translation.
Shin et al. (2013) "Droplet Bisulfite Conversion Platform for Epigenetic Cancer Biomarker Detection" Transducers & Eurosensors XXVII: The 17th International Conference on Solid-State Sensors, Actuators and Microsystems, Barcelona, Spain, Jun. 16-20, 2013, pp. 2181-2184.
Sommer and Tautz (1989) "Minimal homology requirements for PCR primers" Nucleic Acids Research, 17(16): 6749.
Tost et al. (2003) "Analysis and quantification of multiple methylation variable positions in CpG islands by Pyrosequencing™" BioTechniques 35(1): 152-154 & 156.
Uccella et al. (2009) "MGMT methylation in diffuse large B-cell lymphoma: validation of quantitative methylation-specific PCR and comparison with MGMT protein expression" J Clin Pathol, 62:715-723.
US Corrected Notice of Allowability dated Sep. 24, 2021, in U.S. Appl. No. 15/839,731.
US Final Office Action dated Aug. 18, 2020 issued in U.S. Appl. No. 15/182,394.
US Final Office Action dated Jan. 28, 2020 issued in U.S. Appl. No. 15/182,394.
US Final Office Action dated Mar. 30, 2021 issued in U.S. Appl. No. 15/182,394.
U.S. Non-Final Office Action dated Nov. 22, 2021, in U.S. Appl. No. 15/182,394.
US Notice of Allowance dated Jun. 21, 2021 issued in U.S. Appl. No. 15/839,731.
US Office Action dated Jun. 4, 2018 issued in U.S. Appl. No. 15/182,394.
US Office Action dated Oct. 23, 2020 issued in U.S. Appl. No. 15/839,731.
Warnecke et al. (1997) "Detection and measurement of PCR bias in quantitative methylation analysis of bisulphite-treated DNA." Nucleic Acids Res., 25(21): 4422-4426.
Watts et al. (1997) "Methylation of Discrete Regions of the O6-Methylguanine DNA Methyltransferase (MGMT) CpG Island Is Associated with Heterochromatinization of the MGMT Transcription Start Site and Silencing of the Gene" Molecular and Cellular Biology, 17(9): 5612-5619.
Wojdacz and Dobrovic (2007) "Methylation-sensitive high resolution melting (MS-HRM): a new approach for sensitive and high-throughput assessment of methylation" Nucleic Acids Res. 35(6): e41 (7 pages).

* cited by examiner

| # | Name | Initial Vol. (uL) | Current Vol. (uL) |
|---|---|---|---|
| 1 | PEG | 0 | 0 |
| 2 | Sample | 2500 | 0 |
| 3 | Wash | 4000 | 0 |
| 4 | Bisulfite | 100 | 0 |
| 5 | Tris | 4000 | 0 |
| 6 | Air2 | 0 | 0 |
| 7 | Master Mix | 35 | 0 |
| 8 | Waste | 1000 | 0 |
| 9 | Internal Beads | 0 | 0 |
| 10 | KOH | 500 | 0 |
| 11 | External Beads | 0 | 0 |
| 12 | Air1 | 0 | 0 |

| | Seq + | Seq - | |
|---|---|---|---|
| Meth + | 18 | 4 | 22 |
| Meth - | 2 | 24 | 26 |
| | 20 | 28 | 48 |

| | Seq + | Seq - | |
|---|---|---|---|
| Meth + | 15 | 1 | 16 |
| Meth - | 2 | 20 | 22 |
| | 17 | 21 | 38 |

SEQUENCE LISTING

<160> NUMBER OF SEQ ID NOS: 390

<210> SEQ ID NO 1
<211> LENGTH: 162
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1
cgcgtttcgg atatgttggg atagttcgcg tttttagaac gttttgcgtt tcgacgttcg 60
taggttttcg cggtgcgtat cgtttgcgat ttggtgagtg tttgggtcgt ttcgttttcg 120
gaagagtgcg gagttttttt tcgggacggt ggtagtttcg ag 162

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2
gcgttgaagt cggggttc 18

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
cccgtacttc gctaacttta aacg 24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
acaaacgcga accgaacgaa acca 24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
ttagggtaga ttgtggatat tag 23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
atactaacaa ctatccaata caac 24

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
caggttgaaa ttagtatgtg ttattttggt atgg 34

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
aatagttcgt aagtttatcg gcg 23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
cttcacgcca ccgataaccg a 21

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
tacttacgcg aaactttacc gccga 25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
gatttagagt tggatgtgtg gat 23

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
accaccatac taataatcaa atcta 25

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
aaatatcact catcaccaaa taaatccaa 29

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
gtaagaagac ggtcgaggcg 20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
acaactctac tcgccctcga a 21

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
aacgaaccac ttctcgtacc aacga 25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
tgtatgagtt tgtggtgaat aatg 24

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
aactcaccat caaacacttt ccc 23

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
tacaaaccca acatcctcta tctattc 27

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
gcgcgttaat cgtaggcgtt t 21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
cccaatacga tacgacctta ac 22

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
cgtaccttta aataacccgt aaaatcga 28

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
tttgttgatg ttttgtggaa gtaag 25

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
attcatcaat actttcaaat aacaca 26

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
caaatacatt atcctaccac taacaataca 30

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
cgggattttg ggttttcgtc g 21

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
cgacgaataa cgacgcaaaa ac 22

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
aaccgaacga taacgaaaac gacgaa 26

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
gttagttttg tagtgtattg agtat 25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
catcttccac aataaacttc caatt 25

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
taactccacc tattctacct accattt 27

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
cgtttagcgg gatgcggtga 20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
acacgaaaac cccgataacc g 21

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
aaacactcat cgcaaccgcc gcg 23

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
ttagatgttg attggttgtg tttg 24

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
atcatcataa aactcaacaa tcaatt 26

```
<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

ccaaacatca aatctttaac ttttaccaa                                   29


<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

aggttgaaat tagtatgtgt tattttggta tgg                              33


<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

aggttgaaat tagtatgtgt tattttggta tgg                              33


<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

aggttgaaat tagtatgtgt tattttggta tgg                              33


<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

gttttatagt ttttgtattt agg                                         23


<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

aactcaataa actcaaactc cc                                          22
```

```
<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

gtgtgtgttt ttattgtaaa tgg                                             23


<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

ataaaatttc ttcacrccac c                                               21


<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

gagggagtta gttgggttat                                                 20


<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

cctccaaaaa atacataccc                                                 20


<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

gtgtaattaa ttagaaggtt tttt                                            24


<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

aacacctacc ttccaaatac                                                 20


<210> SEQ ID NO 49
```

<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
ttagaggyga gagagtagtt 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
aaactactac taaccrcctc 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51 aggagatatyl gttgagggga 20

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
tcactcatac taaaccrcca a 21

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
ttagggtaga ttgtggatat tagatagg 28

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
taatactaac aactatccaa tacaacac 28

<210> SEQ ID NO 55
<211> LENGTH: 22

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
ccgataaccg aaacgctctt ac 22

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
gcgttaatcg taggcgttt 19

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 57
gtttagcggg atgcggtg 18

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
acacgaaaac cccgataac 19

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
gygtaattaa ttagaaggtt tttt 24

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 60
tcgtacgaag taaatagttc gtaag 25

<210> SEQ ID NO 61
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 61
ggatttttga aatattatag gattaattag 30

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
gttttatagt ttttgtattt agg 23

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 63
acaaacgcga naccgaacga aacca 25

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
ctggtttcgt tcggttcgcg 20

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
caggttgaaa ttagtatgtg ttattttggt atgg 34

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
caaactactt acgcgaaact ttaccgcc 28

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (21)..(21)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 67
aaatatcact catcaccaaa ntaaatccaa 30

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
aaacgaacca cttctcgtac caacgac 27

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
caaacccaac atcctctatc tattc 25

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(13)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 70
acgcgtacct ttnaaataac ccgtaaaatc g 31

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
acgcgtacct ttaaataacc cgtaaaatcg 30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
caaatacatt atcctaccac taacaataca 30

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
aaccgaacga taacgaaaac gacga 25

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (21)..(21)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 74
taactccacc tattctacct naccattt 28

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
caaacatcaa atctttaact tttac 25

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
cacgcgtacc tttaaataac ccgtaaaatc g 31

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(19)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 77
aaccgaacga taacgaaana cgacgaa 27

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
aaacactcat cgcaaccgcc gcg 23

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
taaccaccac ccaacacaca ataac 25

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
cccaactact taaaaaacta aaac 24

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
cacctaaaat caaaaattta aaacc 25

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
caaataattc tcctacctca acctc 25

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
cttaactcac tacaacctct acc 23

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
caaaccgaac gacgcgcaca aacac 25

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
gtatataggt tggggaagtt tg 22

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
aactatactc aaccaataaa acc 23

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
tgttatttag gttggagtgt ag 22

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
taataactca tacctataat ccc 23

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
ggttggagtg tagtggtata attttag 27

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
taataactca tacctataat cccaacac 28

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
gtagagatag ggttttatta tgttg 25

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
ggttttatta tgttggttag gttgg 25

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
gtattttggg aggttaaggt ag 22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
atcttactct tattacccaa ac 22

<210> SEQ ID NO 95
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
ggttaaggta ggtagattat ttgagg 26

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
atcttactct tattacccaa actaaaatac 30

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
gttatttagg aggttgaggt ag 22

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 98
gaggtaggag aattatttga atttagg 27

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99
atttgagatt tttgagttgg 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
aaccctactc cctatctacg 20

<210> SEQ ID NO 101

<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 101
gcgcgcgttt ttttttgaag 20

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 102
ggcgtagata gggagtaggg tt 22

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 103
gtgatggagg aggtttagta agtt 24

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 104
ccaataaaac ctactcctcc cttaa 25

<210> SEQ ID NO 105
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 105
ccataccaaa ataacacatc taatttcaac ct 32

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 106
caaatacatt atcctaccac taacaataca 30

<210> SEQ ID NO 107
<211> LENGTH: 31

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cacgcgtacc tttaaataac ccgtaaaatc g 31

<210> SEQ ID NO 108
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cacgcgtacc tttaaataac ccgtaaaatc g 31

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ctaacaaaca caaaccaaac aaaacca 27

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ctaacaaaca caaaccaaac aaaacca 27

<210> SEQ ID NO 111
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 111
aactacttac acaaaacttn taccaccaa 29

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aactacttac acaaaacttt accac 25

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
aaacaaacca cttctcatac caacaac 27

<210> SEQ ID NO 114
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
cacatacctt taaataaccc ataaaatcaa c 31

<210> SEQ ID NO 115
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
cacatacctt taaataaccc ataaaatcaa c 31

<210> SEQ ID NO 116
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (24)..(24)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 116
caacaaaaac ccaaaatccc aacnaaacca ca 32

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
caaaatccca acaaaccaca taaca 25

<210> SEQ ID NO 118
<211> LENGTH: 25
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 118
aaacactcat cacaaccacc acacc 25

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tggtgtgtta attgtaggtg tttt 24

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cccaatacaa tacaacctta acc 23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gtggtgtgta ttgtgtagtg tta 23

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
caaaccaaac aataacaaaa acaac 25

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tgtttagtgg gatgtggtga ag 22

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
acacaaaaac cccaataacc aca 23

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
gtttaaagtt agtgaagtat gggttt 26

<210> SEQ ID NO 126
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
tgtatgaagt aaatagtttg taagtttatt gg 32

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
tttgttgatg ttttgtggaa gtaag 25

<210> SEQ ID NO 128
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
attcatcaat actttcaaat aacaca 26

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
aaacgaacca cttctcgtac caacgac 27

<210> SEQ ID NO 130
<211> LENGTH: 25
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 130
caaacccaac atcctctatc tattc 25

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
aaacactcat cgcaaccgcc gcg 23

<210> SEQ ID NO 132
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132
ccaaacatca aatctttaac ttttaccaa 29

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 133
aaacactcat cgcaaccgcc gcg 23

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 134
ggtgttgaag ttggggtttg 20

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 135
cccatacttc actaacttta aac 23

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
gtaaatagtt tgtaagttta ttggtg 26

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
tttcttcaca ccaccaataa ccaa 24

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 138
gagtaagaag atggttgagg tg 22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
caacaactct actcaccctc aa 22

<210> SEQ ID NO 140
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
tcccaactac ttaaaaaact aaaac 25

<210> SEQ ID NO 141
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
tcccaactac ttaaaaaact aaaac 25

<210> SEQ ID NO 142
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
tcccaactac ttaaaaaact aaaac 25

<210> SEQ ID NO 143
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
tcccaactac ttaaaaaact aaaac 25

<210> SEQ ID NO 144
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
tcccaactac ttaaaaaact aaaac 25

<210> SEQ ID NO 145
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
ggataagatt tttgatattg tattttttaa gg 32

<210> SEQ ID NO 146
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146
catattcaaa ctccttaata aacaaacttt tctc 34

<210> SEQ ID NO 147
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
ccgaacaaaa aaaacctaaa taaatccctt c 31

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148
ccaccaccca acacacaata acaaacac 28

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
ggtttagtaa gttttttgga ttgtg 25

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
ccttaaaaat tacaaaaacc acaac 25

<210> SEQ ID NO 151
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
ccaccaccca acacacaata acaaacac 28

<210> SEQ ID NO 152
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (13)..(13)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 152
ccaccaccca acnacacaat aacaaacac 29

<210> SEQ ID NO 153
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (16)..(16)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 153
ccaccaccca acacancaat aacaaacac 29

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
ttcagtgccg gttggtaatg taa 23

<210> SEQ ID NO 155
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 155
caacaacttt aatacctgtt tcaagga 27

<210> SEQ ID NO 156
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
ggtatttttg tatttgttgg tgttg 25

<210> SEQ ID NO 157
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
catacataca ccaaacaatt cattc 25

<210> SEQ ID NO 158
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
gtatggtggt atttttgtat ttgttg 26

<210> SEQ ID NO 159
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
cacacataca tacaccaaac aattc 25

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (18)..(18)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 160
aagatccgat tcacaganca agctccgtca 30

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (18)..(18)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 161
aagatccgat tcacaganca agctccgtca 30

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 162
caaaatcatt tccttcacaa atacactc 28

<210> SEQ ID NO 163
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
ccaaatacca taaccatttt attaataaca c 31

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(19)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 164
aaaatcattt ccttcacana atacactc 28

<210> SEQ ID NO 165
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (18)..(18)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 165
ccaaatacca taaccatntt tattaataac ac 32

<210> SEQ ID NO 166
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166
ccctagtatg ctaggtctct tgctggga 28

<210> SEQ ID NO 167
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 167
cagcctctct gagggtttaa gccca 25

<210> SEQ ID NO 168
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 168
tcagcctatc tgacaccccg gg 22

<210> SEQ ID NO 169
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 169
gactcctgag gagaagtctg ccgtta 26

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
ccttgatacc aacctgccca ggg 23

<210> SEQ ID NO 171
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
aggtgaacgt ggatgaagtt ggtggtg 27

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
caacatcgcg caagagcacg g 21

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
cgtttccttc acgagtacgc tctccga 27

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
accggcgaat acagagatac cg 22

<210> SEQ ID NO 175
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(13)

<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 175
ccaccaccca acnacacaat aacaaacac 29

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
gttggtgttg gagagtgtat ttg 23

<210> SEQ ID NO 177
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
ggagagtgta tttgtgaagg aaatg 25

<210> SEQ ID NO 178
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
ggaaatgatt ttttttatga gatgagtg 28

<210> SEQ ID NO 179
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (16)..(16)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 179
ccaccaccca acacancaat aacaaacac 29

<210> SEQ ID NO 180
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (16)..(16)

```
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 180

ccaccaccca acacancaat aacaaacac                                        29


<210> SEQ ID NO 181
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181

ccaccaccca acacacaata acaaacac                                         28


<210> SEQ ID NO 182
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182

gatggaggag gtttagtaag ttttt                                            25


<210> SEQ ID NO 183
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183

aataaaacct actcctccct taaaaa                                           26


<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Universal purine

<400> SEQUENCE: 184

cttaccataa ctactacnct cc                                               22


<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185

cttaccataa ctactacrct cc                                               22
```

```
<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186

gtgtgtgttt ttattgtaaa tggt                                          24


<210> SEQ ID NO 187
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: Universal purine
<220> FEATURE:
<221> NAME/KEY: modified_base
<222> LOCATION: (10)..(10)
<223> OTHER INFORMATION: Universal purine

<400> SEQUENCE: 187

aacnataacn ataaaatttc ttcac                                         25


<210> SEQ ID NO 188
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188

aacrataacr ataaaatttc ttcac                                         25


<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Universal pyrimidine

<400> SEQUENCE: 189

gtttgtnggg attttgggt                                                19


<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190

gtttgtyggg attttgggt                                                19


<210> SEQ ID NO 191
<211> LENGTH: 21
```

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (3)..(3)
<223> OTHER INFORMATION: Universal purine
<220> FEATURE:
<221> NAME/KEY: modified_base
<222> LOCATION: (10)..(10)
<223> OTHER INFORMATION: Universal purine

<400> SEQUENCE: 191
ccnaactccn aaaaaaaaac c 21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 192
ccraactccr aaaaaaaaac c 21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (10)..(10)
<223> OTHER INFORMATION: Universal pyrimidine
<220> FEATURE:
<221> NAME/KEY: modified_base
<222> LOCATION: (12)..(12)
<223> OTHER INFORMATION: Universal pyrimidine

<400> SEQUENCE: 193
ggtattaagn gnggtttttt g 21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 194
ggtattaagy gyggtttttt g 21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (3)..(3)
<223> OTHER INFORMATION: Universal pyrimidine

<400> SEQUENCE: 195
gtngtttagt ttggattttg g 21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196
gtygtttagt ttggattttg g 21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
tttcgaaggg taagcgttaa g 21

<210> SEQ ID NO 198
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (14)..(14)
<223> OTHER INFORMATION: Universal purine

<400> SEQUENCE: 198
aacataaata accnaaataa cc 22

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
aacataaata accraaataa cc 22

<210> SEQ ID NO 200
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200 cggtttttg agtaagaaga cggtc 25

<210> SEQ ID NO 201
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (17)..(17)
<223> OTHER INFORMATION: Universal purine

<400> SEQUENCE: 201
tacctttaaa taacccntaa aatcgacaa 29

<210> SEQ ID NO 202
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
tacctttaaa taacccrtaa aatcgacaa 29

<210> SEQ ID NO 203
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (17)..(17)
<223> OTHER INFORMATION: Universal purine

<400> SEQUENCE: 203
ataacaaact acttacncga aactttac 28

<210> SEQ ID NO 204
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 204
ataacaaact acttacrcga aactttac 28

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (9)..(9)
<223> OTHER INFORMATION: Universal purine
<220> FEATURE:
<221> NAME/KEY: modified_base
<222> LOCATION: (19)..(19)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 205
aacaaaccna acgataacna aaac 24

<210> SEQ ID NO 206

<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(19)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 206
aacaaaccra acgataacna aaac 24

<210> SEQ ID NO 207
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(19)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 207
cacattctaa taaaaaacna accacttc 28

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (5)..(5)
<223> OTHER INFORMATION: Universal purine

<400> SEQUENCE: 208
aaccnaacga aaccacaaaa c 21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 209
aaccraacga aaccacaaaa c 21

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (15)..(15)

<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 210
caaaaacact catcncaacc gcc 23

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 211
acaaccctcc aaaaaataca ta 22

<210> SEQ ID NO 212
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 212
ccaaatacca taaccatttt attaataaca c 31

<210> SEQ ID NO 213
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
ccaaatacca taaccatttt attaataaca c 31

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: Universal pyrimidine
<220> FEATURE:
<221> NAME/KEY: modified_base
<222> LOCATION: (15)..(15)
<223> OTHER INFORMATION: Universal pyrimidine

<400> SEQUENCE: 214
tttngaaggg taagngttaa g 21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215

```
tttygaaggg taagygttaa g                                              21


<210> SEQ ID NO 216
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Universal purine
<220> FEATURE:
<221> NAME/KEY: modified_base
<222> LOCATION: (16)..(16)
<223> OTHER INFORMATION: Universal purine

<400> SEQUENCE: 216

caacacnaaa accccnata                                                 19


<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217

caacacraaa accccrata                                                 19


<210> SEQ ID NO 218
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218

cctgctgaaa atgactgaat ataaccgcta agaacctctc ggtcagctga t              51


<210> SEQ ID NO 219
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219

cctgctgaaa atgactgaat ataaagtctc attataatcg ttcgagctgt t              51


<210> SEQ ID NO 220
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220

cctgctgaaa atgactgaat ataagcagac ttggcggtag gtccgagctt g              51


<210> SEQ ID NO 221
<211> LENGTH: 51
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cctgctgaaa atgactgaat ataagtatcc tgagcacggt tgcgagctgc t 51

<210> SEQ ID NO 222
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 222
ctcttgccta cgccnccgct aagaacctct cggtc 35

<210> SEQ ID NO 223
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 223
ctcttgccta cgccnagtct cattataatc gttcg 35

<210> SEQ ID NO 224
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 224
ctcttgccta cgccngcaga cttggcggta ggtcc 35

<210> SEQ ID NO 225
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (15)..(15)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 225
ctcttgccta cgccngtatc ctgagcacgg ttgcg 35

<210> SEQ ID NO 226
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 226
ccaccaccca acacacaata acaaacac 28

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 227
cccrcaaacc rcgaaaacct c 21

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
gtttttttty gggagaggta aata 24

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 229
crcctccraa actaaaacaa c 21

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 230
gggttattgt aaagttaggg tg 22

<210> SEQ ID NO 231
<211> LENGTH: 21

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: Universal pyrimidine
<220> FEATURE:
<221> NAME/KEY: modified_base
<222> LOCATION: (15)..(15)
<223> OTHER INFORMATION: Universal pyrimidine

<400> SEQUENCE: 231
gaggtngtgg ttttngtaga t 21

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Universal purine

<400> SEQUENCE: 232
aaacnccaaa aaacttcaaa ac 22

<210> SEQ ID NO 233
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Universal pyrimidine

<400> SEQUENCE: 233
ttttgttggg ataagaagng ttt 23

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
accaaaaact attacaaaac caaa 24

<210> SEQ ID NO 235
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ccgacgaccg acg 13

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 236
gggagaggta aatatcgata c 21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 237
cgcgaaaatt aatacctaac g 21

<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 238
ttagggtgcg ttatcggac 19

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 239
cggaggtgtt tgttttcgtc 20

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 240
cgaaaaaaac aaacaccgac acg 23

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 241
cgttttcggg gttgaggtaa c 21

<210> SEQ ID NO 242

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
ccaaaatacg ctaccgaacg a 21

<210> SEQ ID NO 243
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (16)..(16)
<223> OTHER INFORMATION: Universal purine

<400> SEQUENCE: 243
aaaatatcta cccccncc 18

<210> SEQ ID NO 244
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 244
tattactcac tctactcaaa actctcc 27

<210> SEQ ID NO 245
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 245
atatctttta ccaacaaata ccttcaaa 28

<210> SEQ ID NO 246
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (6)..(6)
<223> OTHER INFORMATION: Universal pyrimidine

<400> SEQUENCE: 246
gttttngttt tggttgcgat gttgt 25

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<221> NAME/KEY: modified_base
<222> LOCATION: (18)..(18)
<223> OTHER INFORMATION: Universal pyrimidine

<400> SEQUENCE: 247
gggatttttt agaagagngg t 21

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (15)..(15)
<223> OTHER INFORMATION: Universal purine

<400> SEQUENCE: 248
tactcactaa taacnaaaac tac 23

<210> SEQ ID NO 249
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (18)..(18)
<223> OTHER INFORMATION: Universal pyrimidine

<400> SEQUENCE: 249
ggttttgtgt tttattgngg ag 22

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (7)..(7)
<223> OTHER INFORMATION: Universal purine

<400> SEQUENCE: 250
cctaacnaac tacaccaata caa 23

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (17)..(17)
<223> OTHER INFORMATION: Universal pyrimidine

<400> SEQUENCE: 251
gagaggggat tttttgngtt t 21

<210> SEQ ID NO 252

<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Universal purine

<400> SEQUENCE: 252
ccnaaaacca attctaaact aatc 24

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tttttagaag agcggtcggc 20

<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ctaataacga aaactacgac gacg 24

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ttgtgtttta ttgcggagtg c 21

<210> SEQ ID NO 256
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
aaccacatat cgatcacgta cg 22

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
gcgttttcgg attttagggt c 21

<210> SEQ ID NO 258
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 258
aactaatcgc cttaaataaa ataccg 26

<210> SEQ ID NO 259
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (6)..(6)
<223> OTHER INFORMATION: Universal purine
<220> FEATURE:
<221> NAME/KEY: modified_base
<222> LOCATION: (17)..(17)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 259
cctccnaacc ttataanaaa taatccc 27

<210> SEQ ID NO 260
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (7)..(7)
<223> OTHER INFORMATION: Universal purine
<220> FEATURE:
<221> NAME/KEY: modified_base
<222> LOCATION: (17)..(17)
<223> OTHER INFORMATION: a, c, t, g, unknown or other
<220> FEATURE:
<223> OTHER INFORMATION: See specification as filed for detailed
description of substitutions and preferred embodiments

<400> SEQUENCE: 260
aaaaacnccc taatccncat ccaac 25

<210> SEQ ID NO 261
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 261
cacttaactt cctctccaaa aatctaaac 29

<210> SEQ ID NO 262
<211> LENGTH: 22
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (11)..(11)
<223> OTHER INFORMATION: Universal pyrimidine
<220> FEATURE:
<221> NAME/KEY: modified_base
<222> LOCATION: (18)..(18)
<223> OTHER INFORMATION: Universal pyrimidine

<400> SEQUENCE: 262
gtttttagaa ngttttgngt tt 22

<210> SEQ ID NO 263
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 263
gtttttagaa ygttttgygt tt 22

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (11)..(11)
<223> OTHER INFORMATION: Universal purine

<400> SEQUENCE: 264
aaaaaactcc ncactcttcc 20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 265
aaaaaactcc rcactcttcc 20

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 266
tttcgacgtt cgtaggtttt cgc 23

<210> SEQ ID NO 267
<211> LENGTH: 22
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 267
gcactcttcc gaaaacgaaa cg 22

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(19)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 268
ccaaacactc accaaatcnc aaac 24

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(19)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 269
ccaaacactc accaaatcnc aaac 24

<210> SEQ ID NO 270
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 270
atatctttta ccaacaaata ccttcaaa 28

<210> SEQ ID NO 271
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (6)..(6)
<223> OTHER INFORMATION: Universal pyrimidine

<400> SEQUENCE: 271
gttttngttt tggttgcgat gttgt 25

<210> SEQ ID NO 272

<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (9)..(9)
<223> OTHER INFORMATION: Universal pyrimidine

<400> SEQUENCE: 272
ggagataang gggtttttgg 20

<210> SEQ ID NO 273
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(19)
<223> OTHER INFORMATION: Universal purine

<400> SEQUENCE: 273
cactaaaaat ataccaacna cc 22

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 274
ggagagttat ttaagaaagg tgg 23

<210> SEQ ID NO 275
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (9)..(9)
<223> OTHER INFORMATION: Universal purine
<220> FEATURE:
<221> NAME/KEY: modified_base
<222> LOCATION: (11)..(11)
<223> OTHER INFORMATION: Universal purine

<400> SEQUENCE: 275
aaaattacnc naaacccac 19

<210> SEQ ID NO 276
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 276
cgtgttcgta gggtttttc gttttc 26

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ccaacgaccc tcgaaaaaaa aacg 24

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gattttgcgg gtacggttta cgc 23

<210> SEQ ID NO 279
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gatccctaaa acgccgaaaa caacg 25

<210> SEQ ID NO 280
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
cgttattttt tttgggtggt ttttcg 26

<210> SEQ ID NO 281
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Universal purine

<400> SEQUENCE: 281
cnaaaaacca cccaaaaaaa ataac 25

<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: Universal pyrimidine

<400> SEQUENCE: 282
ggataaatat ngtaaggtat tgag 24

<210> SEQ ID NO 283
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 283
cgaaatacta aatttctcta attcctc 27

<210> SEQ ID NO 284
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(19)
<223> OTHER INFORMATION: Universal pyrimidine

<400> SEQUENCE: 284 gagtttttt ggttttttng ag 22

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (15)..(15)
<223> OTHER INFORMATION: Universal purine

<400> SEQUENCE: 285
ctaaaataaa taccncaaaa cac 23

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 286
cgcgttcgga ttttttttc ggc 23

<210> SEQ ID NO 287
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 287
aaatttctct aattcctccg aacgcacg 28

<210> SEQ ID NO 288
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 288
gcgtacgttg gtcgtttcgt attttc 26

<210> SEQ ID NO 289
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 289
gcaaaacact aaacaaacga aaaaacgcg 29

<210> SEQ ID NO 290
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (9)..(9)
<223> OTHER INFORMATION: Universal pyrimidine
<220> FEATURE:
<221> NAME/KEY: modified_base
<222> LOCATION: (17)..(17)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 290
gtagttatng agagtgngga gcgattag 28

<210> SEQ ID NO 291
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(7)
<223> OTHER INFORMATION: Universal purine
<220> FEATURE:
<221> NAME/KEY: modified_base
<222> LOCATION: (20)..(20)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 291
ctaatcnctc cgcactctcn ataactac 28

<210> SEQ ID NO 292
<211> LENGTH: 20
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (9)..(9)
<223> OTHER INFORMATION: Universal pyrimidine

<400> SEQUENCE: 292
gtttggagng ttatgagtag 20

<210> SEQ ID NO 293
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (13)..(13)
<223> OTHER INFORMATION: Universal purine

<400> SEQUENCE: 293
cttcatatcc ccnataaaac tc 22

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 294
gggtttttag tcggtttagt g 21

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (8)..(8)
<223> OTHER INFORMATION: Universal purine
<220> FEATURE:
<221> NAME/KEY: modified_base
<222> LOCATION: (17)..(17)
<223> OTHER INFORMATION: Universal purine

<400> SEQUENCE: 295
ctaaaacnta aaactcnaac c 21

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 296
gatttagagc gcgttgttcg c 21

<210> SEQ ID NO 297

<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 297
catatccccg ataaaactca acgactcg 28

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 298
gtcggtttag tgatattgcg ggc 23

<210> SEQ ID NO 299
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 299
ccacgaccta aacgtaaacc taacg 25

<210> SEQ ID NO 300
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(7)
<223> OTHER INFORMATION: Universal pyrimidine

<400> SEQUENCE: 300
gatggtnggg ttgggttttt gtttttgg 28

<210> SEQ ID NO 301
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 301
ccaaaaacaa aaacccaacc cgaccatc 28

<210> SEQ ID NO 302
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (11)..(11)
<223> OTHER INFORMATION: Universal pyrimidine
<220> FEATURE:
<221> NAME/KEY: modified_base
<222> LOCATION: (20)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 302
cgtatatttt nggttttttn gggtttcg 28

<210> SEQ ID NO 303
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Universal purine
<220> FEATURE:
<221> NAME/KEY: modified_base
<222> LOCATION: (18)..(18)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 303
cnaaacccga aaaaaccnaa aatatac 27

<210> SEQ ID NO 304
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Universal pyrimidine

<400> SEQUENCE: 304
ggtagttgtn gtcgggaagg aggttcg 27

<210> SEQ ID NO 305
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Universal purine
<220> FEATURE:
<221> NAME/KEY: modified_base
<222> LOCATION: (18)..(18)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 305
cnaacctcct tcccgacnac aactacc 27

<210> SEQ ID NO 306

<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 306 ggttttttt gtatagatgt ggttaatgg 29

<210> SEQ ID NO 307
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 307
ccattaacca catctataca aaaaaaacc 29

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (15)..(15)
<223> OTHER INFORMATION: Universal pyrimidine

<400> SEQUENCE: 308
ggtttggttt atagngtatt tagg 24

<210> SEQ ID NO 309
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 309
gaggtttagt aagtttttg gattgtg 27

<210> SEQ ID NO 310
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 310
cccttaaaaa ttacaaaaac cacaac 26

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 311
gtagattggg tggttaattt agag 24

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (12)..(12)
<223> OTHER INFORMATION: Universal purine
<220> FEATURE:
<221> NAME/KEY: modified_base
<222> LOCATION: (14)..(14)
<223> OTHER INFORMATION: Universal purine

<400> SEQUENCE: 312
ctataattcc cncnctttc 20

<210> SEQ ID NO 313
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 313
ggtggttaat ttagagtttc gagagac 27

<210> SEQ ID NO 314
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 314
cgttaccacg aaaaccaaaa aactaccg 28

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 315
gatttcgtat tttgagaggt tgttgtttag 30

<210> SEQ ID NO 316
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 316
ctaaacaaca acctctcaaa atacgaaatc 30

<210> SEQ ID NO 317
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 317
ggtagattgg gtggttaatt tagag 25

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 318
ccaaaaaatc tcaacraact c 21

<210> SEQ ID NO 319
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 319
gggtggttaa tttagagttt cgagagac 28

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 320
accacgaaaa ccaaaaaact accg 24

<210> SEQ ID NO 321
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 321
gggattttgt ttaagtatgt taaagg 26

<210> SEQ ID NO 322
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 322
cctaccttac ctctaaatac caacc 25

<210> SEQ ID NO 323
<211> LENGTH: 29
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 323
gtatgttaaa gggttgttgt aagttaagg                                      29

<210> SEQ ID NO 324
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
cctctaaata ccaaccccaa acc                                            23

<210> SEQ ID NO 325
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ccaactactc caaaaaactt ccaaaaacc                                      29

<210> SEQ ID NO 326
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ccaactactc caaaaaactt ccaaaaacc                                      29

<210> SEQ ID NO 327
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gtatgttaaa gggttgttgt aagttaagg                                      29

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
cctctaaata ccaaccccaa acc                                            23

<210> SEQ ID NO 329
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 329
ccaccaccca acacacaata acaaacac 28

<210> SEQ ID NO 330
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 330
ccaccaccca acacacaata acaaacac 28

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 331
atttagagcg cgttgttcgc 20

<210> SEQ ID NO 332
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 332
atatccccga taaaactcaa cgactcg 27

<210> SEQ ID NO 333
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 333
tatccccgat aaaactcaac gactcg 26

<210> SEQ ID NO 334
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 334
atccccgata aaactcaacg actcg 25

<210> SEQ ID NO 335
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 335
gcgttcggat ttttttttcg gc 22

<210> SEQ ID NO 336
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 336
tttctctaat tcctccgaac gcacg 25

<210> SEQ ID NO 337
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 337
ctctaattcc tccgaacgca cg 22

<210> SEQ ID NO 338
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 338
gtgacgatta gagttagatt tagagcgc 28

<210> SEQ ID NO 339
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 339
gtagttatcg agagtgcgga gcgattag 28

<210> SEQ ID NO 340
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 340
ccaacccgac catcaccgcg aacaac 26

<210> SEQ ID NO 341
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 341
ggagagtgta tttgtgaagg aaatg 25

<210> SEQ ID NO 342
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 342
catacataca ccaaacaatt cattc 25

<210> SEQ ID NO 343
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 343
ccaaatacca taaccatttt attaataaca c 31

<210> SEQ ID NO 344
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 344
ccaaatacca taaccatttt attaataaca c 31

<210> SEQ ID NO 345
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 345
ggtttygttg gggatttg 18

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 346
accrctcttc taaaaaatcc 20

<210> SEQ ID NO 347
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 347 aggtttttc ggttagttgc gc 22

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 348
aacgtcgacc gcaaaaaaac g 21

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 349
cgcgatttcg gggattttag g 21

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 350
cctaaaatcc ccgaaatcgc 20

<210> SEQ ID NO 351
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 351
gaagtagttg tgtaattygt tgg 23

<210> SEQ ID NO 352
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352
caccctaacr aactacacc 19

<210> SEQ ID NO 353
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 353
tgcggattag ggcgtttttt attttc 26

<210> SEQ ID NO 354
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 354
tacaaccaca tatcgatcac gtacg 25

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 355
ggagttcgtc gattggttgg g 21

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 356
cccaaccaat cgacgaactc c 21

<210> SEQ ID NO 357
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 357
gagtttttyg gagggttata g 21

<210> SEQ ID NO 358
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 358
caaactacaa aaaacattca atcc 24

<210> SEQ ID NO 359
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 359
gcgtttgggt tttttcggtg tc 22

<210> SEQ ID NO 360
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 360
atcgccgcaa ttaaaaaacc cg 22

<210> SEQ ID NO 361
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 361
ggttcgcgtt ttaattttta ggtattg 27

<210> SEQ ID NO 362
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 362
caatacctaa aaattaaaac gcgaacc 27

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 363
gttatggatt yggaygttag 20

<210> SEQ ID NO 364
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 364
ctccracraa caatcactc 19

<210> SEQ ID NO 365
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 365
gtttggtgtt tagtcgttcg tc 22

<210> SEQ ID NO 366
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 366
cactcgaaat aaacgaaaac acg 23

<210> SEQ ID NO 367
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 367
ggtagtagcg gtagcgtttt tattg 25

<210> SEQ ID NO 368
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 368
caataaaaac gctaccgcta ctacc 25

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 369
ggygtagttt atttyggtt 19

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 370
atttaaccra ctcraccaac 20

<210> SEQ ID NO 371
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 371
gtatgtttcg cggtttcgta gttc 24

<210> SEQ ID NO 372
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 372
actaaaccta acgttcgaaa cg 22

<210> SEQ ID NO 373
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 373
cgttcgttcg gtgtattttt ttttcgg 27

<210> SEQ ID NO 374
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 374
ccgaaaaaaa aatacaccga acgaac 26

<210> SEQ ID NO 375
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 375
gtttgagttg ttttgatttt agtg 24

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 376
ctccaacctc aactctaaac 20

<210> SEQ ID NO 377
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 377
gattttagtg tcgcgtattt tggttc 26

<210> SEQ ID NO 378

<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
ctaaactaaa tcccgcgaac ctcg                                              24

<210> SEQ ID NO 379
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 379
ggttttattg ggggttnatt tcgggtag                                          28

<210> SEQ ID NO 380
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 380
ctacccgaaa taaccccaa ntaaaacc                                           28

<210> SEQ ID NO 381
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ggtttttagt atttttayga aggt                                              24

<210> SEQ ID NO 382
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
cratacraaa acctactctc ta                                                22

<210> SEQ ID NO 383

<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 383
tttggatttt gttcgtcgtt agtgc 25

<210> SEQ ID NO 384
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 384
ctactctcta aacccgcgaa cg 22

<210> SEQ ID NO 385
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 385
ggttttagtc gtcgcggacg atgt 24

<210> SEQ ID NO 386
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 386
acatcgtccg cgacgactaa aacc 24

<210> SEQ ID NO 387
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 387
gagttagatt tagagcgcgt tgttc 25

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 388
gagcgcgttc ggattttttt ttc 23

<210> SEQ ID NO 389
<211> LENGTH: 19

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389

tggygggggt agatatttt                                                19


<210> SEQ ID NO 390
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390

tctactcaaa actctcccct ctcc                                          24
```

INTEGRATED PURIFICATION AND MEASUREMENT OF DNA METHYLATION AND CO-MEASUREMENT OF MUTATIONS AND/OR MRNA EXPRESSION LEVELS IN AN AUTOMATED REACTION CARTRIDGE

CROSS-REFERENCE TO RELATED APPLICATIONS

This application is a continuation of U.S. non-provisional application Ser. No. 15/839,731, filed Dec. 12, 2017, which claims the benefit of prior U.S. provisional application No. 62/433,165, filed Dec. 12, 2016, each of which is hereby incorporated by reference in its entirety.

INCORPORATION BY REFERENCE OF SEQUENCE LISTING PROVIDED AS A TEXT FILE

The instant application contains a Sequence Listing which has been submitted electronically in ASCII format and is hereby incorporated by reference in its entirety. Said ASCII copy, created on Jan. 27, 2022, is named CPHDP011C1US_SL.txt and is 104,271 bytes in size.

BACKGROUND

The genomes of higher eukaryotes contain the modified nucleoside 5-methyl cytosine (5-meC). This modification is usually found as part of the dinucleotide CpG in which cytosine is converted to 5-methylcytosine in a reaction that involves flipping a target cytosine out of an intact double helix and transfer of a methyl group from S-adenosylmethionine by a methyltransferase enzyme (see, e.g., Klimasauskas et al. (1994) Cell 76: 357-369). This enzymatic conversion is the primary epigenetic modification of DNA known to exist in vertebrates and is essential for normal embryonic development (see, e.g., Bird (1992) *Cell* 70: 5-8; Laird and Jaenisch (1994) *Human Mol. Genet.* 3: 1487-1495; and Li et al. (1992) *Cell* 69: 915-926).

In eukaryotes, DNA methylation regulates normal cellular processes such as genomic imprinting, chromosomal instability, and X-chromosome inactivation. Typically, DNA methylation occurs at the fifth carbon position of cytosine at dinucleotide 5'-CpG-3' sites in or near gene promoters termed CpG islands or shores. Methylation controls gene expression by down-regulating transcription either by directly inhibiting transcriptional machinery or indirectly through the recruitment of chromatin remodeling proteins. Chromosomal methylation patterns change dynamically during embryonic development, and the correct methylation patterns have to be maintained throughout an individual's lifetime. Changes in methylation patterns are linked to aging, and errors in DNA methylation are among the earliest changes that occur during oncogenesis. Thus, the detection of methylation at gene promoters is important, inter alia, for diagnosing and/or monitoring patients with cancer.

Epigenetic alterations, including DNA methylation, interrupt the DNA-RNA-protein axis which describes how genetic information is transcribed into messenger RNAs (mRNAs). The correlation between genomic DNA variation, mRNA copy numbers and protein levels may be described by DNA methylation levels. Thus co-measurement of DNA methylation levels and corresponding down-stream mRNA levels can be important to understanding the mechanism of epigenetic cellular regulation.

Several methods have been developed to detect and quantify methylation efficiently and accurately. The most common technique is the bisulfite conversion method which converts unmethylated cytosines to uracil. Once converted, the methylation profile of DNA can be determined by standard PCR techniques, sequencing methods, and the like.

There are several DNA Methylation kits suitable for bisulfite conversion and DNA cleanup (e.g., EZ DNA METHYLATION™ kits from Zymo Research). Most kits involve several steps, reagents, and incubation times and often require purified DNA before conversion although some kits can utilize tissue or plasma/serum as starting material.

Typically the bisulfite conversion process requires at least four steps: 1) DNA Denaturation; 2) Bisulfite Incubation; 3) DNA Purification; and 4) Desulphonation. The final desulphonation step can be completed on-column or in solution followed by an ethanol precipitation. There are currently no methylation kits that allow a user to complete the entire process-DNA purification, bisulfite incubation, desulphonation, second DNA purification, and methylation-specific PCR all in one step.

SUMMARY

Various embodiments contemplated herein may comprise, but need not be limited to, one or more of the following:

Various embodiments contemplated herein may include, but need not be limited to, one or more of the following:

Embodiment 1: A method of determining the methylation state of a nucleic acid, said method comprising:

i) contacting a biological sample comprising a nucleic acid to a first matrix material comprising a first column or filter where said matrix material binds and/or filters nucleic acids in said sample and thereby purifies the DNA;
ii) eluting the bound DNA from the first matrix material and denaturing the DNA to produce eluted denatured DNA;
iii) heating the eluted DNA in the presence of a bisulfite reagent to produce a deaminated nucleic acid;
iv) contacting said deaminated nucleic acid to a second matrix material comprising a second column to bind said deaminated nucleic acid to said second matrix material;
v) desulphonating the bound deaminated nucleic acid and/or simultaneously eluting and desulphonating the nucleic acid by contacting the deaminated nucleic acid with an alkaline solution to produce a converted (e.g., bisulfite converted) nucleic acid;
vi) eluting said bisulfite converted nucleic acid from said second matrix material; and
vii) performing methylation specific PCR and/or nucleic acid sequencing, and/or high resolution melting analysis (HRM) on said converted nucleic acid to determine the methylation of said nucleic acid, wherein at least steps iv) through vi) are performed in a single reaction cartridge.

Embodiment 2: The method of embodiment 1, wherein at least steps iv) through vi) are performed in a single reaction cartridge.

Embodiment 3: The method of embodiment 1, wherein at least steps iii) through vi) are performed in a single reaction cartridge.

Embodiment 4: The method of embodiment 1, wherein at least steps ii) through vi) are performed in a single reaction cartridge.

Embodiment 5: The method of embodiment 1, wherein at least steps i) through vi) are performed in a single reaction cartridge.

Embodiment 6: The method according to any one of embodiments 1-5, wherein step vii is performed in the same reaction cartridge.

Embodiment 7: The method according to any one of embodiments 1-6, wherein said first matrix material and said second matrix material are the same material forming the same column.

Embodiment 8: The method according to any one of embodiments 1-7, wherein said first matrix material and said second matrix material form different columns.

Embodiment 9: The method according to any one of embodiments of embodiment 1-8, wherein said methylation specific PCR, when performed, is performed in said cartridge.

Embodiment 10: The method according to any one of embodiments 1-9, wherein said nucleic acid sequencing, when performed, is performed in said cartridge or in a device coupled to said cartridge.

Embodiment 11: The method according to any one of embodiments 1-10, wherein said cartridge comprises a column comprising said first matrix material, a sample receiving chamber, a temperature controlled channel or chamber, a plurality of chambers containing reagents and/or buffers, and when in use at least one of said chambers contains a desulphonation/elution buffer, and wherein said cartridge optionally comprises a second column comprising said second matrix material.

Embodiment 12: The method of embodiment 11, wherein, when in use, at least one of said chambers contains a reagent that provides bisulfite ions.

Embodiment 13: The method according to any one of embodiments 11-12, wherein said second column is absent.

Embodiment 14: The method according to any one of embodiments 11-13, wherein said second column is present.

Embodiment 15: The method according to any one of embodiments 11-14, wherein said cartridge comprises a thermocycling channel or chamber in addition to said temperature controlled channel or chamber.

Embodiment 16: The method according to any one of embodiments 11-14, wherein said temperature controlled channel or chamber is a thermocycling channel or chamber.

Embodiment 17: The method according to any one of embodiments 11-16, wherein said cartridge comprises one or more chambers containing one or more reagents selected from the group consisting of methylation specific PCR primers, methylation specific PCR probes, PCR enzyme(s), and PCR reaction buffer.

Embodiment 18: The method of embodiment 17, wherein said cartridge comprises one or more chambers containing one or more primers and probes for detection of methylation of a forward strand of a bisulfate-converted DNA.

Embodiment 19: The method according to any one of embodiments 17-18, wherein said cartridge comprises one or more chambers containing one or more primers and probes for detection of methylation of a reverse strand of a bisulfate-converted DNA.

Embodiment 20: The method according to any one of embodiments 11-19, wherein said sample receiving chamber, said column(s), said plurality of chambers, and when present, said temperature controlled channel or chamber and/or thermocycling channel or chamber, are selectively in fluid communication.

Embodiment 21: The method of embodiment 20, wherein said sample receiving chamber, said column(s), said plurality of chambers, and when present, said thermocycling channel or chamber, are selectively in fluid communication by microfluidic channels and valves.

Embodiment 22: The method of embodiment 20, wherein said sample receiving chamber, said column(s), said plurality of chambers, and when present, said thermocycling channel or chamber or a port into said thermocycling channel or chamber, are disposed around a central valve and selectively in fluid communication with a channel in said central valve, wherein said central valve is configured to accommodate a plunger that is capable of drawing fluid into or out of a chamber in fluid communication with said central valve.

Embodiment 23: The method according to any one of embodiments 11-22, wherein said cartridge, when in use, comprises:

a first chamber containing a sample;

a second chamber containing a guanidinium thiocyanate-ethanol (GTC-EtOH) solution;

a third chamber containing a bisulfate reagent;

a fourth chamber containing a buffer;

a fifth chamber containing a rinse solution; and a sixth chamber containing an elution/desulphonation reagent.

Embodiment 24: The method of embodiment 23, wherein first chamber contains said sample in a GTC-EtOH-Tween extraction/precipitation reagent.

Embodiment 25: The method according to any one of embodiments 23-24, wherein the GTC-ETOH-Tween buffer is added at or near the time the sample is placed into the cartridge.

Embodiment 26: The method according to any one of embodiments 23-25, wherein the bisulfite reagent is added to the cartridge at or near the time the sample is placed in the cartridge.

Embodiment 27: The method of embodiment 23, wherein the GTC-ETOH-Tween buffer is provided as a component of the cartridge.

Embodiment 28: The method according to any one of embodiments 23-25, wherein the bisulfite reagent is provided as a component of the cartridge.

Embodiment 29: The method according to any one of embodiments 11-28, wherein said cartridge comprises a seventh chamber containing PCR primers and/or probes and/or PCR enzymes.

Embodiment 30: The method according to any one of embodiments 11-29, wherein said cartridge comprises an eighth chamber also containing PCR primers and/or probes and/or PCR enzymes.

Embodiment 31: The method of embodiments 29-30, wherein said PCR primers, and/or probes, and/or enzymes are provided as beads.

Embodiment 32: The method according to any one of embodiments 1-31, wherein said biological sample comprises one or more samples selected from the group consisting of a cell, a tissue, and a biological fluid containing a nucleic acid.

Embodiment 33: The method of embodiment 32, wherein said biological sample comprises a biological fluid selected from the group consisting of whole blood, plasma, serum, saliva, mucus, urine, sputum, pancreatic juice, and cerebrospinal fluid.

Embodiment 34: The method of embodiment 32, wherein said biological sample comprises a sample selected from the group consisting of a tissue sample, a formalin fixed paraffin embedded (FFPE) tissue, fresh frozen tissue, fine needle aspirates (FNA), and a core biopsy.

Embodiment 35: The method according to any one of embodiments 1-34, wherein said method comprises contacting said biological sample with a lysis solution.

Embodiment 36: The method of embodiment 35, wherein said method comprises providing said sample in said sample receiving chamber and contacting said sample with an extraction/precipitation solution.

Embodiment 37: The method according to any one of embodiments 1-36, wherein said matrix material comprises a column material selected from the group consisting of glass or silica, an ion exchange resin, cellulose, and hydroxyapatite.

Embodiment 38: The method of embodiment 37, wherein said matrix material comprises glass.

Embodiment 39: The method according to any one of embodiments 1-38, wherein said bisulfite ion is provided as compound selected from the group consisting of ammonium bisulfite, sodium metabisulfite, potassium bisulfite, cesium bisulfite, and DABSO.

Embodiment 40: The method of embodiment 39, wherein said bisulfite ion is provided by ammonium bisulfite.

Embodiment 41: The method according to any one of embodiments 1-40, wherein said bisulfite is provided in a reagent mix comprising scavengers to prevent sulfite oxidation and/or catalysts.

Embodiment 42: The method of embodiment 41, wherein said bisulfite is provided in a reagent mix comprising scavengers selected from the group consisting of TROLOX water-soluble analog of vitamin E and hydroquinone.

Embodiment 43: The method according to any one of embodiments 41-42, wherein said bisulfite is provided in a reagent mix comprising polyamines as catalysts.

Embodiment 44: The method according to any one of embodiments 1-43, wherein said eluting the bound DNA comprises eluting and denaturing said DNA using a low concentration of potassium hydroxide or other base.

Embodiment 45: The method of embodiment 44, wherein said eluting the bound DNA comprises eluting and denaturing said DNA with an alkaline solution with a pH greater than about pH 10.5.

Embodiment 46: The method of embodiment 44, wherein said eluting the bound DNA comprises eluting and denaturing said DNA with an alkaline solution with a pH greater than about pH 12.

Embodiment 47: The method of embodiments 45-46, wherein said alkaline solution is a 10-15 mM KOH solution.

Embodiment 48: The method according to any one of embodiments 1-47, wherein said incubating the eluted DNA with bisulfite ions to produce a deaminated nucleic acid comprises incubating the DNA in an ammonium bisulfite solution having a concentration that ranges from about 6M to about 7M.

Embodiment 49: The method of embodiment 48, wherein said incubating the eluted DNA with bisulfite ions to produce a deaminated nucleic acid comprises incubating the DNA in an ammonium bisulfite solution having a concentration of about 6.5M.

Embodiment 50: The method of embodiment 49, wherein said incubating comprises transferring the DNA in a concentrated bisulfite solution into a temperature controlled channel or chamber in said cartridge and heating said mixture.

Embodiment 51: The method of embodiment 50, wherein said incubating comprises thermally cycling the concentrated bisulfite solution from a temperature of about 60° C. to about 95° C.

Embodiment 52: The method according to any one of embodiments 1-51, wherein said contacting said deaminated nucleic acid to a second matrix material comprises mixing the DNA-bisulfite solution with fresh GTC-EtOH and dispensing the solution over said second matrix material.

Embodiment 53: The method of embodiment 52, wherein said method comprises washing the DNA in said second matrix material with fresh GTC-EtOH, and then a rinse solution.

Embodiment 54: The method of embodiment 53, wherein said rinse solution comprises PEG200.

Embodiment 55: The method according to any one of embodiments 1-54, wherein said desulphonating the bound deaminated nucleic acid comprises eluting the DNA from said second column with a high pH desulphonation buffer and incubating said solution.

Embodiment 56: The method of embodiment 55, wherein said incubating is for a period of time ranging from about 1 minute to about 1 hour, or from about 5 minutes to about 30 minutes, or from about 10 minutes to about 20 minutes, or for about 15 minutes.

Embodiment 57: The method of embodiments 55-56, wherein said high pH desulphonation/elution buffer comprises KOH.

Embodiment 58: The method according to any one of embodiments 55-57, wherein said incubation is in a chamber that previously held said high pH desulphonation buffer (e.g., chamber 10).

Embodiment 59: The method according to any one of embodiments 1-58, wherein after the incubation with bisulfite ions, a temperature controlled channel or chamber is washed with a buffer to remove the residual bisulfite and neutralize pH.

Embodiment 60: The method according to any one of embodiments 1-59, wherein high resolution melting analysis (HRM) on said bisulfite-converted nucleic acid is performed to determine the methylation of said nucleic acid.

Embodiment 61: The method according to any one of embodiments 1-60, wherein nucleic acid sequencing of said bisulfite-converted nucleic acid is performed to determine the methylation of said nucleic acid.

Embodiment 62: The method according to any one of embodiments 1-60, wherein methylation specific PCR is performed to determine methylation of target nucleic acid sequences.

Embodiment 63: The method of embodiment 62, wherein said methylation specific PCR (MSP) is performed using primers specific for methylated sequences and/or primers specific for unmethylated sequences.

Embodiment 64: The method of embodiment 62, wherein said methylation specific PCR comprises a MethyLight protocol.

Embodiment 65: The method of embodiment 62, wherein TaqMan PCR reactions are performed with primers specific for bisulfite-converted methylated and/or unmethylated sequences.

Embodiment 66: The method according to any one of embodiments 62-65, wherein said MSP utilizes one or more fluorescent probes that are markers for amplified methylated sequences and/or one or more fluorescent probes that are markers for amplified unmethylated sequences.

Embodiment 67: The method of embodiment 66, wherein said fluorescent probes comprise a fluorescent reporter dye and a quencher dye where the probe provides a signal upon cleavage by 5' to 3' nuclease activity of Taq DNA polymerase.

Embodiment 68: The method according to any one of embodiments 66-67, wherein a methylation signal is determined by the combined signal for a plurality of probes each specific to a different methylated region in an amplified region of interest.

Embodiment 69: The method according to any one of embodiments 66-67, wherein a methylation signal is determined by a plurality of probes specific for the same methylated region in an amplified region of interest.

Embodiment 70: The method according to any one of embodiments 66-67, wherein said plurality of probes comprise 2, 3, 4, 5, 6, 7, 8, 9, 10, or more probes.

Embodiment 71: The method according to any one of embodiments 66-67, wherein a methylation signal is determined by a single probe in the amplified region of interest.

Embodiment 72: The method according to any one of embodiments 66-71, wherein said probes are run in simplex or multiplex.

Embodiment 73: The method according to any one of embodiments 66-71, wherein said probes are run in a multiplex format.

Embodiment 74: The method according to any one of embodiments 66-73, wherein said probes are run as a nested PCR reaction.

Embodiment 75: The method according to any one of embodiments 66-74, wherein said PCR reaction comprises a bisulfite contamination control probe that that undergoes bisulfite-mediated cleavage during PCR if bisulfite is present in the reaction.

Embodiment 76: The method according to any one of embodiments 1-75, wherein PCR is performed for one or more mutated genes.

Embodiment 77: The method according to any one of embodiments 1-76, wherein PCR is performed for unconverted DNA as a control.

Embodiment 78: The method according to any one of embodiments 1-77, wherein PCR is performed for converted DNA as a control.

Embodiment 79: The method of embodiment 77, wherein PCR is performed for unconverted DNA where the unconverted DNA is a target for said method.

Embodiment 80: The method according to any one of embodiments 1-79, wherein a bisulfite reaction and a PCR reaction, or a desulphonation reaction and a PCR reaction, or a bisulfite reaction, a desulphonation reaction and a PCR reaction are all performed in the same reaction tube or chamber.

Embodiment 81: The method according to any one of embodiments 1-80, wherein said contacting a biological sample comprising a nucleic acid to a first matrix material comprises contacting a sample containing RNA to said first matrix material, where said matrix material binds said RNA thereby purifies the RNA.

Embodiment 82: The method of embodiment 81, wherein said method comprises eluting said RNA from said matrix material substantially independently of the DNA.

Embodiment 83: The method of embodiment 82, wherein the RNA is eluted from said first matrix material using a Tris buffered elution.

Embodiment 84: The method according to any one of embodiments 81-83, wherein said RNA is eluted and stored in a chamber.

Embodiment 85: The method according to any one of embodiments 81-84, wherein reverse transcription (RT) is performed on said RNA and qRT-PCR is performed to determine the level of target RNA sequences.

Embodiment 86: The method according to any one of embodiments 82-85, where the RNA fraction is used to elute the bisulfite converted nucleic acid from said second matrix material and mix with the bisulfite-converted DNA, or is mixed with eluted bisulfite-converted DNA.

Embodiment 87: The method of embodiment 86, wherein RT is performed on said RNA prior to, or after, combination with the bisulfite-converted DNA.

Embodiment 88: The method according to any one of embodiments 86-87, wherein qRT-PCR is performed for RT RNA in the mixture to determine the level of target RNA sequences and methylation specific PCR is performed on the mixture to determine methylation of target DNA sequences.

Embodiment 89: The method according to any one of embodiments 1-88, where methylation is determined for a promoter region of a gene selected from the group consisting of MGMT. RASSF1A, ADAMTS1, BNC1, HIST1H3C, HOXB4, RASGRF2, TM6SF1, and AKR1B1.

Embodiment 90: The method according to any one of embodiments 81-89, wherein the expression level of RNA is determined for a methyltransferase.

Embodiment 91: The method of embodiment 90, wherein the expression level of RNA is determined for a methyltransferase selected from the group consisting of DNMT1, DNMT2, DNMT3A, DNMT3B, and TNMT3L.

Embodiment 92: A cartridge for determining the methylation state of a nucleic acid, said cartridge comprising: a column comprising a first matrix material, a sample receiving chamber, a temperature controlled channel or chamber, a plurality of chambers containing reagents and/or buffers, and when in use at least one of said chambers contains a bisulfite reagent, and at least one of said chambers contains a desulphonation/elution buffer, and wherein said cartridge optionally comprises a second column comprising said second matrix material.

Embodiment 93: The cartridge of embodiment 92, wherein said cartridge, when in use, comprises a chamber containing a reagent comprising guanidinium thiocyanate ethanol (GTC-EtOH).

Embodiment 94: The cartridge according to any one of embodiments 92-93, wherein said second column is absent.

Embodiment 95: The cartridge according to any one of embodiments 92-93, wherein said second column is present.

Embodiment 96: The cartridge according to any one of embodiments 92-95, wherein said temperature controlled channel or chamber is a thermocycling channel or chamber.

Embodiment 97: The cartridge according to any one of embodiments 92-96, wherein said cartridge further comprises a second heating channel or chamber.

Embodiment 98: The cartridge according to any one of embodiment 92-97, wherein said bisulfite reagent comprises a compound selected from the group consisting of ammonium bisulfite, sodium metabisulfite, potassium bisulfite, cesium bisulfite, and DABSO.

Embodiment 99: The cartridge of embodiment 98, wherein said bisulfite reagent comprises ammonium bisulfite.

Embodiment 100: The cartridge according to any one of embodiments 92-99, wherein said bisulfite is provided in a reagent mix comprising scavengers to prevent sulfite oxidation and/or catalysts.

Embodiment 101: The cartridge of embodiment 100, wherein said bisulfite is provided in a reagent mix comprising scavengers selected from the group consisting of TROLOX water-soluble analog of vitamin E and hydroquinone.

Embodiment 102: The cartridge according to any one of embodiments 100-101, wherein said bisulfite is provided in a reagent mix comprising polyamines as catalysts.

Embodiment 103: The cartridge according to any one of embodiments 92-102, wherein said first matrix material and/or said second matrix material, when present, comprises a material is selected from the group consisting of glass or silica, an ion exchange resin, and hydroxyapatite.

Embodiment 104: The cartridge according to any one of embodiments 92-103, wherein said cartridge comprises one or more chambers containing one or more reagents selected from the group consisting of methylation specific PCR primers, methylation specific PCR probes, PCR enzyme(s), and PCR reaction buffer.

Embodiment 105: The cartridge of embodiment 104, wherein said cartridge contains at least two chambers containing one or more reagents selected from the group consisting of methylation specific PCR primers, methylation specific PCR probes, PCR enzyme(s), and PCR reaction buffer.

Embodiment 106: The cartridge according to any one of embodiments 92-105, wherein said cartridge contains at least one chamber containing primers and probes for detection of methylation of a forward strand of a converted DNA.

Embodiment 107: The cartridge according to any one of embodiments 92-106, wherein said cartridge contains at least one chamber containing primers and probes for detection of methylation of a reverse strand of a converted DNA.

Embodiment 108: The cartridge according to any of embodiments 104-107, wherein said PCR primers, and/or probes, and/or enzymes are provided as beads.

Embodiment 109: The cartridge according to any one of embodiments 92-108, wherein said sample receiving chamber, said column(s), said plurality of chambers, and said temperature-controlled heating channel or chamber, are selectively in fluid communication.

Embodiment 110: The cartridge of embodiment 109, wherein said sample receiving chamber, said column(s), said plurality of chambers, and said temperature controlled channel or chamber, are selectively in fluid communication by microfluidic channels and valves.

Embodiment 111: The cartridge of embodiment 109, wherein said sample receiving chamber, said column(s), said plurality of chambers, and said temperature controlled channel or chamber or a port into said temperature controlled channel or chamber, are disposed around a central valve and selectively in fluid communication with a channel in said central valve, wherein said central valve is configured to accommodate a plunger that is capable of drawing fluid into or out of a chamber in fluid communication with said central valve.

Embodiment 112: The cartridge according to any one of embodiments 92-111, wherein said cartridge is configured so that, when in use, said cartridge comprises:

- a first chamber containing a sample;
- a second chamber containing a guanidinium thiosulfate-ethanol (GTC-EtOH) solution;
- a third chamber containing a bisulfite reagent;
- a fourth chamber containing a buffer;
- a fifth chamber containing a rinse solution; and
- a sixth chamber containing an elution/desulphonation reagent.

Embodiment 113: The cartridge of embodiment 112, wherein said first chamber contains said sample in a GTC-EtOH-Tween extraction/precipitation reagent.

Embodiment 114: The cartridge according to any one of embodiments 92-113, wherein the cartridge is configured for the bisulfite reagent to be added to the cartridge at or near the time the sample is placed in the cartridge.

Embodiment 115: The cartridge according to any one of embodiments 92-113, wherein the bisulfite reagent is provided as a component of the cartridge.

Embodiment 116: The cartridge according to any one of embodiments 92-115, wherein the cartridge is configured for addition of GTC-ETOH-Tween buffer at or near the time the sample is placed into the cartridge.

Embodiment 117: The cartridge according to any one of embodiments 92-115, wherein the GTC-ETOH-Tween buffer is provided as a component of the cartridge.

Embodiment 118: The cartridge according to any one of embodiments 92-117, wherein said cartridge comprises a seventh chamber containing PCR primers and/or probes and/or PCR enzymes.

Embodiment 119: The cartridge according to any one of embodiments 92-118, wherein said cartridge comprises an eighth chamber also containing PCR primers and/or probes and/or PCR enzymes.

Embodiment 120: The cartridge according to any one of embodiments 92-119, wherein said cartridge comprises one or more chambers containing primers specific for bisulfite-converted methylated and/or unmethylated sequences.

Embodiment 121: The cartridge according to any one of embodiments 92-120, wherein said cartridge comprises one or more chambers containing reagents for TaqMan PCR reactions.

Embodiment 122: The cartridge according to any one of embodiments 92-121, wherein said cartridge comprises one or more chambers containing one or more fluorescent probes that are markers for amplified methylated sequences and/or one or more fluorescent probes that are markers for amplified unmethylated sequences.

Embodiment 123: The cartridge of embodiment 122, wherein said probes comprise a fluorescent reporter dye and a quencher dye, where the probes provides a signal upon cleavage by the 5' to 3' nuclease activity of Taq DNA polymerase.

Embodiment 124: The cartridge according to any one of embodiments 122-123, wherein said cartridge comprises a plurality of probes each specific to a different methylated region in an amplified region of interest.

Embodiment 125: The cartridge according to any one of embodiments 122-123, wherein said cartridge comprises a single probe specific to a methylated region in an amplified region of interest.

Embodiment 126: The cartridge according to any one of embodiments 122-123, wherein said cartridge comprises a plurality of probes each specific to the same methylated region in an amplified region of interest.

Embodiment 127: The cartridge according to any one of embodiments 92-126, wherein said cartridge contains primers and/or probes to determine methylation of a promoter region of a gene selected from the group consisting of MGMT, RASSF1A, ADAMTS1, BNC1, HIST1H3C, HOXB4, RASGRF2, TM6SF1, and AKR1B1.

Embodiment 128: The cartridge according to any one of embodiments 92-126, wherein said cartridge contains one or more primers shown in Tables 5, 9, or 10, and/or one or more probes shown in Tables 5, 9, or 10.

Embodiment 129: The cartridge of embodiment 128, wherein said cartridge contains the following probes and primers for determining methylation of MGMT using a nested PCR reaction:

an external forward primer (248b) comprising the nucleotide sequence (SEQ ID NO: 263)

GTTTT(T*)AGAAYG(T*)TTTGYGTTT;

an external reverse primer (249b) comprising the nucleotide sequence:

(SEQ ID NO: 265)
AAAAAAC(T*)CCRCACTCTTCC;

an internal forward primer (250) comprising the nucleotide sequence (SEQ ID NO: 266)
TTTCGACGTTCGTAGGTTTTCGC;

an internal reverse primer (251) comprising the nucleotide sequence (SEQ ID NO: 267)
GCACTCTTCCGAAAACGAAACG;

and a probe (252a) comprising the nucleotide sequence fluor- (SEQ ID NO: 268)
CCAAACAC(T*)CACCAAATC(N*)CAAAC-blocker.

Embodiment 130: The cartridge according to any one of embodiments 128-129, wherein said cartridge contains the following probes and primers for determining methylation of ACTB (e.g., as a control) using a nested PCR reaction:

an external forward primer (102) comprising the nucleotide sequence:

(SEQ ID NO: 103)
GTGATGGAGGAGGTTTAGTAAGTT;

an external reverse primer (103) comprising the nucleotide sequence:

(SEQ ID NO: 104)
CCAATAAAACCTACTCCTCCCTTAA;

an internal forward primer (148) comprising the nucleotide sequence:

(SEQ ID NO: 149)
GGTTTAGTAAGTTTTTTGGATTGTG;

an internal reverse primer (149) comprising the nucleotide sequence:

(SEQ ID NO: 150)
CCTTAAAAATTACAAAAACCACAAC;

and a probe (178) comprising the nucleotide sequence: fluor- (SEQ ID NO: 179)
CCACCACCCAACACA(N*)CAA(T*)AACAAACAC-blocker.

Embodiment 131: The cartridge according to any one of embodiments 92-130, wherein the cartridge is configured for determination of the expression level of RNA for a methyltransferase.

Embodiment 132: The cartridge of embodiment 131, wherein said methyltransferases is selected from the group consisting of DNMT1, DNMT2, DNMT3A, DNMT3B, and TNMT3L.

Embodiment 133: A system for determining the methylation of a nucleic acid in a biological sample, said system comprising: an enclosure configured to contain one or more sample processing modules, each sample processing module configured to hold a removable cartridge according to any one of embodiments 92-132; where said system is configured to operate the sample processing modules to perform sample processing to determine methylation of one or more target nucleic acids and optionally to determine the level of one or more target DNA sequences within a corresponding removable sample cartridge, wherein said processing on a sample within the corresponding removable sample cartridge performs a method according to any one of embodiments 1-91.

Embodiment 134: The system of embodiment 133, wherein said system is configured to contain one sample processing module.

Embodiment 135: The system of embodiment 133, wherein said system is configured to contain at least two sample processing modules, or at least 4 sample processing modules, or at least 8 sample processing modules, or at least 12 sample processing modules, or at least 16 sample processing modules, or at least 20 sample processing modules, or at least 24 sample processing modules, or at least 28 sample processing modules, or at least 32 sample processing modules, or at least 64 sample processing modules, or at least 128 sample processing modules.

Embodiment 136: The system according to any one of embodiments 133-135, wherein said modules comprise one or more heating plates to heat a temperature controlled chamber or channel in said cartridge.

Embodiment 137: The system according to any one of embodiments 133-136, wherein said modules comprise a fan configured to cool a temperature controlled channel or chamber in said cartridge.

Embodiment 138: The system according to any one of embodiments 133-137, wherein said modules comprise circuitry to pass information (e.g., optical information) to a computer for analysis.

Embodiment 139: The system according to any one of embodiments 133-138, wherein said modules comprise optical blocks to provide excitation and/or detection of one or more optical signals produced by reactions in said cartridge.

Embodiment 140: The system according to any one of embodiments 133-139, wherein said system is configured to operate said cartridge to perform a method according to any one of embodiments 1-91.

Embodiment 141: The system according to any one of embodiments 133-139, wherein said system is configured to operate said cartridge to: bind a sample to a column; elute DNA from the column and combine said DNA with a conversion reagent; heat the DNA/conversion reagent solution in a reaction chamber or tube to produce converted DNA; bind the converted DNA to a column; desulphonate and elute the DNA from the column; and perform PCR on the eluted desulphonated DNA in a reaction chamber or tube.

Embodiment 142: The system of embodiment 141, wherein said PCR is performed in the same reaction chamber or tube where the DNA/conversion reagent solution was previously heated.

Embodiment 143: A cartridge for sample preparation, said cartridge comprising: a channel or chamber comprising an affinity matrix that binds DNA, a plurality of chambers disposed around a central valve assembly and selectively in fluid communication with said central valve assembly where said central valve assembly is configured to accommodate a plunger that is capable of drawing fluid into or out of a chamber in fluid communication with said central valve wherein said plurality of chambers comprises: a chamber configured to receive up to about 5 ml or up to about 4 ml of sample solution; a chamber containing PEG; a chamber containing GTC-EtOH; a chamber containing an alkaline solution; and a chamber containing a buffer.

Embodiment 144: The cartridge of embodiment 143, wherein said plurality of chambers further comprises a chamber containing a bisulfate reagent.

Embodiment 145: The cartridge according to any one of embodiments 143-144, wherein said plurality of chambers comprises a chamber containing a GTC-ethanol wash solution.

Embodiment 146: The cartridge of embodiment 145, wherein said GTC-ethanol wash solution comprises 1.25M guanidinium thiocyanate, 25 mM Tris pH 7.0, and 50% ethanol.

Embodiment 147: The cartridge according to any one of embodiments 143-146, wherein said PEG comprises PEG200.

Embodiment 148: The cartridge according to any one of embodiments 143-147, wherein said alkaline solution comprises KOH.

Embodiment 149: The cartridge according to any one of embodiments 143-148, wherein said buffer comprises Tris.

Embodiment 150: The cartridge according to any one of embodiments 143-149. wherein said plurality of chambers comprises a chamber containing beads comprising one or more PCR primers and/or probes.

Embodiment 151: The cartridge according to any one of embodiments 143-150, wherein said chamber containing PEG contains about 1 ml of PEG.

Embodiment 152. The cartridge according to any one of embodiments 143-151, wherein said chamber containing an alkaline solution contains about 500 μL of solution.

Embodiment 153: The cartridge according to any one of embodiments 143-152, wherein said chamber containing GTC-EtOH contains about 2 ml GTC-EtOH.

Embodiment 154: The cartridge according to any one of embodiments 143-153, wherein said chamber containing a buffer contains about 2 mL of buffer.

Embodiment 155: A high volume sample preparation (HVSP), said cartridge comprising: a channel or chamber comprising an affinity matrix that binds DNA, a plurality of chambers disposed around a central valve assembly and selectively in fluid communication with said central valve assembly where said central valve assembly is configured to accommodate a plunger that is capable of drawing fluid into or out of a chamber in fluid communication with said central valve wherein said plurality of chambers comprises: at least two different chambers each configured to receive up to about 4.5 ml of sample solution; a chamber containing PEG; a chamber containing an alkaline solution; and a chamber containing a buffer.

Embodiment 156: The cartridge of embodiment 155, wherein said plurality of chambers comprises at least three different chambers each configured to receive up to 4 ml of sample solution.

Embodiment 157: The cartridge according to any one of embodiments 155-156, wherein said PEG comprises PEG200.

Embodiment 158: The cartridge according to any one of embodiments 155-157, wherein said basic solution comprises KOH.

Embodiment 159: The cartridge according to any one of embodiments 155-158, wherein said buffer comprises Tris.

Embodiment 160: The cartridge according to any one of embodiments 155-159, wherein said plurality of chambers comprises a chamber containing a wash solution.

Embodiment 161: The cartridge of embodiment 160, wherein said wash solution comprise 1.25M guanidinium thiocyanate, 25 mM Tris pH 7.0, and 50% ethanol.

Embodiment 162: The cartridge according to any one of embodiments 155-161, wherein said cartridge comprises a chamber configured for removal of a processed sample.

Embodiment 163: The cartridge according to any one of embodiments 155-162, wherein said sample chambers, when in use contain sample solution, GTC and isopropanol.

Embodiment 164: The cartridge of embodiment 163, wherein said sample chambers, when in use contain sample solution, GTC and isopropanol in substantially equal volumes.

Embodiment 165: The cartridge according to any one of embodiments 155-164 wherein said cartridge, when in use, comprises 4 ml of sample solution disposed in each of said chambers configured to receive a sample.

Embodiment 166: The cartridge according to any one of embodiments 155-165, wherein said cartridge provides DNA or RNA recovery that is substantially linear with respect to the sample volume between 0.5 ml and about 4 ml of sample.

Embodiment 167: The cartridge according to any one of embodiments 155-166, wherein said cartridge contains or is configured to receive a conversion reagent.

Embodiment 168: The cartridge of embodiment 167, wherein said cartridge, when in use, performs a bisulfate conversion of DNA.

Embodiment 169: A lysis solution for preparation of a DNA sample from serum or plasma, said lysis solution comprising: GTC, a buffer, a detergent, and optionally an anti-foaming agent.

Embodiment 170: The lysis solution of embodiment 169, wherein said lysis solution for serum or plasma comprises GTC, Tris pH 7.0, Tween 20, and antifoam SE15.

Embodiment 171: The lysis solution of embodiment 170, wherein said lysis solution for serum or plasma comprises about 4.5M GTC, about 45 mM Tris pH 7.0, about 1% Tween20, and about 0.01% Antifoam SE15.

Embodiment 172: A lysis solution for preparation of a DNA sample from an FFPE sample.

Embodiment 173: The lysis solution of embodiment 172, wherein said lysis solution for FFPE samples comprises a buffer, a detergent, NaCl, $MgCl_2$, a chelating agent, antifoam SE15, and sodium azide.

Embodiment 174: The lysis solution of embodiment 173, wherein said lysis solution for FFPE samples comprises about 1% Tween20, about 400 mM NaCl, about 25 mM EDTA, about 10 mM $MgCl_2$, about 50 mM HEPES pH 7.2, about 0.01% antifoam SE15, and about 0.01% sodium azide.

Embodiment 175: A kit for the determination of DNA methylation, said kit comprising: a container containing a cartridge for determining the methylation state of a nucleic acid according to any one of embodiments 92-136.

Embodiment 176: The kit of embodiment 175, wherein said kit further comprises a container containing a lysis solution.

Embodiment 177: The kit of embodiment 176, wherein said lysis solution is a lysis solution for serum or plasma according to any one of embodiments 169-171.

Embodiment 178: The kit of embodiment 176, wherein said lysis solution is a lysis solution for an FFPE sample according to any one of embodiments 172-174.

Embodiment 179: The kit according to any one of embodiments 175-178, wherein said kit comprises a container containing proteinase K.

Embodiment 180: The kit according to any one of embodiments 175-179, wherein said kit comprises a conversion reagent in said cartridge or in a container separate from the cartridge.

Embodiment 181: The kit of embodiment 180, wherein said kit comprises said conversion reagent in a container separate from the cartridge.

Embodiment 182: The kit of embodiment 180, wherein said kit comprises said conversion reagent is provided in a chamber of the cartridge.

Embodiment 183: The according to any one of embodiments 180-182, wherein said conversion reagent comprises a compound selected from the group consisting of sodium metabisulfite, potassium bisulfite, cesium bisulfite, ammonium bisulfite, and DABSO.

Embodiment 184: The kit of embodiment 183, wherein said conversion reagent comprises ammonium bisulfite.

Embodiment 185: The kit according to any one of embodiments 175-184, wherein said kit comprises a container containing a sample processing reagent.

Embodiment 186: The kit of embodiment 185, wherein said sample processing reagent comprises guanidium thiocyanate.

Embodiment 187: The kit according to any one of embodiments 185-186, wherein said sample processing reagent comprise ethanol.

Embodiment 188: The kit according to any one of embodiments 175-187, wherein said kit comprises a container containing a cartridge for sample preparation according to any one of embodiments 155-166.

Embodiment 189: The kit according to any one of embodiments 175-188, wherein said kit contains instructional materials teaching the use of said cartridge for the determination of DNA methylation.

Embodiment 190: A cartridge for the detection of methylation markers of a cancer, said cartridge comprising: a plurality of chambers and a thermocycling channel or chamber, wherein said plurality of chambers and a port into said thermocycling channel or chamber are disposed around a central valve assembly and selectively in fluid communication with said central valve assembly where said central valve assembly is configured to accommodate a plunger that is capable of drawing fluid into or out of a chamber or port in fluid communication with said central valve wherein said plurality of chambers comprises: a sample receiving chamber; a chamber containing or configured to receive a bisulfite reagent; a chamber containing a wash solution; a chamber containing a Tris buffer; a chamber containing an alkaline solution comprising KOH; a chamber containing beads that provide a PCR master mix; and a chamber containing beads that provide PCR primers and probes to detect methylation of one or more gene promoters whose methylation state is a marker for a cancer.

Embodiment 191: The cartridge of embodiment 190, wherein said plurality of chambers comprises a chamber disposed to receive waste solutions.

Embodiment 192: The cartridge according to any of embodiments 190-191, wherein said bisulfite reagent comprises a compound selected from the group consisting of sodium metabisulfite, potassium bisulfite, cesium bisulfite, ammonium bisulfite, and DABSO.

Embodiment 193: The cartridge of embodiment 192, wherein said bisulfite reagent comprises ammonium bisulfite.

Embodiment 194: The cartridge according to any of embodiments 190-193, wherein said wash solution comprises 1.25M GTC, 25 mM Tris pH 7.0, and 50% ethanol.

Embodiment 195: The cartridge according to any of embodiments 190-194, wherein said chamber containing beads that provide PCR primers and probes to detect methylation of one or more gene promoters comprises beads that provide PCR primers and probes to detect methylation of one or more gene promoters whose methylation state is a marker for a cancer selected from the group consisting of breast cancer, pancreatic cancer, prostate cancer, brain cancer, and lung cancer.

Embodiment 196: The cartridge of embodiment 195, wherein said chamber containing beads that provide PCR primers and probes to detect methylation of one or more gene promoters comprises beads that provide PCR primers and probes for a nested PCR reaction.

Embodiment 197: The cartridge of embodiment 196, wherein said nested PCR comprises a first PCR reaction specific for converted DNA and a second PCR reaction specific for methylated CpGs.

Embodiment 198: The cartridge according to any one of embodiments 190-197, wherein said chamber containing beads that provide PCR primers and probes chamber contains beads that provide PCR primers and probes to detect methylation of a forward strand of converted DNA.

Embodiment 199: The cartridge according to any one of embodiments 190-198, wherein said chamber containing beads that provide PCR primers and probes chamber contains beads that provide PCR primers and probes to detect methylation of a reverse strand of converted DNA.

Embodiment 200: The cartridge according to any of embodiments 190-199, wherein said chamber containing beads that provide PCR primers and probes to detect methylation of one or more gene promoters comprises beads that provide PCR primers and probes to detect methylation of the promoters of one or more genes selected from the group consisting of RASSF1A, AKR1B1, HOXB4, HIST1H3C, RASGRF2, TM6SF1, BRCA1, BNC1, ADAMTS1, CDO1, SOX17, TAC1, HOXA 7, and MGMT.

Embodiment 201: The cartridge according to any of embodiments 190-200, wherein said chamber containing beads that provide PCR primers and probes to detect methylation of one or more gene promoters comprises beads that provide PCR primers and probes to detect methylation of one or more gene promoters whose methylation state is a marker for pancreatic cancer.

Embodiment 202: The cartridge of embodiment 201, wherein said chamber containing beads that provide PCR primers and probes to detect methylation of one or more gene promoters comprises beads that provide PCR primers and probes to detect methylation of the promoters of ADAMTS1, and/or BNC1.

Embodiment 203: The cartridge of embodiment 202, wherein said chamber containing beads that provide PCR primers and probes to detect methylation of one or more gene promoters comprises beads that provide PCR primers and probes to detect methylation of the promoter of ADAMTS1.

Embodiment 204: The cartridge according to any one of embodiments 202-203, wherein said chamber containing beads that provide PCR primers and probes to detect methylation of one or more gene promoters comprises beads that provide PCR primers and probes to detect methylation of the promoter of BNC1.

Embodiment 205: The cartridge of embodiment 202, wherein said chamber containing beads that provide PCR primers and probes to detect methylation of one or more gene promoters comprises beads that provide one or more PCR primers and/or probes for ADAMTS1 and/or BNC1 shown in Tables 5, or 10.

Embodiment 206: The cartridge according to any of embodiments 190-200, wherein said chamber containing beads that provide PCR primers and probes to detect methylation of one or more gene promoters comprises beads that provide PCR primers and probes to detect methylation of one or more gene promoters whose methylation state is a marker for breast cancer.

Embodiment 207: The cartridge of embodiment 206, wherein said chamber containing beads that provide PCR primers and probes to detect methylation of one or more gene promoters comprises beads that provide PCR primers and probes to detect methylation of the promoters of one, two, three, four, five, or all genes selected from the group consisting of BRCA1, RASSF1A, AKR1B1, HOXB4, HIST1H3C, RASGRF2, and TM6SF1.

Embodiment 208: The cartridge of embodiment 207, wherein said chamber containing beads that provide PCR primers and probes to detect methylation of one or more gene promoters comprises beads that provide PCR primers and probes to detect methylation of the promoter of BRCA1.

Embodiment 209: The cartridge according to any one of embodiments 207-208, wherein said chamber containing beads that provide PCR primers and probes to detect methylation of one or more gene promoters comprises beads that provide PCR primers and probes to detect methylation of the promoter of RASSF1A.

Embodiment 210: The cartridge according to any one of embodiments 207-209, wherein said chamber containing beads that provide PCR primers and probes to detect methylation of one or more gene promoters comprises beads that provide PCR primers and probes to detect methylation of the promoter of AKR1B1.

Embodiment 211: The cartridge according to any one of embodiments 207-210, wherein said chamber containing beads that provide PCR primers and probes to detect methylation of one or more gene promoters comprises beads that provide PCR primers and probes to detect methylation of the promoter of HOXB4.

Embodiment 212: The cartridge according to any one of embodiments 207-211, wherein said chamber containing beads that provide PCR primers and probes to detect methylation of one or more gene promoters comprises beads that provide PCR primers and probes to detect methylation of the promoter of HIST1H3C.

Embodiment 213: The cartridge according to any one of embodiments 207-212, wherein said chamber containing beads that provide PCR primers and probes to detect methylation of one or more gene promoters comprises beads that provide PCR primers and probes to detect methylation of the promoter of RASGRF2.

Embodiment 214: The cartridge according to any one of embodiments 207-213, wherein said chamber containing beads that provide PCR primers and probes to detect methylation of one or more gene promoters comprises beads that provide PCR primers and probes to detect methylation of the promoter of TM6SF1.

Embodiment 215: The cartridge according to any one of embodiments 207-214, wherein said chamber containing beads that provide PCR primers and probes to detect methylation of one or more gene promoters comprises beads that provide one or more PCR primers and/or one or more PCR probes shown in Tables 5, or 9.

Embodiment 216: The cartridge of embodiment 206, wherein said chamber containing beads that provide PCR primers and probes to detect methylation of one or more gene promoters comprises beads that provide PCR primers and probes to detect methylation of the promoters of BRCA1.

Embodiment 217: The cartridge according to any of embodiments 190-200, wherein said chamber containing beads that provide PCR primers and probes to detect methylation of one or more gene promoters comprises beads that provide PCR primers and probes to detect methylation of one or more gene promoters whose methylation state is a marker for lung cancer.

Embodiment 218: The cartridge of embodiment 217, wherein said chamber containing beads that provide PCR primers and probes to detect methylation of one or more gene promoters comprises beads that provide PCR primers and probes to detect methylation of the promoters of one, two, three, or all genes selected from the group consisting of CDO1, SOX17, TAC1, and HOXA7.

Embodiment 219: The cartridge of embodiment 218, wherein said chamber containing beads that provide PCR primers and probes to detect methylation of one or more gene promoters comprises beads that provide PCR primers and probes to detect methylation of the promoter of CDO1.

Embodiment 220: The cartridge according to any one of embodiments 218-219, wherein said chamber containing beads that provide PCR primers and probes to detect methylation of one or more gene promoters comprises beads that provide PCR primers and probes to detect methylation of the promoter of SOX17.

Embodiment 221: The cartridge according to any one of embodiments 218-220, wherein said chamber containing beads that provide PCR primers and probes to detect methylation of one or more gene promoters comprises beads that provide PCR primers and probes to detect methylation of the promoter of TAC1.

Embodiment 222: The cartridge according to any one of embodiments 218-221, wherein said chamber containing beads that provide PCR primers and probes to detect methylation of one or more gene promoters comprises beads that provide PCR primers and probes to detect methylation of the promoter of HOXA7.

Embodiment 223: The cartridge according to any of embodiments 190-200, wherein said chamber containing beads that provide PCR primers and probes to detect methylation of one or more gene promoters comprises beads that provide PCR primers and probes to detect methylation of one or more gene promoters whose methylation state is a marker for brain cancer.

Embodiment 224: The cartridge of embodiment 223, wherein said chamber containing beads that provide PCR primers and probes to detect methylation of one or more gene promoters comprises beads that provide PCR primers and probes to detect methylation of the promoter of MGMT.

Embodiment 225: The cartridge of embodiment 224, wherein said chamber containing beads that provide PCR primers and probes to detect methylation of one or more gene promoters comprises beads that provide one or more PCR primers and/or probes for MGMT shown in Tables 5, or 10.

Embodiment 226: The cartridge of embodiment 225, wherein said cartridge contains the following probes and primers for determining methylation of MGMT using a nested PCR reaction:

an external forward primer (248b) comprising the nucleotide sequence (SEQ ID NO: 263)
GTTTT(T*)AGAAYG(T*)TTTGYGTTT;

an external reverse primer (249b) comprising the nucleotide sequence (SEQ ID NO: 265)
AAAAAAC(T*)CCRCACTCTTCC;

an internal forward primer (250) comprising the nucleotide sequence (SEQ ID NO: 266)
TTTCGACGTTCGTAGGTTTTCGC;

an internal reverse primer (251) comprising the nucleotide sequence (SEQ ID NO: 267)
GCACTCTTCCGAAAACGAAACG;

and a probe (252a) comprising the nucleotide sequence fluor- (SEQ ID NO: 268)
CCAAACAC(T*)CACCAAATC(N*)CAAAC-blocker.

Embodiment 227: The cartridge according to any one of embodiments 225-226, wherein said cartridge contains the following probes and primers for determining methylation of ACTB (e.g., as a control) using a nested PCR reaction:

an external forward primer (102) comprising the nucleotide sequence (SEQ ID NO: 103)
GTGATGGAGGAGGTTTAGTAAGTT;

an external reverse primer (103) comprising the nucleotide sequence (SEQ ID NO: 104)
CCAATAAAACCTACTCCTCCCTTAA;

an internal forward primer (148) comprising the nucleotide sequence (SEQ ID NO: 149)
GGTTTAGTAAGTTTTTTGGATTGTG;

an internal reverse primer (149) comprising the nucleotide sequence (SEQ ID NO: 150)
CCTTAAAAATTACAAAAACCACAAC;

and a probe (178) comprising the nucleotide sequence fluor- (SEQ ID NO: 179)
CCACCACCCAACACA(N*)CAA(T*)AACAAACAC-blocker.

Embodiment 228: A method of preparing a sample of cfDNA from serum or plasma, said method comprising:

combining a proteinase K treated sample of serum or plasma with a lysis solution according to any one of embodiments 169-171, and an alcohol to form a sample solution;

loading said sample solution into a sample receiving chamber in a cartridge according to any one of embodiments 143-154, or into a sample receiving chamber in a cartridge according to any one of embodiments 155-168; and operating said cartridge to bind DNA in said sample to said affinity matrix and then to wash and release said DNA from said matrix.

Embodiment 229: The method of embodiment 228, wherein said combining a proteinase K treated sample of serum or plasma comprises combining said sample, lysis solution and alcohol in proportions corresponding to about 1.3 ml proteinase K treated serum or plasma, 2.2 mL lysis solution; and about 1.5 ml alcohol.

Embodiment 230: The method according to any one of embodiments 228-229, wherein said alcohol comprises isopropanol.

Embodiment 231: The method according to any one of embodiments 228-230, wherein said sample comprises serum.

Embodiment 232: The method according to any one of embodiments 228-231, wherein said sample comprises plasma.

Embodiment 233: The method according to any one of embodiments 228-232, wherein said sample comprises serum.

Embodiment 234: The method according to any one of embodiments 228-233, wherein operating said cartridge comprises introducing said cartridge into a sample processing module in a system according to any one of embodiments 133-139.

Embodiment 235: The method according to any one of embodiments 228-234, wherein said method further comprises operating said cartridge to convert said DNA for methylation detection.

Embodiment 236: The method according to any one of embodiments 228-235, wherein said method further comprises operating said cartridge to perform one or more PCR reactions using said DNA or converted DNA a template.

Embodiment 237: The method according to any one of embodiments 228-234, wherein said loading comprises loading said sample solution into one or more sample receiving chambers in a cartridge according to any one of embodiments 155-165.

Embodiment 238: The method of embodiment 237, wherein said method further comprises transferring the released DNA to a second cartridge for methylation detection and/or PCR.

Embodiment 239: The method of embodiment 238, wherein said second cartridge is a cartridge according to any one of embodiments 92-132.

Embodiment 240: The method according to any one of embodiments 238-239, wherein said method further comprises operating said second cartridge to convert said DNA for methylation detection.

Embodiment 241: The method according to any one of embodiments 238-240, wherein said method further comprises operating said second cartridge to perform one or more PCR reactions using said DNA or converted DNA as a template.

Embodiment 242: The method according to any one of embodiments 238-241, wherein said operating said second cartridge comprises introducing said second cartridge into a sample processing module in a system according to any one of embodiments 133-139.

Embodiment 243: A method of preparing a DNA from an FFPE sample, said method comprising:

- combining a formalin-fixed paraffin embedded sample with a lysis solution according to any one of embodiments 172-174;
- heating said lysis solution containing said sample; adding an alcohol to said sample to form a sample solution; loading said sample solution into a sample receiving chamber in a cartridge according to any one of embodiments 143-154, or into a sample receiving chamber in a cartridge according to any one of embodiments 155-168; and
- operating said cartridge to bind DNA in said sample to said affinity matrix and then to wash and release said DNA from said matrix.

Embodiment 244: The method of embodiment 243, wherein said heating comprises adding proteinase K to said sample and heating said sample.

Embodiment 245: The method of embodiment 244, wherein said heating comprises adding about 50 μL proteinase K to about 1.2 mL of FFPE lysis solution containing a FFPE sample.

Embodiment 246: The method according to any one of embodiments 243-245, wherein said heating comprises heating said lysis solution to a temperature ranging from about 50° C. to about 60° C.

Embodiment 247: The method of embodiment 246, wherein said heating comprises heating said lysis solution to a temperature of about 56° C.

Embodiment 248: The method according to any one of embodiments 243-247, wherein said heating is for a period of time ranging up to about 4 hours, or up to about 5 hours, or up to about 6 hours.

Embodiment 249: The method of embodiment 248, wherein said heating is for about 4 hours.

Embodiment 250: The method according to any one of embodiments 243-249, wherein said alcohol comprises ethanol.

Embodiment 251: The method according to any one of embodiments 243-250, wherein said method comprises adding alcohol to said lysis solution in a volume ratio of about 1:1 lysis solution:alcohol.

Embodiment 252: The method according to any one of embodiments 243-251, wherein operating said cartridge comprises introducing said cartridge into a sample processing module in a system according to any one of embodiments 133-139.

Embodiment 253: The method according to any one of embodiments 243-252, wherein said method further comprises operating said cartridge to convert said DNA for methylation detection.

Embodiment 254: The method according to any one of embodiments 243-253, wherein said method further comprises operating said cartridge to perform one or more PCR reactions using said DNA or converted DNA as a template.

Embodiment 255: The method according to any one of embodiments 243-251, wherein said loading comprise loading said sample solution into one or more sample receiving chambers in a cartridge according to any one of embodiments 155-165.

Embodiment 256: The method of embodiment 255, wherein said method further comprises transferring the released DNA to a second cartridge for methylation detection and/or PCR.

Embodiment 257: The method of embodiment 256, wherein said second cartridge is a cartridge according to any one of embodiments 92-132.

Embodiment 258: The method according to any one of embodiments 256-257, wherein said method further comprises operating said second cartridge to convert said DNA for methylation detection.

Embodiment 259: The method according to any one of embodiments 256-258, wherein said method further comprises operating said second cartridge to perform one or more PCR reactions using said DNA or converted DNA as a template.

Embodiment 260: The method according to any one of embodiments 256-259, wherein said operating said second cartridge comprises introducing said second cartridge into a sample processing module in a system according to any one of embodiments 133-139.

Embodiment 261: A method of detecting a cancer, and/or staging a cancer, and/or detecting the predisposition to a cancer in a subject, said method comprising:

- providing a biological sample from said subject, wherein said biological sample comprises a DNA;
- utilizing a cartridge according to any one of embodiments 190-225 to detect methylation of one or more gene promoters in said DNA whose methylation state is a marker for a cancer, where an increase in methylation of said one or more gene promoters is indicative of the presence of a cancer or a predisposition to a cancer or a stage of a cancer or precancer.

Embodiment 262: The method of embodiment 261, wherein said subject is a human.

Embodiment 263: The method according to any one of embodiments 261-262, wherein said cancer is a cancer selected from the group consisting of breast cancer, pancreatic cancer, prostate cancer, brain cancer, a lung cancer, a B cell lymphoma, a bronchus cancer, a colorectal cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma.

Embodiment 264: The method according to any one of embodiments 261-262, wherein said cancer is a cancer selected from the group consisting of breast cancer, pancreatic cancer, prostate cancer, brain cancer, a lung cancer.

Embodiment 265: The method according to any one of embodiments 261-264, wherein said sample comprise a sample from serum or plasma.

Embodiment 266: The method according to any one of embodiments 261-264, wherein said sample comprise an FFPE sample.

Embodiment 267: The method according to any one of embodiments 261-266, wherein said one or more gene promoters comprise the promoters of one or more genes selected from the group consisting of RASSF1A, AKR1B1, HOXB4, HIST1H3C, RASGRF2, TM6SF1, BRCA1, BNC1, ADAMTS1, CDO1, SOX17, TAC1, HOXA7, and MGMT.

Embodiment 268: The method according to any one of embodiments 261-266, wherein said cancer is pancreatic cancer and said one or more gene promoters comprise the promoters of one, two, three, or four genes selected from the group consisting of ADAMTS1, and BNC1.

Embodiment 269: The method of embodiment 268, wherein said one or more gene promoters comprise the promoter of ADAMTS1.

Embodiment 270: The method according to any one of embodiments 268-269, wherein said one or more gene promoters comprise the promoter of BNC1.

Embodiment 271: The method according to any one of embodiments 261-266, wherein said cancer is breast cancer and said one or more gene promoters comprise the promoters of one, two, three, four, five, or all genes selected from the group consisting of BRCA1, RASSF1A, AKR1B1, HOXB4, HIST1H3C, RASGRF2, and TM6SF1.

Embodiment 272: The method of embodiment 271, wherein said one or more gene promoters comprise the promoter of BRCA1.

Embodiment 273: The method according to any one of embodiments 271-272, wherein said one or more gene promoters comprise the promoter of RASSF1A.

Embodiment 274: The method according to any one of embodiments 271-273, wherein said one or more gene promoters comprise the promoter of AKR1B1.

Embodiment 275: The method according to any one of embodiments 271-274, wherein said one or more gene promoters comprise the promoter of HOXB4.

Embodiment 276: The method according to any one of embodiments 271-275, wherein said one or more gene promoters comprise the promoter of HIST1H3C.

Embodiment 277: The method according to any one of embodiments 271-276, wherein said one or more gene promoters comprise the promoter of RASGRF2.

Embodiment 278: The method according to any one of embodiments 271-277, wherein said one or more gene promoters comprise the promoter of TM6SF1.

Embodiment 279: The method according to any one of embodiments 261-266, wherein said cancer is breast cancer and said one or more gene promoters comprise the promoter of BRCA1.

Embodiment 280: The method according to any one of embodiments 261-266, wherein said cancer is lung cancer and said one or more gene promoters comprise the promoters of one, two, three, for all genes selected from the group consisting of CDO1, SOX17, TAC1, and HOXA7.

Embodiment 281: The method of embodiment 280, wherein said one or more gene promoters comprise the promoter of CDO1.

Embodiment 282: The method according to any one of embodiments 280-281, wherein said one or more gene promoters comprise the promoter of SOX17.

Embodiment 283: The method according to any one of embodiments 280-282, wherein said one or more gene promoters comprise the promoter of TAC1.

Embodiment 284: The method according to any one of embodiments 280-283, wherein said one or more gene promoters comprise the promoter of HOXA7.

Embodiment 285: The method according to any one of embodiments 261-266, wherein said cancer is brain cancer and said one or more gene promoters comprise the promoter of MGMT.

Embodiment 286: A method of converting cytosine residues in a DNA to uracil, while leaving 5-methylcytosine residues substantially unaffected, said method comprising:

contacting a sample comprising DNA with DABSO to convert said DNA;

desulphonating the converted DNA, to produce a DNA in which cytosine residues are converted to uracil, but 5-methylcytosine residues substantially unaffected.

Embodiment 287: The method of embodiment 286, wherein said contacting comprises contacting said DNA with DABSO at a concentration ranging from about 2 M up to about 5 M.

Embodiment 288: The method of embodiment 286, wherein said contacting comprises contacting said DNA with DABSO at a concentration of about 2.5 M.

Embodiment 289: The method according to any one of embodiments 286-288, wherein said DABSO is dissolved in an alkaline aqueous solution.

Embodiment 290: The method of embodiment 289, wherein said DABSO is dissolved in a solution comprising KOH.

Embodiment 291: The method according to any one of embodiments 286-290, wherein said contacting comprises heating the DABSO/DNA solution to a temperature ranging from about 55° C. to about 90° C.

Embodiment 292: The method according to any one of embodiments 286-291, wherein said DABSO is reacted with the DNA for a period of time ranging from about 15 minutes up to about 90 minutes.

Embodiment 293: The method according to any one of embodiments 286-292, wherein said desulphonating comprises contacting said converted DNA with an alkaline reagent.

Embodiment 294: The method of embodiment 293, wherein said alkaline reagent comprises KOH.

Embodiment 295: The method according to any one of embodiments 286-294, wherein said conversion and/or desulphonation is performed on the DNA bound to a column.

Embodiment 296: The method according to any one of embodiments 286-294, wherein said conversion and/or desulphonation is performed on the DNA in solution.

Embodiment 297: A method of analyzing DNA methylation, said method comprising:

providing a DNA sample;

converting DNA in said sample according to the method of any one of embodiments 286-296; and performing methylation specific PCR and/or nucleic acid sequencing, and/or high resolution melting analysis (HRM) on the converted nucleic acid to determine the methylation of said nucleic acid.

Embodiment 298: The method of embodiment 297, wherein said providing a DNA sample comprises preparing a sample according to any one of embodiments 228-234 or according to any one of embodiments 243-252.

Embodiment 299: A kit for detection of methylation state of a DNA, said kit comprising:

a container containing a conversion reagent comprising DABSO; and a container containing a desulphonation reagent.

Embodiment 300: The kit of embodiment 299, wherein said kit comprises a column comprising an affinity matrix.

Embodiment 301: The kit according to any one of embodiments 299-300, wherein said kit comprises a container containing a binding buffer.

Embodiment 302: The kit according to any one of embodiments 299-301, wherein said kit comprises a container containing an elution buffer.

Embodiment 303: The kit according to any one of embodiments 299-302, wherein said kit comprises a container containing a wash buffer.

Embodiment 304: The kit according to any one of embodiments 299-303, wherein said kit comprises a container containing a lysis solution according to any one of embodiments 169-171, and/or a container containing a lysis solution according to any one of embodiments 172-174.

Embodiment 305: The kit according to any one of embodiments 299-304, wherein said kit comprises a cartridge according to any one of embodiments 143-155 and/or a cartridge according to any one of embodiments 155-166.

Embodiment 306: The kit according to any one of embodiments 299-305, said kit comprising instructional materials teaching the use of said kit to convert a nuclei acid for determination of the methylation state of said nucleic acid.

Embodiment 307: A set of primers and probes for the determination of methylation of MGMT using a nested PCR reaction, said set comprising the following primers and probes:

an external forward primer comprising the nucleotide sequence (SEQ ID NO: 263)
GTTTT(T*)AGAAYG(T*)TTTGYGTTT;

an external reverse primer comprising the nucleotide sequence (SEQ ID NO: 265)
AAAAAAC(T*)CCRCACTCTTCC;

an internal forward primer comprising the nucleotide sequence (SEQ ID NO: 266)
TTTCGACGTTCGTAGGTTTTCGC;

an internal reverse primer comprising the nucleotide sequence (SEQ ID NO: 267)
GCACTCTTCCGAAAACGAAACG;

and a probe comprising the nucleotide sequence fluor- (SEQ ID NO: 268)
CCAAACAC(T*)CACCAAATC(N*)CAAAC-blocker.

Embodiment 308: A set of primers and probes for the determination of methylation of ACTB (e.g., as a control) using a nested PCR reaction, said set comprising the following primers and probes:

an external forward primer (102) comprising the nucleotide sequence (SEQ ID NO: 103)
GTGATGGAGGAGGTTTAGTAAGTT;

an external reverse primer (103) comprising the nucleotide sequence (SEQ ID NO: 104)
CCAATAAAACCTACTCCTCCCTTAA;

an internal forward primer (148) comprising the nucleotide sequence (SEQ ID NO: 149)
GGTTTAGTAAGTTTTTTGGATTGTG;

and an internal reverse primer (149) comprising the nucleotide sequence (SEQ ID NO: 150)
CCTTAAAAATTACAAAAACCACAAC;

and a probe (178) comprising the nucleotide sequence fluor- (SEQ ID NO: 179)
CCACCACCCAACACA(N*)CAA(T*)AACAAACAC-blocker.

Embodiment 309: A set of primers and probes for the determination of methylation of MGMT using a nested PCR reaction with determination of the methylation of ACTB as a control, comprising the primers and probes of embodiment 307 and the primers and probes of embodiment 308.

Embodiment 310: A method of determining the methylation of MGMT using methylation specific PCR said method comprising:

providing a converted (e.g., bisulfite converted) DNA containing a promoter region of the MGMT gene;

performing methylation specific PCR for MGMT methylation using a nested PCR reaction comprising the following primers and probes:

an external forward primer comprising the nucleotide sequence GTT (SEQ ID NO: 263)
TT(T*)AGAAYG(T*)TTTGYGTTT;

an external reverse primer comprising the nucleotide sequence (SEQ ID NO: 265)
AAAAAAC(T*)CCRCACTCTTCC;

an internal forward primer comprising the nucleotide sequence (SEQ ID NO: 266)
TTTCGACGTTCGTAGGTTTTCGC;

an internal reverse primer comprising the nucleotide sequence (SEQ ID NO: 267)
GCACTCTTCCGAAAACGAAACG;

and a probe comprising the nucleotide sequence fluor- (SEQ ID NO: 268)
CCAAACAC(T*)CACCAAATC(N*)CAAAC-blocker;

and detecting and/or quantifying the PCR amplification product to provide determine methylation of said MGMT gene.

Embodiment 311: The method of embodiment 310, wherein said method further comprises:

providing a converted (e.g., bisulfite converted) DNA containing a promoter region of the ACTB gene (e.g., as a control);

performing methylation specific PCR for ACTB methylation using a nested PCR reaction comprising the following primers and probes:

an external forward primer comprising the nucleotide sequence (SEQ ID NO: 103)
GTGATGGAGGAGGTTTAGTAAGTT;

an external reverse primer comprising the nucleotide sequence (SEQ ID NO: 104)
CCAATAAAACCTACTCCTCCCTTAA;

an internal forward primer comprising the nucleotide sequence (SEQ ID NO: 149)
GGTTTAGTAAGTTTTTTGGATTGTG;

an internal reverse primer comprising the nucleotide sequence (SEQ ID NO: 150)
CCTTAAAAATTACAAAAACCACAAC;

and a probe comprising the nucleotide sequence fluor- (SEQ ID NO: 179)
CCACCACCCAACACA(N*)CAA(T*)AACAAACAC-blocker;

and detecting and/or quantifying the PCR amplification product to provide determine methylation of said ACTB gene.

Embodiment 312: The method according to any one of embodiments 310-311, wherein said methylation specific PCR for MGMT methylation and said methylation specific PCR for ACTB methylation are performed in a single multiplex PCR reaction.

Embodiment 313: The method according to any one of embodiments 310-312, wherein said methylation specific PCR is performed using a cartridge according to any one of embodiments 92-132.

Embodiment 314: The method of embodiment 313, wherein: said providing a converted DNA containing a promoter region of the MGMT gene comprises introducing an unconverted DNA containing a promoter region of the MGMT gene into said cartridge and operating said cartridge to convert said DNA in said cartridge using a conversion reagent; and/or said providing a converted DNA containing a promoter region of the ACTB gene comprises introducing an unconverted DNA containing a promoter region of the ACTB gene into said cartridge and operating said cartridge to convert said DNA in said cartridge using a conversion reagent.

Embodiment 315: The method of embodiment 314, wherein said conversion reagent comprises a compound selected from the group consisting of ammonium bisulfite, sodium metabisulfite, potassium bisulfite, cesium bisulfite, and DABSO.

Embodiment 316: The method according to any one of embodiments 313-315, wherein said operating said cartridge comprises heating said DNA and said conversion reagent in a thermocycling channel or chamber that is later used to perform said nested PCR reaction.

Embodiment 317: A set of cartridges for determining the methylation state of a nucleic acid, said set of cartridges comprising: a first cartridge comprising:

a sample receiving chamber;

a column comprising a first matrix material;

a temperature controlled channel or chamber;

a sample removal chamber; and a plurality of chambers containing reagents and/or buffers, wherein when in use at least one of said chambers contains a bisulfite reagent; and a second cartridge comprising:

a sample receiving chamber;

a column comprising a second matrix material;

a temperature controlled channel or chamber; and a plurality of chambers containing reagents and/or buffers, wherein when in use at least one of said chambers contains a desulphonation and/or elution reagent.

Embodiment 318: The set of cartridges of embodiment 317, wherein the temperature controlled channel or chamber in said first cartridge is a thermocycling channel or chamber.

Embodiment 319: The set of cartridges according to any one of embodiments 317-318, wherein the temperature controlled channel or chamber in said second cartridge is a thermocycling channel or chamber.

Embodiment 320: The set of cartridges according to any one of embodiments 317-319, wherein said bisulfite reagent comprises a compound selected from the group consisting of ammonium bisulfite, sodium metabisulfite, potassium bisulfite, cesium bisulfite, and DABSO.

Embodiment 321: The set of cartridges of embodiment 320, wherein said bisulfite reagent comprises ammonium bisulfite.

Embodiment 322: The set of cartridges according to any one of embodiments 317-321, wherein said bisulfite is provided in a reagent mix comprising scavengers to prevent sulfite oxidation and/or catalysts.

Embodiment 323: The set of cartridges of embodiment 322, wherein said bisulfite is provided in a reagent mix comprising scavengers selected from the group consisting of TROLOX water-soluble analog of vitamin E and hydroquinone.

Embodiment 324: The set of cartridges according to any one of embodiments 322-323, wherein said bisulfite is provided in a reagent mix comprising polyamines as catalysts.

Embodiment 325: The set of cartridges according to any one of embodiments 317-324, wherein said first cartridge is configured for the bisulfite reagent to be added to the cartridge at or near the time the sample is placed in the cartridge.

Embodiment 326: The set of cartridges according to any one of embodiments 317-325, wherein the bisulfite reagent is provided as a component in one of said plurality of chambers in said first the cartridge.

Embodiment 327: The set of cartridges according to any one of 317-326, wherein said first matrix material and/or said second matrix material, independently comprise a material is selected from the group consisting of glass or silica, an ion exchange resin, and hydroxyapatite.

Embodiment 328: The set of cartridges of embodiment 327, wherein said first matrix material comprises glass fibers.

Embodiment 329: The set of cartridges according to any one of 327-328, wherein said second matrix material comprises glass fibers.

Embodiment 330: The set of cartridges according to any one of embodiments 317-329, wherein said first cartridge comprises two sample receiving chambers.

Embodiment 331: The set of cartridges according to any one of 317-330, wherein at least one chamber comprising the plurality of chambers in said second cartridge contains PCR primers, and/or PCR probes, and/or a PCR master mix.

Embodiment 332: The set of cartridges according to any one of 317-331, wherein, when said cartridge is in use, a chamber comprising the plurality of chambers in said first cartridge contains GTC-EtOH in a buffer.

Embodiment 333: The set of cartridges according to any one of 317-332, wherein, when said cartridge is in use, a chamber comprising the plurality of chambers in said second cartridge contains GTC-EtOH in a buffer.

Embodiment 334: The set of cartridges according to any one of 332-333, wherein the first cartridge is configured for addition of GTC-ETOH in a buffer at or near the time the sample is placed into the cartridge.

Embodiment 335: The set of cartridges according to any one of 332-333, wherein the GTC-ETOH in a buffer is provided as a component in a chamber comprising the plurality of chambers of the first cartridge.

Embodiment 336: The set of cartridges according to any one of 332-335, wherein the second cartridge is configured for addition of GTC-ETOH in a buffer at or near the time the sample is placed into the cartridge.

Embodiment 337: The set of cartridges according to any one of 332-336, wherein the GTC-ETOH in a buffer is provided as a component in a chamber comprising the plurality of chambers of the second cartridge.

Embodiment 338: The set of cartridges according to any one of embodiments 317-337, wherein said second cartridge comprises one or more chambers containing one or more reagents selected from the group consisting of methylation specific PCR primers, methylation specific PCR probes, PCR enzyme(s), and PCR reaction buffer.

Embodiment 339: The set of cartridges of embodiment 338, wherein said second cartridge contains at least two chambers containing one or more reagents selected from the group consisting of methylation specific PCR primers, methylation specific PCR probes, PCR enzyme(s), and PCR reaction buffer.

Embodiment 340: The set of cartridges according to any one of embodiments 317-339, wherein said second cartridge contains at least one chamber containing primers and probes for detection of methylation of a forward strand of a converted DNA.

Embodiment 341: The set of cartridges according to any one of embodiments 317-340, wherein said second cartridge contains at least one chamber containing primers and probes for detection of methylation of a reverse strand of a converted DNA.

Embodiment 342: The set of cartridges according to any of embodiments 338-341, wherein said PCR primers, and/or probes, and/or enzymes are provided as beads.

Embodiment 343: The set of cartridges according to any one of embodiments 317-342, wherein:

in said first cartridge said sample receiving chamber, said column, said plurality of chambers, said sample removal chamber, and said temperature-controlled heating channel or chamber, are selectively in fluid communication; and/or in said second cartridge said sample receiving chamber, said column, said plurality of chambers, and said temperature-controlled heating channel or chamber, are selectively in fluid communication.

Embodiment 344: The set of cartridges of embodiment 343, wherein in said first cartridge, said sample receiving chamber, said column, said plurality of chambers, said sample removal chamber, and said temperature controlled channel or chamber, are selectively in fluid communication by microfluidic channels and valves; and/or in said second cartridge, said sample receiving chamber, said column, said plurality of chambers, and said temperature controlled channel or chamber, are selectively in fluid communication by microfluidic channels and valves.

Embodiment 345: The set of cartridges of embodiment 343, wherein in said first cartridge, said sample receiving chamber, said column, said plurality of chambers, said sample removal chamber, and said temperature controlled channel or chamber or a port into said temperature controlled channel or chamber, are disposed around a central valve and selectively in fluid communication with a channel in said central valve, wherein said central valve is configured to accommodate a plunger that is capable of drawing fluid into or out of a chamber in fluid communication with said central valve; and/or in said second cartridge, said sample receiving chamber, said column, said plurality of chambers, and said temperature controlled channel or chamber or a port into said temperature controlled channel or chamber, are disposed around a central valve and selectively in fluid communication with a channel in said central valve, wherein said central valve is configured to accommodate a plunger that is capable of drawing fluid into or out of a chamber in fluid communication with said central valve.

Embodiment 346: The set of cartridges according to any one of embodiments 317-345, wherein said first cartridge is configured so that, when in use, said first cartridge comprises:

a first chamber containing a sample;

a second chamber containing a guanidinium thiosulfate-ethanol (GTC-EtOH) solution;

a third chamber containing a bisulfate reagent;

a fourth chamber containing a Tris buffer;

a fifth chamber polyethyleneglycol (PEG); and a sixth chamber containing KOH.

Embodiment 347: The set of cartridges of embodiment 346, wherein said first chamber in said first cartridge contains said sample in a GTC-EtOH-Tween extraction/precipitation reagent.

Embodiment 348: The set of cartridges according to any one of embodiments 346-347, wherein said a second chamber containing a guanidinium thiosulfate-ethanol (GTC-EtOH) solution contains GTC-Tris (pH 7), ethanol.

Embodiment 349: The set of cartridges according to any one of embodiments 317-336, wherein said second cartridge is configured so that, when in use, said second cartridge comprises:

a first chamber containing a sample;

a second chamber containing a guanidinium thiosulfate-ethanol (GTC-EtOH) solution;

a third chamber containing a Tris buffer;

a fourth chamber containing polyethylene glycol (PEG);

a fifth chamber containing KOH; and a sixth chamber containing a PCR enzyme bead.

Embodiment 350: The set of cartridges of embodiment 349, wherein said second cartridge comprises a seventh chamber containing a Tris bead, and an enzyme bead.

Embodiment 351: The set of cartridges according to any one of embodiments 349-350, wherein said said a second chamber containing a guanidinium thiosulfate-ethanol (GTC-EtOH) solution contains GTC-Tris (pH 7), ethanol.

Embodiment 352: The set of cartridges according to any one of embodiments 317-351, wherein said second cartridge comprises a chamber containing PCR primers and/or probes and/or PCR enzymes.

Embodiment 353: The set of cartridges according to any one of embodiments 317-352, wherein said second cartridge comprises an eighth chamber also containing PCR primers and/or probes and/or PCR enzymes.

Embodiment 354: The set of cartridges according to any one of embodiments 317-353, wherein said second cartridge comprises one or more chambers containing primers specific for bisulfate-converted methylated and/or unmethylated sequences.

Embodiment 355: The set of cartridges according to any one of embodiments 317-354, wherein said second cartridge comprises one or more chambers containing reagents for TaqMan PCR reactions.

Embodiment 356: The set of cartridges according to any one of embodiments 317-355, wherein said second cartridge comprises one or more chambers containing one or more fluorescent probes that are markers for amplified methylated sequences and/or one or more fluorescent probes that are markers for amplified unmethylated sequences.

Embodiment 357: The set of cartridges of embodiment 356, wherein said probes comprise a fluorescent reporter dye and a quencher dye, where the probes provides a signal upon cleavage by the 5' to 3' nuclease activity of Taq DNA polymerase.

Embodiment 358: The set of cartridges according to any one of embodiments 356-357, wherein said second cartridge comprises a plurality of probes each specific to a different methylated region in an amplified region of interest.

Embodiment 359: The set of cartridges according to any one of embodiments 356-357, wherein said second cartridge comprises a single probe specific to a methylated region in an amplified region of interest.

Embodiment 360: The set of cartridges according to any one of embodiments 356-357, wherein said second cartridge comprises a plurality of probes each specific to the same methylated region in an amplified region of interest.

Embodiment 361: The set of cartridges according to any one of embodiments 317-360, wherein said second cartridge contains primers and/or probes to determine methylation of a promoter region of a gene selected from the group consisting of MGMT, RASSF1A, ADAMTS1, BNC1, HIST1H3C, HOXB4, RASGRF2, TM6SF1, and AKR1B1.

Embodiment 362: The set of cartridges according to any one of embodiments 317-360, wherein said second cartridge contains one or more primers shown in Tables 5, 9, or 10, and/or one or more probes shown in Tables 5, 9, or 10.

Embodiment 363: The set of cartridges of embodiment 362, wherein said second cartridge contains the following probes and primers for determining methylation of MGMT using a nested PCR reaction:

an external forward primer (248b) comprising the nucleotide sequence

```
                                    (SEQ ID NO: 263)
GTTTT(T*)AGAAYG(T*)TTTGYGTTT;
```

an external reverse primer (249b) comprising the nucleotide sequence:

```
                                    (SEQ ID NO: 265)
AAAAAAC(T*)CCRCACTCTTCC;
```

an internal forward primer (250) comprising the nucleotide sequence

```
                                    (SEQ ID NO: 266)
TTTCGACGTTCGTAGGTTTTCGC;
```

an internal reverse primer (251) comprising the nucleotide sequence

```
                                    (SEQ ID NO: 267)
GCACTCTTCCGAAAACGAAACG;
```

and a probe (252a) comprising the nucleotide sequence fluor-

```
                                    (SEQ ID NO: 268)
CCAAACAC(T*)CACCAAATC(N*)CAAAC-blocker.
```

Embodiment 364: The set of cartridges according to any one of embodiments 362-363, wherein said second cartridge contains the following probes and primers for determining methylation of ACTB (e.g., as a control) using a nested PCR reaction:

an external forward primer (102) comprising the nucleotide sequence

```
                                    (SEQ ID NO: 103)
GTGATGGAGGAGGTTTAGTAAGTT;
```

an external reverse primer (103) comprising the nucleotide sequence

```
                                    (SEQ ID NO: 104)
CCAATAAAACCTACTCCTCCCTTAA;
```

an internal forward primer (148) comprising the nucleotide sequence

```
                                    (SEQ ID NO: 149)
GGTTTAGTAAGTTTTTTGGATTGTG;
```

an internal reverse primer (149) comprising the nucleotide sequence

```
                                    (SEQ ID NO: 150)
CCTTAAAAATTACAAAAACCACAAC;
```

and a probe (178) comprising the nucleotide sequence fluor-

```
                                    (SEQ ID NO: 179)
CCACCACCCAACACA(N*)CAA(T*)AACAAACAC-blocker.
```

Embodiment 365: The set of cartridges according to any one of embodiments 317-360, wherein said second cartridge comprises one or more chambers containing beads that provide PCR primers and probes to detect methylation of one or more gene promoters.

Embodiment 366: The set of cartridges of embodiment 365, wherein said second cartridge comprises one or more chambers containing beads that provide PCR primers and probes to detect methylation of one or more gene promoters whose methylation state is a marker for a cancer selected from the group consisting of breast cancer, pancreatic cancer, prostate cancer, brain cancer, and lung cancer.

Embodiment 367: The set of cartridges according to any of embodiments 365-366, wherein said chamber containing beads that provide PCR primers and probes to detect methylation of one or more gene promoters comprises beads that provide PCR primers and probes to detect methylation of one or more gene promoters whose methylation state is a marker for a cancer selected from the group consisting of breast cancer, pancreatic cancer, prostate cancer, brain cancer, and lung cancer.

Embodiment 368: The set of cartridges of embodiment 367, wherein said chamber containing beads that provide PCR primers and probes to detect methylation of one or more gene promoters comprises beads that provide PCR primers and probes for a nested PCR reaction.

Embodiment 369: The set of cartridges of embodiment 368, wherein said nested PCR comprises a first PCR reaction specific for converted DNA and a second PCR reaction specific for methylated CpGs.

Embodiment 370: The set of cartridges according to any one of embodiments 349-369, wherein said chamber containing beads that provide PCR primers and probes chamber contains beads that provide PCR primers and probes to detect methylation of a forward strand of converted DNA.

Embodiment 371: The set of cartridges according to any one of embodiments 349-370, wherein said chamber containing beads that provide PCR primers and probes chamber contains beads that provide PCR primers and probes to detect methylation of a reverse strand of converted DNA.

Embodiment 372: The set of cartridges according to any of embodiments 349-371, wherein said chamber containing beads that provide PCR primers and probes to detect methylation of one or more gene promoters comprises beads that provide PCR primers and probes to detect methylation of the promoters of one or more genes selected from the group consisting of RASSF1A, AKR1B1, HOXB4, HIST1H3C, RASGRF2, TM6SF1, BRCA1, BNC1, ADAMTS1, CDO1, SOX17, TAC1, HOXA7, and MGMT.

Embodiment 373: The set of cartridges according to any of embodiments 349-372, wherein said chamber containing beads that provide PCR primers and probes to detect methylation of one or more gene promoters comprises beads that provide PCR primers and probes to detect methylation of one or more gene promoters whose methylation state is a marker for pancreatic cancer.

Embodiment 374: The set of cartridges of embodiment 373, wherein said chamber containing beads that provide PCR primers and probes to detect methylation of one or more gene promoters comprises beads that provide PCR primers and probes to detect methylation of the promoters of ADAMTS1, and/or BNC1.

Embodiment 375: The set of cartridges of embodiment 374, wherein said chamber containing beads that provide PCR primers and probes to detect methylation of one or more gene promoters comprises beads that provide PCR primers and probes to detect methylation of the promoter of ADAMTS1.

Embodiment 376: The set of cartridges according to any one of embodiments 374-375, wherein said chamber containing beads that provide PCR primers and probes to detect methylation of one or more gene promoters comprises beads that provide PCR primers and probes to detect methylation of the promoter of BNC1.

Embodiment 377: The set of cartridges of embodiment 374, wherein said chamber containing beads that provide PCR primers and probes to detect methylation of one or more gene promoters comprises beads that provide one or more PCR primers and/or probes for ADAMTS1 and/or BNC1 shown in Tables 5, or 10.

Embodiment 378: The set of cartridges according to any of embodiments 349-372, wherein said chamber containing beads that provide PCR primers and probes to detect methylation of one or more gene promoters comprises beads that provide PCR primers and probes to detect methylation of one or more gene promoters whose methylation state is a marker for breast cancer.

Embodiment 379: The set of cartridges of embodiment 378, wherein said chamber containing beads that provide PCR primers and probes to detect methylation of one or more gene promoters comprises beads that provide PCR primers and probes to detect methylation of the promoters of one, two, three, four, five, or all genes selected from the group consisting of BRCA1, RASSF1A, AKR1B1, HOXB4, HIST1H3C, RASGRF2, and TM6SF1.

Embodiment 380: The set of cartridges of embodiment 379, wherein said chamber containing beads that provide PCR primers and probes to detect methylation of one or more gene promoters comprises beads that provide PCR primers and probes to detect methylation of the promoter of BRCA1.

Embodiment 381: The set of cartridges according to any one of embodiments 379-380, wherein said chamber containing beads that provide PCR primers and probes to detect methylation of one or more gene promoters comprises beads that provide PCR primers and probes to detect methylation of the promoter of RASSF1A.

Embodiment 382: The set of cartridges according to any one of embodiments 379-381, wherein said chamber containing beads that provide PCR primers and probes to detect methylation of one or more gene promoters comprises beads that provide PCR primers and probes to detect methylation of the promoter of AKR1B1.

Embodiment 383: The set of cartridges according to any one of embodiments 379-382, wherein said chamber containing beads that provide PCR primers and probes to detect methylation of one or more gene promoters comprises beads that provide PCR primers and probes to detect methylation of the promoter of HOXB4.

Embodiment 384: The set of cartridges according to any one of embodiments 379-383, wherein said chamber containing beads that provide PCR primers and probes to detect methylation of one or more gene promoters comprises beads that provide PCR primers and probes to detect methylation of the promoter of HIST1H3C.

Embodiment 385: The set of cartridges according to any one of embodiments 379-384, wherein said chamber containing beads that provide PCR primers and probes to detect methylation of one or more gene promoters comprises beads that provide PCR primers and probes to detect methylation of the promoter of RASGRF2.

Embodiment 386: The set of cartridges according to any one of embodiments 379-385, wherein said chamber containing beads that provide PCR primers and probes to detect methylation of one or more gene promoters comprises beads that provide PCR primers and probes to detect methylation of the promoter of TM6SF1.

Embodiment 387: The set of cartridges according to any one of embodiments 379-386, wherein said chamber containing beads that provide PCR primers and probes to detect methylation of one or more gene promoters comprises beads that provide one or more PCR primers and/or one or more PCR probes shown in Tables 5, or 9.

Embodiment 388: The set of cartridges of embodiment 378, wherein said chamber containing beads that provide PCR primers and probes to detect methylation of one or more gene promoters comprises beads that provide PCR primers and probes to detect methylation of the promoters of BRCA1.

Embodiment 389: The set of cartridges according to any of embodiments 349-372, wherein said chamber containing beads that provide PCR primers and probes to detect methylation of one or more gene promoters comprises beads that provide PCR primers and probes to detect methylation of one or more gene promoters whose methylation state is a marker for lung cancer.

Embodiment 390: The set of cartridges of embodiment 389, wherein said chamber containing beads that provide PCR primers and probes to detect methylation of one or more gene promoters comprises beads that provide PCR primers and probes to detect methylation of the promoters of one, two, three, or all genes selected from the group consisting of CDO1, SOX17, TAC1, and HOXA7.

Embodiment 391: The set of cartridges of embodiment 390, wherein said chamber containing beads that provide PCR primers and probes to detect methylation of one or more gene promoters comprises beads that provide PCR primers and probes to detect methylation of the promoter of CDO1.

Embodiment 392: The set of cartridges according to any one of embodiments 390-391, wherein said chamber containing beads that provide PCR primers and probes to detect methylation of one or more gene promoters comprises beads that provide PCR primers and probes to detect methylation of the promoter of SOX17.

Embodiment 393: The set of cartridges according to any one of embodiments 390-392, wherein said chamber containing beads that provide PCR primers and probes to detect methylation of one or more gene promoters comprises beads that provide PCR primers and probes to detect methylation of the promoter of TAC1.

Embodiment 394: The set of cartridges according to any one of embodiments 390-393, wherein said chamber containing beads that provide PCR primers and probes to detect methylation of one or more gene promoters comprises beads that provide PCR primers and probes to detect methylation of the promoter of HOXA7.

Embodiment 395: The set of cartridges according to any of embodiments 349-372, wherein said chamber containing beads that provide PCR primers and probes to detect methylation of one or more gene promoters comprises beads that provide PCR primers and probes to detect methylation of one or more gene promoters whose methylation state is a marker for brain cancer.

Embodiment 396: The set of cartridges of embodiment 395, wherein said chamber containing beads that provide PCR primers and probes to detect methylation of one or more gene promoters comprises beads that provide PCR primers and probes to detect methylation of the promoter of MGMT.

Embodiment 397: The set of cartridges of embodiment 396, wherein said chamber containing beads that provide PCR primers and probes to detect methylation of one or more gene promoters comprises beads that provide one or more PCR primers and/or probes for MGMT shown in Tables 5, or 10.

Embodiment 398: The set of cartridges of embodiment 397, wherein said cartridge contains the following probes and primers for determining methylation of MGMT using a nested PCR reaction:

an external forward primer (248b) comprising the nucleotide sequence

```
                                    (SEQ ID NO: 263)
GTTTT(T*)AGAAYG(T*)TTTGYGTTT;
```

an external reverse primer (249b) comprising the nucleotide sequence

```
                                    (SEQ ID NO: 265)
AAAAAAC(T*)CCRCACTCTTCC;
```

an internal forward primer (250) comprising the nucleotide sequence

```
                                    (SEQ ID NO: 266)
TTTCGACGTTCGTAGGTTTTCGC;
```

an internal reverse primer (251) comprising the nucleotide sequence

```
                                    (SEQ ID NO: 267)
GCACTCTTCCGAAAACGAAACG;
```

and a probe (252a) comprising the nucleotide sequence fluor-

```
                                    (SEQ ID NO: 268)
CCAAACAC(T*)CACCAAATC(N*)CAAAC-blocker.
```

Embodiment 399: The set of cartridges according to any one of embodiments 397-398, wherein said cartridge contains the following probes and primers for determining methylation of ACTB (e.g., as a control) using a nested PCR reaction:

an external forward primer (102) comprising the nucleotide sequence:

```
                                    (SEQ ID NO: 103)
GTGATGGAGGAGGTTTAGTAAGTT;
```

an external reverse primer (103) comprising the nucleotide sequence:

```
                                    (SEQ ID NO: 104)
CCAATAAAACCTACTCCTCCCTTAA;
```

an internal forward primer (148) comprising the nucleotide sequence:

```
                                    (SEQ ID NO: 149)
GGTTTAGTAAGTTTTTTGGATTGTG;
```

an internal reverse primer (149) comprising the nucleotide sequence:

(SEQ ID NO: 150)
CCTTAAAAATTACAAAAACCACAAC;

and an probe (178) comprising the nucleotide sequence: fluor- (SEQ ID NO: 179)
CCACCACCCAACACA(N*)CAA(T*)AACAAACAC-blocker.

Embodiment 400: A system for determining the methylation of a nucleic acid in a biological sample, said system comprising:

an enclosure configured to contain one or more sample processing modules, each sample processing module configured to hold a removable cartridge first cartridge and/or second cartridge of said set of cartridges according to any one of embodiments 317-399;

where said system is configured to:

operate the sample processing modules to perform sample processing to operate the first cartridge of said set of cartridges to perform a bisulfate conversion of a nucleic acid in a sample introduced into said first cartridge; and/or to perform a desulphonation and to determine methylation of one or more target nucleic acids within a corresponding removable sample cartridge.

Embodiment 401: The system of embodiment 400, wherein said system is configured to contain one sample processing module.

Embodiment 402: The system of embodiment 400, wherein said system is configured to contain at least two sample processing modules, or at least 4 sample processing modules, or at least 8 sample processing modules, or at least 12 sample processing modules, or at least 16 sample processing modules, or at least 20 sample processing modules, or at least 24 sample processing modules, or at least 28 sample processing modules, or at least 32 sample processing modules, or at least 64 sample processing modules, or at least 128 sample processing modules.

Embodiment 403: The system according to any one of embodiments 400-402, wherein said modules comprise one or more heating plates to heat a temperature controlled chamber or channel in said cartridge.

Embodiment 404: The system according to any one of embodiments 400-403, wherein said modules comprise a fan configured to cool a temperature controlled channel or chamber in said cartridge.

Embodiment 405: The system according to any one of embodiments 400-404, wherein said modules comprise circuitry to pass information (e.g., optical information) to a computer for analysis.

Embodiment 406: The system according to any one of embodiments 400-405, wherein said modules comprise optical blocks to provide excitation and/or detection of one or more optical signals produced by reactions in said cartridge.

Embodiment 407: The system according to any one of embodiments 400-406, wherein said system is configured to operate said first cartridge of said set of cartridges to:

bind a sample to a column;

elute DNA from the column and combine said DNA with a conversion reagent;

heat the DNA/conversion reagent solution in a reaction chamber or tube to produce converted DNA; and to deliver the converted DNA to a sample removal chamber in the first cartridge.

Embodiment 408: The system according to any one of embodiments 400-407, wherein said system is configured to operate said second cartridge in said set of cartridges to:

bind the converted DNA to a column;

wash, rinse, and elute the converted DNA;

elute the DNA from the column; and defulphonate the converted DNA.

Embodiment 409: The system of embodiment 408, wherein said system is configured to operate said second cartridge in said set of cartridges to perform PCR on the eluted desulphonated DNA in a reaction chamber or tube.

Embodiment 410: A method of determining the methylation state of a nucleic acid, said method comprising: providing a biological sample in a sample chamber of a first cartridge in a set of cartridges according to any one of embodiments 317-399; and operating said first cartridge to:

bind DNA in said sample to said first matrix material;

wash the bound DNA; elute the bound DNA off of the matrix material; combine the eluted DNA with said bisulfite reagent;

heat the mixture of DNA and bisulfite reagent in said temperature controlled channel or chamber perform a bisulfite conversion of said DNA; and deliver the bisulfite-converted DNA into the sample removal chamber of said first cartridge.

Embodiment 411: The method of embodiment 410, wherein said method further comprise:

providing bisulfite converted DNA in a sample chamber of a second cartridge in a set of cartridges according to any one of embodiments 317-399; and operating said second cartridge to:

bind said bisulfite converted DNA to said second matrix material;

wash the bound bisulfite-converted DNA;

elute the washed bisulfite-converted DNA from said second matrix material; and desulphonate the bisulfite converted DNA.

Embodiment 412: The method of embodiment 411, wherein said second cartridge is operated to elute the bisulfite-converted DNA from said second matrix material before desulphonation.

Embodiment 413: The method of embodiment 411, wherein said second cartridge is operated to elute the bisulfite-converted DNA from said second matrix material after or during desulphonation.

Embodiment 414: The method according to any one of embodiments 411-413, wherein said method comprises operating said second cartridge to perform methylation specific PCR and/or nucleic acid sequencing, and/or high resolution melting analysis (HRM) on said converted nucleic acid to determine the methylation of said nucleic acid.

Embodiment 415: The method according to any one of embodiments 410-414, wherein said sample comprises one or more samples selected from the group consisting of a cell, a tissue, and a biological fluid containing a nucleic acid.

Embodiment 416: The method of embodiment 415, wherein said biological sample comprises a biological fluid selected from the group consisting of whole blood, plasma, serum, saliva, mucus, urine, sputum, pancreatic juice, and cerebrospinal fluid.

Embodiment 417: The method of embodiment 415, wherein said biological sample comprises a sample selected from the group consisting of a tissue sample, a formalin fixed paraffin embedded (FFPE) tissue, fresh frozen tissue, fine needle aspirates (FNA), and a core biopsy.

Embodiment 418: The method according to any one of embodiments 410-417, wherein said method comprises contacting said biological sample with a lysis solution.

Embodiment 419: The method according to any one of embodiments 410-418, wherein operating said first cartridge comprises introducing said first cartridge into a sample processing module in a system according to any one of embodiments 400-409.

Embodiment 420: The method according to any one of embodiments 410-419, wherein operating said second cartridge comprises introducing said second cartridge into a sample processing module in a system according to any one of embodiments 400-409.

Embodiment 421: The method according to any one of embodiments 410-420, wherein said providing a biological sample in a sample chamber of a first cartridge comprises loading a sample into one or more sample receiving chambers in said first cartridge.

Embodiment 422: The method according to any one of embodiments 410-421, wherein said providing bisulfite converted DNA in a sample chamber of a second cartridge comprises transferring bisulfite-converted DNA from a sample removal chamber in said first cartridge into a sample receiving chamber of said second cartridge.

Embodiment 423: The method according to any one of embodiments 410-422, wherein said eluting the bound DNA in said first cartridge comprises eluting and denaturing said DNA using a low concentration of potassium hydroxide or other base.

Embodiment 424: The method of embodiment 423, wherein said eluting the bound DNA in said first cartridge comprises eluting and denaturing said DNA with an alkaline solution with a pH greater than about pH 10.5.

Embodiment 425: The method of embodiment 423, wherein said eluting the bound DNA in said first cartridge comprises eluting and denaturing said DNA with an alkaline solution with a pH greater than about pH 12.

Embodiment 426: The method of embodiments 424-425, wherein said alkaline solution is a 10-15 mM KOH solution.

Embodiment 427: The method according to any one of embodiments 410-426, wherein said combining the eluted DNA with a bisulfite reagent in said first cartridge comprises incubating the DNA in an ammonium bisulfite solution having a concentration that ranges from about 6M to about 7M.

Embodiment 428: The method of embodiment 427, wherein said combining the eluted DNA with a bisulfite reagent in said first cartridge comprises incubating the DNA in an ammonium bisulfite solution having a concentration of about 6.5M.

Embodiment 429: The method of embodiment 428, wherein said combining the eluted DNA with a bisulfite reagent in said first cartridge comprises transferring the DNA in a concentrated bisulfite solution into a temperature controlled channel or chamber in said first cartridge and heating said mixture.

Embodiment 430: The method of embodiment 429, wherein said incubating comprises thermally cycling the concentrated bisulfite solution from a temperature of about 60° C. to about 95° C.

Embodiment 431: The method according to any one of embodiments 411-430, wherein said binding the bisulfite converted DNA to the second matrix material comprises mixing the DNA-bisulfite solution with fresh GTC-EtOH in said second column, and dispensing the solution over said second matrix material.

Embodiment 432: The method of embodiment 431, wherein said method comprises washing the DNA in said second matrix material with fresh GTC-EtOH, and then a rinse solution.

Embodiment 433: The method of embodiment 432, wherein said rinse solution comprises PEG200.

Embodiment 434: The method according to any one of embodiments 411-433, wherein said desulphonating the converted DNA comprises eluting the DNA from said second matrix material with a high pH desulphonation buffer and incubating said solution.

Embodiment 435: The method of embodiment 434, wherein said incubating is for a period of time ranging from about 1 minute to about 1 hour, or from about 5 minutes to about 30 minutes, or from about 10 minutes to about 20 minutes, or for about 15 minutes.

Embodiment 436: The method of embodiments 434-435, wherein said high pH desulphonation/elution buffer comprises KOH.

Embodiment 437: The method according to any one of embodiments 411-436, wherein said method comprises operating said second cartridge to perform one or more PCR reactions using said converted DNA as a template.

Embodiment 438: The method of embodiment 437, wherein methylation specific PCR is performed to determine methylation of target nucleic acid sequences.

Embodiment 439: The method of embodiment 438, wherein said methylation specific PCR (MSP) is performed using primers specific for methylated sequences and/or primers specific for unmethylated sequences.

Embodiment 440: The method of embodiment 438, wherein said methylation specific PCR comprises a MethyLight protocol.

Embodiment 441: The method of embodiment 438, wherein TaqMan PCR reactions are performed with primers specific for bisulfate-converted methylated and/or unmethylated sequences.

Embodiment 442: The method according to any one of embodiments 438-441, wherein said methylation specific PCR (MSP) utilizes one or more fluorescent probes that are markers for amplified methylated sequences and/or one or more fluorescent probes that are markers for amplified unmethylated sequences.

Embodiment 443: The method of embodiment 442, wherein said fluorescent probes comprise a fluorescent reporter dye and a quencher dye where the probe provides a signal upon cleavage by 5' to 3' nuclease activity of Taq DNA polymerase.

Embodiment 444: The method according to any one of embodiments 442-443, wherein a methylation signal is determined by the combined signal for a plurality of probes each specific to a different methylated region in an amplified region of interest.

Embodiment 445: The method according to any one of embodiments 442-443, wherein a methylation signal is determined by a plurality of probes specific for the same methylated region in an amplified region of interest.

Embodiment 446: The method according to any one of embodiments 442-443, wherein said plurality of probes comprise 2, 3, 4, 5, 6, 7, 8, 9, 10, or more probes.

Embodiment 447: The method according to any one of embodiments 442-443, wherein a methylation signal is determined by a single probe in the amplified region of interest.

Embodiment 448: The method according to any one of embodiments 442-447, wherein said probes are run in simplex or multiplex.

Embodiment 449: The method according to any one of embodiments 442-447, wherein said probes are run in a multiplex format.

Embodiment 450: The method according to any one of embodiments 442-449, wherein said probes are run as a nested PCR reaction.

Embodiment 451: The method according to any one of embodiments 442-450, wherein said PCR reaction comprises a bisulfite contamination control probe that that undergoes bisulfite-mediated cleavage during PCR if bisulfite is present in the reaction.

Embodiment 452: The method according to any one of embodiments 411-451, wherein PCR is performed for one or more mutated genes.

Embodiment 453: The method according to any one of embodiments 411-452, wherein PCR is performed for unconverted DNA as a control.

Embodiment 454: The method according to any one of embodiments 411-453, wherein PCR is performed for converted DNA as a control.

Embodiment 455: The method of embodiment 453, wherein PCR is performed for unconverted DNA where the unconverted DNA is a target for said method.

Embodiment 456: The method according to any one of embodiments 410-455, where methylation is determined for a promoter region of a gene selected from the group consisting of MGMT. RASSF1A, ADAMTS1, BNC1, HIST1H3C, HOXB4, RASGRF2, TM6SF1, and AKR1B1.

Embodiment 457: A method of detecting a cancer or the predisposition to a cancer in a subject, said method comprising:

- providing a biological sample from said subject, wherein said biological sample comprises a DNA;
- utilizing a set of cartridges according to any one of embodiments 317-399, wherein said first cartridge of said set of cartridges is used to perform a bisulfite conversion of said DNA; and said second cartridge of said set of cartridges is used to desulphonate the converted DNA and to detect methylation of one or more gene promoters in said DNA whose methylation state is a marker for a cancer, where an increase in methylation of said one or more gene promoters is indicative of the presence of a cancer or a predisposition to a cancer or a stage of a cancer or precancer.

Embodiment 458: The method of embodiment 457, wherein said subject is a human.

Embodiment 459: The method according to any one of embodiments 457-458, wherein said cancer is a cancer selected from the group consisting of breast cancer, pancreatic cancer, prostate cancer, brain cancer, a lung cancer, a B cell lymphoma, a bronchus cancer, a colorectal cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma.

Embodiment 460: The method according to any one of embodiments 457-458, wherein said cancer is a cancer selected from the group consisting of breast cancer, pancreatic cancer, prostate cancer, brain cancer, a lung cancer.

Embodiment 461: The method according to any one of embodiments 457-460, wherein said sample comprise a sample from serum or plasma.

Embodiment 462: The method according to any one of embodiments 457-460, wherein said sample comprise an FFPE sample.

Embodiment 463: The method according to any one of embodiments 457-462, wherein said one or more gene promoters comprise the promoters of one or more genes selected from the group consisting of RASSF1A, AKR1B1, HOXB4, HIST1H3C, RASGRF2, TM6SF1, BRCA1, BNC1, ADAMTS1, CDO1, SOX17, TAC1, HOXA 7, and MGMT.

Embodiment 464: The method according to any one of embodiments 457-462, wherein said cancer is pancreatic cancer and said one or more gene promoters comprise the promoters of one, two, three, or four genes selected from the group consisting of ADAMTS1, and BNC1.

Embodiment 465: The method of embodiment 464, wherein said one or more gene promoters comprise the promoter of ADAMTS1.

Embodiment 466: The method according to any one of embodiments 464-465, wherein said one or more gene promoters comprise the promoter of BNC1.

Embodiment 467: The method according to any one of embodiments 457-462, wherein said cancer is breast cancer and said one or more gene promoters comprise the promoters of one, two, three, four, five, or all genes selected from the group consisting of BRCA1, RASSF1A, AKR1B1, HOXB4, HIST1H3C, RASGRF2, and TM6SF1.

Embodiment 468: The method of embodiment 467, wherein said one or more gene promoters comprise the promoter of BRCA1.

Embodiment 469: The method according to any one of embodiments 467-468, wherein said one or more gene promoters comprise the promoter of RASSF1A.

Embodiment 470: The method according to any one of embodiments 467-469, wherein said one or more gene promoters comprise the promoter of AKR1B1.

Embodiment 471: The method according to any one of embodiments 467-470, wherein said one or more gene promoters comprise the promoter of HOXB4.

Embodiment 472: The method according to any one of embodiments 467-471, wherein said one or more gene promoters comprise the promoter of HIST1H3C.

Embodiment 473: The method according to any one of embodiments 467-472, wherein said one or more gene promoters comprise the promoter of RASGRF2.

Embodiment 474: The method according to any one of embodiments 467-473, wherein said one or more gene promoters comprise the promoter of TM6SF1.

Embodiment 475: The method according to any one of embodiments 457-462, wherein said cancer is breast cancer and said one or more gene promoters comprise the promoter of BRCA1.

Embodiment 476: The method according to any one of embodiments 457-462, wherein said cancer is lung cancer and said one or more gene promoters comprise the promoters of one, two, three, for all genes selected from the group consisting of CDO1, SOX17, TAC1, and HOXA7.

Embodiment 477: The method of embodiment 476, wherein said one or more gene promoters comprise the promoter of CDO1.

Embodiment 478: The method according to any one of embodiments 476-477, wherein said one or more gene promoters comprise the promoter of SOX17.

Embodiment 479: The method according to any one of embodiments 476-478, wherein said one or more gene promoters comprise the promoter of TAC1.

Embodiment 480: The method according to any one of embodiments 476-479, wherein said one or more gene promoters comprise the promoter of HOXA7.

Embodiment 481: The method according to any one of embodiments 457-462, wherein said cancer is brain cancer and said one or more gene promoters comprise the promoter of MGMT.

Embodiment 482: A kit for the determination of DNA methylation, said kit comprising: a container containing a first cartridge and/or a second cartridge of set of cartridges according to any one of embodiments 317-399.

Embodiment 483: The kit of embodiment 482, wherein said first cartridge and said second cartridge are contained in the same container.

Embodiment 484: The kit of embodiment 482, wherein said first cartridge and said second cartridge are in separate containers.

Embodiment 485: The kit of embodiment 482, wherein said kit further comprises a container containing a lysis solution.

Embodiment 486: The kit of embodiment 485, wherein said lysis solution is a lysis solution for serum or plasma.

Embodiment 487: The kit of embodiments 485, wherein said lysis solution is a lysis solution for an FFPE sample.

Embodiment 488: The kit according to any one of embodiments 482-487, wherein said kit comprises a container containing proteinase K.

Embodiment 489: The kit according to any one of embodiments 482-488, wherein said kit comprises a conversion reagent in said cartridge or in a container separate from the cartridge.

Embodiment 490: The kit of embodiment 489, wherein said kit comprises said conversion reagent in a container separate from the cartridge.

Embodiment 491: The kit of embodiment 489, wherein said kit comprises said conversion reagent is provided in a chamber of the cartridge.

Embodiment 492: The according to any one of embodiments 489-491, wherein said conversion reagent comprises a compound selected from the group consisting of sodium metabisulfite, potassium bisulfite, cesium bisulfite, ammonium bisulfite, and DABSO.

Embodiment 493: The kit of embodiment 492, wherein said conversion reagent comprises ammonium bisulfite.

Embodiment 494: The kit according to any one of embodiments 482-493, wherein said kit comprises a container containing a sample processing reagent.

Embodiment 495: The kit of embodiment 494, wherein said sample processing reagent comprises guanidium thiocyanate.

Embodiment 496: The kit according to any one of embodiments 494-495, wherein said sample processing reagent comprise ethanol.

Embodiment 497: The kit according to any one of embodiments 482-496, wherein said kit contains instructional materials teaching the use of said cartridge for the determination of DNA methylation.

In certain embodiments the methods and/or cartridges expressly exclude magnetic materials including magnetic glass, magnetic hydroxyapatite, and magnetic matrix materials. In certain embodiments the methods and/or cartridges expressly exclude magnetic materials for DNA isolation.

BRIEF DESCRIPTION OF THE DRAWINGS

FIG. 3A illustrates a module for operation of a GENEXPERT® cartridge. FIG. 3B illustrates some components of one embodiment of a module for operation of a cartridge for the analysis of DNA methylation. FIG. 3C illustrates a system (e.g., processing unit) incorporating a plurality of modules.

FIG. 4A, modified from Eads et al. 92000) *Nucleic Acids. Res.,* 28(8): e32) schematically illustrates MethyLight technology. DNA is modified by sodium bisulfate which generates methylation-dependent sequence differences, e.g., at CpG dinucleotides by converting unmethylated cytosine residues (locations indicated by white circles) to uracil, while methylated cytosine residues (locations indicated by black circles) are retained as cytosine. Fluorescence-based PCR is then performed with primers that either overlap methylation sites or that do not overlap any methylation sites. Sequence discrimination can occur either at the level of the PCR amplification process (panel D) or at the level of the probe hybridization process (panel B), or both (panel D). Sequence discrimination at the PCR amplification level utilizes primers and probes (panel D), or just primers (panel C), to overlap potential methylation sites (e.g., CpG dinucleotides). Only two (fully methylated (M) and fully unmethylated (U)) of the many theoretical methylation permutations are shown. The MethyLight assay can also be designed such that sequence discrimination does not occur at the PCR amplification level. If neither the primers nor the probe overlap sites of methylation (e.g., CpG dinucleotides) (panel A), then no methylation-dependent sequence discrimination occurs at the PCR amplification or probe hybridization level. This reaction represents amplification of the converted genomic DNA without bias to methylation status, which can serve as a control for the amount of input DNA. When just the probe overlaps methylation sites (panel B), then sequence discrimination can occur through probe hybridization. FIG. 4B illustrates a MethyLight approach using a single, e.g., methylation-specific, probe (PR3) along with methylation specific forward (FW) and reverse (RV) primers. FIG. 4C illustrates a MethyLight approach using multiple probes (PR1 . . . PR5) that each target different regions. FIG. 4D illustrates a MethyLight approach using multiple probes (PR1 . . . PR5) that each target the same region, but provide signals for different methylation patterns.

FIG. 7A shows the results for 25 ng of HSDNA or 5000 cells without bisulfite conversion. FIG. 7B shows the results of 20 cycles of nested qPCR for the bisulfite converted methylated targets using DNA from MBA-453 cells. FIG. 7C shows the results of 20 cycles of nested qPCR for the bisulfite converted methylated targets using DNA from MBA-453 cells in a carrier (1 μg of SS and 10 ng of HS DNA). Fallouts occur at around 25-50 copies or around 100 cells.

DEFINITIONS

Figure 1A:
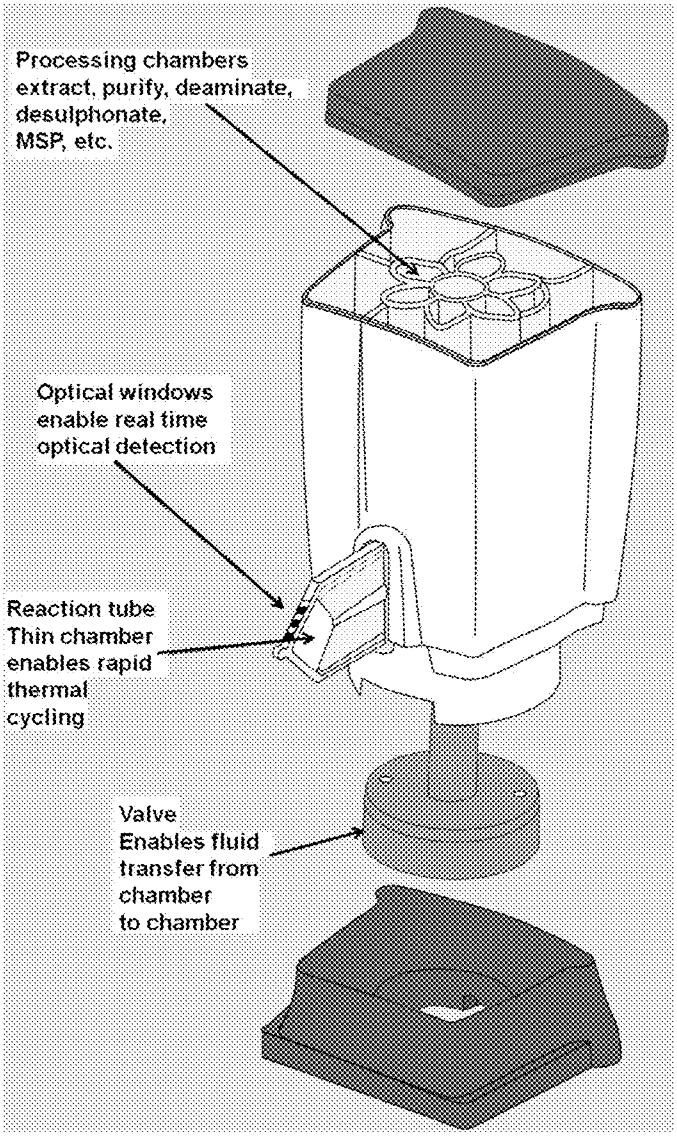
FIG. 1A illustrates major components of a cartridge (e.g., a GENEXPERT® cartridge) suitable for use with the methods described herein.

To facilitate an understanding of the present invention, a number of terms and phrases are defined below:

As used herein, the terms “detect”, “detecting” or “detection” may describe either the general act of discovering or discerning or the specific observation of a detectably labeled composition.

As used herein, the term “detectably different” or “spectrally distinguishable” refers to a set of labels (such as dyes/fluorophores) that can be detected and distinguished simultaneously.

DNA methylation DNA methylation refers to the addition of a methyl group (CH3) covalently to the base cytosine (C) typically in the dinucleotide 5'-CpG-3'. The term CpG refers to the base cytosine (C) linked by a phosphate bond to the base guanine (G) in the DNA nucleotide sequence.

The term “conversion reagent” refers to a reagent that deaminates cytosine to uracil in single stranded DNA, while leaving 5-MeC essentially unaffected. Illustrative conversion reagents include bisulfites (e.g., sodium metabisulfite, potassium bisulfite, cesium bisulfite, ammonium bisulfite, etc.) and/or compounds that can produce a bisulfite under appropriate reaction conditions (e.g., DABSO).

The phrase “detecting methylation of a gene” generally refers to the detection of methylation of cytosine, typically in CPG islands, in the promoter region of the gene.

As used herein, the terms “patient” and “subject” are typically used interchangeably to refer to a human. In some embodiments, the methods described herein may be used on samples from non-human animals, e.g., a non-human primate, canine, equine, feline, porcine, bovine, lagomorph, and the like.

As used herein, the terms “oligonucleotide,” “polynucleotide,” “nucleic acid molecule,” and the like, refer to nucleic acid-containing molecules, including but not limited to, DNA. The terms encompass sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term “oligonucleotide,” refers to a single-stranded polynucleotide typically having fewer than 500 nucleotides. In some embodiments, an oligonucleotide is 8 to 200, 8 to 100, 12 to 200, 12 to 100, 12 to 75, or 12 to 50 nucleotides long. Oligonucleotides may be referred to by their length, for example, a 24 residue oligonucleotide may be referred to as a “24-mer.”

As used herein, the term “complementary” to a target gene (or target region thereof), and the percentage of “complementarity” of the probe sequence to the target gene sequence is the percentage “identity” to the sequence of target gene or to the complement of the sequence of the target gene. In determining the degree of “complementarity” between probes used in the compositions described herein (or regions thereof) and a target gene, such as those disclosed herein, the degree of “complementarity” is expressed as the percentage identity between the sequence of the probe (or region thereof) and sequence of the target gene or the complement of the sequence of the target gene that best aligns therewith. The percentage is calculated by counting the number of aligned bases that are identical as between the 2 sequences, dividing by the total number of contiguous nucleotides in the probe, and multiplying by 100. When the term “complementary” is used, the subject oligonucleotide is at least 90% complementary to the target molecule, unless indicated otherwise. In some embodiments, the subject oligonucleotide is at least 91%, at least 92%, at least 93%, at least 94%, at least 95%, at least 96%, at least 97%, at least 98%, at least 99%, or 100% complementary to the target molecule.

A “primer” or “probe” as used herein, refers to an oligonucleotide that comprises a region that is complementary to a sequence of at least 8 contiguous nucleotides of a target nucleic acid molecule, such as a target gene. In some embodiments, a primer or probe comprises a region that is complementary to a sequence of at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 29, at least 30, at least 319, at least 32, at least 33, at least 34, at least 35, at least 36, at least 37, at least 38, at least 39, or at least 40 contiguous nucleotides of a target molecule. When a primer or probe comprises a region that is “complementary to at least x contiguous nucleotides of a target molecule,” the primer or probe is at least 95% complementary to at least x contiguous nucleotides of the target molecule. In some embodiments, the primer or probe is at least 96%, at least 97%, at least 98%, at least 99%, or 100% complementary to the target molecule.

The term “nucleic acid amplification,” encompasses any means by which at least a part of at least one target nucleic acid is reproduced, typically in a template-dependent manner, including without limitation, a broad range of techniques for amplifying nucleic acid sequences, either linearly or exponentially. Exemplary means for performing an amplifying step include polymerase chain reaction (PCR), ligase chain reaction (LCR), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), digital amplification, and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or, in certain embodiments, can be performed isothermally.

The term "hybridize" is typically used herein refer to "specific hybridization" which is the binding, duplexing, or hybridizing of a nucleic acid molecule preferentially to a particular nucleotide sequence, in some embodiments, under stringent conditions. The term "stringent conditions" refers to conditions under which a probe will hybridize preferentially to its target sequence, and to a lesser extent to, or not at all to, other sequences. A "stringent hybridization" and "stringent hybridization wash conditions" in the context of nucleic acid hybridization are sequence-dependent and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. ("Tijssen"). Generally, highly stringent hybridization and wash conditions for filter hybridizations are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. In certain embodiments very stringent conditions are selected to be equal to the $T_m$ for a particular probe. Dependency of hybridization stringency on buffer composition, temperature, and probe length are well known to those of skill in the art (see, e.g., Sambrook and Russell (2001) *Molecular Cloning: A Laboratory Manual* (3rd ed.) Vol. 1-3, Cold Spring Harbor Laboratory, Cold Spring Harbor Press, N.Y.).

A "sample," as used herein, generally refers to a biological sample including biological fluids (e.g., blood or blood fractions, serum, plasma, pancreatic juice, cerebrospinal fluid, oral fluid, lymph, intraocular fluid, and the like) and/or tissue samples including, but not limited to biopsy samples, frozen tissue samples, formalin fixed paraffin embedded (FFPE) samples from various tissues including but not limited to breast tissue, endocervical tissue, vaginal tissue, colon/rectal tissue, throat tissue, and other types of human samples, such as blood, stool, and biopsy samples. The term sample also includes diluted and/or buffered forms of the above samples, for example, a buffer into which a swab sample has been placed, a urine sample to which a buffer has been added, and the like.

As used herein, the phrase "is indicative of the presence of a cancer or a predisposition to a cancer" means that a particular result tends to indicate that a cancer is present, and/or a precancerous condition is present or likely present. This phrase does not imply a definitive determination that the condition is present. A definitive determination can be made based on further examination or testing that a medical practitioner deems appropriate. Furthermore, this phrase does not require that a determination be made as to which condition may be present based only on the particular result. Rather, it is contemplated that a positive result will be considered in light of other examination or text results to arrive at a differential diagnosis.

The term "tubefill procedure" refers to a procedure that is run using standard laboratory instrumentation rather than on a cassette (e.g., rather than with a GENEXPERT®, or modified GENEXPERT® cartridge described herein).

DETAILED DESCRIPTION

In various embodiments devices and methods are provided that facilitate the rapid detection and/or characterization of methylation in DNA samples. In certain embodiments automated reaction cartridges are provided as are methods that that utilize the automated reaction cartridge(s) to facilitate analysis of the methylation of a DNA sample and, optionally, to measure mRNA levels along with the determination of DNA methylation. In various embodiments the DNA methylation is determined by bisulfite conversion and analysis of the bisulfite converted DNA (e.g., via methylation specific PCR, nucleic acid sequencing, melting point analysis, and the like). In certain embodiments the cartridge performs all or a part of the bisulfite conversion of DNA and all or a part of the analysis of the bisulfite converted DNA. In certain embodiments the cartridge performs all of the steps involved in bisulfite conversion and all or a part of the analysis of the bisulfite-converted DNA. In certain embodiments the cartridge performs all of the steps involved in bisulfite conversion and all of the analysis of the bisulfite-converted DNA. In certain embodiments the cartridge additionally performs an isolation and purification of the DNA to be analyzed.

There are several advantages to automating the methylation analysis including for example, reduction in overall processing time, improvements in efficiency, decreased user error and variability, minimization of loss between steps, and an improved ability to use smaller amounts of sample. Use of a cartridge-based process, as described herein, allows for rapid and easy testing of not only multiple sample types but also for evaluating methylation changes observed in several different types of cancers including, but not limited to breast cancer, colorectal cancer, prostate cancer, and lung cancer.

The cartridge-based methods described herein additionally permit measurement of mRNA derived from the same sample. Measurement of corresponding upstream and/or downstream mRNA involved in DNA methylation can be important to understand the mechanism and activity of the epigenetic modification. For example, the measurement of DNA methyltransferases (DNMT) mRNA has been studied along with DNA methylation for several cancers (see Table 1).

TABLE 1

Illustrative DNA methyltransferases and their importance in particular cancers (from Subramaniam et al. (2014) Front Oncol., 4: Article 80, doi: 10.3389/fonc.2014.00080).

| Methyltransferase | Cancers |
|---|---|
| DNMT1 | Leukemia: upregulated - 5.3-fold expression |
| | Gastric cancer - 64.8% localized in the cytoplasm and nuclei |
| | Breast cancer - 16.6% |
| | Hepatocellular carcinoma - 100% |
| | Pancreatic cancer - highly expressed - Gli target gene |
| | Colon cancer - highly expressed |
| | Glioblastoma - overexpressed |
| DNMT2 or TRDMT1 | Hepatocellular carcinoma - reduced expression |
| | Colorectal and stomach cancers - lower mRNA expression |
| DNMT3A | Acute myeloid leukemia - 22.1% mutations and affect translation |
| | Gastric cancer - 70.4% localized in the cytoplasm |
| | Breast cancer - 14% |
| | Hepatocellular carcinoma - 60% |
| | Pancreatic cancer - highly expressed - regulated by Gli 1 |
| | Colon cancer - highly expressed |
| DNMT3B | Leukemia: upregulated - 11.7-fold expression |
| | Gastric cancer - 51.9% localized in the cytoplasm |
| | Breast cancer - 81.8% poor prognosis |
| | Breast cancer cell lines - hypermethylation defect resulted in aberrant - overexpression DNMT activity |
| | Hepatocellular carcinoma (60%) and mRNA levels high |
| | Colon cancer - highly expressed |
| | Prostate cancer - overexpressed |
| | Glioblastoma - overexpressed |
| DNMT3L | Cervical cancer - promising biomarker |
| | Embryonal carcinoma - novel biomarker |

Often separate independent extractions for DNA or RNA are used for studying and measuring genes and transcripts. Co-detection from the same sample preparation would be ideal to minimize sample preparation, assay to assay, sample-to-sample and cell-to-cell variability.

Cartridge-Based Bisulfite Conversion of DNA

In certain embodiments the extraction of DNA, bisulfite conversion, and methylation specific PCR are all performed in the cartridge. In one illustrative embodiment, the user will add the sample to a lysis/binding reagent, then mix/vortex the reagent briefly, and then add the sample to a sample port or chamber in the cartridge. Illustrative, but non-limiting lysis reagents (including reagents particularly well suited for FFPE sections) are described in PCT Patent Publication No: WO/2014/052551 (PCT/US2013/061863), which is incorporated herein by reference for the reagents described therein.

Additional illustrative lysis reagents for serum or plasma and for formalin-fixed paraffin embedded (FFPE) samples are shown in Example (Tables 13, and 14, respectively).

Figure 11:
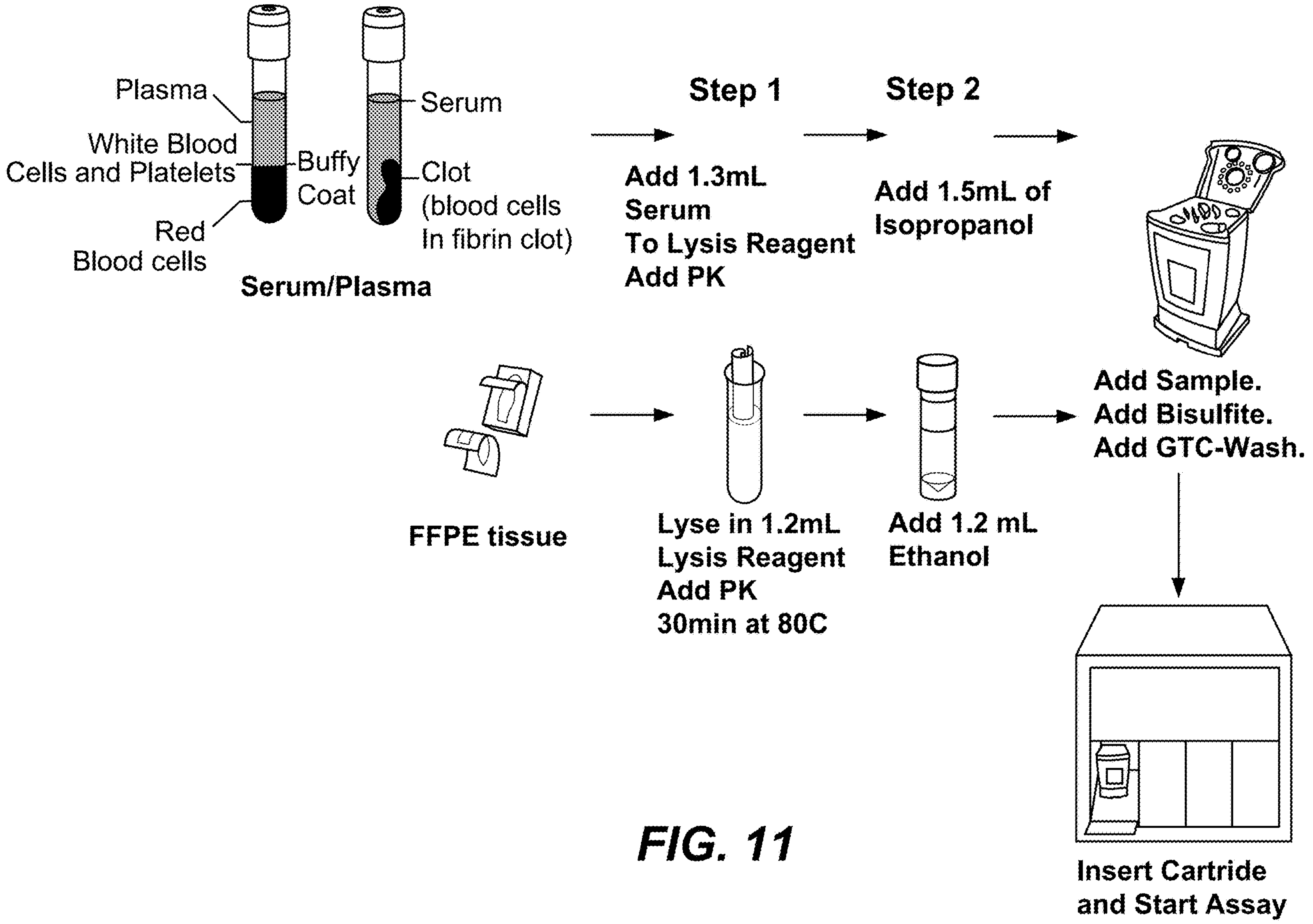
FIG. 11 shows illustrative but non-limiting workflows for analysis of methylation using a cartridge (e.g., a GENEXPERT® cartridge). Top illustrates one work flow for analysis of DNA methylation in a serum or plasma sample. Bottom illustrates one work flow for analysis of DNA methylation in a tissue section (e.g., frozen or formalin-fixed paraffin embedded (FFPE) section).

In certain embodiments the cartridge is placed into a processing module and the assay is initiated by clicking through a set of selections within software controlling the processing module (see, e.g., FIGS. 11A and 11B). The cartridge then performs the bisulfate conversion process and analysis of the bisulfate-converted DNA. In certain embodiments mRNA is also determined. While in certain embodiments, all of the operations are performed in the cartridge, in other embodiments, subsets of the various operations are performed in the cartridge as described below.

The sample can comprise any biological sample that contains DNA whose methylation state is to be evaluated. Illustrative samples include, but are not limited to isolated DNA and/or isolated total nucleic acids, a cell, a tissue, a biological fluid containing a nucleic acid, and the like. In certain embodiments the biological sample comprises a biological fluid selected from the group consisting of plasma, serum, amniotic fluid saliva, mucus, urine, pancreatic juice, and cerebrospinal fluid. In certain embodiments the sample comprises a tissue sample from a healthy tissue, or a tissue sample from a diseased sample. In certain embodiments the tissue sample is from a fetus, a neonate, a child, an adolescent, or an adult. In certain embodiments the tissue sample comprises tumor cell and/or is derived from a biopsy of a tumor (e.g., a breast cancer, a prostate cancer, a brain cancer, a cervical cancer, an ovarian cancer, a pancreatic cancer, a colon cancer, a gastric cancer, a hepatocellular cancer and the like. In certain embodiments the sample comprises a fixed tissue, e.g., a formalin fixed tissue sample. In certain embodiments the sample comprises an embedded tissue sample (e.g., a formalin-fixed paraffin embedded (FFPE) tissue sample).

Bisulfite conversion of DNA typically involves four steps:

1) DNA purification;
2) DNA denaturation;
3) DNA conversion (e.g., bisulfite deamination); and
4) Alkali desulphonation.

Typically DNA conversion (e.g., using a conversion reagent such as a bisulfite) involves: 1) Sulphonation: The addition of bisulphite to the 5-6 double bond of cytosine; and 2) Hydrolic Deamination: hydrolytic deamination of the resulting cytosine-bisulphite derivative to give a uracil-bisulphite derivative. This is followed by Alkali Desulphonation: Removal of the sulphonate group by an alkali treatment, to give uracil as indicated above.

As noted above, in certain embodiments, the DNA purification can be performed prior to placing a sample in the cartridge, or alternatively, can be performed by the cartridge itself. Accordingly, in certain embodiments the sample is added directly to the reaction cartridge, while in other embodiments, the sample is mixed with one or more reagents. In certain embodiments DNA preparation typically involves preparing substantially isolated DNA. This may involve lysing cells to release DNA, removing particulates and cellular debris, and/or removing protein components to provide a sample comprising substantially pure nucleic acids (e.g., substantially pure DNA and/or a substantially pure combination of DNA and RNA). In one illustrative, but non-limiting, embodiment, the sample (e.g., a tissue sample) is added to a lysis reagent, agitated and then inserted into the cartridge for further processing.

In certain embodiments, all of the reagents necessary to perform bisulfite conversion of the DNA are provided in the cartridge. In certain embodiments, to avoid degradation of reagents over time in the cartridge, certain reagents may be added to the cartridge immediately before use. Thus, for example in certain embodiments, it is contemplated that the cartridge may be loaded with a conversion reagent (e.g., a bisulfite reagent) and/or a guanidium thiocynanate reagent (e.g., GTC-EtOH-Tween) at or about the time the sample is loaded into the cartridge. In certain embodiments, the guanidinium thiocyanate reagent (e.g., GTC-EtOH-Tween) is combined with the sample and added to the cartridge in the sample receiving chamber (e.g., chamber 2 in the GENEXPERT® cartridge).

In certain embodiments when performing the bisulfite conversion of DNA using a reaction cartridge (e.g., GENEXPERT® cartridge), the method comprises i) contacting a biological sample comprising a nucleic acid to a first matrix material comprising a first column or filter where said matrix material binds and/or filters nucleic acids in said sample and thereby purifies the DNA;

ii) eluting the bound DNA from the first matrix material (e.g., using an alkaline solution) and denaturing the DNA to produce eluted denatured DNA;

iii) heating the eluted DNA in the presence of a conversion reagent (e.g., a reagent that provides bisulfite ions) to produce a converted (e.g., a deaminated) nucleic acid;

iv) contacting the converted nucleic acid to a second matrix material comprising a second column to bind said deaminated nucleic acid to said second matrix material (note in certain embodiments the second column can be a column different than the first column, or in other embodiments, the same column used a second time);

v) desulphonating the bound deaminated nucleic acid and/or simultaneously eluting and desulphonating the nucleic acid by contacting the deaminated nucleic acid with an alkaline solution to produce a converted (e.g., bisulfite converted) nucleic acid; and vi) eluting the converted nucleic acid from said second matrix material, wherein at least steps iv) through vi) are performed in a one reaction cartridge.

In certain embodiments the method further includes the analysis of the converted DNA. Accordingly, in certain embodiments, the method further comprises:

vii) performing methylation specific PCR and/or nucleic acid sequencing, and/or high resolution melting analysis (HRM) on the converted nucleic acid to determine the methylation of the nucleic acid, wherein at least steps iv) through vi) are performed in a single reaction cartridge.

In certain embodiments at least steps iii) through vi) are performed in one reaction cartridge.

In certain embodiments at least steps ii) through vi) are performed in one reaction cartridge.

In certain embodiments at least steps i) through vi) are performed in one reaction cartridge.

In certain embodiments at least steps i) through vii) are performed in one reaction cartridge.

It is noted that the first column and, where present, the second column can refer to discrete columns. However, particularly when integrated into a reaction cartridge, the "column" can simply be a matrix material disposed in a chamber or channel in the cartridge. In various embodiments the "columns" act as filters and/or as affinity columns that bind nucleic acids. Accordingly, in certain embodiments the column contains a matrix material that binds a nucleic acid (e.g., DNA and/or RNA). Illustrative matrix materials include, but are not limited to, glass (silica), an ion exchange resin, hydroxyapatite, and the like. It will be recognized that the matrix materials can take a number of forms. Thus, in certain embodiments, the matrix material comprises a fibrous material a particulate material (e.g., microbeads, nanobeads, etc.), a structured material (e.g., porous "baffle" system", a serpentine channel, and the like). In certain embodiments the first column and second column are different columns (chambers or channels). In other embodiments the first column and the second column are the same column (chamber or channel) that is used twice (e.g., a first time and a second time).

In certain embodiments, the use of one or more additional filters, e.g., to clean up the initial sample prior to contacting with the first matrix material, is contemplated. Thus, for example, in certain embodiments, a filter matrix (e.g., polycarbonate filter, nylon filter, polypropylene filter, polyester filter, nylon filter, ceramic filter, polytetrafluoroethylene filter, and the like) is disposed in the sample receiving chamber or "downstream" from the sample receiving chamber and before the first "column". It is also recognized, that in certain embodiments, the sample, can be lysed and/or filtered prior to deposition into a sample receiving chamber.

In certain illustrative, but non-limiting embodiments, the methods described herein can be performed using a GENEXPERT® cartridge (Cepheid, Inc., Sunnyvale, CA) or a variant thereof. In various embodiments sample extraction, and/or amplification, and/or DNA conversion, and/or detection can all be carried out within this self-contained "laboratory in a cartridge" (see, e.g., U.S. Pat. Nos. 5,958,349, 6,403,037, 6,440,725, 6,783,736, and 6,818,185, each of which is herein incorporated by reference in its entirety). In various embodiments components of the cartridge can include, but are not limited to, processing chambers containing reagents, filters, and capture technologies useful to extract, purify, and amplify target nucleic acids. A valve enables fluid transfer from chamber to chamber and contains nucleic acids lysis and filtration components. An optical window enables real-time optical detection (e.g., of PCR amplification products). A reaction tube can be provided that permits very rapid heating and/or thermal cycling.

In certain embodiments an illustrative GENEXPERT® cartridge comprises a plurality of chambers disposed around a central valve assembly and selectively in fluid communication with the central valve assembly where the central valve assembly is configured to accommodate a plunger that is capable of drawing fluid into or out of a chamber in fluid communication with the central valve. Rotation of the valve assembly determines which chamber are in fluid communication with the central valve. One illustrative GENEXPERT® cartridge is illustrated in FIG. 1A which show the cartridge, processing/reagent chambers, a reaction tube (e.g., heating and/or thermocycling tube), optional optical windows, and a valve that facilitates fluid transfer from chamber to chamber.

Figure 1B:
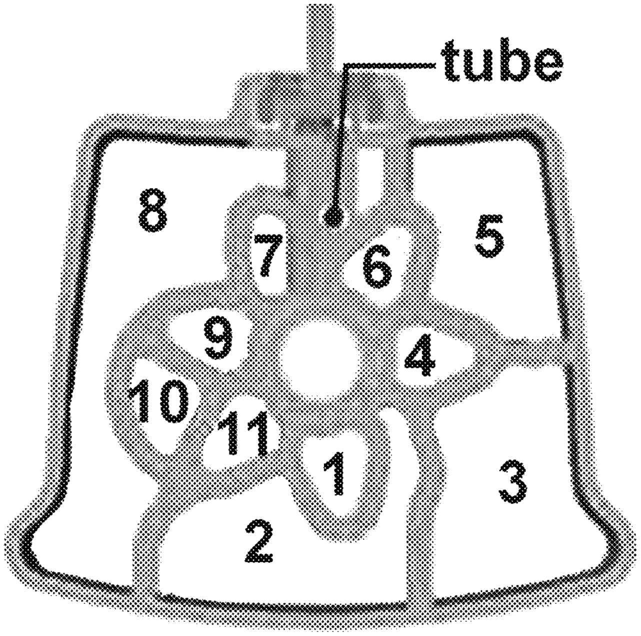
FIG. 1B shows a top view of the cartridge illustrating chambers disposed around a central valve.

An illustrative layout of the cartridge is shown in FIG. 1B which provides a top view of the cartridge identifying various chambers by number. In one illustrative, but non-limiting embodiment, the components of the chambers comprising the cartridge are as listed in Table 2. It will be recognized that this disposition of reagents and chamber is illustrative and non-limiting. Using the teachings provided herein other reagent dispositions and/or other chamber configurations will be available to one of skill in the art.

TABLE 2

One illustrative embodiment showing chamber contents for use of a GENEXPERT ® cartridge for measurement of DNA methylation.

| Chamber # | Chamber Contents | Initial Volume (μL) |
|---|---|---|
| 1 | | — |
| 2* | Sample chamber (sample mixed with e.g., GTC-EtOH-Tween precipitation reagent) | |
| 3** | GTC-EtOH | |
| 4*** | Bisulfite reagent (e.g., 8M ammonium bisulfite) | |
| 5 | Buffer e.g., 50 mM Tris pH 8.5 | |
| 6 | | — |
| 7 | | — |
| 8 | Rinse (e.g., PEG 200) | |
| 9 | Beads (e.g., polymerase, primer, probe) | |
| 10 | Elution/Desulphonation reagent (e.g., 15 mM KOH) | |
| 11 | Beads (e.g., polymerase, primer, probe) | |

*Sample is added to chamber 2 by user

**In certain embodiments, GTC-EtOH is added at time of use (e.g., when sample is added). In certain embodiments GTC-EtOH is provided as reagent already disposed in cartridge.

***In certain embodiments, bisulfite reagent is added at time of use (e.g., when sample is added). In certain embodiments bisulfite reagent is already disposed in cartridge.

Figure 1C:
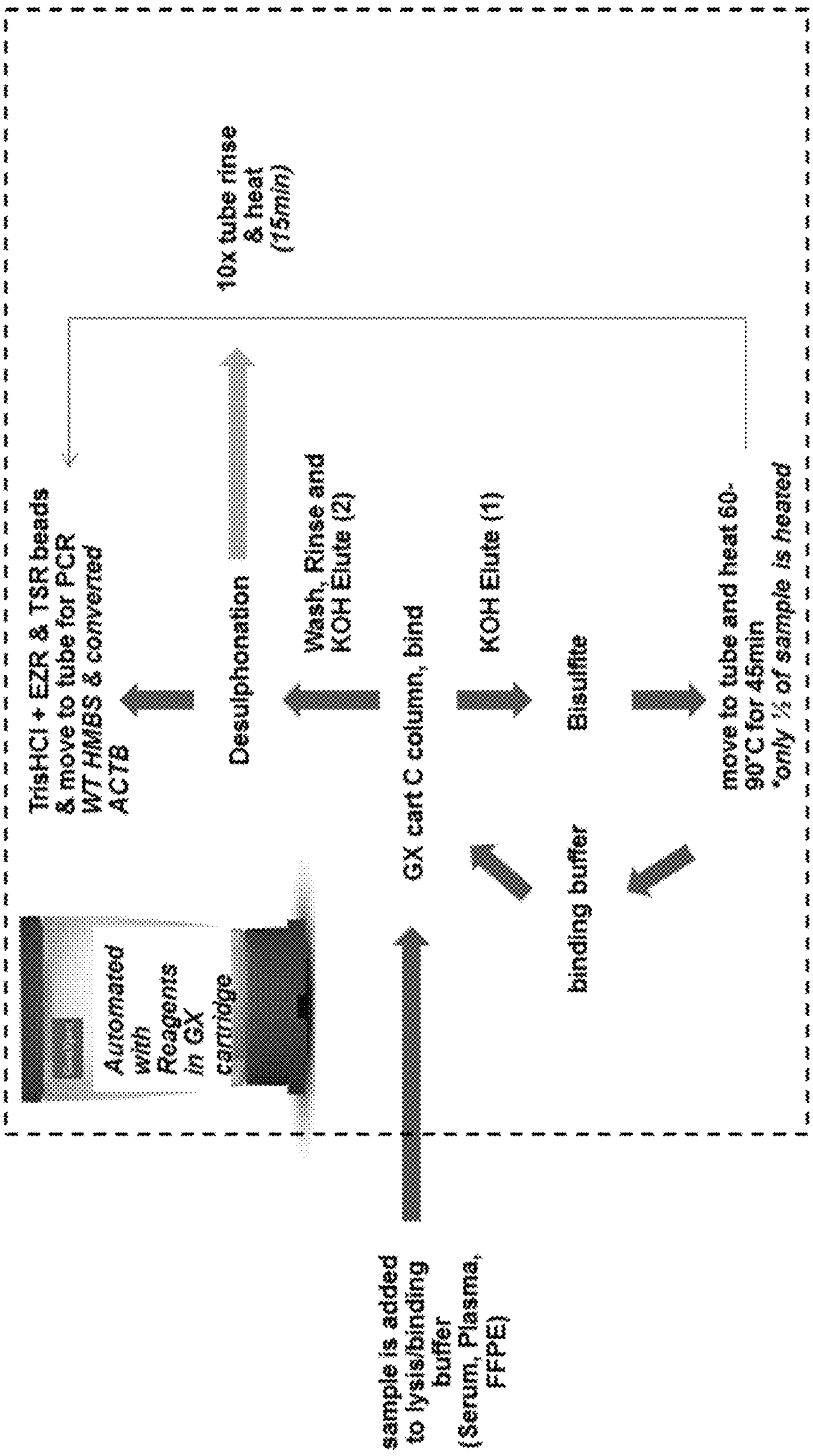
FIG. 1C shows an illustrative workflow for the determination of DNA methylation utilizing the reaction cartridge.

One embodiment of a step-by-step workflow for the determination of DNA methylation utilizing such a cartridge is shown in FIG. 1C. In this cartridge configuration, there are five chambers that, in use (e.g., when the cartridge is operating to determine DNA methylation), will hold reagents and buffers (e.g., chambers 3, 4, 5, 8, and 10), one chamber that will hold the sample added by the user (e.g., chamber 2), and one or two (or more) chambers holding analysis reagents (e.g., MSP reagents such as enzyme reaction, template specific reaction, and/or or 200 mM Tris pH 7.0, e.g., as beads) (e.g., chambers 9, and 11). In certain embodiments, the reagents (e.g., polymerase, reverse transcriptase, primer, probe) are provided in solution. In certain embodiments the reagents are provided as lyophilized powders. In certain embodiments the reagents are provided as lyophilized beads. The beads can further comprise agents to that improve reagent stability and/or activity (see, e.g., U.S. Patent Publication No: 2006/0068399 which is incorporated herein by reference for the beads, bead fabrication, and bead formulations described therein.

In certain embodiments the cartridge, as provided contains all of the reagents necessary to run the cartridge and only the sample (e.g., sample in buffer/lysis/precipitation solution) is added to the cartridge. In certain embodiments the cartridge is provided without the GTC-EtOH and/or the bisulfite reagents and one or both are added at the time of use. Thus, in certain embodiments, the GTC-EtOH reagent is added to the cartridge at the time of use, in certain embodiments the bisulfite reagent (in addition to the sample) is added to the chamber at the time of use, and in certain embodiments, both the GTC-EtOH and the bisulfite reagent (in addition to the sample) are added to the cartridge at the time of use. In certain embodiments these reagents are added directly to the desired chambers (see, e.g., Table 2). In certain embodiments ports are provided for loading the reagents and the ports are configured to deliver the reagent(s) to the desired chambers.

At the start of the assay, the cartridge dispenses the sample, e.g. from chamber 2 over a glass fiber column (e.g. the first column) in the cartridge. DNA is eluted off the column and simultaneously denatured by an alkali solution, e.g., a low concentration of potassium hydroxide from chamber 10 into a concentrated bisulfite reagent (e.g., concentrated ammonium bisulfite) in Chamber 4. In certain embodiments the DNA is eluted with an alkaline solution of KOH with a pH greater than about 10.5, or a pH greater than about pH 12. In certain embodiments the DNA is eluted with 10-15 mM KOH.

Figure 16:
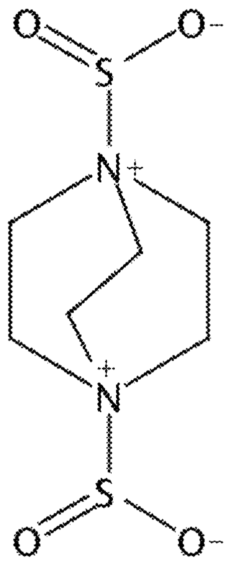
FIG. 16 illustrates the structure of DABSO (1,4-diazoniabicyclo[2.2.2]octane-1,4-disulfinate).

As indicated above, the DNA is eluted (optionally with a burst of sonication) into the bisulfite reagent. In various embodiments the conversion reagent (e.g., bisulfite reagent) is present at a concentration ranging from about 4 M to about 10 M, or from about 5 M to about 8 M, or from about 6 M or about 7 M. In certain embodiments the bisulfite solution comprises sodium metabisulfite, or potassium bisulfite, or ammonium bisulfite, or cesium bisulfite, or DABSO (1,4-diazoniabicyclo[2.2.2]octane-1,4-disulphinate, see, e.g., FIG. 16). In certain embodiments the conversion reagent (e.g., bisulfite reagent) contains radical scavengers, including, but not limited to one or more chemicals to prevent sulfite oxidation to sulfate (TROLOX and hydroquinone), and/or catalysts (polyamines).

The DNA-bisulfite (DNA/conversion reagent) mix is then introduced into a temperature controlled chamber or channel and incubated at a temperature ranging from about 40° C. to about 95° C. In certain embodiments the mix is incubated at a constant temperature, while in other embodiments, e.g., where the temperature controlled chamber or channel is a thermocycling chamber or channel (e.g., a smartcycler tube in the back of the cartridge), the mix is thermally cycled (e.g., between 60° C. and 95° C.). The mix is incubated until the DNA is converted (e.g., deaminated). In certain embodiments the incubation is for a period of time that ranges from about 5 minutes up to about 4 hours, or preferably from about 15 minutes up to about 45 minutes.

Following incubation the DNA/conversion reagent) (e.g., DNA-bisulfite) solution is mixed with fresh guanidinium thiocyanate-EtOH, e.g., from chamber 3 and dispensed over a matrix material. In certain embodiments the first column is reused, hence there is only one column and the second column and the first column are the same. In certain embodiments the second column is a separate column different than the first column.

The DNA bound to the second column matrix material is washed with fresh GTC-EtOH (e.g., from chamber 3) and rinsed (e.g., with a PEG 200 rinse, e.g., from chamber 8). The DNA is then desulphonated on the column, or is simultaneously eluted and desulphonated by contacting the deaminated nucleic acid with an alkaline solution (e.g., KOH from chamber 10 to produce a bisulfite converted nucleic acid. In certain embodiments the incubation is for a period of time ranging from about 1 minute to about 1 hour, or from about 5 minutes to about 30 minutes, or from about 10 minutes to about 20 minutes, or for about 15 minutes.

Where the initial incubation was in a thermocycling chamber that is to be further used, the thermocycling chamber or channel is washed with a buffer to remove residual bisulfite and neutralize pH. It was a surprising discovery that incubation with a conversion reagent (e.g., a bisulfite reagent), and/or desulphonation can be performed in a channel or chamber that is later used for PCR without bisulfite contamination substantially interfering with the later PCR reaction(s).

The eluted desulphonated bisulfite-converted DNA can be mixed with an appropriate buffer and analyzed for methylation. In certain embodiments the converted DNA is mixed with concentrated Tris, enzyme reaction, and template specific beads (e.g., beads comprising primers and/or probes for the PCR or nested PCR reaction(s)) in chambers 9 and 11, and the final mixture is aspirated into the thermocycling tube or chamber for the methylation specific quantitative PCR reaction.

Figure 14:
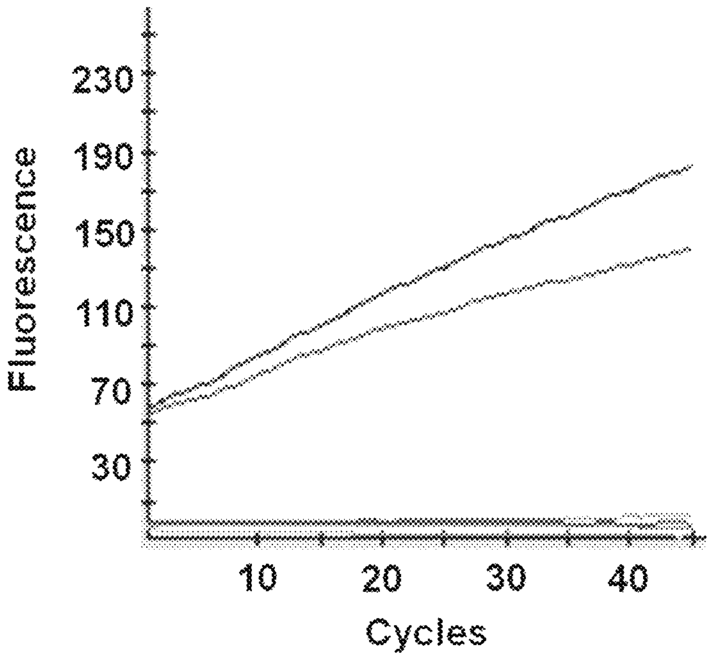
FIG. 14 illustrates a run in which some samples contain bisulfite contamination.

Bisulfite contamination during the qPCR step can be the primary failure mode of the methylation cartridge. Residual bisulfite can result from either direct contamination of the PCR reaction tube (e.g., during the bisulfite conversion step) or from indirect contamination (e.g. cross contamination during bisulfite fluidic movements between chambers). Residual bisulfite contamination, if present, can be measured by bisulfite-mediated probe cleavage during the qPCR step, which results in an increase in fluorescence during the earlier qPCR cycles (cycles 1-10) typically used for background subtraction. Accordingly, in certain embodiments, the cartridge comprises beads that provide one or more probes that are cleavable during PCR if bisulfite is present. Results of a run containing bisulfite contamination are shown in FIG. 14.

While the methods above (and in Example 4, see, e.g., FIG. 13A) are described with respect to specific chambers in the GENEXPERT® cartridge, it will be recognized that the particular reagent/chamber assignments can be varied depending on the particularities of the methylation analysis protocol applied.

Figure 13A:
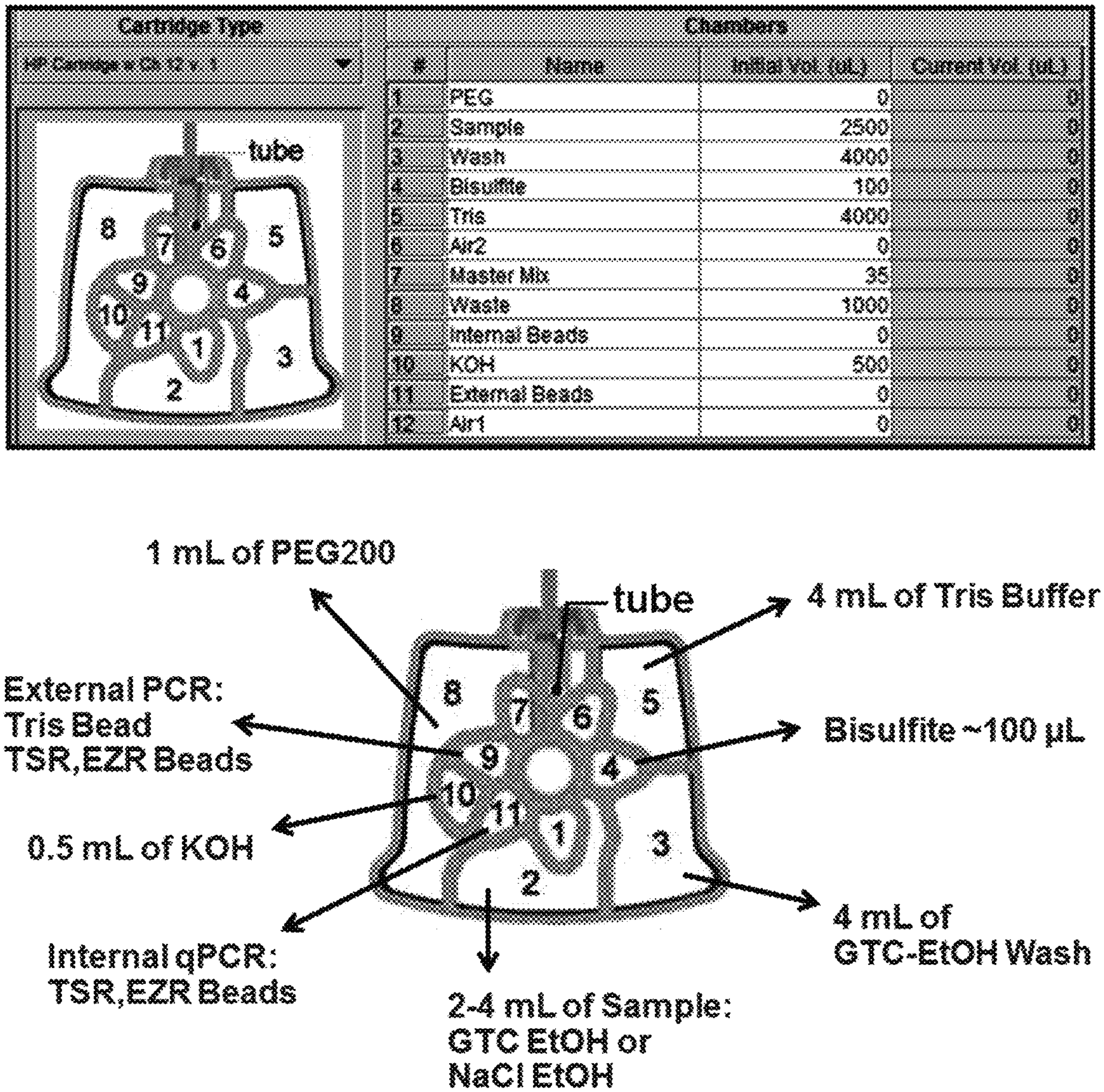
FIG. 13A illustrates a cartridge layout and FIG. 13B illustrates a flow chart of the protocol used in Example 4.
Figure 13B:
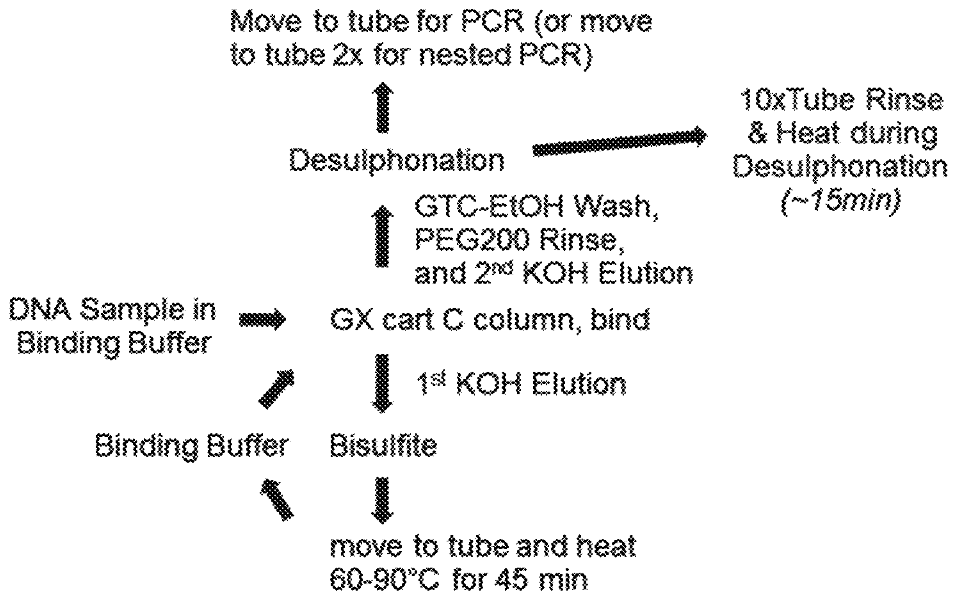

Thus, for example, operation of a methylation analysis cartridge (e.g., a GENEXPERT® cartridge can be generally described by a flow chart (see, e.g., FIGS. 1C and 13B). In the illustrative, but non-limiting embodiment shown in FIG. 13B, the DNA sample is provided in a binding buffer (e.g., a buffer comprising GTC-EtoH, in certain embodiments after the sample is processed with proteinase K and/or a lysis solution). In certain embodiments the sample is obtained from a sample preparation cartridge as described herein (see, e.g., FIG. 20).

The sample in binding buffer is introduced into a sample receiving chamber of the cartridge. In operation the cartridge is operated to deliver the sample solution to a matrix ("column") that binds the DNA. The bound DNA is then eluted from the column using an alkaline reagent (e.g., KOH solution) combined with a bisulfite reagent and moved to a heating tube (typically the PCR reaction tube) in the cartridge where the bisulfite reaction proceeds (e.g., at about 50° C. or about 60° C. to about 90° C. for about 45 minutes (or up to about 90 minutes), in this illustrative protocol). The reacted DNA is combined with a binding buffer (e.g., 2.25 M Guanidinium thiocyanate, 22.5 mM Tris pH 7.0, 0.5% Tween20, 50% Ethanol, and 0.005% SE-15 antifoam (a 10% emulsion of an active silicon antifoam and non-ionic emulsifiers)) and moved back to the same column, or to a different column, where it again binds to the column matrix. The reacted DNA is washed with GTC-EtOH, rinsed with PEG (e.g., PEG200) and eluted again from the column using an alkaline reagent (e.g., KOH) which also desulphonates the DNA. While the DNA is desulphonating the reaction tube (e.g., PCR reaction tube) can be heated and rinsed (e.g., 10× rinse) to remove any bisulfite reagent. The eluted DNA (or a portion thereof) can be moved to a reaction tube for PCR and/or nested PCR.

It will be appreciated that these operations can be performed on the entire sample or on a portion of the DNA sample. In the latter case a portion of the sample can be stored in one or more chambers and used as a control, or subjected to a different analysis/protocol.

Co-Purification and Detection of both RNA Expression and DNA Methylation.

In certain embodiments methods for co-purification and detection of both altered RNA expression of genes along with DNA methylation (MSP) in a cartridge-based assay (e.g., utilizing a GENEXPERT® cartridge) are provided. In certain embodiments these assays would identify altered expression of e.g. DNMT correlated with tumor-specific methylation from the same sample preparation. In certain embodiments these assays can be used to verify expression and methylation status.

We have shown that we can elute nucleic acids off the column using a Tris buffered elution that retains a portion of nucleic acids on the column. In one illustrative embodiment, an RNA fraction is eluted and retained, e.g., in a chamber in the cartridge using a Tris solution.

After saving the RNA fraction, NaOH or KOH elution which will strip the column and elute and denature the DNA which would go into bisulfite for conversion as described above. Then, ether using the RNA elution fraction to elute the bisulfite converted DNA from the column or using the KOH elution mix the two fractions (RNA and converted DNA products) are mixed for RNA plus bisulfite converted qRT-PCR. This involves incorporating a reverse transcriptase (RT) step for the RNA plus MSP (or other analytic method) in the same tube from the same sample. Alternative methods include, but are not limited to performing the RT step independently prior to mixing with DNA (combine cDNA and DNA) for qPCR, or PCR for DNA or RT RNA could be done independently/serially using one thermocycling tube/chamber or simultaneously using multiple thermocycling tubes/chambers in the cartridge.

Analysis of Converted DNA

Numerous analytic methods can be performed in the cartridge to evaluate DNA methylation. Alternatively, in certain embodiments, the cartridge can be coupled to another device and/or system for further analysis of the converted (e.g., bisulfite or DABSO converted) DNA. Illustrative methods include, but are not limited to methylation specific PCR (MSP), direct sequencing, high resolution melting analysis (HRM), pyrosequencing (sequencing by addition), base-specific cleavage analysis (e.g. base-specific MALDI-TOF), and the like.

Methylation-Specific PCR (MSP).

In various embodiments methylation-specific PCR can be used to evaluate methylation status of the target DNA. MSP utilized primer and/or probe sets designed to be "methylated-specific" by including sequences complementing only unconverted 5-methylcytosines, or, on the converse, "unmethylated-specific", complementing thymines converted from unmethylated cytosines. Methylation is then determined by the ability of the specific primer to achieve amplification. This method is particularly effective for interrogating CpG islands in regions of high methylation density, because increased numbers of unconverted methylcytosines within the target to be amplified increase the specificity of the PCR. In certain embodiments placing the CpG pair at the 3'-end of the primer also improves the specificity.

In certain embodiments methylation is evaluated using a MethyLight method. The MethyLight method is based on MSP, but provides a quantitative analysis using quantitative PCR (see, e.g., Eades et al. (2000) *Nucleic Acids Res.,* 28(8): E32. doi:10.1093/nar/28.8.e32). Methylated-specific primers are used, and a methylated-specific fluorescence reporter probe is also used that anneals to the amplified region. In alternative fashion, the primers or probe can be designed without methylation specificity if discrimination is needed between the CpG pairs within the involved sequences. Quantitation can be made in reference to a methylated reference DNA. One modification to this protocol to increase the specificity of the PCR for successfully bisulphite-converted DNA (ConLight-MSP) uses an additional probe to bisulphite-unconverted DNA to quantify this non-specific amplification (see, e.g., Rand et al. (2002) *Methods* 27(2): 114-120).

In various embodiments the MethyLight methods utilize TAQMAN® technology, which is based on the cleavage of a dual-labeled fluorogenic hybridization probe by the 5' nuclease activity of Taq-polymerase during PCR amplification (Eads et al. (1999) *Cancer Res.,* 59: 2302-2306; Livak et al. (1995) *PCR Meth. Appl.,* 4: 357-362; Lee et al. (1993) *Nucleic Acids Res.,* 21: 3761-3766; Fink et al. (1998) *Nat. Med.,* 4: 1329-1333). The use of three different oligonucleotides in the TAQMAN® technology (forward and reverse PCR primers and the fluorogenic hybridization probe) offers the opportunity for several sequence detection strategies.

Figure 4A:
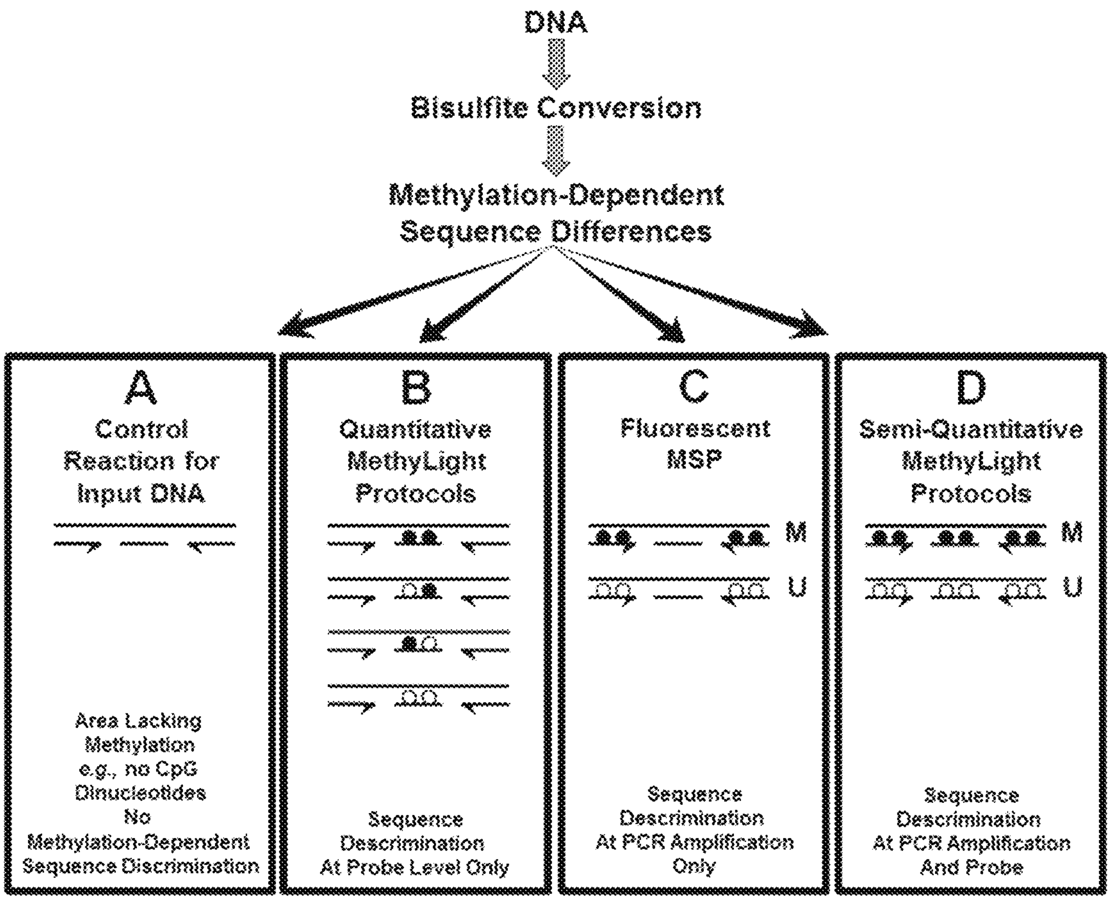
FIGS. 4A-4D illustrate various strategies for the use of MethyLight protocols to detect/quantify DNA phosphorylation.

For example, the sequence discrimination can occur at the level of the PCR amplification process (see, e.g., FIG. 4A, panel C) and/or at the level of the fluorogenic probe hybridization (see, e.g., FIG. 4A, panel B). In both steps, the discrimination is based on the differential annealing of the perfectly matched, versus mismatched oligonucleotides. In the MethyLight technology, sequence discrimination at the PCR amplification level occurs by designing the primers and probe, or just primers, or just probes, to overlap potential sites of DNA methylation (e.g., CpG dinucleotides). One approach is simply a fluorescence-based version of the MSP technique (Herman et al. (1996) *Proc. Natl. Acad. Sci. USA,* 93: 9821-9826). Each oligonucleotide (primers and probe) can cover anywhere from zero to multiple CpG dinucleotides. Each CpG dinucleotide can result in two different sequence variations following bisulfate conversion, depending on whether that particular site was methylated (mCpG) or unmethylated (UpG). For example, if an oligonucleotide overlaps two CpG dinucleotides, then the number of possible sequence variants in the genomic DNA within the region covered by that oligonucleotide is 2×2=4. If both of the primers and the probe each overlap two CpGs, then the total number of variants contained within the sequence covered by the oligonucleotides is 4×4×4=64. In theory, one could design separate PCR reactions to analyze the relative amounts of each of these potential 64 sequence variants. However, significant methylation information can be derived from the analysis of a much smaller number of variants by designing reactions for the fully methylated and fully unmethylated molecules, which represent the two most extreme sequence variants this hypothetical example. The ratio between these two reactions or the ratio between the methylated reaction and a control reaction provides a measure of the prevalence of methylated molecules at this locus.

The MethyLight technology can also be modified to avoid sequence discrimination at the PCR amplification level. If the neither the primers nor the probe overlie any CpG dinucleotides, then the reaction represents unbiased amplification and can serve as a control for the amount of input DNA. One illustrative useful control reaction is one in which the entire amplicon is devoid of any CpG dinucleotides in the unconverted genomic sequence. When just the probe is designed to cover CpG dinucleotides, then sequence discrimination occurs solely at the level of probe hybridization. In this version, all sequence variants resulting from the sodium bisulfate conversion step are amplified with equal efficiency, as long as there is no amplification bias (see, e.g., Wamecke et al. (1997) *Nucleic Acids Res.,* 25: 4422-1426). In this case, the design of separate probes for each of the different sequence variants associated with a particular methylation pattern (2×2=4 probes in the case of two CpGs) allows a quantitative determination of the relative prevalence of each sequence permutation in the mixed pool of PCR products.

In certain embodiments the analysis methods also provide PCR specific for unconverted DNA. This PCR may interrogate SNPs, mutations, and/or translocations, etc. In this regard, it is noted that the detection of mutations and methylation in a single cartridge is illustrated in Example 12 (see, e.g., FIGS. 27A and 27B). Detection of SNPs, mutations, translocations and the like can readily be accomplished by the inclusion of primers and probe sets specific for the detection of these targets.

Nested PCR and Multiplex PCR Assays.

In certain embodiments methylated DNA can be detected using an PCR methods well known to those of skill in the art. In certain embodiments a nested PCR reaction is used to detect methylation targets. In one illustrative, but non-limiting, embodiment (see, e.g., Example 4), a nested PCR protocol can be used where the first 15-20 cycle PCR reaction is not specific for methylation but only the converted DNA sequences (i.e., they do not cross CpGs or in instances when they do a R=purine or Y=pyrimidine is used to catch both methylated and unmethylated template sequences). The second qPCR reaction (e.g., a 45 cycle qPCR reaction) can contain both primers and probes that are specific for typically 2-3 methylated CpGs.

Figure 4B:
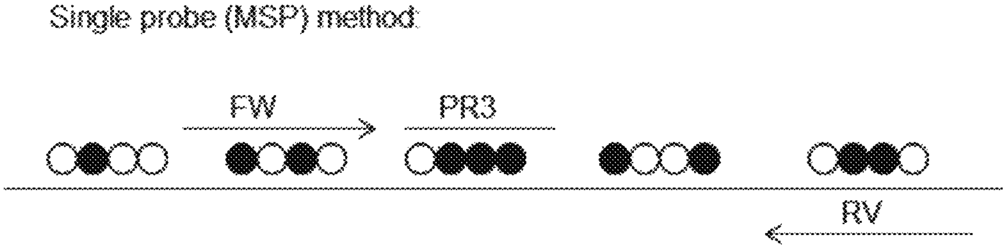

It will be noted that in certain embodiments, a MethyLight analysis is performed using a single probe (see, e.g., FIG. 4B). In this approach, using a single, e.g., methylation-specific, probe (PR3) along with methylation specific forward (FW) and reverse (RV) primers, methylation specific PCR for the probe (PR3) provides a signal that is dependent on methylation and bisulfite conversion for the FW, RV and PR3 sequences.

Figure 4C:
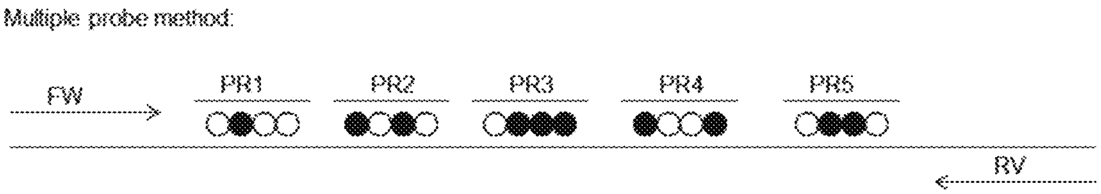
Figure 4D:
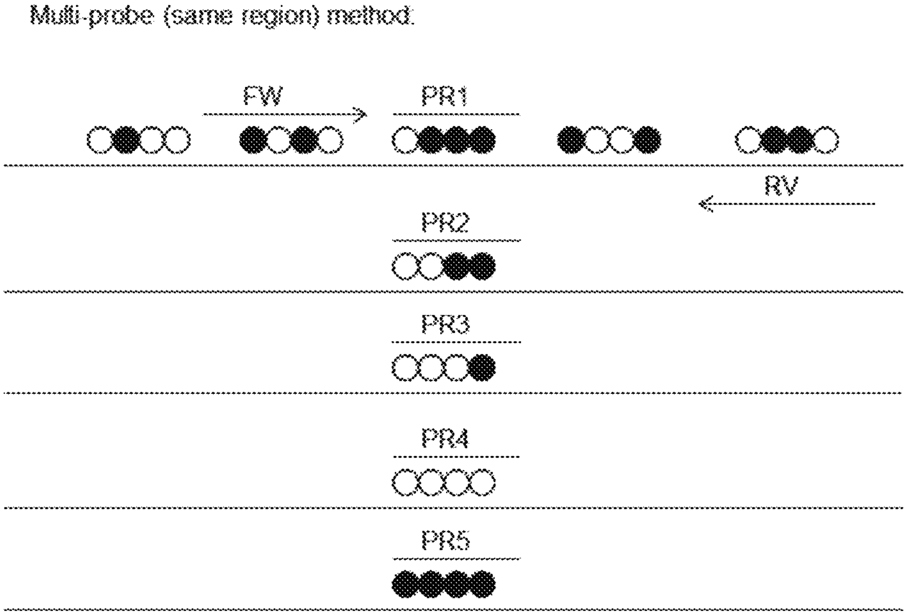

In various embodiments, multiplexed PCR assays are contemplated. By way of illustration, FIG. 4C illustrates a MethyLight approach using multiple probes (PR1, PR2, . . . PR5) that each target different regions. The combined signal from all the probes (PR1, PR2, PR3, PR4, and PR5) yields a measure of the amount/degree of methylation. In certain embodiments each probe has its own specific dye/fluor so that it is detectable independently of the other probes. Thus, even where one target is not methylated, a signal may still be detected, e.g., if PR3 is not methylated there will be no/less signal from the remaining probes. FIG. 4D illustrates a MethyLight approach using multiple probes (PR1 . . . PR5) that each target the same region, but provide signals for different methylation patterns. While the approach illustrated in FIG. 4C can provide detection from a larger region, this multi-probe approach on a single smaller region could be accomplished with sequence specific primers or probes interrogating the extent of methylation across a specific sequence after bisulfite conversion.

Figure 26:
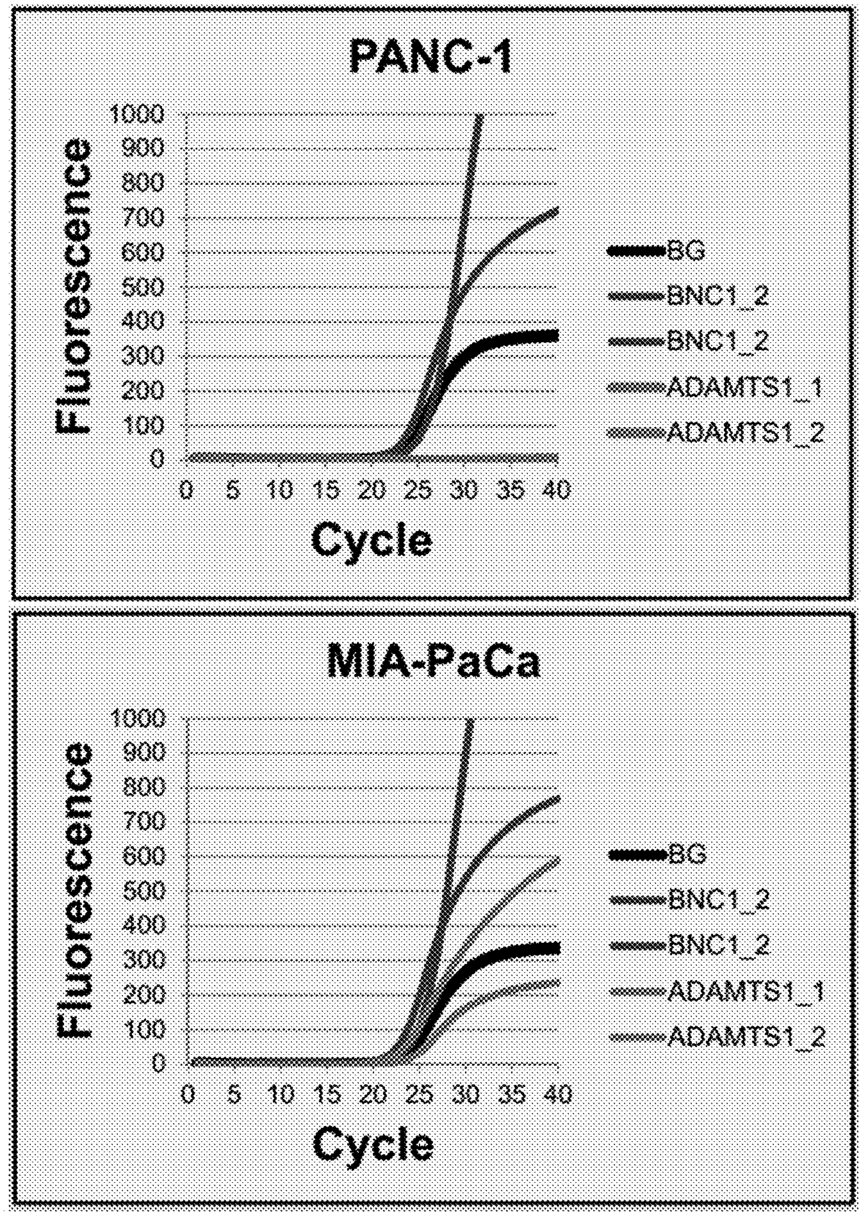
FIG. 26 illustrates the results for a reverse complement multiplex assay for both strands (curves from highest to lowest fluorescence: top panel—BNC1_2, BNC1_2, BG, ADAMTS1_1/ADAMTS1_2; bottom panel—BNC1_2, BNC1_2, ADAMTS1_1/ADAMTS1_2, BG, ADAMTS1_1/ADAMTS1_2).

In certain embodiments a reverse complement multiplex assay for both strands can be used (see, e.g., FIG. 26). Following bisulfite conversion, both strands lose their complementarity. Thus, primer and probe sets can be designed for one strand or the other, and result in unique amplicons. In addition to providing "more opportunities" for detection, this approach can potentially help with sensitivity (at LOD, if only one strand or the other ends up in the tube, this approach would ensure the signal gets picked up). This approach permits the multiplex assay to be expanded to detect different CpGs at the same promoter site. The reverse complement multiplex provides more opportunities to detect target methylation and to pick up heterogenous methylation.

The foregoing methods are illustrative and non-limiting. Using the teachings provided herein numerous variations of MSP and/or MethyLight analysis will be available to one of skill in the art and implementable on a reaction cartridge, e.g. as described herein.

Direct Sequencing

In certain embodiments methylation status of the DNA can be determined using direct sequencing methods. In certain embodiments, the method can utilize PCR and standard dideoxynucleotide DNA sequencing to directly determine the nucleotides resistant to bisulphite conversion (see, e.g., Frommer et al. (1992) *Proc. Natl. Acad. Sci. USA,* 89 (5): 1827-1831). In various embodiments primers are designed to be strand-specific as well as bisulphite-specific (e.g., primers containing non-CpG cytosines such that they are not complementary to non-bisulphite-treated DNA), flanking (but not involving) the methylation site of interest. Therefore, it will amplify both methylated and unmethylated sequences, in contrast to methylation-specific PCR. All sites of unmethylated cytosines are displayed as thymines in the resulting amplified sequence of the sense strand, and as adenines in the amplified antisense strand. In certain embodiments nested PCR methods can be used to enhance the product for sequencing.

In certain embodiments the sequencing can be performed in the cartridge. In other embodiments, the cartridge can be coupled (e.g., fluidic coupled) to a sequencing machine to provide the sequencing analysis. Alternatively, in certain embodiments, the amplified product can be manually transferred from the cartridge to the sequencing system.

High Resolution Melting Analysis (HRM)

In certain embodiments high-resolution melting analysis (HRM) can be used to differentiate converted from unconverted bisulphite-treated DNA. HRM is a quantitative PCR technique in which the PCR amplicons are analyzed directly by temperature ramping and resulting liberation of an intercalating fluorescent dye during melting (see, e.g., Wojdacz and Dobrovic (2007) *Nucleic Acids Res.* 35(6): e41). The degree of methylation, as represented by the C-to-T content in the amplicon, determines the rapidity of melting and consequent release of the dye. This method allows direct quantitation, but assesses methylation in the amplified region as a whole rather than at specific CpG sites.

Pyrosequencing

In certain embodiments pyrosequencing (sequencing by synthesis) can be used to analyze bisulphite-treated DNA without using methylation-specific PCR (see, e.g., Colella et al. (2003). *BioTechniques* 35(1): 146-150; Tost et al. (2003) *BioTechniques* 35(1): 152-156; and the like). Sequencing by synthesis differs from Sanger sequencing in that it utilizes the detection of phosphate release on nucleotide incorporation, rather than chain termination with dideoxynucleotides. The DNA sequence is able to be determined by light emitted upon incorporation of the next complementary nucleotide by the fact that typically only one out of four of the possible A/T/C/G nucleotides are added and available at a time so that only one letter can be incorporated on the single stranded template (which is the sequence to be determined).

Following PCR amplification of the region of interest, pyrosequencing can be used to determine the bisulphite-converted sequence of specific regions (e.g., CpG sites). In certain embodiments the ratio of C-to-T at individual sites can be determined quantitatively based on the amount of C and T incorporation during the sequence extension.

A modification of this technique can utilize allele-specific primers that incorporate single-nucleotide polymorphisms (SNPs) into the sequence of the sequencing primer(s), thus allowing for separate analysis of maternal and paternal alleles (see, e.g., Wong et al. (2006) *BioTechniques* 41(6): 734-739). This modification is particularly of use for genomic imprinting analysis.

Base-Specific Cleavage Analysis.

In certain embodiments, base-specific cleavage/MALDI-TOF takes advantage of bisulphite-conversions by adding a base-specific cleavage step to enhance the information gained from the nucleotide changes (Ehrich et al. (2005) *Proc. Natl. Acad. Sci. USA,* 102 (44): 15785-15790). By first using in vitro transcription of the region of interest into RNA (by adding an RNA polymerase promoter site to the PCR primer in the initial amplification), RNase A can be used to cleave the RNA transcript at base-specific sites. RNase A cleaves RNA specifically at cytosine and uracil ribonucleotides and base-specificity is achieved by adding incorporating cleavage-resistant dTTP when cytosine-specific (C-specific) cleavage is desired, and incorporating dCTP when uracil-specific (U-specific) cleavage is desired. The cleaved fragments can then be analyzed by MALDI-TOF or other methods. Bisulphite treatment results in either introduction/removal of cleavage sites by C-to-U conversions or shift in fragment mass by G-to-A conversions in the amplified reverse strand. C-specific cleavage will cut specifically at all methylated CpG sites. By analyzing the sizes of the resulting fragments (e.g., using MALDI-TOF, capillary electrophoresis, microchip electrophoresis, and the like), it is possible to determine the specific pattern of DNA methylation of CpG sites within the region, rather than determining the extent of methylation of the region as a whole.

Methylation-Sensitive Single-Strand Conformation Analysis (MS-SSCA).

Methylation-sensitive single strand conformation analysis (MS-SSCA) is based on the single-strand conformation polymorphism analysis (SSCA) method developed for single-nucleotide polymorphism (SNP) analysis (Bianco et al. (1999) *Hum. Mutat.* 14(4): 289-293). SSCA differentiates between single-stranded DNA fragments of identical size but distinct sequence based on differential migration in non-denaturating electrophoresis. In MS-SSCA, this is used to distinguish between bisulphite-treated, PCR-amplified regions containing the CpG sites of interest. Although SSCA lacks sensitivity when only a single nucleotide difference is present, bisulphite treatment frequently makes a number of C-to-T conversions in most regions of interest, and the resulting sensitivity can be high. In certain embodiments MS-SSCA can also provide semi-quantitative analysis of the degree of DNA methylation based on the ratio of band intensities. Typically, however, MS-SSCA assesses all CpG sites as a whole in the region of interest rather than individual methylation sites.

Methylation Targets.

As noted above, DNA methylation is of interest in a wide number of contexts. In certain embodiments, the amount of DNA methylation is of clinical interest particularly in oncology. Aberrant DNA methylation patterns (hypermethylation and hypomethylation compared to normal tissue) have been associated with a large number of human malignancies. Hypermethylation typically occurs at CpG islands in the promoter region and is associated with gene inactivation. A lower level of leukocyte DNA methylation is associated with many types of cancer (Zhang et al. (2011) Epigenetics, 6(3): 293-299). Global hypomethylation has also been implicated in the development and progression of cancer through different mechanisms. Typically, there is hypermethylation of tumor suppressor genes and hypomethylation of oncogenes (see, e.g., Lund et al. (2004) *J. Biol. Chem.* 279(28): 29147-29154).

In this regard, it is noted that DNA methylation provides a prognostic indicator for Stage I Non-Small-Cell Lung Cancer (NSCLC). In particular, it was discovered that hypermethylation of five genes was significantly associated with shorter relapse-free survival (RFS) in stage I NSCLC: HIST1H4F, PCDHGB6, NPBWR1, ALX1, and HOXA9. A signature based on the number of hypermethylated events distinguished patients with high- and low-risk stage I NSCLC (see, e.g., Sandoval et al. (2013) *J. Clin. Oncol.,* 4140-4147).

Similarly it has been observed that malignant gliomas may have the MGMT gene inactivated due to methylation of its promoter region. The prediction, born out by current research, is that by methylating the MGMT gene, a better response to chemotherapy can occur (as the tumor has no means to repair the DNA damage induced by the alkylating agent). In gliomas, MGMT promoter methylation is a favorable prognostic marker in the setting of either radiation or chemotherapy (see, e.g., //neurosurgery.ucsd.edu/brain-tumor-research-mgmt/).

By way of further illustration, Table 3 illustrates various genes that are hypermethylated in certain cancers.

TABLE 3 shows illustrative, but non-limiting examples of genes hypermethylated in sporadic cancers (see, e.g., Baylin (2005) *Nature Clinical Practice Oncology*, 2: S4-S11).

| Gene or gene product | Tumor type |
|---|---|
| Rb | Retinoblastoma |
| APC | Colorectal and other cancers |
| p14/ARF | Colorectal cancer |
| p15/CDKN2B | Leukemias |
| p16/CDKN2A | Various cancers |
| BRCA1 | Breast, ovarian cancer |
| VHL | Renal cell cancers |
| hMLH1 | Colorectal, gastric, endometrial cancers |
| ER-α | Breast, colorectal, other cancers |

In various illustrative, but non-limiting, embodiments measurement of methylation of any one of more of the promoters of the following genes is contemplated: APC, ARF, CDKN2B, CDKN2A, BRCA1, VLH, hMLH1, MGMT. RASSF1A, ADAMTS1, BNC1, HIST1H3C, HOXB4, RASGRF2, TM6SF1, AKR1B1, HIST1H4F, PCDHGB6, NPBWR1, ALX1, and HOXA9.

Pancreatic Cancer.

In certain embodiments methylation status is determined for one or more promoters where methylation status is a marker for the presence and/or prognosis of pancreatic cancer. It was determined that the frequency of methylation of one or more of ADAMTS1, or BNC1, can be used to detect and/or stage pancreatic cancer. Thus, illustrative, but non-limiting methylation markers for pancreatic cancer include, but are not limited to ADAMTS1 and/or BNC1. Illustrative primers and probes for the detection of methylation at the promoters of these genes are shown in Table 4, below (referencing Table 5 for particular sequences), and in Table 12 in Example 4). In certain embodiments primers and probes are provided for the detection of methylation in the forward strand of the converted DNA and/or for the detection of methylation in the reverse strand of the converted DNA.

Breast Cancer.

In certain embodiments methylation status is determined for one or more promoters where methylation status is a marker for the presence and/or prognosis of breast cancer. Illustrative methylation markers for breast cancer include, but are not limited to RASSF1A, and/or AKR1B1, and/or HOXB4, and/or HIST1H3C, and/or RASGRF2, and/or TM6SF1. Illustrative primers and probes for the detection of methylation at the promoters of these genes are shown in Table 4, below (referencing Table 5 for particular sequences), and in Table 11 in Example 4.

In certain embodiments methylation status is determined for one or more promoters where methylation status is a marker for the presence or likelihood of lung cancer. Illustrative methylation markers for lung cancer include, but are not limited to CDO1, SOX17, TAC1, and/or HOXA7.

The methods described herein are not limited to determining methylation of the promoters of these genes. Using the methods described herein methylation of essentially any target of interest is possible.

It will be noted, however that measurement of DNA methylation need not be limited to measurement of methylation at CPG islands in promoters. For example, it has been demonstrated that gene body methylation can also alter gene expression and can provide a therapeutic target in cancer (see, e.g., Yang et al. (2014) Cancer Cell, 26(4): 577-590).

Additionally, measurement of DNA methylation has prognostic/therapeutic applications for pathologies other than cancer. For example, aberrant methylation on regions on chromosomes 13, 18, 21, X, and Y can be used to diagnose Down syndrome (see, e.g., Patsalis et al. (2012) *Exp. Opin. Biol. Ther.* 12(Suppl. 1): S155-S161). Because fetal DNA and maternal DNA are differentially methylated, cell-free DNA in maternal plasma can provide a source of fetal DNA, which can be obtained non-invasively and utilized to assess the methylation state of the aforementioned chromosomes (or other chromosomes or genes).

As noted above, in certain embodiments, the cartridges and methods described herein are also used to determine mRNA levels, e.g., to determine expression of various methyltransferases. In certain embodiments, expression level of RNA is determined for a methyltransferase selected from the group consisting of DNMT1, DNMT2, DNMT3A, DNMT3B, and TNMT3L.

Primers/Probes and Multiplex Analysis

In various embodiments the methods described herein can involve nested PCR reactions and the cartridges described herein can contain reagents (e.g., primers and probes) for such nested PCR reactions. For example, in certain embodiments, methylation is detected for one, two, three, four, five, or six genes (gene promoters). Since bisulfite conversion of a DNA changes cytosine resides to uracil, but leave 5-methyl cytosine residues unaffected, the forward and reverse strands of converted (bisulfite-converted) DNA are no longer complementary. Accordingly, it is possible to interrogate the forward and revers strands independently (e.g., in a multiplex PCR reaction) to provide additional specificity and sensitivity to methylation detection. In such instances, assaying of a single target can involve a two-plex multiplex assay, while assaying of two, three, four, five, or six target genes can involve four-plex, six-plex, 8-plex, 10-plex, or 12-plex multiplex assays. In certain embodiments the assays can be divided into two multiplex reactions, e.g., to independently assay forward and reverse strands. However, it will be recognized that when split into multiple multiplex assays, the grouping of assays need not be by forward or reverse, but can simply include primer/probe sets that are most compatible for particular PCR reaction conditions.

As indicated above, numerous cancers can be identified, and/or staged and/or a prognosis therefor determined by the detection/characterization of the methylation state on the forward and/or reverse strand of gene promoters whose methylation (or lack thereof) is associated with a cancer. Illustrative gene (promoter) targets associated with various cancers are described above and shown below in Table 4. It will be recognized that methylation (forward strand and/or reverse strand) of one or more of the genes shown in Table 4 for each cancer can be determined to identify, and/or stage, and/or provide a prognosis for the indicated cancer. In certain embodiments methylation status of all of the genes shown for a particular cancer (forward and/or reverse strand) can be determined in a single multiplex PCR reaction.

TABLE 4

Illustrative primers and probes for the detection of methylation at the promoters of genes associated with various cancers using the devices and methods described herein. Primer and probe numbers refer to primer/probe numbers (primer/probe num) shown in Table 5, below.

| Indication/ Gene | External Primers | Internal Primers | Probe |
|---|---|---|---|
| Breast Cancer | | | |
| AKR1B1: | 58/183 | 19/20 | 193 |
| HIST1H3C: | 42/43, | 59/54 | 194 |
| HOXB4: | 186/187, | 25/26 | 76 |
| RASGRF2: | 188/199, | 192/14 | 67 |
| RASSF1A: | 189/1, | 1/2 | 63 |
| TM6SF1: | 202/51, | 31/57 | 77 |
| BG: | 175/158, | 176/156 | 164 |

TABLE 4-continued

Illustrative primers and probes for the detection of methylation at the promoters of genes associated with various cancers using the devices and methods described herein. Primer and probe numbers refer to primer/probe numbers (primer/probe num) shown in Table 5, below.

| Indication/ Gene | External Primers | Internal Primers | Probe |
|---|---|---|---|
| Pancreatic Cancer Set 1: | | | |
| BNC1 | 213/214, | 221/222 | 229 |
| ADAMTS1: | 219/220, | 227/228 | 265 |
| ACTB: | 102/103, | 320/321 | 150 |
| Pancreatic Cancer Set 2: | | | |
| BNC1: | 217/218, | 225/226 | 264 |
| ADAMTS1: | 215/216, | 223/224 | 230 |
| ACTB: | 102/103, | 320/321 | 150 |
| Lung CPHD Set 2: | | | |
| CDO1: | 283/284, | 287/288 | 291 |
| TAC1: | 293/294, | 386/388 | 301 |
| SOX17: | 303/304, | 382/385 | 312 |
| ACTB: | 102/103, | 320/321 | 150 |
| Prostate: | | | |
| GSTP1: | 233/234, | 239/240 | 245 |
| APC: | 235/236, | 241/242 | 246 |
| PTGS2: | 237/238, | 243/244 | 247 |
| ACTB: | 102/103, | 320/321 | 150 |
| BRCA1: | | | |
| BRCA1: | 328/329, | 330/331 | 327 |
| ACTB: | 102/103, | 320/321 | 150 |
| MGMT: | | | |
| MGMT: | 248b/249b, | 250/251 | 252 |
| ACTB: | 102/103, | 320/321 | 150 |

Illustrative primers and probes for the detection of methylation at the promoters of various genes are shown below in Table 5, below, and in Tables 11 and 12 in Example 4. In certain embodiments these primers and/or probes are particularly suitable for use in a multiplex amplification.

TABLE 5

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 1 | RASSF1A | I | GCGTTGAAGTCGGGGTTC | 2 |
| 2 | RASSF1A | I | CCCGTACTTCGCTAACTTTAAACG | 3 |
| 3 | RASSF1A | P | ACAAACGCGAACCGAACGAAACCA-quencher/blocker | 4 |
| 4 | RASSF1A STD | I | fluor-TTAGGGTAGATTGTGGATATTAG | 5 |
| 5 | RASSF1A STD | I | ATACTAACAACTATCCAATACAAC | 6 |
| 6 | RASSF1A STD | P | fluor-(C*)AGGTTGAAATTAG(T-quencher)ATGTGTTATTTTGGTATGG | 7 |
| 7 | HIST1H3C | I | AATAGTTCGTAAGTTTATCGGCG | 8 |
| 8 | HIST1H3C | I | CTTCACGCCACCGATAACCGA | 9 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 9 | HIST1H3C | P | fluor-TACTTACGCGAAACTTTACCGCCGA-quencher/blocker | 10 |
| 10 | HIST1H3C STD | I | GATTTAGAGTTGGATGTGTGGAT | 11 |
| 11 | HIST1H3C STD | I | ACCACCATACTAATAATCAAATCTA | 12 |
| 12 | HIST1H3C STD | P | fluor-AAATATCACTCATCACCAAATAAATCCAA-quencher/blocker | 13 |
| 13 | RASGRF2 | I | GTAAGAAGACGGTCGAGGCG | 14 |
| 14 | RASGRF2 | I | ACAACTCTACTCGCCCTCGAA | 15 |
| 15 | RASGRF2 | P | fluor-AACGAACCACTTCTCGTACCAACGA-quencher/blocker | 16 |
| 16 | RASGRF2 STD | I | TGTATGAGTTTGTGGTGAATAATG | 17 |
| 17 | RASGRF2 STD | I | AACTCACCATCAAACACTTTCCC | 18 |
| 18 | RASGRF2 STD | P | fluor-TACAAACCCAACATCCTCTATCTATTC-quencher/blocker | 19 |
| 19 | AKR1B1 | I | GCGCGTTAATCGTAGGCGTTT | 20 |
| 20 | AKR1B1 | I | CCCAATACGATACGACCTTAAC | 21 |
| 21 | AKR1B1 | P | fluor-CGTACCTTTAAATAACCCGTAAAATCGA-quencher/blocker | 22 |
| 22 | AKR1B1 STD | I | TTTGTTGATGTTTTGTGGAAGTAAG | 23 |
| 23 | AKR1B1 STD | I | ATTCATCAATACTTTCAAATAACACA | 24 |
| 24 | AKR1B1 STD | P | fluor-(C*)AAATACATTATCC(T-quencher)ACCACTAACAATACA | 25 |
| 25 | HOXB4 | I | CGGGATTTTGGGTTTTCGTCG | 26 |
| 26 | HOXB4 | I | CGACGAATAACGACGCAAAAAC | 27 |
| 27 | HOXB4 | P | fluor-AACCGAACGATAACGAAAACGACGAA-quencher/blocker | 28 |
| 28 | HOXB4 STD | I | GTTAGTTTTGTAGTGTATTGAGTAT | 29 |
| 29 | HOXB4 STD | I | CATCTTCCACAATAAACTTCCAATT | 30 |
| 30 | HOXB4 STD | P | fluor-TAACTCCACCTATTCTACCTACCATTT-quencher/blocker | 31 |
| 31 | TM6SF1 | I | CGTTTAGCGGGATGCGGTGA | 32 |
| 32 | TM6SF1 | I | ACACGAAAACCCCGATAACCG | 33 |
| 33 | TM6SF1 | P | fluor-AAACACTCATCGCAACCGCCGCG-quencher/blocker | 34 |
| 34 | TM6SF1 STD | I | TTAGATGTTGATTGGTTGTGTTTG | 35 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 35 | TM6SF1 STD | I | ATCATCATAAAACTCAACAATCAATT | 36 |
| 36 | TM6SF1 STD | P | fluor-CCAAACATCAAATCTTTAACTTTTACCA A-quencher/blocker | 37 |
| 37 | RASSF1A STD | P | fluor-AGGTTGAAATTAGTATG(T-quencher)GTTATTTTGGTATGG-quencher/blocker | 38 |
| 38 | RASSF1A STD | P | fluor-AGGTTGAAATTAGTATGTGT(T-quencher)ATTTTGGTATGG-quencher/blocker | 39 |
| 39 | RASSF1A STD | P | fluor-AGGTTGAAATTAGTATGTGTTA(T-quencher)TTTGGTATGG-quencher/blocker | 40 |
| 40 | RASSF1A | E | GTTTTATAGTTTTTGTATTTAGG | 41 |
| 41 | RASSF1A | E | AACTCAATAAACTCAAACTCCC | 42 |
| 42 | HIST1H3C | E | GTGTGTGTTTTTATTGTAAATGG | 43 |
| 43 | HIST1H3C | E | ATAAAATTTCTTCACRCCACC | 44 |
| 44 | RASGRF2 | E | GAGGGAGTTAGTTGGGTTAT | 45 |
| 45 | RASGRF2 | E | CCTCCAAAAAATACATACCC | 46 |
| 46 | AKR1B1 | E | GTGTAATTAATTAGAAGGTTTTTT | 47 |
| 47 | AKR1B1 | E | AACACCTACCTTCCAAATAC | 48 |
| 48 | HOXB4 | E | TTAGAGGYGAGAGAGTAGTT | 49 |
| 49 | HOXB4 | E | AAACTACTACTAACCRCCTC | 50 |
| 50 | TM6SF1 | E | AGGAGATATYGTTGAGGGGA | 51 |
| 51 | TM6SF1 | E | TCACTCATACTAAACCRCCAA | 52 |
| 52 | RASSF1A STD | I | TTAGGGTAGATTGTGGATATTAGATAGG | 53 |
| 53 | RASSF1A STD | I | TAATACTAACAACTATCCAATACAACAC | 54 |
| 54 | HIST1H3C | I | CCGATAACCGAAACGCTCTTAC | 55 |
| 55 | AKR1B1 | I | GCGTTAATCGTAGGCGTTT | 56 |
| 56 | TM6SF1 | I | GTTTAGCGGGATGCGGTG | 57 |
| 57 | TM6SF1 | I | ACACGAAAACCCCGATAAC | 58 |
| 58 | AKR1B1 | E | GYGTAATTAAT(T*)AGAAGGTTTTTT | 59 |
| 59 | HIST1H3C | I | TCGTACGAAGTAAATAGTTCGTAAG | 60 |
| 60 | HIST1H3C | E | GGATTTTTGAAATATTATAGGATTAATT AG | 61 |
| 61 | RASSF1A | E | GTTTTATAGTT(T*)TTGTATTTAGG | 62 |
| 62 | RASSF1A | P | fluor-ACAAACGCGA(N*)ACCGAA(C**)GAAAC CA-quencher/blocker | 63 |
| 63 | RASSF1A | P | fluor-(C*)TGGTTTCGT(T-quencher)CGGT(T*)CGCG-quencher/blocker | 64 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 64 | RASSF1A STD | P | fluor-(C*)AGGTTGAAATTAGTA(T-quencher)GTGTTAT(T*)TTGG(T*)ATGG-quencher/blocker | 65 |
| 65 | HIST1H3C | P | fluor-CAAACTACTTACGCGAAACTT(T*)ACCGCC-quencher/blocker | 66 |
| 66 | HIST1H3C STD | P | fluor-AAATATCACTCA(T*)CACCAAA(N*)TAAA(T*)CCAA-quencher/blocker | 67 |
| 67 | RASGRF2 | P | fluor-AAACGAACCACTTCTCG(T*)ACCAACGAC-quencher/blocker | 68 |
| 68 | RASGRF2 STD | P | fluor-CAAACCCAACATCCTC(T*)ATC(T*)ATTC-quencher/blocker | 69 |
| 69 | AKR1B1 | P | fluor-A(C*)GCGTACCTTT(N*)AAA(T*)AACCCG(T*)AAAATCG-quencher/blocker | 70 |
| 70 | AKR1B1 | P | fluor-A(C*)GCGTACCTT(T-quencher)AAA(T*)AACCCG(T*)AAAATCG-quencher/blocker | 71 |
| 71 | AKR1B1 STD | P | fluor-(C*)AAATACATTATCC(T-quencher)ACCAC(T*)AACAA(T*)ACA-quencher/blocker | 72 |
| 72 | HOXB4 | P | fluor-AACCGAACGATAACGAAAA(C**)GACGA-quencher/blocker | 73 |
| 73 | HOXB4 STD | P | fluor-TAACTCCACCTATTC(T*)ACCT(N*)ACCA(T*)TT-quencher/blocker | 74 |
| 74 | TM6SF1 STD | P | fluor-CAAACATCAAATCT(T*)TAAC(T*)TT(T*)AC-quencher/blocker | 75 |
| 75 | AKR1B1 | P | fluor-(C*)A(C*)GCGTACCT(T-quencher)TAAA(T*)AACCCG(T*)AAAATCG-quencher/blocker | 76 |
| 76 | HOXB4 | P | fluor-AACCGAACGA(T*)AACGAAA(N*)ACGACGAA-quencher/blocker | 77 |
| 77 | TM6SF1 | P | fluor-AAACACTCATCGCAACCGCCGCG-quencher/blocker | 78 |
| 78 | ACTB | P | fluor-TAACCACCACCCAACACA(C**)AATAAC-quencher/blocker | 79 |
| 79 | ALU Long Set 1 | P | fluor-CCCAACTACT(T*)AAAAAAC(T*)AAAAC-quencher/blocker | 80 |
| 80 | ALU Short Set 1 | P | fluor-CACCTAAAA(T*)CAAAAATT(T*)AAAACC-quencher/blocker | 81 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 81 | ALU Long Set 2 | P | fluor-CAAATAATTCTCC(T*)ACCTCAACC(T*)C-quencher/blocker | 82 |
| 82 | ALU Short Set 2 | P | fluor-CTTAACTCAC(T*)ACAACCTC(T*)ACC-quencher/blocker | 83 |
| 83 | INSL6 | P | fluor-CAAACCGAACGACGCGCACAAACAC-quencher/blocker | 84 |
| 84 | ACTB | E | GTATATAGGTTGGGGAAGTTTG | 85 |
| 85 | ACTB | E | AACTATACTCAACCAATAAAACC | 86 |
| 86 | ALU Long Set 1 | E | TGTTATTTAGGTTGGAGTGTAG | 87 |
| 87 | ALU Long Set 1 | E | TAATAACTCATACCTATAATCCC | 88 |
| 88 | ALU Long Set 1 | I | GGTTGGAGTGTAGTGGTATAATTTTAG | 89 |
| 89 | ALU Long Set 1 | I | TAATAACTCATACCTATAATCCCAACAC | 90 |
| 90 | ALU Short Set 1 | E | GTAGAGATAGGGTTTTATTATGTTG | 91 |
| 91 | ALU Short Set 1 | I | GGTTTTATTATGTTGGTTAGGTTGG | 92 |
| 92 | ALU Long Set 2 | E | GTATTTTGGGAGGTTAAGGTAG | 93 |
| 93 | ALU Long Set 2 | E | ATCTTACTCTTATTACCCAAAC | 94 |
| 94 | ALU Long Set 2 | I | GGTTAAGGTAGGTAGATTATTTGAGG | 95 |
| 95 | ALU Long Set 2 | I | ATCTTACTCTTATTACCCAAACTAAAATA C | 96 |
| 96 | ALU Short Set 2 | E | GTTATTTAGGAGGTTGAGGTAG | 97 |
| 97 | ALU Short Set 2 | E | GAGGTAGGAGAATTATTTGAATTTAGG | 98 |
| 98 | INSL6 | E | ATTTGAGATTTTTGAGTTGG | 99 |
| 99 | INSL6 | E | AACCCTACTCCCTATCTACG | 100 |
| 100 | INSL6 | I | GCGCGCGTTTTTTTTTGAAG | 101 |
| 101 | INSL6 | I | GGCGTAGATAGGGAGTAGGGTT | 102 |
| 102 | ACTB | I | GTGATGGAGGAGGTTTAGTAAGTT | 103 |
| 103 | ACTB | I | CCAATAAAACCTACTCCTCCCTTAA | 104 |
| 104 | RASSF1A STD | P | fluor-(C*)(C*)ATACCAAAA(T-quencher)AACACA(T*)CTAAT(T*)TCAACC T-quencher/blocker | 105 |
| 105 | AKR1B1 STD | P | fluor-(C*)AAATACAT(T*)ATCC(T-quencher)ACCAC(T*)AACAA(T*)ACA-quencher/blocker | 106 |
| 106 | AKR1B1 | P | fluor-(C*)ACGCGTACCTT(T-quencher)AAA(T*)AACCCG(T*)AAAATCG-quencher/blocker | 107 |
| 107 | AKR1B1 | P | fluor-(C*)ACGCGTACCTT(T*)AAA(T-quencher)AACCCG(T*)AAAATCG-quencher/blocker | 108 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 108 | RASSF1A UM | P | fluor-CTAACAAACA(C-quencher)AAA(C**)CAAA(C**)AAAACCA-quencher/blocker | 109 |
| 109 | RASSF1A UM | P | fluor-CTAACAAACA(C**)AAA(C-quencher)CAAA(C**)AAAACCA-quencher/blocker | 110 |
| 110 | HIST1H3C UM | P | fluor-AACTACTTACA(C**)AAAACTT(N*)TAC(C**)ACCAA-quencher/blocker | 111 |
| 111 | HIST1H3C UM | P | fluor-AACTACTTA(C**)ACAAAA(C**)TTTACCAC-quencher/blocker | 112 |
| 112 | RASGRF2 UM | P | fluor-AAACAAACCAC(T*)TCTCA(T*)ACCAACAAC-quencher/blocker | 113 |
| 113 | AKR1B1 UM | P | fluor-(C*)ACATACCTTTAAA(T-quencher)AACCCA(T*)AAAA(T*)CAAC-quencher/blocker | 114 |
| 114 | AKR1B1 UM | P | fluor-(C*)ACATACCTT(T-quencher)AAA(T*)AACCCA(T*)AAAATCAAC-quencher/blocker | 115 |
| 115 | HOXB4 UM | P | fluor-CAACAAAAACCCAAAA(T*)CCCAAC(N*)AAACCACA-quencher/blocker | 116 |
| 116 | HOXB4 UM | P | fluor-CAAAATCCCAA(C**)AAACCA(C**)ATAACA-quencher/blocker | 117 |
| 117 | TM6SF1 UM | P | fluor-AAACACTCATCACAACCA(C**)CACACC-quencher/blocker | 118 |
| 118 | AKR1B1 UM | I | TGGTGTGTTAATTGTAGGTGTTTT | 119 |
| 119 | AKR1B1 UM | I | CCCAATACAATACAACCTTAACC | 120 |
| 120 | HOXB4 UM | I | GTGGTGTGTATTGTGTAGTGTTA | 121 |
| 121 | HOXB4 UM | I | CAAACCAAACAATAACAAAAACAAC | 122 |
| 122 | TM6SF1 UM | I | TGTTTAGTGGGATGTGGTGAAG | 123 |
| 123 | TM6SF1 UM | I | ACACAAAAACCCCAATAACCACA | 124 |
| 124 | RASSF1A UM | I | GTTTAAAGTTAGTGAAGTATGGGTTT | 125 |
| 125 | HIST1H3C UM | I | TGTATGAAGTAAATAGTTTGTAAGTTTATTGG | 126 |
| 126 | AKR1B1 STD | I | TTTGTTGATGTTTTGTGGAAG(T*)AAG | 127 |
| 127 | AKR1B1 STD | I | ATTCATCAATACTTTCAAA(T*)AACACA | 128 |
| 128 | RASGRF2 | P | fluor-AAACGAACCACTTCTCG(T*)ACCAACGAC-quencher/blocker | 129 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 129 | RASGRF2 STD | P | fluor-CAAACCCAACATCCTC(T*)ATC(T*)ATTC-quencher/blocker | 130 |
| 130 | TM6SF1 | P | fluor-AAACACTCATCGCAACCGCCGCG-quencher/blocker | 131 |
| 131 | TM6SF1 STD | P | fluor-CCAAACATCAAATCT(T*)TAACTT(T*)TA CCAA-quencher/blocker | 132 |
| 132 | TM6SF1 | P | fluor-AAACACTCATCGCAACCGCCGCG-quencher/blocker | 133 |
| 133 | RASSF1A UM | I | GGTGTTGAAGTTGGGGTTTG | 134 |
| 134 | RASSF1A UM | I | CCCATACTTCACTAACTTTAAAC | 135 |
| 135 | HIST1H3C UM | I | GTAAATAGTTTGTAAGTTTATTGGTG | 136 |
| 136 | HIST1H3C UM | I | TTTCTTCACACCACCAATAACCAA | 137 |
| 137 | RASGRF2 UM | I | GAGTAAGAAGATGGTTGAGGTG | 138 |
| 138 | RASGRF2 UM | I | CAACAACTCTACTCACCCTCAA | 139 |
| 139 | | P | fluor-TCCCAACTACT(T*)AAAAAAC(T*)AAAAC-quencher/blocker | 140 |
| 140 | ALU Long Set 1 | P | fluor-TCCCAACTACT(T*)AAAAAAC(T*)AAAAC-quencher/blocker | 141 |
| 141 | ALU Long Set 1 | P | fluor-TCCCAACTACT(T*)AAAAAAC(T*)AAAAC-quencher/blocker | 142 |
| 142 | ALU Long Set 1 | P | fluor-TCCCAACTACT(T*)AAAAAAC(T*)AAAAC-quencher/blocker | 143 |
| 143 | ALU Long Set 1 | P | fluor-TCCCAACTACT(T*)AAAAAAC(T*)AAAAC-quencher/blocker | 144 |
| 144 | HMBS | I | GGATAAGATTTTTGATATTGTATTTTTTA AGG | 145 |
| 145 | HMBS | I | CATATTCAAACTCCTTAATAAACAAACT TTTCTC | 146 |
| 146 | HMBS | P | fluor-CCGAACAAAAAAAA(C-quencher)CTAAA(T*)AAATCCC(T*)TC-quencher/blocker | 147 |
| 147 | ACTB | P | fluor-CCACCACCCAACACACAA(T*)AACAAAC AC-quencher/blocker | 148 |
| 148 | ACTB | I | GGTTTAGTAAGTTTTTTGGATTGTG | 149 |
| 149 | ACTB | | CCTTAAAAATTACAAAAACCACAAC | 150 |
| 150 | ACTB | P | fluor-CCACCACCCAACA(C-quencher)ACAA(T*)AACAAACAC-quencher/blocker | 151 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 151 | ACTB | P | fluor- CCACCACCCAAC(N*)ACA(C**)AATAA(C**) AAACAC-quencher/blocker | 152 |
| 152 | ACTB | P | fluor- CCACCACCCAACACA(N*)CAA(T*)AACA AACAC-quencher/blocker | 153 |
| 153 | BG | I | TTCAGTGCCGGTTGGTAATGTAA- quencher/blocker | 154 |
| 154 | BG | I | CAACAACTTTAATACCTGTTTCAAGGA | 155 |
| 155 | BG conv | I | GGTATTTTTGTATTTGTTGGTGTTG | 156 |
| 156 | BG conv | I | CATACATACACCAAACAATTCATTC | 157 |
| 157 | BG conv | E | GTATGGTGGTATTTTTGTATTTGTTG | 158 |
| 158 | BG conv | E | CACACATACATACACCAAACAATTC | 159 |
| 159 | BG | P | fluor- AAGATCCGATTCACAGA(N*)CAAGCTCC GTCA-quencher/blocker | 160 |
| 160 | BG | I | fluor- AAGATCCGATTCACAGA(N*)CAAGCTCC GTCA-quencher/blocker | 161 |
| 161 | BG conv | P | fluor-(C*)AAAATCATTT(C- quencher)CTT(C**)ACAAATA(C**)ACTC- quencher/blocker | 162 |
| 162 | BG conv | P | fluor-CCAAATACCA(T- quencher)AACCA(T*)TTTATTAA(T*)AACA C-quencher/blocker | 163 |
| 163 | BG conv | P | fluor- AAAATCATTTCCTT(C**)ACA(N*)AATA(C**) ACTC-quencher/blocker | 164 |
| 164 | BG conv | P | fluor- CCAAATACCA(T*)AACCAT(N*)TTTATTA A(T*)AACAC-quencher/blocker | 165 |
| 165 | short HMBS | I | CCCTAGTATGCTAGGTCTCTTGCTGGGA | 166 |
| 166 | short HMBS | I | CAGCCTCTCTGAGGGTTTAAGCCCA | 167 |
| 167 | short HMBS | P | fluor- TCAGCC(T*)ATC(T*)GACACCCCGGG- quencher/blocker | 168 |
| 168 | short β-Globin | I | GACTCCTGAGGAGAAGTCTGCCGTTA | 169 |
| 169 | short β-Globin | I | CCTTGATACCAACCTGCCCAGGG | 170 |
| 170 | short β-Globin | P | fluor- AGGTGAACG(T*)GGATGAAGT(T*)GGTG GTG-quencher/blocker | 171 |
| 171 | short BG | I | CAACATCGCGCAAGAGCACGG | 172 |
| 172 | short BG | I | CGTTTCCTTCACGAGTACGCTCTCCGA | 173 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 173 | short BG | P | fluor-ACCGGCGAA(T*)ACAGAGA(T*)ACCG-quencher/blocker | 174 |
| 174 | ACTB | P | fluor-CC(A*)CC(A*)CCCAAC(N*)ACA(C**)AAT AA(C**)AAACAC-quencher/blocker | 175 |
| 175 | BG conv | I | GTTGGTGTTGGAGAGTGTATTTG | 176 |
| 176 | BG conv | I | GGAGAGTGTATTTGTGAAGGAAATG | 177 |
| 177 | BG conv | I | GGAAATGATTTTTTTATGAGATGAGTG | 178 |
| 178 | ACTB | P | fluor-CCACCACCCAACACA(N*)CAA(T*)AACA AACAC-quencher/blocker | 179 |
| 179 | ACTB | P | fluor-CCACCACCCAACACA(N*)CAA(T*)AACA AACAC-quencher/blocker | 180 |
| 180 | ACTB | P | fluor-CCACCACCCAACACACAA(T*)AACAAAC AC-quencher/blocker | 181 |
| 181 | ACTB | I | GATGGAGGAGGTTTAGTAAGTTTTT | 182 |
| 182 | ACTB | I | AATAAAACCTACTCCTCCCTTAAAAA | 183 |
| 183a | AKR1B1 | E | CTTACCATAACTACTAC(dK)CTCC | 184 |
| 183b | AKR1B1 | E | CTTACCATAACTACTACRCTCC | 185 |
| 184 | HIST1H3C | E | GTGTGTGTTTTTATTGTAAATGGT | 186 |
| 185a | HIST1H3C | E | AAC(dK)ATAAC(dK)ATAAAATTTCTTCAC | 187 |
| 185b | HIST1H3C | E | AACRATAACRATAAAATTTCTTCAC | 188 |
| 186a | HOXB4 | E | GTTTGT(dP)GGGATTTTGGGT | 189 |
| 186b | HOXB4 | E | GTTTGTYGGGATTTTGGGT | 190 |
| 187a | HOXB4 | E | CC(dK)AACTCC(dK)AAAAAAAAACC | 191 |
| 187b | HOXB4 | E | CCRAACTCCRAAAAAAAAACC | 192 |
| 188a | RASGRF2 | E | GGTATTAAG(dP)G(dP)GGTTTTTTG | 193 |
| 188b | RASGRF2 | E | GGTATTAAGYGYGGTTTTTTG | 194 |
| 189a | RASSF1A | E | GT(dP)GTTTAGTTTGGATTTTGG | 195 |
| 189b | RASSF1A | E | GTYGTTTAGTTTGGATTTTGG | 196 |
| 190 | TM6SF1 | E | TTTCGAAGGGTAAGCGTTAAG | 197 |
| 191a | TM6SF1 | E | AACATAAATAACC(dK)AAA(T*)AACC | 198 |
| 191b | TM6SF1 | E | AACATAAATAACCRAAA(T*)AACC | 199 |
| 192 | RASGRF2 | I | CGGTTTTTTGAGTAAGAAGACGGTC | 200 |
| 193a | AKR1B1 | P | fluor-TACCTTTAAA(T-quencher)AACCC(dK)(T*)AAAA(T*)CGACA A-quencher/blocker | 201 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 193b | AKR1B1 | P | fluor-TACCTTTAAA(T-quencher)AACCCR(T*)AAAA(T*)CGACAA-quencher/blocker | 202 |
| 194a | HIST1H3C | P | fluor-ATAACAAACTACT(T*)AC(dK)CGAAAC(T*)TTAC-quencher/blocker | 203 |
| 194b | HIST1H3C | P | fluor-ATAACAAACTACT(T*)ACRCGAAAC(T*)T TAC-quencher/blocker | 204 |
| 195a | HOXB4 | P | fluor-AACAAACC(dK)AA(C**)GA(T*)AAC(N*)A AAAC-quencher/blocker | 205 |
| 195b | HOXB4 | P | fluor-AACAAACCRAA(C**)GA(T*)AAC(N*)AAA AC-quencher/blocker | 206 |
| 196 | RASGRF2 | P | fluor-CACATTCTAA(T*)AAAAAAC(N*)AACCA C(T*)TC-quencher/blocker | 207 |
| 197a | RASSF1A | P | fluor-AACC(dK)AA(C**)GAAA(C-quencher)CA(C**)AAAAC-quencher/blocker | 208 |
| 197b | RASSF1A | P | fluor-AACCRAA(C**)GAAA(C-quencher)CA(C**)AAAAC-quencher/blocker | 209 |
| 198 | TM6SF1 | P | fluor-CAAAAACAC(T*)CATC(N*)CAACCGCC-quencher/blocker | 210 |
| 199 | RASGRF2 | E | ACAACCCTCCAAAAAATACATA | 211 |
| 200 | BG conv | P | fluor-CCAAATACCATAACCA(T*)TTTATTAA(T*)AACAC-quencher/blocker | 212 |
| 201 | BG conv | P | fluor-CCAAATACCATAACCA(T*)TTTATTAA(T*)AACAC-quencher/blocker | 213 |
| 202a | TM6SF1 | E | TTT(dP)GAAGGGTAAG(dP)GTTAAG | 214 |
| 202b | TM6SF1 | E | TTTYGAAGGGTAAGYGTTAAG | 215 |
| 203a | TM6SF1 | E | CAACAC(dK)AAAACCCC(dK)ATA | 216 |
| 203b | TM6SF1 | E | CAACACRAAAACCCCRATA | 217 |
| 204 | KRAS Multi | E | CCTGCTGAAAATGACTGAATATAACCGC TAAGAACCTCTCGGTCAGCTGAT | 218 |
| 205 | KRAS Multi | E | CCTGCTGAAAATGACTGAATATAAAGTC TCATTATAATCGTTCGAGCTGTT | 219 |
| 206 | KRAS Multi | E | CCTGCTGAAAATGACTGAATATAAGCAG ACTTGGCGGTAGGTCCGAGCTTG | 220 |
| 207 | KRAS Multi | E | CCTGCTGAAAATGACTGAATATAAGTAT CCTGAGCACGGTTGCGAGCTGCT | 221 |
| 208 | KRAS Multi | I | CTCTTGCCTACGCC(N*)CCGCTAAGAACC TCTCGGTC | 222 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 209 | KRAS Multi | I | CTCTTGCCTACGCC(N*)AGTCTCATTATA ATCGTTCG | 223 |
| 210 | KRAS Multi | I | CTCTTGCCTACGCC(N*)GCAGACTTGGCG GTAGGTCC | 224 |
| 211 | KRAS Multi | I | CTCTTGCCTACGCC(N*)GTATCCTGAGCA CGGTTGCG | 225 |
| 212 | ACTB | P | fluor-CCACCACCCAACACACAA(T*)AACAAAC AC-quencher/blocker | 226 |
| 213 | BNC1 | E | CCCRCAAACCRCGAAAACCTC | 227 |
| 214 | BNC1 | E | GTTTTTTTTYGGGAGAGGTAAATA | 228 |
| 215 | ADAMTS1 | E | CRCCTCCRAAACTAAAACAAC | 229 |
| 216 | ADAMTS1 | E | GGGTTATTGTAAAGTTAGGGTG | 230 |
| 217 | BNC1 | E | GAGGT(dP)GTGGTTTT(dP)GTAGAT | 231 |
| 218 | BNC1 | E | AAAC(dK)CCAAAAAACTTCAAAAC | 232 |
| 219 | ADAMTS1 | E | TTTTGTTGGGATAAGAAG(dP)GTTT | 233 |
| 220 | ADAMTS1 | E | ACCAAAAACTATTACAAAACCAAA | 234 |
| 221 | BNC1 | I | CCGACGACCGACG | 235 |
| 222 | BNC1 | I | GGGAGAGGTAAATATCGATAC | 236 |
| 223 | ADAMTS1 | I | CGCGAAAATTAATACCTAACG | 237 |
| 224 | ADAMTS1 | I | TTAGGGTGCGTTATCGGAC | 238 |
| 225 | BNC1 | I | CGGAGGTGTTTGTTTTCGTC | 239 |
| 226 | BNC1 | I | CGAAAAAAACAAACACCGACACG | 240 |
| 227 | ADAMTS1 | I | CGTTTTCGGGGTTGAGGTAAC | 241 |
| 228 | ADAMTS1 | I | CCAAAATACGCTACCGAACGA | 242 |
| 229 | BNC1 | P | fluor-AAAAT(A*)TCT(A*)(C**)CCC(C**)(dK)CC-quencher/blocker | 243 |
| 230 | ADAMTS1 | P | fluor-TATTACTCACTCTAC(T*)CAAAAC(T*)CT CC-quencher/blocker | 244 |
| 231 | BNC1 | P | fluor-ATATCTTTTACCAACAAA(T*)ACCT(T*)C AAA-quencher/blocker | 245 |
| 232 | ADAMTS1 | P | fluor-GTTTT(dP)GTTTTGGTTGCGA(T*)GTTGT-quencher/blocker | 246 |
| 233 | GSTP1 | E | GGGATTTTTTAGAAGAG(dP)GGT | 247 |
| 234 | GSTP1 | E | TACTCACTAATAAC(dK)AAAAC(T*)AC | 248 |
| 235 | APC | E | GGTTTTGTGTTTTATTG(dP)GGAG | 249 |
| 236 | APC | E | CCTAAC(dK)AACTACACCAATACAA | 250 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 237 | PTGS2 | E | GAGAGGGGATTTTTTG(dP)GTTT | 251 |
| 238 | PTGS2 | E | CC(dK)AAAACCAATTCTAAACTAATC | 252 |
| 239 | GSTP1 | I | TTTTTAGAAGAGCGGTCGGC | 253 |
| 240 | GSTP1 | I | CTAATAACGAAAACTACGACGACG | 254 |
| 241 | APC | I | TTGTGTTTTATTGCGGAGTGC | 255 |
| 242 | APC | I | AACCACATATCGATCACGTACG | 256 |
| 243 | PTGS2 | I | GCGTTTTCGGATTTTAGGGTC | 257 |
| 244 | PTGS2 | I | AACTAATCGCCTTAAATAAAATACCG | 258 |
| 245 | GSTP1 | P | fluor-CCTCC(dK)AACCTTA(T*)AA(N*)AAA(T*)AATCCC-quencher/blocker | 259 |
| 246 | APC | P | fluor-AAAAAC(dK)CCCTAATCC(N*)CA(T*)CCAAC-quencher/blocker | 260 |
| 247 | PTGS2 | P | fluor-CACTTAACTTCCTC(T*)CCAAAAATC(T*)AAAC-quencher/blocker | 261 |
| 248a | MGMT | E | GTTTT(T*)AGAA(dP)G(T*)TTTG(dP)GTTT | 262 |
| 248b | MGMT | E | GTTTT(T*)AGAAYG(T*)TTTGYGTTT | 263 |
| 249a | MGMT | E | AAAAAAC(T*)CC(dK)CACTCTTCC | 264 |
| 249b | MGMT | E | AAAAAAC(T*)CCRCACTCTTCC | 265 |
| 250 | MGMT | I | TTTCGACGTTCGTAGGTTTTCGC | 266 |
| 251 | MGMT | I | GCACTCTTCCGAAAACGAAACG | 267 |
| 252a | MGMT | P | fluor-CCAAACAC(T*)CACCAAATC(N*)CAAAC-quencher/blocker | 268 |
| 252b | MGMT | P | fluor-CCAAACAC(T*)CACCAAATC(N*)CAAAC-quencher/blocker | 269 |
| 264 | BNC1 | P | fluor-ATATCTTTTACCAA(C-quencher)AAA(T*)ACCT(T*)CAAA-quencher/blocker | 270 |
| 265 | ADAMTS1 | P | fluor-GTTTT(dP)GTTTTGGTTGCGA(T*)GTTGT-quencher/blocker | 271 |
| 283 | CDO1 | E | GGAGATAA(dP)GGGGTTTTTGG | 272 |
| 284 | CDO1 | E | CACTAAAAATATACCAAC(dK)ACC | 273 |
| 285 | CDO1 | E | GGAGAGTTATTTAAGAAAGGTGG | 274 |
| 286 | CDO1 | E | AAAATTAC(dK)C(dK)AAACCCAC | 275 |
| 287 | CDO1 | I | CGTGTTCGTAGGGTTTTTTCGTTTTC | 276 |
| 288 | CDO1 | I | CCAACGACCCTCGAAAAAAAAACG | 277 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 289 | CDO1 | I | GATTTTGCGGGTACGGTTTACGC | 278 |
| 290 | CDO1 | I | GATCCCTAAAACGCCGAAAACAACG | 279 |
| 291 | CDO1 | P | fluor-(C*)GTTATTTTT(T-quencher)TTGGG(T*)GGTT(T*)TTCG-quencher/blocker | 280 |
| 292 | CDO1 | P | fluor-C(dK)AAAAACCACC(C-quencher)AAAAAAA(T*)AAC-quencher/blocker | 281 |
| 293 | TAC1 | E | GGATAAATAT(dP)GTAAGGTATTGAG | 282 |
| 294 | TAC1 | E | CGAAATACTAAATTTCTCTAATTCCTC | 283 |
| 295 | TAC1 | E | GAGTTTTTTTGGTTTTTT(dP)GAG | 284 |
| 296 | TAC1 | E | CTAAAATAAATACC(dK)CAAAACAC | 285 |
| 297 | TAC1 | I | CGCGTTCGGATTTTTTTTTCGGC | 286 |
| 298 | TAC1 | I | AAATTTCTCTAATTCCTCCGAACGCACG | 287 |
| 299 | TAC1 | I | GCGTACGTTGGTCGTTTCGTATTTTC | 288 |
| 300 | TAC1 | I | GCAAAACACTAAACAAACGAAAAAAACGCG | 289 |
| 301 | TAC1 | P | fluor-GTAGTTAT(dP)GAGAG(T*)G(N*)GGAGCGA(T*)TAG-quencher/blocker | 290 |
| 302 | TAC1 | P | fluor-CTAATC(dK)CTCCGCAC(T*)CTC(N*)A(T*)AACTAC-quencher/blocker | 291 |
| 303 | SOX17 | E | GTTTGGAG(dP)GTTATGAGTAG | 292 |
| 304 | SOX17 | E | CTTCATATCCCC(dK)ATAAAACTC | 293 |
| 305 | SOX17 | E | GGGTTTTTAGTCGGTTTAGTG | 294 |
| 306 | SOX17 | E | CTAAAAC(dK)TAAAACTC(dK)AACC | 295 |
| 307 | SOX17 | I | GATTTAGAGCGCGTTGTTCGC | 296 |
| 308 | SOX17 | I | CATATCCCCGATAAAACTCAACGACTCG | 297 |
| 309 | SOX17 | I | GTCGGTTTAGTGATATTGCGGGC | 298 |
| 310 | SOX17 | I | CCACGACCTAAACGTAAACCTAACG | 299 |
| 311 | SOX17 | P | fluor-GATGGT(dP)GGGTTGGGTT(T*)TTGTTTTTGG-quencher/blocker | 300 |
| 312 | SOX17 | P | fluor-CCAAAAACAAAAACCCAA(C**)CCGACCATC-quencher/blocker | 301 |
| 313 | CDO1 | P | fluor-(C*)GTATATTTT(dP)GGTT(T*)TTT(N*)GGGT(T*)TCG-quencher/blocker | 302 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 314 | CDO1 | P | fluor-C(dK)AAACC(C**)GAAAAAA(C**)C(N*)AAAATATAC-quencher/blocker | 303 |
| 315 | TAC1 | P | fluor-GGTAGTTGT(dP)G(T*)CGGGAAGGAGGTTCG-quencher/blocker | 304 |
| 316 | TAC1 | P | fluor-C(dK)AACCTCCTTCCCGAC(N*)ACAAC(T*)ACC-quencher/blocker | 305 |
| 317 | SOX17 | P | fluor-GGTTTTTTTTGTA(T*)AGATGTGGT(T*)AATGG-quencher/blocker | 306 |
| 318 | SOX17 | P | fluor-CCATTAACCACA(T*)CTA(T*)ACAAAAAAACC-quencher/blocker | 307 |
| 319 | SOX17 | E | GGTTTGGTTTATAG(dP)GTATTTAGG | 308 |
| 320 | ACTB | I | GAGGTTTAG(T*)AAGTTTTTTGGATTGTG | 309 |
| 321 | ACTB | I | CCCTTAAAAAT(T*)ACAAAAACCACAAC | 310 |
| 322 | BRCA1 | E | GTAGATTGGGTGGTTAATTTAGAG | 311 |
| 323 | BRCA1 | E | CTATAATTCCC(dK)C(dK)CTTTTC | 312 |
| 324 | BRCA1 | I | GGTGGTTAATTTAGAGTTTCGAGAGAC | 313 |
| 325 | BRCA1 | I | CGTTACCACGAAAACCAAAAAACTACCG | 314 |
| 326 | BRCA1 | P | fluor-GATTTCGTATTT(T*)GAGAGG(T*)TGTTGTTTAG-quencher/blocker | 315 |
| 327 | BRCA1 | P | fluor-CTAAACAACAACC(T*)CTCAAAA(T*)ACGAAATC-quencher/blocker | 316 |
| 328 | BRCA1 | E | GGTAGATTGGGTGGTTAATTTAGAG | 317 |
| 329 | BRCA1 | E | CCAAAAAATCTCAACRAACTC | 318 |
| 330 | BRCA1 | I | GGGTGGTTAATTTAGAGTTTCGAGAGAC | 319 |
| 331 | BRCA1 | I | ACCACGAAAACCAAAAAACTACCG | 320 |
| 336 | MGMT | E | GGGATTTTGTTTAAGTATGTTAAAGG | 321 |
| 337 | MGMT | E | CCTACCTTACCTCTAAATACCAACC | 322 |
| 338 | MGMT | I | GTATGTTAAAGGGTTGTTGTAAGTTAAGG | 323 |
| 339 | MGMT | I | CCTCTAAATACCAACCCCAAACC | 324 |
| 340 | MGMT | P | fluor-CCAACTACTC(C-quencher)AAAAAACTTCCAAAAACC-quencher/blocker | 325 |
| 341 | MGMT | P | fluor-CCAAC(T*)ACTC(C-quencher)AAAAAC(T*)TCCAAAAACC-quencher/blocker | 326 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 342 | MGMT | I | GTATGTTAAAGGGTTGT(T*)GTAAGTTAA GG | 327 |
| 343 | MGMT | I | CCTCTAAATACCAA(C**)CCCAAACC | 328 |
| 380 | ACTB | P | fluor- CCACCACCCAACACACAA(T*)AACAAAC AC-quencher/blocker | 329 |
| 381 | ACTB | P | fluor- CCACCACCCAACACACAA(T*)AACAAAC AC-quencher/blocker | 330 |
| 382 | SOX17 | I | ATTTAGAGCGCGTTGTTCGC | 331 |
| 383 | SOX17 | I | ATATCCCCGATAAAACTCAACGACTCG | 332 |
| 384 | SOX17 | I | TATCCCCGATAAAACTCAACGACTCG | 333 |
| 385 | SOX17 | I | ATCCCCGATAAAACTCAACGACTCG | 334 |
| 386 | TAC1 | I | GCGTTCGGATTTTTTTTTCGGC | 335 |
| 387 | TAC1 | I | TTTCTCTAATTCCTCCGAACGCACG | 336 |
| 388 | TAC1 | I | CTCTAATTCCTCCGAACGCACG | 337 |
| 389 | SOX17 | I | GTGACGATTAGAGTTAGATTTAGAGCGC | 338 |
| 390 | TAC1 | P | fluor- GTAGTTATCGAGAG(T*)GCGGAGCGA(T*) TAG-quencher/blocker | 339 |
| 391 | SOX17 | P | fluor- CCAACCCGACCATCACCGCGAACAAC- quencher/blocker | 340 |
| 392 | BG converted | I | GGAGAGTGTATTTG(T*)GAAGGAAATG | 341 |
| 393 | BG converted | I | CATACATACACCAAACAA(T*)TCATTC | 342 |
| 394 | BG converted | P | fluor- CCAAATACCA(T*)AACCATTTTATTAA(T*) AACAC-quencher/blocker | 343 |
| 395 | BG converted | P | fluor- CCAAATACCA(T*)AACCATTTTATTAA(T*) AACAC-quencher/blocker | 344 |
| 396 | GSTP1 (Fwd) | E | GGTTTYGTTGGGGATTTG | 345 |
| 397 | GSTP1 (Fwd) | E | ACCRCTCTTCTAAAAAATCC | 346 |
| 398 | GSTP1 (Fwd) | I | AGGTTTTTTCGGTTAGTTGCGC | 347 |
| 399 | GSTP1 (Fwd) | I | AACGTCGACCGCAAAAAAACG | 348 |
| 400 | GSTP1 (Fwd) | P | fluor-(C*)GCGAT(T*)T(C- quencher)GGGGA(T*)T(T*)TAGG- quencher/blocker | 349 |
| 401 | GSTP1 (Fwd) | P | fluor-CC(T*)AAAA(T*)C(C- quencher)CCGAAA(T*)CGC-quencher/blocker | 350 |
| 402 | APC (Fwd) | E | GAAGTAGTTGTGTAATTYGTTGG | 351 |
| 403 | APC (Fwd) | E | CACCCTAACRAACTACACC | 352 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 404 | APC (Fwd) | I | TGCGGATTAGGGCGTTTTTTATTTTC | 353 |
| 405 | APC (Fwd) | I | TACAACCACATATCGATCACGTACG | 354 |
| 406 | APC (Fwd) | P | fluor-GGAGTTCGTCGA(T*)TGG(T*)TGGG-quencher/blocker | 355 |
| 407 | APC (Fwd) | P | fluor-CCCAACCAA(T*)CGACGAAC(T*)CC-quencher/blocker | 356 |
| 408 | EYA4 (Fwd) | E | GAGTTTTTYGGAGGGTTATAG | 357 |
| 409 | EYA4 (Fwd) | E | CAAACTACAAAAAACATTCAATCC | 358 |
| 410 | EYA4 (Fwd) | I | GCGTTTGGGTTTTTTCGGTGTC | 359 |
| 411 | EYA4 (Fwd) | I | ATCGCCGCAATTAAAAAACCCG | 360 |
| 412 | EYA4 (Fwd) | P | fluor-GGTTCGCGTTTTAAT(T*)TTTAGG(T*)ATTG-quencher/blocker | 361 |
| 413 | EYA4 (Fwd) | P | fluor-CAATACC(T*)AAAAAT(T*)AAAACGCGAACC-quencher/blocker | 362 |
| 414 | OLIG2(Fwd) | E | GTTATGGATTYGGAYGTTAG | 363 |
| 415 | OLIG2(Fwd) | E | CTCCRACRAACAATCACTC | 364 |
| 416 | OLIG2(Fwd) | I | GTTTGGTGTTTAG(T*)CGTTCGTC | 365 |
| 417 | OLIG2(Fwd) | I | CACTCGAAATAAA(C**)GAAAACACG | 366 |
| 418 | OLIG2(Fwd) | P | fluor-GGTAGTAGCGG(T*)AGCGTT(T*)TTATTG-quencher/blocker | 367 |
| 419 | OLIG2(Fwd) | P | fluor-CAATAAAAACGC(T*)ACCGC(T*)ACTACC-quencher/blocker | 368 |
| 420 | ADAMTS12(Fwd) | E | GGYGTAGTTTATTTYGGTT | 369 |
| 421 | ADAMTS12(Fwd) | E | ATTTAACCRACTCRACCAAC | 370 |
| 422 | ADAMTS12(Fwd) | I | GTATGTTTCGCGGTTTCGTAGTTC | 371 |
| 423 | ADAMTS12(Fwd) | I | ACTAAACCTAACG(T*)TCGAAACG | 372 |
| 424 | ADAMTS12(Fwd) | P | fluor-(C*)GTTCGTTCGG(T-quencher)G(T*)ATTTTTT(T*)TTCGG-quencher/blocker | 373 |
| 425 | ADAMTS12(Fwd) | P | fluor-CCGAAAAAAAAA(T-quencher)A(C**)ACCGAA(C**)GAAC-quencher/blocker | 374 |
| 426 | POU4F1(Fwd) | E | GTTTGAGTTGTTTTGATTTTAGTG | 375 |
| 427 | POU4F1(Fwd) | E | CTCCAACCTCAACTCTAAAC | 376 |
| 428 | POU4F1(Fwd) | I | GATTTTAGTGTCGCGTATTTTGGTTC | 377 |
| 429 | POU4F1(Fwd) | I | CTAAACTAAATCCCGCGAACCTCG | 378 |

TABLE 5-continued

Illustrative primers and probes for the detection of methylation of various gene promoters. Note Y is C/T; R is A/G; C* is an optionally functionalized (e.g., to alter probe $T_m$) C; T* is an optionally functionalized (e.g., to alter probe $T_m$) T; A* is an optionally functionalized (e.g., to alter probe $T_m$) A; N* is a nucleotide optionally a quencher; dP is a universal pyrimidine; dK is a universal purine.

| Primer/ Probe Num | Target | Type | Sequence | SEQ ID NO |
|---|---|---|---|---|
| 430 | POU4F1(Fwd) | P | fluor- GGTTTTAT(T*)GGGGGTT(N*)AT(T*)TCG GGTAG-quencher/blocker | 379 |
| 431 | POU4F1(Fwd) | P | fluor- CTACCCGAAATAACCC(C**)CAA(N*)TAA AA(C**)C-quencher/blocker | 380 |
| 432 | ABCB1(Fwd) | E | GGTTTTTAGTATTTTTAYGAAGGT | 381 |
| 433 | ABCB1(Fwd) | E | CRATACRAAAACCTACTCTCTA | 382 |
| 434 | ABCB1(Fwd) | I | TTTGGATTTTGTTCGTCGTTAGTGC | 383 |
| 435 | ABCB1(Fwd) | I | CTACTCTCTAAACCCGCGAACG | 384 |
| 436 | ABCB1(Fwd) | P | fluor- GGTTTTAGTCG(T*)CGCGGACGATGT- quencher/blocker | 385 |
| 437 | ABCB1(Fwd) | P | fluor- ACATCGTCCGCGACGAC(T*)AAAACC- quencher/blocker | 386 |
| 438 | SOX17 | I | GAGTTAGATTTAGAGCGCGTTGTTC | 387 |
| 439 | TAC1 | I | GAGCGCGTTCGGATTTTTTTTTC | 388 |

It is noted that these primers and probes identify the locations of various fluorophores and quenchers. However, it will be recognized that the particular fluorophores and quenchers are illustrative and not limiting and numerous amplification and/or detection strategies can be employed in the cartridges described herein. Accordingly, in various embodiments the methods and devices described herein can employ many different nucleic acid hybridization probes. Typically, for signal generation, the probes utilize a change in the fluorescence of a fluorophore due to a change in its interaction with another molecule or moiety brought about by changing the distance between the fluorophore and the interacting molecule or moiety. Alternatively, other methods of detecting a polynucleotide in a sample, including, but not limited to, the use of radioactively-labeled probes, are contemplated.

Fluorescence-based assays typically rely for signal generation on fluorescence resonance energy transfer, or "FRET", according to which a change in fluorescence is caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction typically requires that the absorption spectrum of one member of the pair overlaps the emission spectrum of the other member, the first fluorophore. If the interacting molecule or moiety is a quencher, its absorption spectrum typically overlaps the emission spectrum of the fluorophore (see, e.g., Stryer (1978) *Ann. Rev. Biochem.* 47: 819-846; Selvin (1995) *Meth. Enzymol.* 246: 300-335; and the like). Efficient FRET interaction is typically achieved when the absorption and emission spectra of the pair have a large degree of overlap. The efficiency of FRET interaction is linearly proportional to that overlap. Typically, a large magnitude of signal (i.e., a high degree of overlap) is desired. FRET pairs, including fluorophore-quencher pairs, are therefore typically chosen on that basis.

A variety of labeled nucleic acid hybridization probes and detection assays that utilize FRET and FRET pairs are known. One such scheme is described by Cardullo et al. (1988) *Proc. Natl. Acad. Sci. USA,* 85: 8790-8794 and in Heller et al. EP 0070685. It uses a probe comprising a pair of oligodeoxynucleotides complementary to contiguous regions of a target DNA strand. One probe molecule contains a fluorescent label, a fluorophore, on its 5' end, and the other probe molecule contains a different fluorescent label, also a fluorophore, on its 3' end. When the probe is hybridized to the target sequence, the two labels are brought very close to each other. When the sample is stimulated by light of an appropriate frequency, fluorescence resonance energy transfer from one label to the other occurs. FRET produces a measurable change in spectral response from the labels, signaling the presence of targets. One label could be a "quencher," which can be, inter alia, an interactive moiety (or molecule) that releases the accepted energy as heat.

Another type of nucleic acid hybridization probe assay utilizing a FRET pair is the "TaqMan®" assay described in Gelfand et al. U.S. Pat. No. 5,210,015, and Livak et al. U.S.

Pat. No. 5,538,848. The probe is typically a single-stranded oligonucleotide labeled with a FRET pair. In a TaqMan® assay, a DNA polymerase releases single or multiple nucleotides by cleavage of the oligonucleotide probe when it is hybridized to a target strand. That release provides a way to separate the quencher label and the fluorophore label of the FRET pair.

In certain embodiments non-FRET fluorescent probes, such as those described in, e.g., Tyagi et al., U.S. Pat. No. 6,150,097 can also be used. For example, the Tiyagi et al. patent describes how changes in the absorption spectra of the label pair can be used as a detectable signal as an alternative to change in fluorescence. When change in absorption is utilized, the label pair may include any two chromophores, that is, fluorophores, quenchers and other chromophores. The label pair may even be identical chromophores.

In some embodiments, dyes and other moieties, such as quenchers, are introduced into primers and/or probes used in the methods and cartridges described herein. In certain embodiments such dyes and quenchers include, but are not limited to dyes (fluors) suitable for use as FRET probes. In certain embodiments the dyes and/or quenchers comprise modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In some embodiments, the modified nucleotide includes one or more reactive groups that can react with a dye or quencher before, during, or after incorporation of the modified nucleotide into the nucleic acid. In some embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In some embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink. An illustrative, but non-limiting list of suitable fluors is shown in Table 6.

TABLE 6

Illustrative, but non-limiting fluorophores (fluorescent labels) for use in the primers and/or probes described herein.

| Dye | Absorbance Wavelength | Emission Wavelength |
|---|---|---|
| Alexa fluor | 345 | 442 |
| Alexa fluor 430 | 430 | 545 |
| Alexa fluor 488 | 494 | 517 |
| Alexa fluor 532 | 530 | 555 |
| Alexa fluor 546 | 556 | 573 |
| Alexa fluor 555 | 556 | 573 |
| Alexa fluor 568 | 578 | 603 |
| Alexa fluor 594 | 590 | 617 |

TABLE 6-continued

Illustrative, but non-limiting fluorophores (fluorescent labels) for use in the primers and/or probes described herein.

| Dye | Absorbance Wavelength | Emission Wavelength |
|---|---|---|
| Alexa fluor 633 | 621 | 639 |
| Alexa fluor 633 | 650 | 668 |
| Alexa fluor 660 | 663 | 690 |
| Alexa fluor 680 | 679 | 702 |
| Allophycocyanin | 650 | 660 |
| Aminocoumarin | 350 | 445 |
| Cy2 | 490 | 510 |
| Cy3 | 550 | 570 |
| Cy3.5 581 | 581 | 596 |
| Cy5 | 650 | 670 |
| Cy5.5 | 675 | 694 |
| Cy7 | 743 | 770 |
| FAM | 495 | 516 |
| Fluorescein FITC | 495 | 518 |
| HEX | 535 | 556 |
| Hydroxycoumarin | 325 | 386 |
| Methoxycoumarin | 360 | 410 |
| Red 613 | 480; 565 | 613 |
| Rhodamine Red-X | 560 | 580 |
| Rox | 575 | 602 |
| R-phycoerythrin (PE) | 480; 565 | 578 |
| Tamara | 565 | 580 |
| Texas Red | 615 | 615 |
| TRITC | 547 | 572 |
| TruRed | 490; 675 | 695 |

If the assay is designed to detect one target DNA sequence then only one fluorescent hybridization probe needs to be used and, in certain embodiments, FAM, TET, or HEX (or one of their alternatives listed in Table 7) will be a good fluorophore to label the probe. These fluorophores can readily be excited and detected in various spectrofluorometric thermal cyclers. In addition, because of the availability of phosphoramidites derivatives of these fluorophores and the availability of quencher-linked control-pore glass columns, fluorescent hybridization probes with these labels can be entirely synthesized in an automated DNA synthesis process, with the advantage of relatively less expensive and less labor intensive probe manufacture.

TABLE 7

Additional illustrative fluorophore labels for fluorescent hybridization probes.

| Fluorophore | Alternative Fluorophore | Excitation (nm) | Emission (nm) |
|---|---|---|---|
| Cy3[3] | NED[2], Quasar 570[1], Oyster 556[4] | 550 | 570 |
| Cy5[3] | LC red 670[5], Quasar 670[1], Oyster 645[4] | 650 | 670 |
| HEX | JOE, VIC [B], CAL Fluor Orange 560[1] | 535 | 555 |
| LC red 640[5] | CAL Fluor Red 635 [A] | 625 | 640 |
| LC red 705[5] | Cy5.5[3] | 680 | 710 |
| ROX | LC red 610[5], CAL Fluor Red 610[1] | 575 | 605 |
| TET | CAL Fluor Gold 540[1] | 525 | 540 |
| Texas red | LC red 610[5], CAL Fluor Red 610[1] | 585 | 605 |
| TMR | CAL Fluor Red 590[1] | 555 | 575 |

[1]CAL and Quasar fluorophores are available from Biosearch Technologies;
[2]VIC and NED are available from Applied Biosystems;
[3]Cy dyes are available from Amersham Biosciences;
[4]Oyster fluorophores are available from Integrated DNA Technologies; and
[5]LC (Light Cycler) fluorophores are available from Roche Applied Science.

In certain embodiments, multiple target genes are detected in a single multiplex reaction. In some embodiments, each probe that is targeted to a different gene is spectrally distinguishable (detectably different) from the other probes utilized in the multiplex reaction. Probe combinations suitable for multiplex detection are known to those of skill in the art. For example, illustrative combinations of detectably different fluorphores in four target multiplex systems include, but are not limited to:

1) FAM, TMR, Texas red, and Cy5;

2) FAM, TET, TMR, and Texas Red;

3) FAM, HEX, Texas red, and Cy5; and

4) FAM, Cy3, Texas red, and Cy5.

An illustrative combination of detectably different fluorphores in a five target multiplex systems is FAM, TET, TMR, Texas Red, and Cy5. Illustrative combinations of detectable different fluorophores in a six target multiplex system include, but are not limited to:

1) FAM, TET, HEX, TMR, ROX, and Texas red; and

2) FAM, HEX, LC red 610, LC red 640, LC red 670, and LC red 705.

It will be recognized that these combinations of fluorophores are illustrative and non-limiting and numerous other fluorophores will be available to those of skill in the art.

As noted above, for the design of fluorescent hybridization probes that utilize fluorescence resonance energy transfer (FRET), fluorophore-quencher pairs that have sufficient spectral overlap should be chosen. Fluorophores with an emission maximum between 500 and 550 nm, such as FAM, TET and HEX, are best quenched by quenchers with absorption maxima between 450 and 550 nm, such as dabcyl, BHQ-1, and the like (see, e.g., Table 8 for illustrative quencher labels). Fluorophores with an emission maximum above 550 nm, such as rhodamines (including TMR, ROX and Texas red) and Cy dyes (including Cy3 and Cy5) are effectively quenched by quenchers with absorption maxima above 550 nm (including BHQ-2).

For the design of fluorescent hybridization probes that utilize contact quenching, any non-fluorescent quencher can serve as a good acceptor of energy from the fluorophore. For example, Cy3 and Cy5 are effectively quenched by the BHQ-1 and BHQ-2 quenchers.

TABLE 8

Illustrative quencher labels for fluorescent hybridization probes.

| Quencher | Absorption Maximum (nm) |
|---|---|
| BHQ-1[4] | 534 |
| BHQ-2[4] | 580 |
| BHQ-3[4] | 670 |
| Dabcyl | 475 |
| DDQ-I[1] | 430 |
| DDQ-II[1] | 630 |
| Eclipse[2] | 530 |
| Iowa Black FQ[3] | 532 |
| Iowa Black RQ[3] | 645 |
| QSY-21[5] | 660 |
| QSY-7[5] | 571 |

[1]DDQ or Deep Dark Quenchers are available from Eurogentec;
[2]Eclipse quenchers are available from Epoch Biosciences;
[3]Iowa quenchers are available from Integrated DNA Technologies;
[4]BHQ or Black Hole quenchers are available from Biosearch Technologies; and
[5]QSY quenchers are available from Molecular Probes.

In certain embodiments nucleotides can quench the fluorescence of fluorophores, with guanosine being the most efficient quencher, followed by adenosine, cytidine and thymidine. In general, fluorophores with an excitation wavelength between 500 and 550 nm are quenched more efficiently by nucleotides than fluorophores with longer excitation wavelengths. In designing fluorescent hybridization probes, it can be desirable to avoid placing a fluorophore label directly next to a guanosine, to ensure higher fluorescence signals from the fluorophore.

The stabilizing effect of some fluorophore-quencher pairs that interact by contact quenching can have important consequences for the design of hybridization probes (see, e.g., Marras et al. (2002) *Nucleic Acids Res.* 30: e122; Johansson et al. (2002) *J. Am. Chem. Soc.* 124: 6950-6956). For example, it has been observed that hybridization probes labeled with a fluorophore quenched by either BHQ-1 or BHQ-2 show an increase in hybrid melting temperature of about 4° C., compared to hybridization probes with the same probe sequence, but labeled with fluorophores quenched by dabcyl. It is also noted that strong affinity has been observed between the Cy dyes, Cy3 and Cy5, and the Black Hole quenchers, BHQ-1 and BHQ-2.

In view of the foregoing and the Examples and teachings provided herein, numerous primer/probe combinations will be available for use in the methods and cartridges described herein.

Cartridge, Modules, and Systems for DNA Methylation Analysis.

In certain embodiments cartridges are provided for performing the methods described herein (e.g., determination of DNA methylation and, optionally RNA expression). In certain embodiments the cartridge comprises a column comprising a first matrix material, a sample receiving chamber, a temperature controlled channel or chamber, a plurality of chambers containing reagents and/or buffers, and when in use at least one of said chambers contains a DNA conversion reagent (e.g., DABSO and/or a bisulfite reagent), and at least one of said chambers contains a desulphonation/elution buffer, and wherein said cartridge optionally comprises a second column comprising said second matrix material. In certain embodiments the cartridge is configured so that in use, the cartridge comprises a chamber containing a reagent comprising guanidinium thiocyanate ethanol (GTC-EtOH). In certain embodiments the second column is absent, while in other embodiments the second column is present. In certain embodiments the temperature controlled channel or chamber can simply be a heating channel or chamber, or it can be a thermocycling channel or chamber. In certain embodiments the cartridge further comprises a second heating channel or chamber (e.g., a second thermocycling channel or chamber). In certain embodiments the cartridge is configured so that a DNA conversion step (e.g., bisulfite incubation) and/or a desulphonation step occurs in the same reaction tube or chamber in which one or more PCR reactions are later performed.

In certain embodiments the bisulfite reagent is provided as a component of the cartridge. In certain other embodiments the cartridge is configured for the bisulfite reagent to be added to the cartridge at or near the time the sample is placed in the cartridge. In certain instances, the bisulfite reagent is added directly into a chamber in the cartridge, while in other embodiments, the bisulfite reagent is introduced into a loading port on the cartridge (e.g., an injection port) to introduce the bisulfite reagent into the cartridge. In certain embodiments the bisulfite reagent is introduced into the cartridge by the system operating the cartridge (e.g., a processing module) while the cartridge is operating to determine DNA methylation.

In certain embodiments the reagent comprising guanidinium thiocyanate (e.g., GTC-EtOH) is provided as a component of the cartridge. In certain other embodiments the cartridge is configured for the reagent comprising guanidinium thiocyanate to be added to the cartridge at or near the time the sample is placed in the cartridge. In certain instances, the reagent comprising guanidinium thiocyanate is added directly into a chamber in the cartridge, while in other embodiments, the reagent comprising guanidinium thiocyanate is introduced into a loading port on the cartridge (e.g., an injection port) to introduce the bisulfite reagent into the cartridge. In certain embodiments the reagent comprising guanidinium thiocyanate is introduced into the cartridge by the system operating the cartridge (e.g., a processing module) while the cartridge is operating to determine DNA methylation.

In various illustrative, but non-limiting embodiments, the conversion reagent (e.g., bisulfite reagent) comprises a compound selected from the group consisting of sodium metabisulfite, potassium bisulfite, cesium bisulfite, DABSO, and ammonium bisulfite. In certain embodiments the bisulfite is provided in a reagent mix comprising scavengers (e.g., TROLOX water-soluble analog of vitamin E, hydroquinone, etc.) to prevent sulfite oxidation and/or catalysts. In certain embodiments the bisulfite is provided in a reagent mix comprising polyamines as catalysts.

In various embodiments the first matrix material and/or said second matrix material, when present, comprises a material selected from the group consisting of glass or silica, an ion exchange resin, and hydroxyapatite.

In various embodiments the cartridge comprises one or more chambers (e.g., 1 chamber, 2 chambers, 3 chambers, 4 chambers, etc.) each containing one or more reagents selected from the group consisting of methylation specific PCR primers, methylation specific PCR probes, PCR enzyme(s) (e.g., polymerase), reverse transcriptase, and PCR reaction buffer.

In certain embodiments the cartridge contains one or more chambers containing primers specific for bisulfite-converted methylated and/or unmethylated sequences. In certain embodiments the cartridge comprises one or more chambers containing primers and probes for a MethyLight PCR protocol. In certain embodiments the cartridge comprises one or more chambers containing reagents for TaqMan PCR reactions. In certain embodiments the cartridge comprises one or more chambers containing one or more fluorescent probes that are markers for amplified methylated sequences and/or one or more fluorescent probes that are markers for amplified unmethylated sequences. In certain embodiments the probes comprise a fluorescent reporter dye and a quencher dye, where the probes provides a signal upon cleavage by the 5' to 3' nuclease activity of Taq DNA polymerase. In certain embodiments the cartridge comprises a plurality of probes each specific to a different methylated region in an amplified region of interest. In certain embodiments the cartridge comprises a single probe specific to a methylated region in an amplified region of interest. In certain embodiments the cartridge comprises a plurality of probes each specific to the same methylated region in an amplified region of interest.

Illustrative primers and probes include, but are not limited to primers and/or probes to determine methylation of a promoter region of a gene selected from the group consisting of APC, ARF, CDKN2B, CDKN2A, BRCA1, VLH, hMLH1, MGMT. RASSF1A, ADAMTS1, BNC1, HIST1H3C, HOXB4, RASGRF2, TM6SF1, AKR1B1, HIST1H4F, PCDHGB6, NPBWR1, ALX1, and HOXA9. In certain embodiments the primers and/or probes are selected to determine methylation of a promoter region of a gene selected from the group consisting of MGMT, RASSF1A, ADAMTS1, BNC1, HIST1H3C, HOXB4, RASGRF2, TM6SF1, and AKR1B1. In various embodiments the PCR primers, and/or probes, and/or enzymes are provided as beads, e.g., as described in U.S. Patent Publication No: 2006/0068399, which is incorporated herein by reference for the beads and bead formulations described therein.

In various embodiments the cartridge is configured so that the sample receiving chamber, said column(s), the plurality of chambers, and the temperature controlled channel or chamber, are selectively in fluid communication. In certain embodiments the selective fluid communication is provided by microfluidic channels and valves. In certain embodiments the selective fluid communication is provided by providing the sample receiving chamber, said column(s), said plurality of chambers, the heating channel or chamber or a port into the heating channel or chamber, disposed around a central valve and selectively in fluid communication with a channel in said central valve.

In certain embodiments the cartridge is configured so that, when in use, the cartridge comprises: a first chamber containing a sample; a second chamber containing a guanidinium thiosulfate-ethanol (GTC-EtOH) solution; a third chamber containing a bisulfate reagent; a fourth chamber containing a buffer; a fifth chamber containing a rinse solution; and a sixth chamber containing an elution/desulphonation reagent. In certain embodiments the cartridge comprises a seventh chamber containing PCR primers and/or probes and/or PCR enzymes. In certain embodiments the cartridge comprises an eighth chamber also containing PCR primers and/or probes and/or PCR enzymes.

Figure 2:
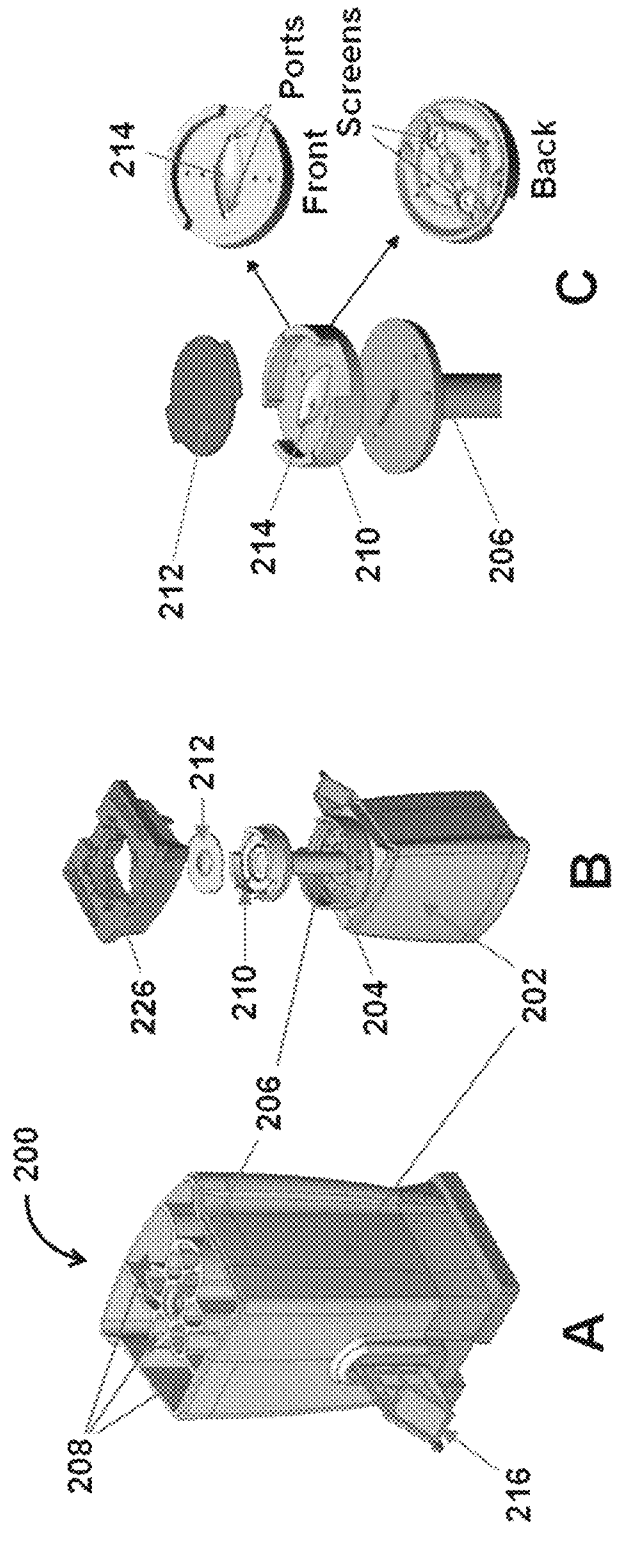
FIG. 2, panels A-C, illustrates one embodiment of a GENEXPERT® cartridge suitable for the determination of DNA methylation as described herein.

FIGS. 1A, 1B and 2 illustrate one cartridge suitable for practice of the methods described herein. The illustrated cartridges are based on the GENEXPERT® cartridge (Cepheid, Inc., Sunnyvale, CA). As shown in FIG. 2, panel A the cartridge 200 comprises a cartridge body 202 containing a plurality of reagent and/or buffer chambers 208. The chambers are disposed around a central syringe barrel 206 that is in fluid communication with a valve body 210 (panel B and FIG. 1B) and that is sealed with a gasket 204. The valve body 210 can comprise a cap 212 and the entire cartridge body can be supported on a cartridge base 226. A "plunger" not shown can be operated to draw fluid into the syringe barrel 206 and rotation of the syringe barrel 206 and associated valve body 212 provides selective fluid communication between the chambers 208 a cavity 214 that can contain a matrix material as described herein and function as a column. In various embodiments the cartridge further comprises one or more temperature controlled channels or chambers 216 that can, in certain embodiments, function as thermocycling chambers. The temperature controlled channels or chambers are also selectively in fluid communication with the cavity 214 and/or the chambers 208. As shown in FIG. 1A, in certain embodiments, the cartridge provides optical windows to provide real-time detection of, e.g., amplification products, base identity in sequencing operations, and the like.

Figure 3A:
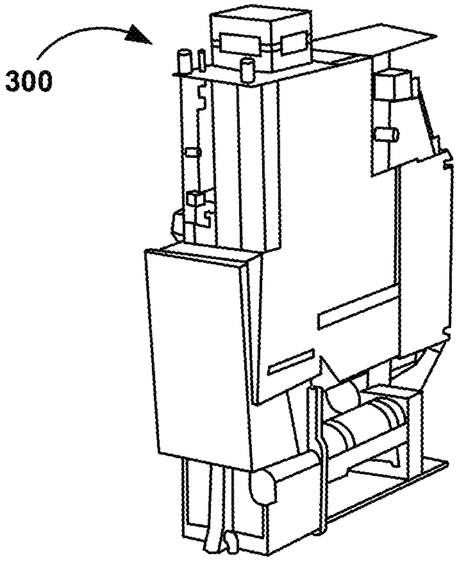
FIGS. 3A-3C show illustrative, but non-limiting embodiments of the modules, and systems (e.g., processing units) for the determination of DNA methylation.
Figure 3B:
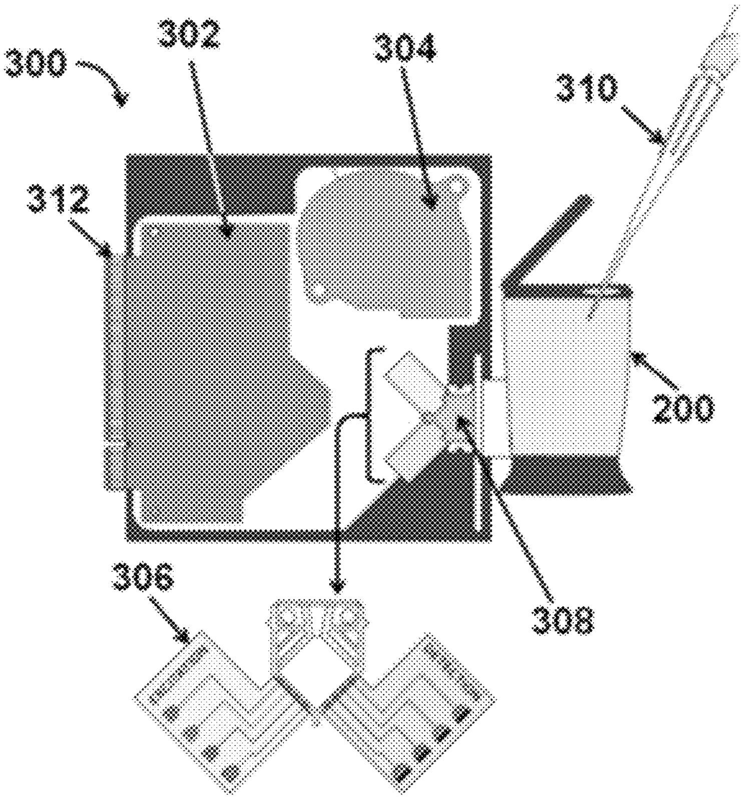

In certain embodiments the cartridge 200 is configured for insertion into a reaction module 300, e.g., as shown in FIG. 3A. As illustrated in FIG. 3B the module is configured to receive the cartridge 200. In certain embodiments the reaction module provides heating plates 308 to heat the temperature controlled chamber or channel. The module can optionally additionally include a fan 304 to provide cooling where the temperature controlled channel or chamber is a thermocycling channel or chamber. Electronic circuitry 302 can be provided to pass information (e.g., optical information) top a computer for analysis. In certain embodiments the module can contain optical blocks 306 to provide excitation and/or detection of one or more (e.g., 1, 2, 3, 4, or more) optical signals representing, e.g., various nucleic acid targets. In various embodiments an electrical connector 312 can be provided for interfacing the module with a system (e.g. system controller or with a discrete analysis/controller unit. As illustrated, in FIG. 3B the sample can be introduced into the cartridge using a pipette 310.

In certain embodiments, the module also contains a controller that operates a plunger in the syringe barrel and the rotation of the valve body.

Figure 3C:
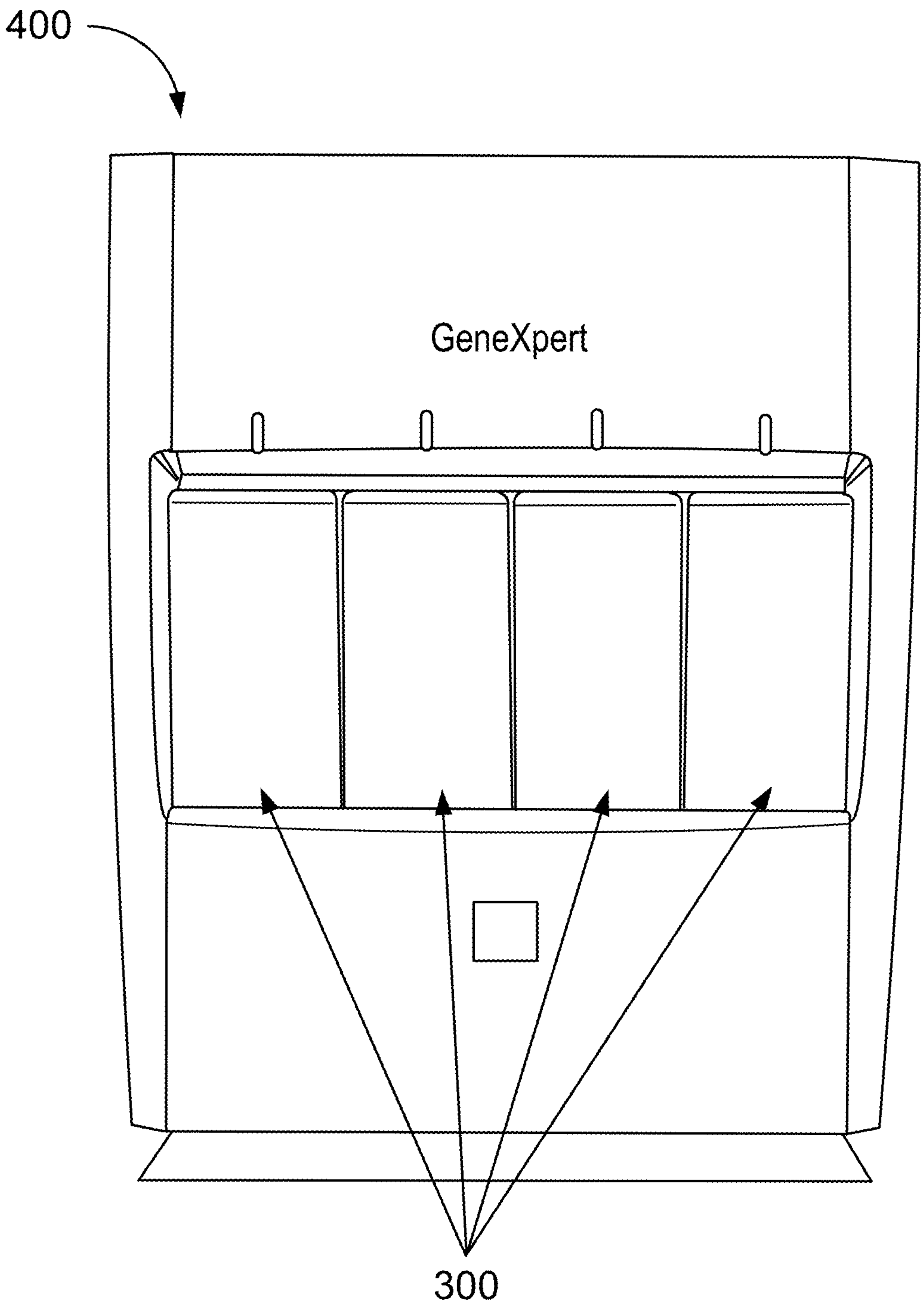

In certain embodiments a system (e.g., a processing unit) is provided. One illustrative, but non-limiting embodiment is shown in FIG. 3C. In certain embodiments, the processing unit comprises an enclosure configured to contain one or more sample processing modules where each processing module is configured to hold and operate a removable cartridge as described herein. In certain embodiments the system is configured to operate the sample processing modules to perform sample processing to determine methylation of one or more target nucleic acids and optionally to determine the level of one or more target RNA/DNA sequences within a corresponding removable sample cartridge, wherein the processing on a sample within the corresponding removable sample cartridge performs a method as described herein. In certain embodiments the system is configured to contain one sample processing module. In certain embodiments the system is configured to contain at least two sample processing modules, or at least 4 sample processing modules, or at least 8 sample processing modules, or at least 12 sample processing modules, or at least 16 sample processing modules, or at least 20 sample processing modules, or at least 24 sample processing modules, or at least 28 sample processing modules, or at least 32 sample processing modules, or at least 64 sample processing modules, or at least 128 sample processing modules. In certain embodiments the system provides a user interface that allows the user input operational instructions and/or to monitor operation of the cartridges to determine DNA methylation.

While the methods described herein are described primarily with reference to the GENEXPERT® cartridge by Cepheid Inc. (Sunnyvale, CA) (see, e.g., FIG. 1A), it will be recognized, that in view of the teachings provided herein the methods can be implemented on other cartridge/microfluidic systems. Such cartridge/microfluidic systems can include, for example microfluidic systems implemented using soft lithography, micro/nano-fabricated microfluidic systems implemented using hard lithography, and the like.

High Volume Sample Preparation (HVSP) Cartridge.

In various embodiments cartridges are provided for the preparation of large sample volumes. In certain embodiments the sample preparation cartridges comprise GENEXPERT® cartridges modified for high volume sample preparation (e.g., as shown in FIG. 20). In certain embodiments, e.g., when the cartridge is based on a GENEXPERT® cartridge comprises one or more channels or chambers comprising an affinity matrix that binds DNA, a plurality of chambers disposed around a central valve assembly and selectively in fluid communication with said central valve assembly where the central valve assembly is configured to accommodate a plunger that is capable of drawing fluid into or out of a chamber in fluid communication with the central valve wherein said plurality of chambers comprises at least two different chambers each configured to receive up to about 4 ml (or up to about 5 ml) of sample solution (in certain embodiments chamber 2 has a maximum volume of about 4 ml, while chamber 3 has a maximum volume of about 4.5 ml), a chamber containing PEG (e.g., PEG200), a chamber containing an alkaline solution (e.g., KOH solution), and a chamber containing a buffer (e.g., Tris). In certain embodiments the plurality of chambers comprises at least three different chambers each configured to receive up to about 4 ml (or up to about 5 ml) of sample solution. In certain embodiments the plurality of chambers comprises a chamber containing a wash solution (e.g., GTC-ethanol wash solution which is typically 1.25M guanidinium thiocyanate, 25 mM Tris pH 7.0, 50% ethanol). In certain embodiments the cartridge comprises a chamber configured for removal of a processed sample. In certain embodiments the sample chambers, when in use, contain sample solution, GTC and alcohol(e.g., isopropanol). In certain embodiments the sample chambers, when in use contain sample solution, GTC and alcohol in substantially equal volumes. In certain embodiments the cartridge, when in use, comprises 4 ml of sample solution GTC and isopropanol disposed in each of said chambers configured to receive a sample. In certain embodiments the cartridge provides DNA or RNA recovery that is substantially linear with respect to the sample volume between 0.5 ml and about 4 ml of sample.

In certain embodiments the HVSP cartridge is configured to perform a DNA conversion (e.g., bisulfite conversion) to provide a methylation analysis. Accordingly in certain embodiments, the HVSP cartridge is configured to contain, or to receive immediately or shortly prior to use, a conversion reagent (e.g. a bisulfite reagent, DABSO, etc.). In certain embodiments, the HVSP cartridge can be configured to also contain reagents for and to provide a desulphonation of converted DNA. Alternatively, in certain embodiments, the conversion is performed in the HSVP cartridge while the desulphonation and methylation analysis (e.g., PCR) is performed in the second cartridge (e.g., as illustrated in the work flows shown in FIG. 20B).

Two-Cartridge Methylation Analysis

Figure 20A:
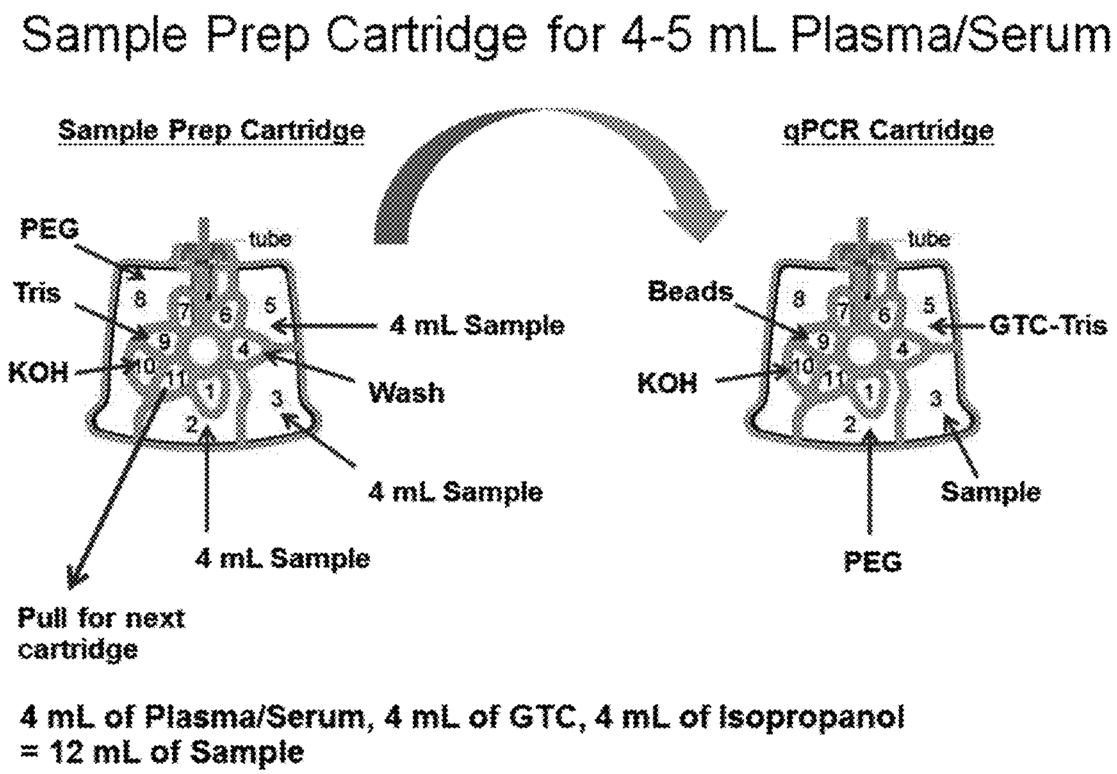
FIG. 20A illustrates one embodiment of a high-volume (e.g., up to 12 ml) sample preparation (HVSP) cartridge that can be used with a qPCR cartridge and/or with a methylation detection cartridge.
Figure 20B:
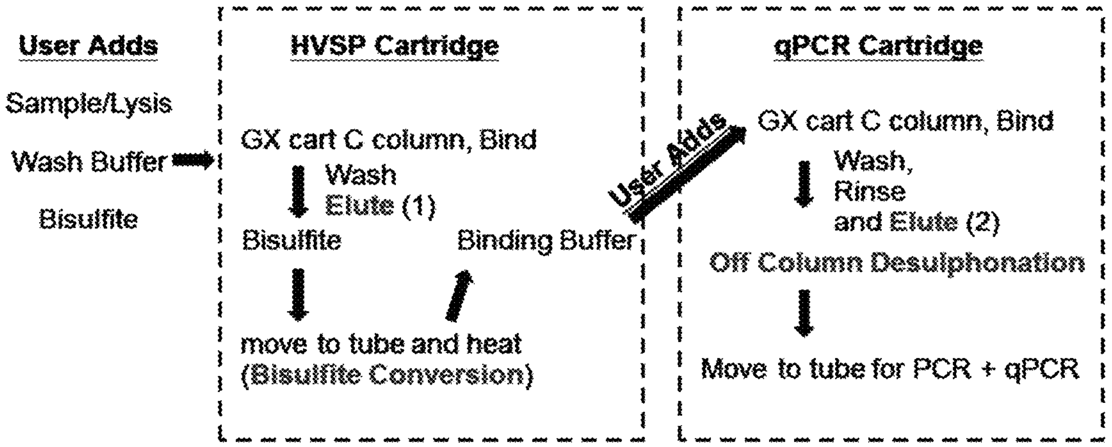
FIG. 20B schematically illustrates one variation of work flows in the HVSP cartridge when used in combination with a qPCR cartridge to perform a methylation analysis.

In various embodiments the methylation analysis methods described herein are performed using a two-cartridge system (a set of two cartridges such as a “first” cartridge (e.g., a high volume sample preparation cartridge), and a “second” cartridge (e.g., a qPCR cartridge)), e.g., as illustrated in FIG. 20B. As illustrated in this figure, in certain embodiments, sample preparation and bisulfite conversion can be performed in a first cartridge. The converted DNA is then transferred to second cartridge wherein it is washed and desulphonated. In certain embodiments the second cartridge is additionally utilized to analyze the converted (or unconverted) DNA, e.g., via PCR (e.g., methylation-specific PCR).

In certain embodiments the first cartridge can be a high-volume sample cartridge as described above where the sample preparation cartridge contains a bisulfite conversion reagent as described herein. In certain embodiments the high-volume cartridge provides a larger sample chamber or multiple sample chambers to permit cleanup and conversion of larger amounts of DNA.

In certain embodiments the first cartridge of the two-cartridge set comprises a sample receiving chamber, a “column” comprising a first matrix material, a temperature controlled channel or chamber, a sample removal chamber, and a plurality of chambers containing reagents and/or buffers. Typically, in use, at least one of the chambers contains a bisulfite reagent (e.g., as described herein). In certain embodiments the second cartridge of the two-cartridge set comprises a sample receiving chamber, a “column” comprising a matrix material, a temperature controlled channel or chamber, a plurality of chambers containing reagents and/or buffers. Typically, in use, at least one of the plurality of chambers in the second cartridge contains a desulphonation and/or elution reagent. In certain embodiments the second cartridge contains reagents for PCR amplification (e.g., methylation specific PCR) and the detection of an amplification product.

In certain embodiments illustrative, but non-limiting embodiments, the first cartridge is used for sample preparation (e.g., binding of DNA to a first matrix material (e.g., glass fiber), washing and eluting of the bound DNA) and bisulfite conversion of the washed DNA. In certain embodiments the bisulfite conversion comprise combining the washed DNA with a bisulfite reagent and heating the mixture in the temperature-controlled channel or chamber. The resulting converted DNA is then mixed with a wash buffer (e.g., 1.25M GTC, 25 mM Tris pH 7.0, 50% ethanol) and moved into a sample removal chamber (e.g., chamber 2) where it can be removed (e.g., removed using a pipette, a syringe or syringe, pump, and the like).

In certain embodiments the bisulfite converted DNA in wash buffer is introduced into a sample receiving chamber of the second cartridge. The second cartridge is operated to bind the DNA to a second matrix material (e.g., glass fiber "column"), to wash and elute the bound DNA and to desulphonate the DNA. In certain embodiments the DNA is desulphonated on the column or as it is eluted from the second matrix material. In certain embodiments the DNA is desulphonated after removal from the second matrix material. In certain embodiments the desulphonated DNA is then mixed, e.g., with enzyme and primer/probe beads for PCR in the second cartridge. In certain embodiments the desulphonated DNA is removed and can be introduced into a third cartridge or other reaction system for further analysis (e.g., sequencing).

In certain embodiments, in the first cartridge, the sample receiving chamber, column, plurality of chambers, sample removal chamber, and temperature-controlled heating channel or chamber, are selectively in fluid communication (e.g., by microfluidic channels and/or valves); and/or, in the second cartridge, the sample receiving chamber, the column, the plurality of chambers, and the temperature-controlled heating channel or chamber, are selectively in fluid communication (e.g., by microfluidic channels and/or valves).

In certain embodiments, in the first cartridge, the sample receiving chamber, the column, the plurality of chambers, the sample removal chamber, and the temperature controlled channel or chamber or a port into the temperature controlled channel or chamber, are disposed around a central valve and selectively in fluid communication with one or more channels in the central valve. The central valve can be configured to accommodate a plunger that is capable of drawing fluid into or out of a chamber(s) in fluid communication with the central valve. In certain embodiments, in the second cartridge, the sample receiving chamber, the column, the plurality of chambers, and the temperature controlled channel or chamber or a port into the temperature controlled channel or chamber, are disposed around a central valve and selectively in fluid communication with one or more channels in the central valve. In certain embodiments the central valve is configured to accommodate a plunger that is capable of drawing fluid into or out of one or more chambers in fluid communication with the central valve.

In certain embodiments the first cartridge and/or the second cartridge is a GENEXPERT® cartridge, or a modified GENEXPERT® cartridge (e.g., as illustrated in FIGS. 1A, 1B, 2, 13A, 17, and 20A). In certain, illustrative, but non-limiting embodiments, the first cartridge is configured as shown in Table 9. In certain embodiments the chamber numbering corresponds to the chambers illustrated in FIG. 1B.

TABLE 9

One illustrative, but non-limiting configuration of a "first" cartridge for DNA preparation and bisulfite conversion.

| Chamber # | Reagent | Volume |
|---|---|---|
| Chamber 1 | Empty | N/A |
| Chamber 2 | Sample in GTC Tween | 2.5 mL |
| Chamber 3 | 1.25M GTC, 25 mM Tris pH 7.0, 50% Ethanol | 3.0 mL |
| Chamber 4 | NH4 Bisulfite | ~150 μL |
| Chamber 5 | Tris pH 8.5 | 2.0 mL |
| Chamber 6 | Empty | N/A |
| Chamber 7 | Empty | N/A |
| Chamber 8 | PEG200 | 1.0 mL |
| Chamber 9 | Empty | N/A |
| Chamber 10 | 15 mM KOH | 500 μL |
| Chamber 11 | Empty | N/A |

In certain, illustrative, but non-limiting embodiments, the second cartridge is configured as shown in Table 10. In certain embodiments the chamber numbering corresponds to the chambers illustrated in FIG. 1B.

TABLE 10

One illustrative, but non-limiting configuration of a "second" cartridge for desulphonation of converted DNA and optional PCR of the desulphonated product.

| Chamber # | Reagent | Volume |
|---|---|---|
| Chamber 1 | Empty | N/A |
| Chamber 2 | 1.25M GTC, 25 mM Tris pH 7.0, 50% Ethanol | 2.0 mL |
| Chamber 3 with funnel | Sample from 1st Cartridge | ~1.6 mL |
| Chamber 4 | Empty | N/A |
| Chamber 5 | Tris pH 8.5 | 2.0 mL |
| Chamber 6 | Empty | N/A |
| Chamber 7 | Empty | N/A |
| Chamber 8 | PEG200 | 1.0 mL |
| Chamber 9 | Enzyme Bead, 1× Internal Bead | 2× Beads |
| Chamber 10 | 15 mM KOH | 500 μL |
| Chamber 11 | Tris Bead, Enzyme Bead, 1× External Bead | 3× Beads |

In certain embodiments the second cartridge is configured to use one or more of the following genes as control genes: MYOD1, COL2A1, NONO, and/or TUBB.

In certain embodiments using the two-cartridge format is possible, inter alia, to run a non-nested PCR reaction or a methylation specific preamp in the $2^{nd}$ cartridge.

The foregoing configurations are illustrative and non-limiting. Using the teaching provided herein numerous other two-cartridge formats will be available to one of skill in the art.

Figure 35:
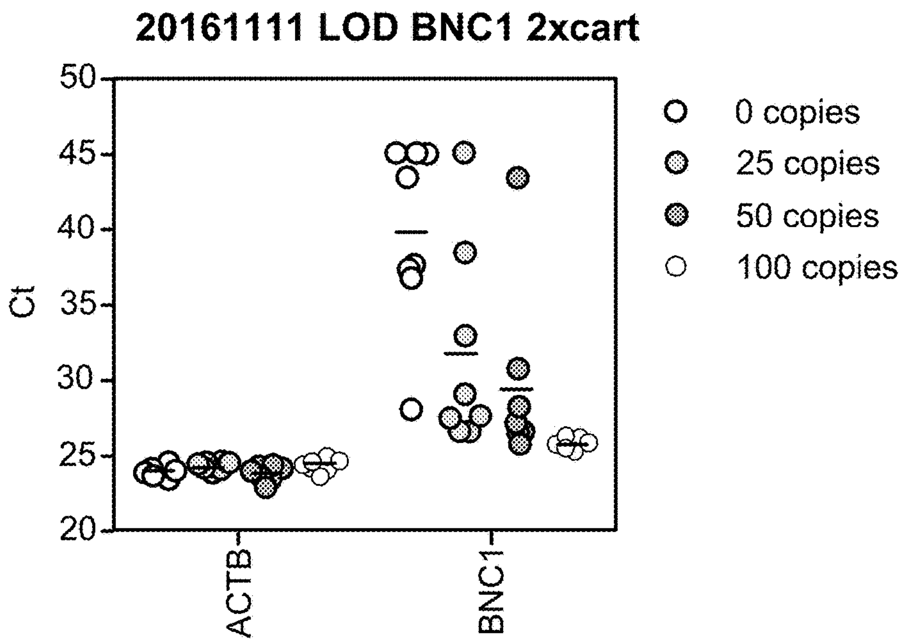
FIG. 35 shows the results of a two-cartridge methylation analysis of BNC1 and ACTB.
Figure 36:
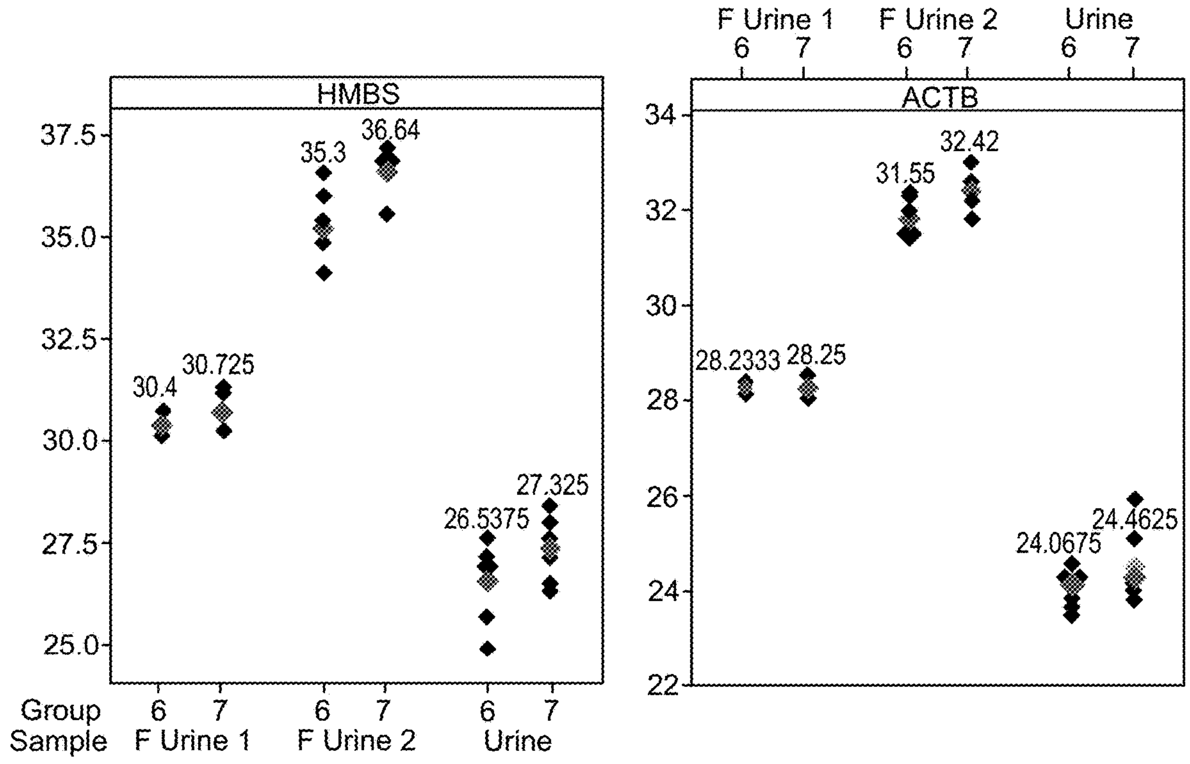
FIG. 36 shows the results of bisulfite conversion analysis of normal urine samples.
Figure 37:
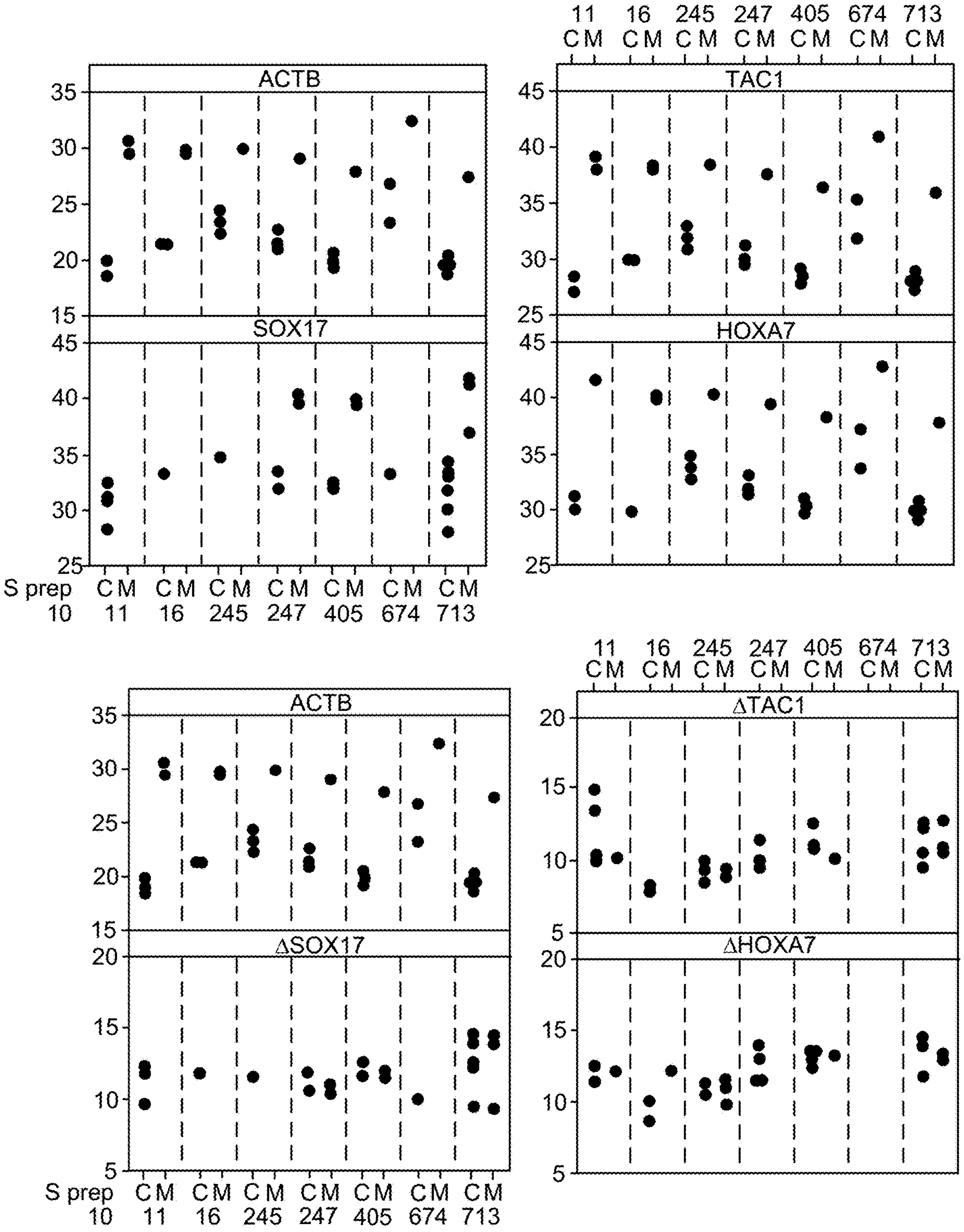
FIG. 37 shows the results of methylation analysis of normal and cancer sputum samples.

By way of illustration, data showing the results of a two-cartridge analysis of urine and sputum samples are shown in FIGS. 35, 36, and 37. In particular, FIG. 35 shows a two-cartridge methylation analysis of BNC1 and ACTB. 0, 25, 50, and 100 copies of 100% methylated control DNA was spiked into serum and processed in the 1st sample prep cartridge (see, e.g., Table 9), and then qPCR was run on the extracted, converted DNA sample in the second cartridge (see, e.g., Table 10) containing primer and probe sets for the methylated BNC1 promoter and a methylation independent primer and probe set for the ACTB promoter.

FIG. 36 shows the results of bisulfite conversion analysis of normal urine samples. 2.0 mL of normal urine was mixed with 1.5 mL of Lysis Buffer [4.5M GTC, 1% Tween20] and 0.5 mL of Ethanol in Condition #6. 1.5 mL of normal urine was mixed with 1.25 mL of Lysis Buffer and 1.25 mL of Ethanol in Condition #7. The 4.0 mL samples were pipetted into Chamber 2 of the methylation analysis cartridge 2 and analyzed for converted ACTB (right) and unconverted HMBS (left).

FIG. 37 shows the results of methylation analysis of normal and cancer sputum samples. Seven sputum samples were tested for SOX17, TAC1, and HOXA7 methylation using the GENEXPERT® methylation cartridge (C) and a comparative assay (M). Both raw Ct's and a deltaCt (to ACTB) are reported in this figure.

The foregoing configurations are illustrative and non-limiting. Using the teaching provided herein numerous other two-cartridge formats will be available to one of skill in the art.

cfDNA Sample Preparation Cartridge.

Figure 17:
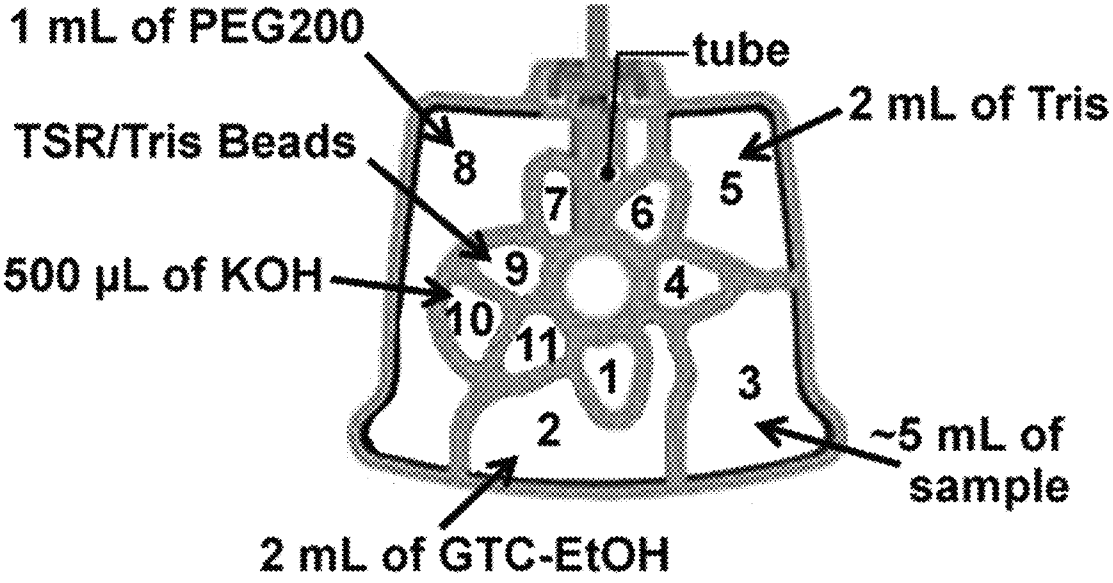
FIG. 17 illustrates one embodiment of a cfDNA sample preparation cartridge. The cartridge is effective for both DNA and RNA isolation. The cartridge provides three GTC-ethanol washes (GTC-ethanol washes are typically 1.25M guanidinium thiocyanate, 25 mM Tris pH 7.0, 50% ethanol), a PEG200 rinse, and a 15 mM KOH elution.

In certain embodiments a sample preparation cartridge is provided that is articular well suited to the preparation (and optional analysis) of nucleic acids from plasma or serum is provide. One illustrative, but non-limiting embodiment is shown in FIG. 17. As illustrated therein in certain embodiments the cartridge comprises a channel or chamber comprising an affinity matrix that binds DNA, a plurality of chambers disposed around a central valve assembly and selectively in fluid communication with the central valve assembly where the central valve assembly is configured to accommodate a plunger that is capable of drawing fluid into or out of a chamber in fluid communication with the central valve where the plurality of chambers comprises: a chamber configured to receive up to about 5 ml or up to about 4 ml of sample solution; a chamber containing PEG (e.g., PEG200); a chamber containing GTC-EtOH; a chamber containing an alkaline solution (e.g., KOH); and a chamber containing a buffer (e.g., Tris). In certain embodiments the plurality of chambers further comprises a chamber containing a conversion reagent (e.g., a bisulfite reagent). In certain embodiments the plurality of chambers comprises a chamber containing a wash solution (e.g., GTC-ethanol wash (typically 1.25M guanidinium thiocyanate, 25 mM Tris pH 7.0, 50% ethanol)). In certain embodiments the plurality of chambers comprises a chamber containing beads comprising one or more PCR primers and/or probes. In certain embodiments the chamber containing PEG contains about 1 ml of PEG. In certain embodiments the chamber containing an alkaline solution contains about 500 μL of solution. In certain embodiments the chamber containing GTC-EtOH contains about 2 ml GTC-EtOH. In certain embodiments the chamber containing a buffer contains about 2 mL of buffer.

It will be recognized that this configuration is illustrative, and using the teaching provided herein numerous other preparation cartridge configurations will be available to one of skill in the art.

Use of DABSO as an Alternative to Bisulfite

It was a surprising discovery that DABSO can be used to perform a conversion of DNA in a manner analogous to the use of bisulfites for the conversion of DNA and detection of methylation. Accordingly, in certain embodiments, methods of utilizing DABSO to converting cytosine residues in a DNA to uracil, while leaving 5-methylcytosine residues substantially unaffected are provided. In certain embodiments the methods involve contacting a sample comprising DNA with DABSO to convert the DNA, and desulphonating the converted DNA, to produce a DNA in which cytosine residues are converted to uracil, but 5-methylcytosine residues substantially unaffected. In certain embodiments the DABSO is provided at a concentration ranging from about 2 M up to about 5 M. In certain embodiments the DABSO is provided at a concentration of about 2.5 M. In certain embodiments the DABSO is dissolved in an alkaline aqueous solution (e.g., a KOH solution). In certain embodiments the reagent comprising DABSO comprises DABSO dissolved in a solution comprising KOH.

In certain embodiments the methods involve heating the DABSO/DNA solution to a temperature ranging from about 55° C. to about 90° C. In certain embodiments the DABSO is reacted with the DNA for a period of time ranging from about 15 minutes up to about 90 minutes. After the DNA is converted, it is desulphonated (e.g., by contacting the converted DNA with an alkaline reagent (e.g., KOH solution). In certain embodiments the conversion and/or desulphonation is performed on the DNA bound to a column, while in other embodiments the conversion and/or desulphonation is performed on the DNA in solution.

Also provided are methods of analyzing DNA methylation, where the methods involve providing a DNA sample, converting DNA in the sample using a DABSO reagent, e.g., as described above, and performing methylation specific PCR and/or nucleic acid sequencing, and/or high resolution melting analysis (HRM) on the converted nucleic acid to determine the methylation of said nucleic acid. In certain embodiments the providing of a DNA sample comprises preparing a sample as described herein (e.g., using lysis solutions and/or preparation cartridges as described herein.

Kits.

Kits for Methylation Detection.

In certain embodiments kits are provided for performing the methods described herein. In one illustrative embodiment, the kits comprise a container containing a reaction cartridge as described herein, a container containing a sample processing reagent as described herein, and a container containing a conversion reagent (e.g., a bisulfite reagent) as described herein. In certain embodiments the bisulfite reagent is provided in a chamber of the cartridge. In certain embodiments the bisulfite reagent is provided in a container separate from the cartridge. In certain embodiments, the sample processing reagent is provided in a chamber of the cartridge. In certain embodiments, particularly where the sample processing reagent comprises guanidinium thiocyanate the sample processing reagent is provided in a container separate from the cartridge.

In certain embodiments the kits can contain the cartridges for a two-cartridge set as described herein. Thus, in certain embodiments the kits can contain a "first" cartridge that is a sample preparation cartridge configured to prepare a sample and perform a bisulfite conversion of DNA in the sample (see, e.g., FIG. 20B, left panel) and a "second" cartridge configured to desulphonated the converted DNA and, in certain embodiments, perform a subsequent analysis (e.g., methylation-specific PCR) (see, e.g., FIG. 20B, right panel). In certain embodiments the first cartridge and the second cartridge are provided in separate containers in the kit, while in other embodiments, the first cartridge and second cartridge are provided in the same container. In certain embodiments the two-cartridge kits can contain devices (e.g., funnels, pipette tips, etc.) to facilitate transfer of a sample from the sample removal chamber of the first cartridge to the sample receiving chamber of the second cartridge.

In addition, the kits optionally include labeling and/or instructional materials providing directions (i.e., protocols)

for the use of the cartridges described herein to determine DNA methylation and, optionally, RNA expression.

In certain embodiments a kit for the determination of DNA methylation is provided where the kit comprises a container containing a cartridge for determining the methylation state of a nucleic acid as described herein. In certain embodiments the kit further comprises a lysis solution as described herein (e.g., a lysis solution for serum or plasma, e.g., as described in Table 13, and/or a lysis solution for FFPE samples, e.g., as described in Table 14). In certain embodiments the kit comprises a container containing proteinase K. In certain embodiments the kit contains a conversion reagent (e.g., a bisulfite reagent) in the cartridge or in a container separate from the cartridge. In certain embodiments the separate container can contain a pre-measured volume of conversion reagent suitable for one "run" of the cartridge. In certain embodiments the conversion reagent comprises a compound selected from the group consisting of sodium metabisulfite, potassium bisulfite, cesium bisulfite, ammonium bisulfite, and DABSO. In certain embodiments the kit comprises a container containing a sample processing reagent. In certain embodiments the sample processing reagent comprises guanidium thiocyanate and/or ethanol.

In various embodiments the kit can additionally contain a cartridge for sample preparation as described herein (e.g., as illustrated in FIG. 20).

In certain embodiments the kit contains instructional materials teaching the use of a cartridge for the determination of DNA methylation. Where a sample preparation cartridge is included in the kit the kit can additionally contain instructional materials teaching the use and operation of the sample preparation cartridge.

Kits for DABSO DNA Conversion and Methylation Detection.

In certain embodiments kits are provided for the use of DABSO as a conversion reagent, e.g., in the detection of the methylation state of a DNA. In certain embodiments the kits comprise a container containing a conversion reagent comprising DABSO, and a container containing a desulphonation reagent. In certain embodiments the kit comprises a column comprising an affinity matrix (e.g., a silica matrix material). In certain embodiments the kits comprise a container containing a binding buffer and/or a container containing an elution buffer. In certain embodiments the kit comprises a container containing a wash buffer.

In certain embodiments the kit further comprises a lysis solution as described herein (e.g., a lysis solution for serum or plasma, e.g., as described in Table 13, and/or a lysis solution for FFPE samples, e.g., as described in Table 14). In certain embodiments the kit comprises a container containing proteinase K.

In various embodiments the kit can additionally contain a cartridge for sample preparation as described herein (e.g., as illustrated in FIG. 20).

In certain embodiments the kit contains instructional materials teaching the use of the kit to convert a nuclei acid for determination of the methylation state of the nucleic acid.

While the instructional materials in the kits described above typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

To validate the method human genomic DNA (HGDNA) was used as a starting sample to monitor sample preparation, bisulfate conversion, sample cleanup, and methylation specific qPCR in a Cepheid GENEXPERT® cartridge. In order to measure bisulfite conversion efficiency, half of the DNA-bisulfite mix was loaded and heated in the 50 μL cartridge tube during the bisulfite conversion step. Therefore, under optimal conversion conditions approximately half of the HGDNA is converted and the other half remains unconverted.

Primers and Taqman probes for the qPCR step were designed for one unconverted gene (HMBS (hydroxymethylbilane synthase housekeeping gene)) and one converted gene (ACTB (beta actin)), and the conversion efficiency was then quantitated by comparison of cycle threshold values (Cts). Both ACTB and HMBS are commonly used as single or low copy reference genes, and thus we expect similar copy numbers per ng of HGDNA.

Figure 5:
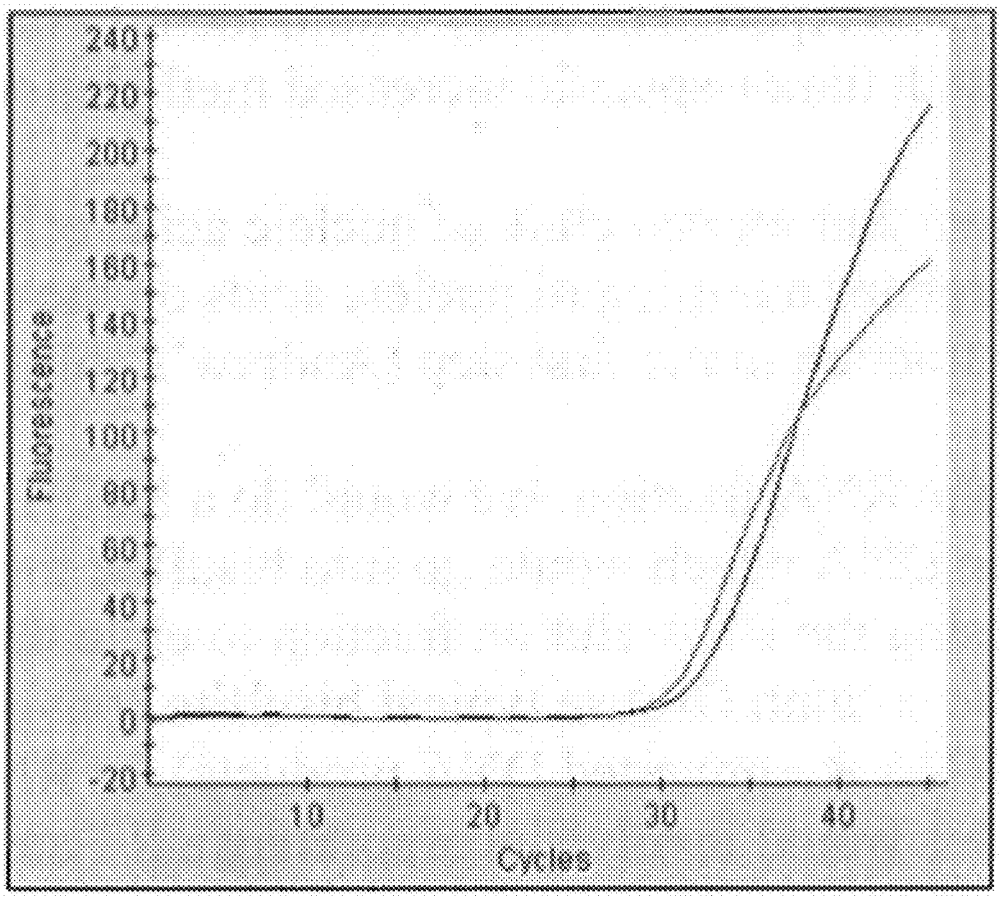
FIG. 5 illustrates results from a representative GeneXpert run from 300 ng of HGDNA showing an ACTB qPCR curve and an HMBS qPCR curve.

A representative GENEXPERT® run from 300 ng of HGDNA is shown below in FIG. 5, with the ACTB qPCR curve in green and the HMBS qPCR curve in blue. The qPCR reaction was run for 45 cycles with a 3 temperature cycle of 96° C. for 5 seconds, 60° C. for 15 seconds, and 72° C. for 15 seconds. At a manual threshold setting of 20 fluorescence units we observed a Ct of 31.7 for the converted ACTB gene and a Ct of 32.7 for the unconverted HMBS gene. Importantly, this result demonstrates that we are able to achieve near-optimal bisulfite conversion efficiency of HGDNA in our cartridge at physiological relevant concentrations of DNA found in FFPE tissue slices and plasma/serum samples. Further specificity for fully converted sequences can be achieved through a nested qPCR reaction or by heating the entire sample. However, neither option would be absolutely required for methylation specific qPCR in the GENEXPERT® because primer and probe sets are designed to amplify only the converted sequences. Thus remaining unconverted DNA sequences would act as carrier DNA, which notably is frequently added during bisulfite conversion, DNA isolation, and PCR methods.

Example 2

Figure 6A:
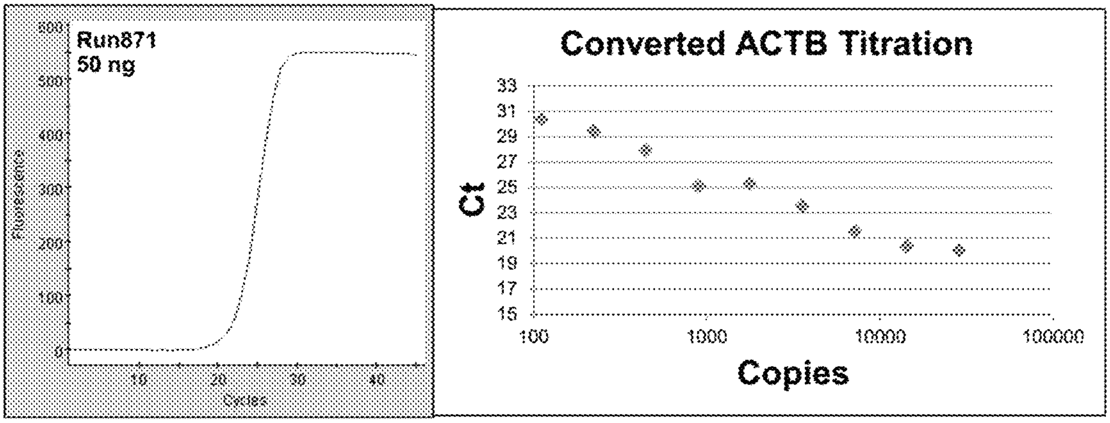
FIGS. 6A and 6B illustrate the results of a titration for bisulfate-converted ACTB using human genomic DNA (hgDNA) in a 15 cycle nested qPCR (FIG. 6A) and a 20 cycle nested qPCR (FIG. 6B).
Figure 6B:
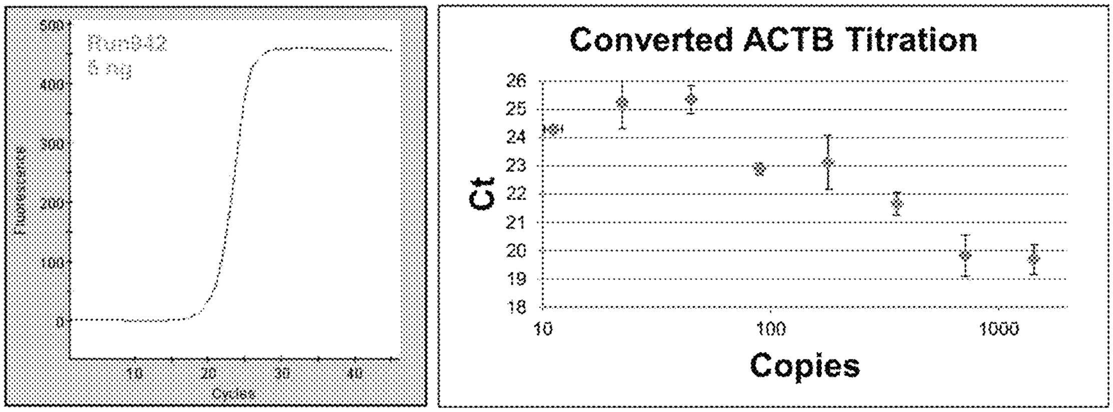

FIGS. 6A and 6B show the linearity of converted ACTB. In particular, FIG. 6A shows the results of a 15 cycle nested qPCR for ACTB using hgDNA. As can be seen from the panel on the right the signal (Ct value) is substantially linear between about 25,000 copies and about 100 copies. FIG. 6B shows the results of a 20 cycle nested qPCR for ACTB using hgDNA. These plots demonstrate the sensitivity of the cartridge for hgDNA. Dropouts start occurring around 20-50 copies with a sensitivity of about 25 copies of converted DNA.

Figure 7A:
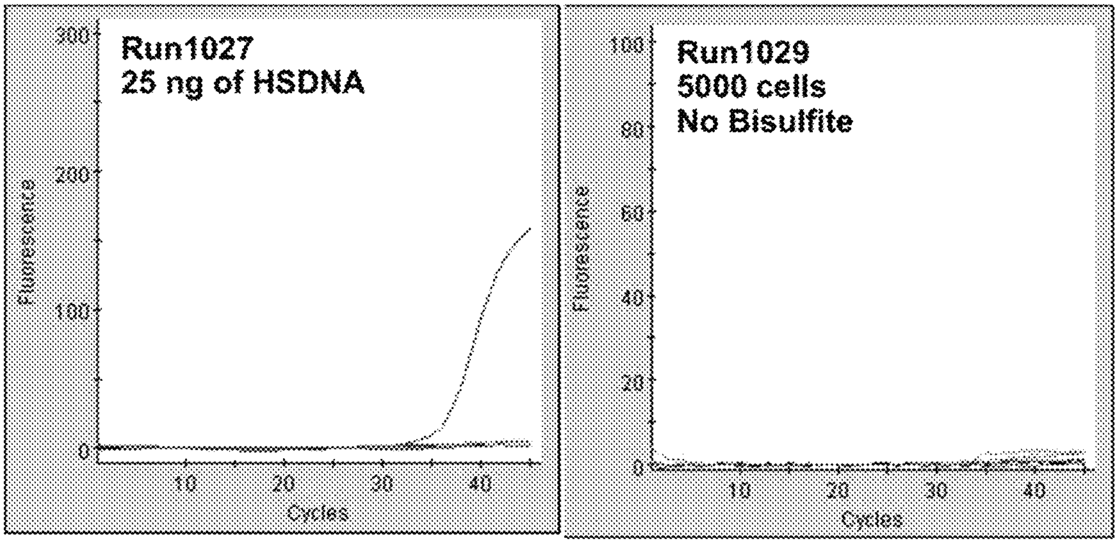
FIGS. 7A-7C shows the result of 20 cycles of nested qPCR (in the cartridge) for six methylated targets (AKR1B1, HOXB4, TM6SF1, RAASGRF2, and RASSF1A).
Figure 7B:
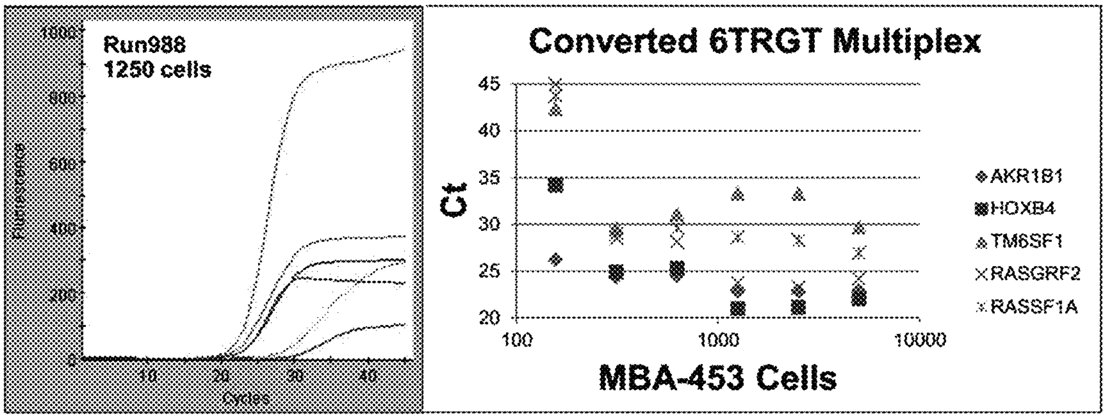
Figure 7C:
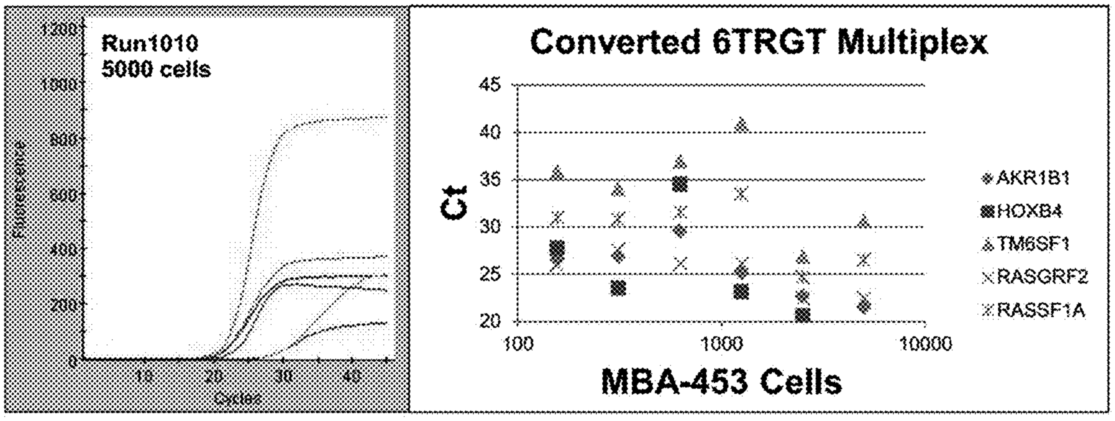

FIGS. 7A, 7B, and 7C show the results of qPCR for six methylated targets (AKR1B1, HOXB4, TM6SF1, RASGRF2, and RASSF1A). FIG. 7A show the results of 20 cycle nested qPCR for controls (25 ng of HSDNA, and 5000 MBA-453 cells whose DNA is not bisulfite-converted). FIG. 7B shows the results of 20 cycle nested qPCR for the six methylated targets using DNA from MBA-453 cells that has been bisulfite converted. A strong signal is shown for all targets. HIST1H3C was not reliably detected. FIG. 7C shows the results of 20 cycle nested qPCR for the six methylated targets using DNA from MBA-453 cells that has been bisulfite converted and is in a carrier comprising 1 µg of SS and 10 ng of HS DNA. Dropouts were observed at about 100 cells and below, however, with the carrier, there were significantly fewer dropouts.

Example 3

Figure 8:
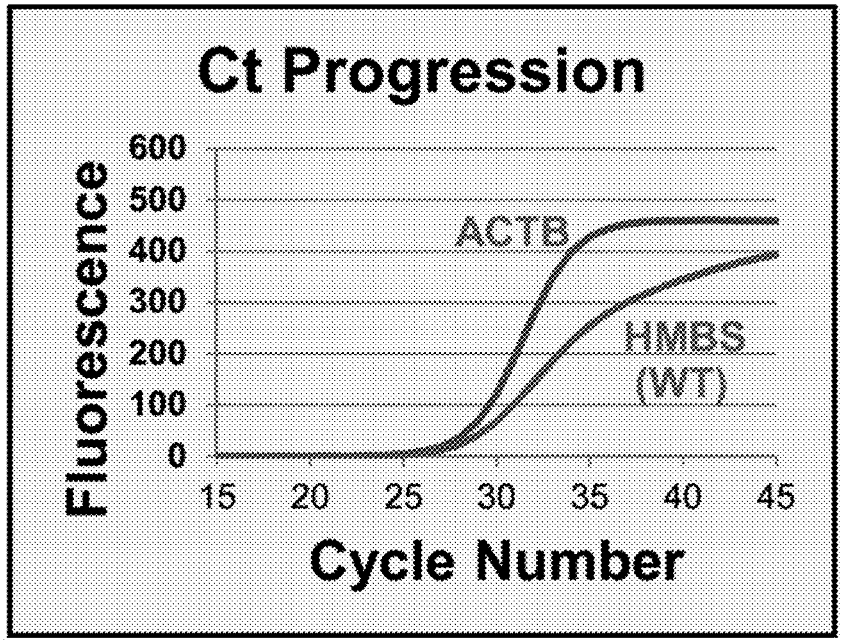
FIG. 8 illustrates the results of a determination of conversion efficiency. The conversion efficiency is about 66% (~1 Ct) the difference between unconverted HMBS and converted ACTB.

FIG. 8 illustrates the results of a determination of conversion efficiency. The conversion efficiency is about 66% (~1 Ct) the difference between unconverted HMBS and converted ACTB. Ideal Ct with 100% binding/elution, 100% conversion, and 100% binding elution is about 24-25. The experiments appear to show a 50% binding/elution, 50-66% conversion, and 50% binding/elution for a 10-fold reduction and a Ct of about 27.

Figure 9:
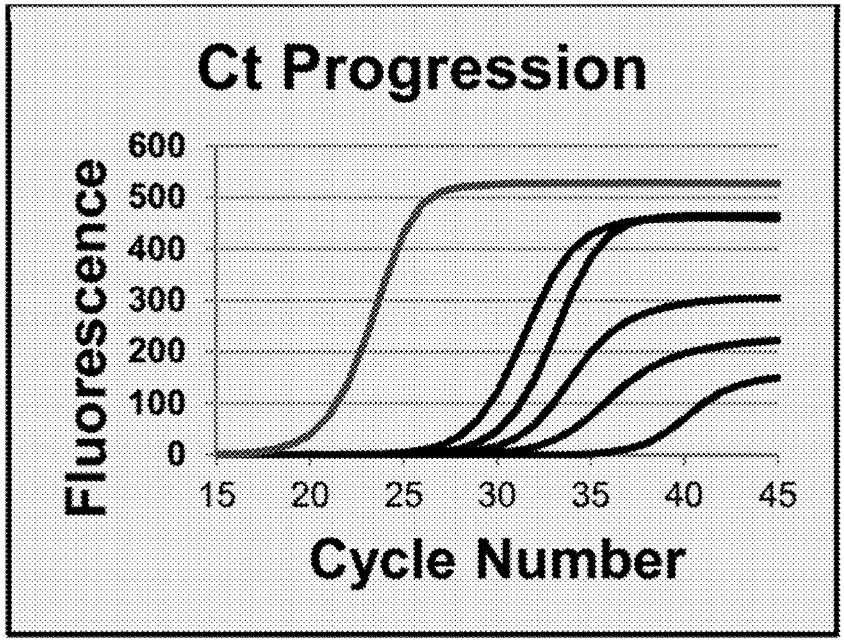
FIG. 9 illustrates the increase in specificity for converted DNA produced by nested qPCR.

FIG. 9 illustrates the increase in specificity for converted DNA produced by nested qPCR. Nested PCR appears to increase the specificity for converted DNA, to increase the specificity for methylated DNA and to reduce contamination issues.

Figure 10:
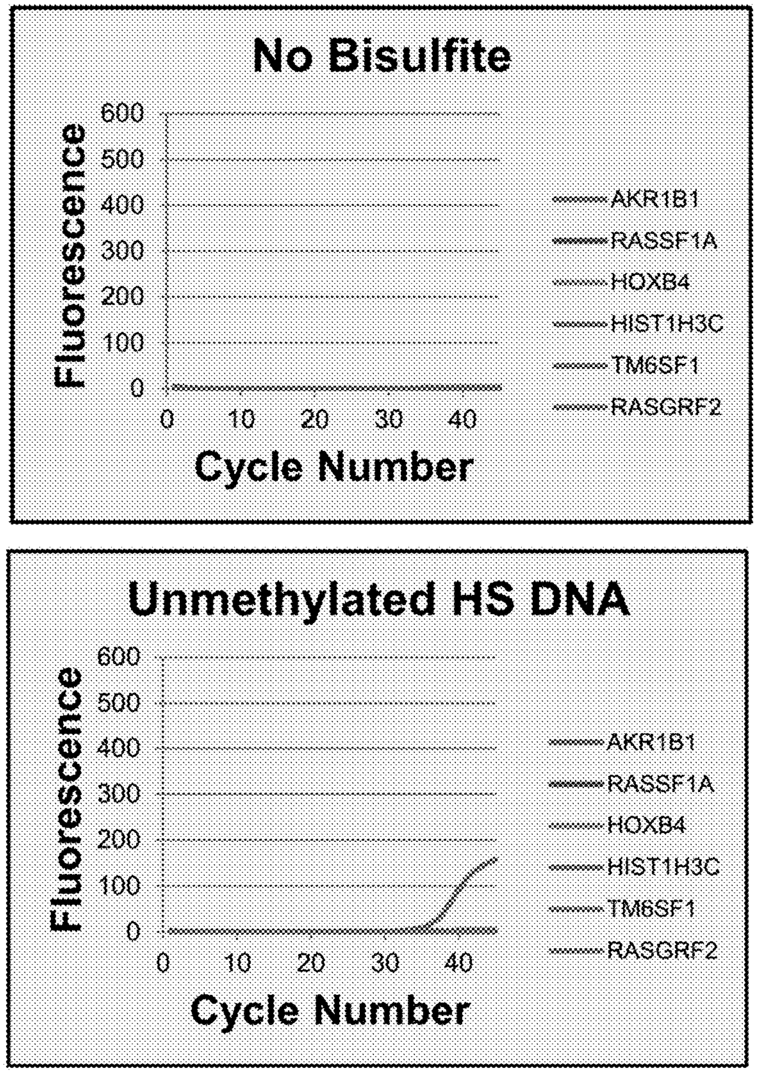
FIG. 10 illustrates the specificity of the methylation cartridge. There is no priming off of unconverted DNA (top panel) or unmethylated DNA (bottom panel) except for HIST1H3C.

FIG. 10 illustrates the specificity of the methylation cartridge. No specificity is shown for unconverted DNA (top panel) or unmethylated DNA (bottom panel) except for HIST1H3C.

FIGS. 11A and 11B show some illustrative but non-limiting workflows for analysis of methylation using a cartridge (e.g., a GENEXPERT® cartridge). FIG. 11A illustrates one work flow for analysis of DNA methylation in a serum sample. As illustrated in this workflow, serum is added to a lysis reagent vial and mixed/vortexed. The sample is then dispensed into a sample port in the cartridge. The cartridge is placed in the system for analysis.

FIG. 11A illustrates one work flow for analysis of DNA methylation in a tissue section (e.g., frozen or formalin-fixed paraffin embedded (FFPE) section). As shown therein, in one embodiment, a tissue section (e.g., a 4 µm FFPE section) is provided. FFPE lysis reagents are added (see, e.g., PCT/US2013/061863 (WO/2014/052551 for illustrative lysis reagents) and the mixture can be heated. Ethanol can be added and the mixture vortexed. The sample is then dispensed into a sample port in the cartridge. The cartridge is placed in the system for analysis.

Figure 12:
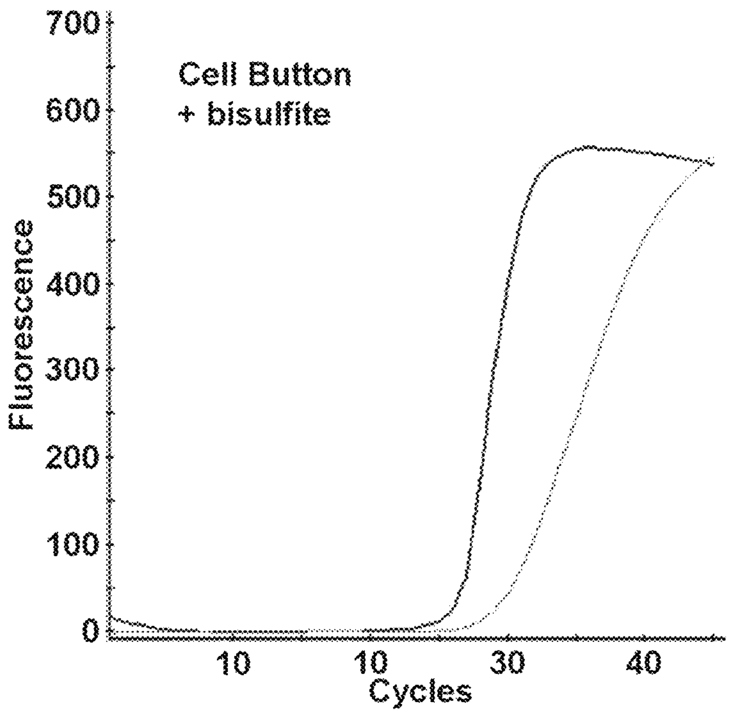
FIG. 12 illustrates the results for a FFPE cell button for converted ALU (left-most curve) and methylated RASSF1A (right-most curve).

FIG. 12 illustrates the results for a FFPE cell button for converted ALU and methylated RASSF1A.

Example 4

Detection of Markers for Breast Cancer Monitoring

Materials and Methods:

Either 1000 MBA-453 cells or 25 ng of human sperm (HS) DNA were added to 2.5 mL of binding buffer (2.25 M Guanidinium thiocyanate, 22.5 mM Tris pH 7.0, 0.5% Tween20, 50% Ethanol, and 0.005% SE-15 antifoam). The 2.5 mL solution of cells or DNA was added to chamber 2 of the Cepheid methylation cartridge (layout in FIG. 13A). The remaining chambers in the methylation cartridge were filled as follows: Chamber 3—3.2 mL of Wash buffer (1.25M Guanidinium thiocyanate, 25 mM Tris pH 7.0, 50% Ethanol), Chamber 4—90 µL of 7M Ammonium Bisulfite, Chamber 5—4 mL of 50 mM Tris pH 8.5, Chamber 8—1 mL of PEG200 Rinse, Chamber 9—quantitative PCR beads including EZR (Taq) and TSR (6 target breast cancer multiplex for RASSF1A, AKR1B1, HOXB4, HIST1H3C, RASGRF2, TM6SF1, see Table 11, below), Chamber 10—500 µL of 15 mM KOH, and Chamber 11—nested beads including EZR (Taq) and TSR (6 target breast cancer multiplex for RASSF1A, AKR1B1, HOXB4, HIST1H3C, RASGRF2, TM6SF1). The methylation cartridge was then loaded into a Cepheid GeneXpert and the entirety of the methylation assay was completed by the GeneXpert—the first DNA sample prep, the bisulfate conversion, the second post conversion DNA sample prep, the desulphonation, and the 20 cycle nested and quantitative PCR reactions.

A flow chart illustrating the methylation protocol is shown in FIG. 13B. It is noted that the PEG200 was filled in the waste chamber 8, and after the assay starts the PEG200 is dispensed into Chamber 1. The PEG200 is a viscous liquid that cannot easily be directly loaded in the smaller chamber 1. Additionally, chamber 1 acts as an air chamber when the cartridge is first loaded before becoming the PEG200 chamber. Thus, the assay begins with Chamber 1=air and Chamber 8=PEG200 and is quickly switched to Chamber 1=PEG200 and Chamber 8=Waste after cartridge loading.

The numbers shown in the “Initial Vol.” column of FIG. 13A just refer to liquid volumes. In this case there are just 2× beads in chamber 11—1× TSR bead (primer and probes for the 6 targets) and 1×EZR bead (Phoenix Taq). These beads are for the final qPCR reaction. Similarly, there are 3× beads in chamber 9—1×TSR bead (primers for the 6 targets), 1× Tris bead (to quench KOH) and 1×EZR bead (Phoenix Taq). These beads are for the first 15-20 cycle PCR reaction.

It is also noted that Chamber 6 is an air chamber throughout the entire assay and is never filled. Chamber 7 is used as sort of a gateway to the PCR tube in the back of the cartridge. It is not filled to start the assay but is filled during the assay on 3 occasions before loading into the tube—1) the DNA-bisulfite mix that is heated in the tube for conversion 2) the 15-20 cycle PCR reaction and 3) the final qPCR reaction.

The primers shown in the Table 11 provided shows five sequences for each gene—two extension primers and 2 qPCR primers for each nested amplification and one probe. The first 15-20 cycle PCR reaction was not specific for methylation but only the converted DNA sequences (i.e., they do not cross CpGs and in a couple instances when they do we use an R=purine or Y=pyrimidine to catch both methylated and unmethylated). The second 45 cycle qPCR reaction contains both primers and probes that are specific for typically 2-3 methylated CpGs.

Figure 15A:
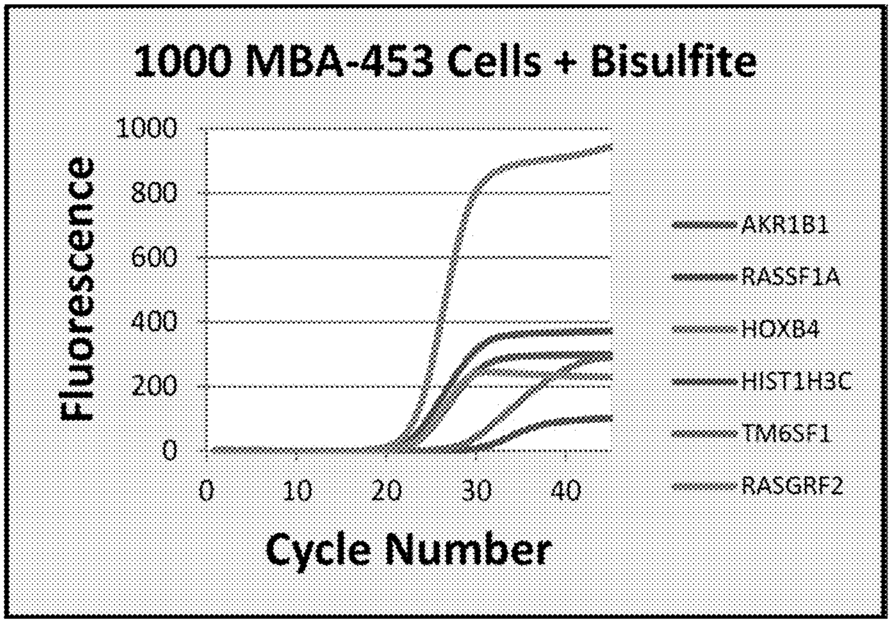
FIG. 15A illustrates the results of 1000 MBA-453 cells with bisulfite conversion (with HOXB4 giving the greatest signal).
Figure 15B:
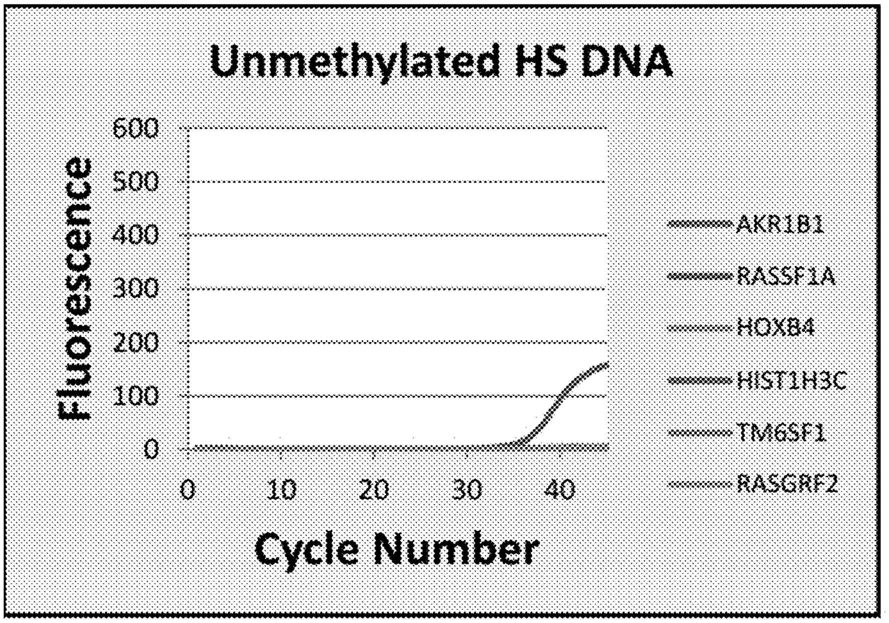
FIG. 15B illustrates results of 25 ng of HS DNA control (with only HIST1H3C showing a detectable signal).

Results:

The methylation cartridge was run using 1000 MBA-453 cells with and without bisulfite (FIGS. 15A-15B) and 25 ng of HS DNA with bisulfite (FIG. 15C) that was primarily unmethylated at each gene promoter with the exception of HIST1H3C. There was little or no amplification of any of the targets in either the no bisulfite or unmethylated HS DNA control reactions (FIGS. 15A, 15C). With the addition of bisulfite, the methylation cartridge picked up high levels of methylation at multiple gene promoters from 1000 MBA-453 cells, specifically AKR1B1, RASSF1A, HOXB4, and RASGRF2.

TABLE 11

Nested primers for R4SSF1A, AKR1B1, HOXB4, HIST1H3C, RASGRF2, and TM6SF1. C*, T* are optionally functionalized (e.g., to alter probe $T_m$) bases.

| Gene/ Probe name | Type | SEQUENCE | SEQ ID NO |
|---|---|---|---|
| RASSF1A | | | |
| olAK61 | ext primer | GTTTTATAGTT(T*)TTGTATTTAGG | 62 |
| olAK41 | ext primer | AACTCAATAAACTCAAACTCCC | 42 |
| olAK1 | qPCR primer | GCGTTGAAGTCGGGGTTC | 2 |
| olAK2 | qPCR primer | CCCGTACTTCGCTAACTTTAAACG | 3 |
| olAK63 | qPCR probe | fluor-(C*)TGGTTTCGT(T-quencher)CGGT(T*)CGCG-quencher/blocker | 64 |
| HIST1H3C | | | |
| olAK60 | ext primer | GGATTTTTGAAATATTATAGGATTAATTAG | 61 |
| olAK43 | ext primer | ATAAAATTTCTTCACRCCACC | 44 |
| olAK59 | qPCR primer | TCGTACGAAGTAAATAGTTCGTAAG | 60 |
| olAK54 | qPCR primer | CCGATAACCGAAACGCTCTTAC | 55 |
| olAK65 | qPCR probe | fluor-CAAACTACTTACGCGAAACTT(T*)ACCGCC-quencher/blocker | 66 |
| RASGRF2 | | | |
| olAK44 | ext primer | GAGGGAGTTAGTTGGGTTAT | 45 |
| olAK45 | ext primer | CCTCCAAAAAATACATACCC | 46 |
| olAK13 | qPCR primer | GTAAGAAGACGGTCGAGGCG | 14 |
| olAK14 | qPCR primer | ACAACTCTACTCGCCCTCGAA | 15 |
| olAK67 | qPCR probe | fluor-AAACGAACCACTTCTCG(T*)ACCAACGAC-quencher/blocker | 129 |
| AKR1B1 | | | |
| olAK58 | ext | GYGTAATTAAT(T*)AGAAGGTTTTTT | 59 |
| olAK47 | ext | AACACCTACCTTCCAAATAC | 48 |
| olAK19 | qPCR | GCGCGTTAATCGTAGGCGTTT | 20 |
| olAK20 | qPCR | CCCAATACGATACGACCTTAAC | 21 |
| olAK75 | qPCR | fluor-(C*)A(C*)GCGTACCT(T-quencher)TAAA(T*)AACCCG(T*)AAAATCG-quencher/blocker | 76 |
| HOXB4 | | | |
| olAK48 | ext primer | TTAGAGGYGAGAGAGTAGTT | 49 |
| olAK49 | ext primer | AAACTACTACTAACCRCCTC | 50 |
| olAK25 | qPCR primer | CGGGATTTTGGGTTTTCGTCG | 26 |
| olAK26 | qPCR primer | CGACGAATAACGACGCAAAAAC | 27 |
| olAK76 | qPCR probe | fluor-AACCGAACGA(T*)AACGAAA(N*)ACGACGAA-quencher/blocker | 77 |
| TM6SF1 | | | |
| olAK50 | ext primer | AGGAGATATYGTTGAGGGGA | 51 |
| olAK51 | ext primer | TCACTCATACTAAACCRCCAA | 52 |

TABLE 11-continued

Nested primers for R4SSF1A, AKR1B1, HOXB4, HIST1H3C, RASGRF2, and TM6SF1. C*, T* are optionally functionalized (e.g., to alter probe $T_m$) bases.

| Gene/ Probe name | Type | SEQUENCE | SEQ ID NO |
|---|---|---|---|
| olAK56 | qPCR primer | GTTTAGCGGGATGCGGTG | 57 |
| olAK57 | qPCR primer | ACACGAAAACCCCGATAAC | 58 |
| olAK77 | qPCR probe | fluor-AAACACTCATCGCAACCGCCGCG-quencher/blocker | 34 |

The primers shown in Table 11 are illustrative and not limiting. Numerous other primers and nested primer sets will be available to those of skill in the art. By way of example, illustrative primers for the detection of methylation of ADAMTS1 and BNC1 genes associated with pancreatic cancer and for the detection of methylation of the MGMT gene associated with glioma are shown in Table 12.

TABLE 12

Illustrative primers for the detection of methylation of ADAMTS1 and BNC1 genes associated with pancreatic cancer and for the detection of methylation of the MGMT gene associated with glioma.

| Gene/ Probe name | Type | SEQUENCE | SEQ ID NO |
|---|---|---|---|
| BNC1 | ext | CCCRCAAACCRCGAAAACCTC | 227 |
| | ext | CCGACGACCGACG | 235 |
| | qPCR | GTTTTTTTTYGGGAGAGGTAAATA | 228 |
| | qPCR | GGGAGAGGTAAATATCGATAC | 236 |
| | qPCR | fluor-TGGYGGGGG(T*)AGA(T*) ATTTT-quencher/blocker | 389 |
| ADAMTS1 | ext | CRCCTCCRAAACTAAAACAAC | 229 |
| | ext | CGCGAAAATTAATACCTAACG | 237 |
| | qPCR | GGGTTATTGTAAAGTTAGGGTG | 230 |
| | qPCR | TTAGGGTGCGTTATCGGAC | 238 |
| | qPCR | fluor-TCTACTCAAAACTCTCCCCTCT CC-quencher/blocker | 390 |
| MGMT | ext1 | GTTTT(T*)AGAAYG(T*)TTTGYGTTT | 263 |
| | ext2 | AAAAAAC(T*)CCRCACTCTTCC | 265 |
| | qPCR | TTTCGACGTTCGTAGGTTTTCGC | 266 |
| | qPCR | GCACTCTTCCGAAAACGAAACG | 267 |
| | qPCR probe | fluor-CCAAACAC(T*)CACCAAATC(N*)CAA AC-quencher/blocker | 268 |

Example 5

Sample Preparation for Plasma and FFPE Samples

FIG. 17 illustrates one configuration of a cartridge that can be used to prepare DNA samples for PCR and/or methylation detection. The sample, obtained from serum or plasma, or an FFPE sample can simply be introduced into a sample chamber of the cartridge (e.g., chamber 3) and operation of the cartridge as described herein provides a sample ready for PCR and/or methylation detection.

Sample Preparation

In one illustrative, but non limiting embodiment, a serum or plasma sample is prepared (e.g., for analysis of cfDNA) by treating the serum or plasma with proteinase K. Then the proteinase K treated serum/plasma is mixed with a lysis solution comprising guanidinium thiocyanate (GTC), buffer (e.g., Tris pH 7.0), a detergent (e.g., Tween 20), and an optional antifoam (e.g., antifoam SE15). An alcohol (e.g., isopropanol) is added to the solution which is then introduced into the cartridge for sample processing. In one embodiment the lysis solution is formulated as shown in Table 13. The proteinase K treated serum/plasma can be mixed with lysis solution and alcohol in a ratio corresponding to 1.3 mL proteinase K treated serum/plasma, 2.2 mL lysis solution, and 1.5 ml alcohol. In certain embodiments the serum/plasma sample is treated with proteinase K for about 15 minutes. The lysis solution is added cold and held/mixed for about 10 minutes. Then isopropanol is added to the mixture which is then loaded into the cartridge for processing.

As noted above, for serum/plasma the alcohol (e.g., isopropanol) precipitations are typically done at RT, and in particular typically not performed with "salty" solutions. In certain embodiments longer room temperature precipitation times can be used.

TABLE 13

Lysis solution for serum or plasma.

| Reagent | Amount |
|---|---|
| Guanidine thiocyanate (GTC) | 4.5M |
| Buffer (e.g., Tris) pH 7.0 | 45 mM |
| Detergent (e.g., Tween20) | 1% |
| Antifoam SE15 | 0.01% |

In another illustrative, but non-limiting embodiment, a formalin fixed paraffin-embedded (FFPE) sample is prepared by combining the FFPE sample with proteinase K and a lysis solution comprising a buffer (e.g., HEPES), a chelator (e.g., EDTA), NaCl, $MgCl_2$, and optionally sodium azide and/or an antifoaming agent. The solution is heated (e.g., at 70° C. to 90° C.) for a period of time ranging, for example from about 10 minutes up to about 4 hours. An alcohol is added to the solution and the solution is then introduced into the cartridge for sample processing. In one embodiment the lysis solution is formulated as shown in Table 14. In one illustrative, but non-limiting embodiment, 1.2 mL of the lysis solution shown in Table 14 is added to the FFPE section(s). Proteinase K is added and the mixture is heated, e.g. at 80° C. for about 15 minutes. In certain embodiments heating is performed at 56° C. for 2 hours followed by 90° C. for 30 minutes. Then 1.2 mL of ethanol is added to the mixture and the mixture is loaded into a sample chamber of the cartridge for processing.

TABLE 14

| Lysis buffer for formalin fixed paraffin embedded (FFPE) sample. | |
|---|---|
| Tween20 | 1% |
| NaCl | 400 mM |
| EDTA | 25 mM |
| $MgCl_2$ | 10 mM |
| HEPES pH 7.2 | 50 mM |
| Sodium Azide | 0.01% |
| SE15 | 0.01% |

Cartridge Operation and Extraction Performance.

Figure 18:
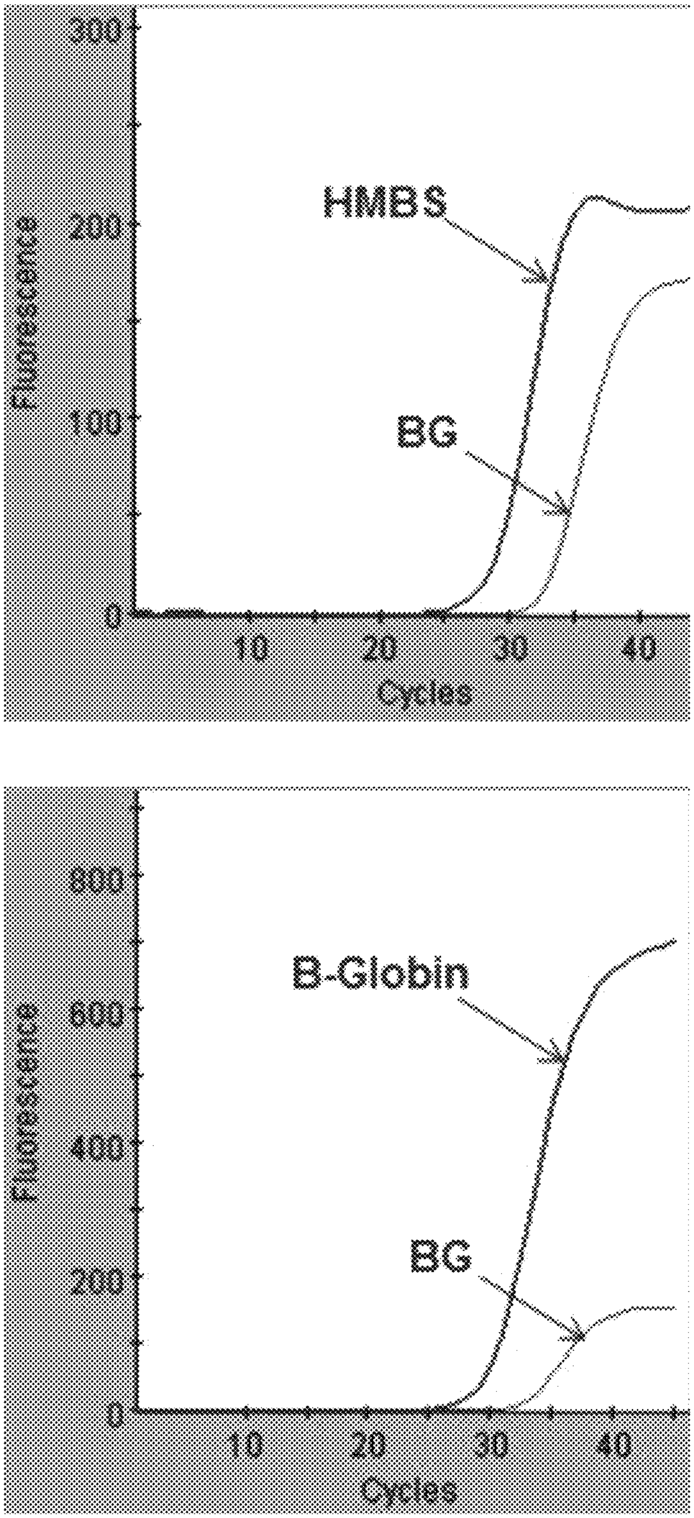
FIG. 18 illustrates controls for cfDNA extraction.

When cfDNA is being prepared, in certain embodiments, it is possible to include extraction controls to permit monitoring of the quality of the DNA preparation. As illustrated in FIG. 18, there are two different bead sets. One bead set contains an endogenous HMBS primer and probe set for a SAC (sample assay control) and exogenous BG primer and probe set for a SPC (sample prep control). The other contains an endogenous Beta-Globin PP set for SAC (as well as BG SPC).

It was discovered, inter alia, that the use of GTC in the cartridge may be less important for serum than plasma samples. Without being bound by a particular theory it is believed that this may be due to the fact that serum contains less protein. Accordingly, in certain embodiments, the cartridge may contain less GTC or may omit GTC.

Figure 19A:
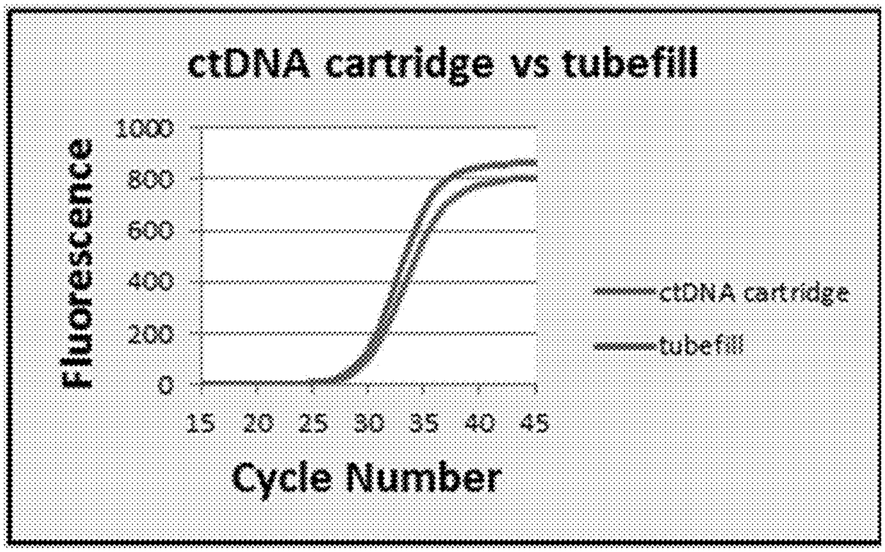
FIG. 19A shows a comparison of cfDNA preparation using a sample preparation cartridge as described herein compared to a standard tube-fill (i.e. tube-based kit) preparation (left-most curve). The cartridge preparation yield is very comparable to that obtained using a tube fill method (right-most curve).
Figure 19B:
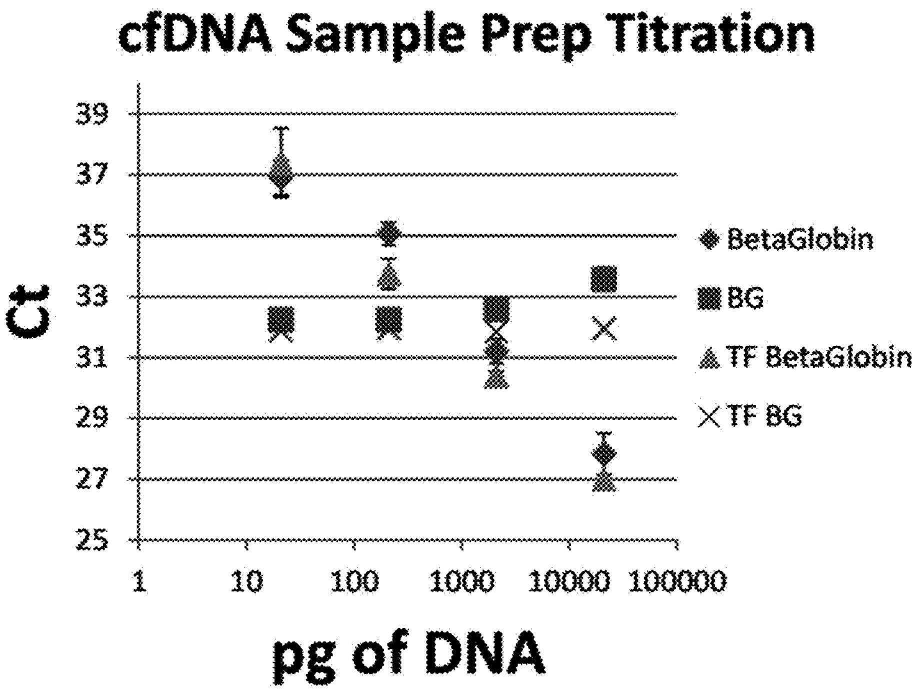
FIG. 19B shows a comparison of the amount of extracted DNA detected using a cartridge-based DNA cleanup as compared to a standard tube-fill as a function of DNA amount. The cartridge-based method is conservatively within 1 Ct of the tube-fill methods and is believed to be closer at higher DNA concentration.

FIGS. 19A and 19B show a comparison of the results of cfDNA preparation performed using a cartridge as described herein compared to the results obtained using a conventional "tubefill" procedure. As illustrated in the qPCR results shown in FIG. 19A, the binding and elution efficiencies obtained using the cartridge are extremely close (within one Ct) to those obtained using the tubefill protocol. As illustrated in FIG. 19B titrations of sample concentrations show that the cartridge preparation is conservatively within 1 Ct of the tubefill preparation down to a sample concentration as low as about 10 pg. It is believe the cartridge preparation is even closer to the tubefill protocol at higher sample concentrations.

Example 6

Testing a High-Volume Sample Preparation Cartridge

In certain embodiments high volume sample preparation (HSVP) cartridges are provided for the preparation of large volumes of sample (e.g., up to about 12 ml to 15 ml). This is particularly useful where the sample contains DNA at a low concentration (e.g., cfDNA in serum or plasma). One such cartridge is schematically illustrated in FIG. 20A. As shown therein the cartridge provides three chambers (chambers 2, 3, and 5) that can be used to receive a sample. In the illustrated embodiment, each of these chambers can receive about 4 mL of sample and, in certain embodiments, the sample comprises 4 mL of plasma/serum combined with 4 mL of GTC and 4 mL of alcohol (e.g., isopropanol).

The sample is introduced into these chambers and the cartridge is operated as described herein to prepare the sample for PCR and/or methylation analysis. By way of illustration, in certain embodiments, operation of this cartridge can comprise binding DNA to an affinity column (e.g., for cleanup) and eluting the DNA. In certain embodiments where a methylation analysis is to be performed, the operation of the cartridge can further comprise combining the DNA with a conversion reagent (e.g., a bisulfate as described herein) and heating the mixture to convert the DNA. In certain embodiments, the HSVP cartridge can also be configured to desulphonates the converted DNA. In other embodiments, the DNA can be desulphonated in the second (e.g., qPCR) cartridge as schematically illustrated in FIG. 20B. The second cartridge can also perform the methylation analysis (e.g. a qPCR analysis).

Figure 21:
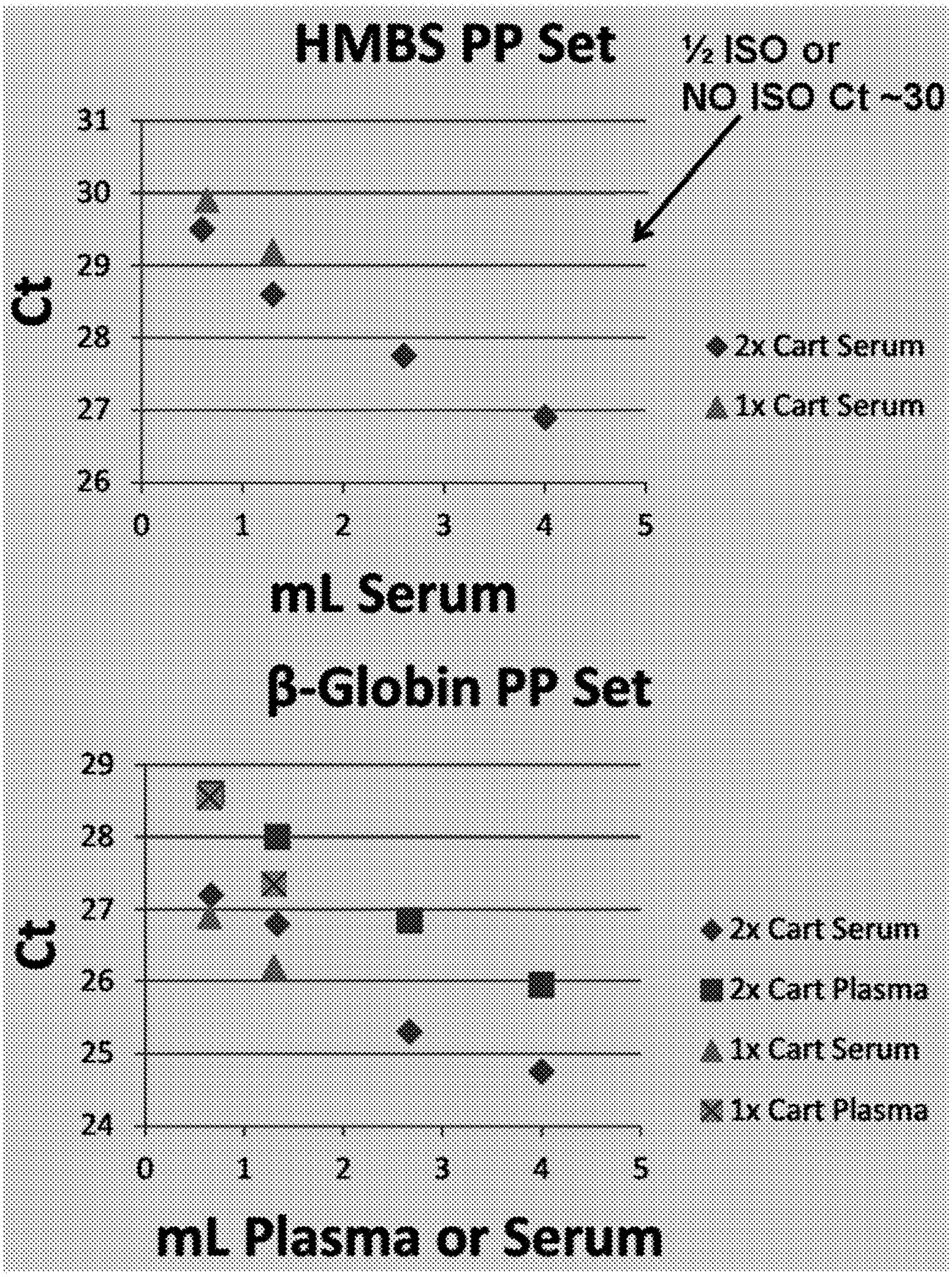
FIG. 21 illustrates the detection of HBMS or β-globin using a two cartridge cleanup using a high-volume sample preparation cartridge (see, e.g., FIG. 20) where the sample is transferred from the high volume cartridge to the PCR analysis cartridge compared to detection using a sample applied to a single PCR analysis cartridge resulting in less sample volume.

FIG. 21 shows a comparison of sample preparation results of DNA from plasma and serum between one cartridge and two cartridge protocols using the HMBS or β-globin primer and probe set. As shown therein, there was a linear increase in DNA recovery between 0.5 mL and 4 mL of serum or plasma. Moreover there was little to no loss when using one cartridge for the preparation and analysis or when using separate cartridges for preparation and analysis/

Example 7

Optimizing Bisulfate Conversion

In certain embodiments when using a cartridge for a methylation analysis as described herein one potential issue is the optimization of elution efficiently using the smallest volume possible. Small elution volumes are easier to deal with using spin columns. This problem can be addressed by using multiple heating steps to process larger sample volumes.

A second technical concern arises when heating a larger sample (e.g., minimum 100 μL) when using a smaller (e.g., 50 μL) heating tube or chamber. In certain instances, pressurizations between heating steps can make it difficult to reproducibly account for volume aspirates and dispenses. Secondly, the absence of pressurization can lead to to volume changes and bubbles especially at higher temperatures. Thirdly, it is possible to pick up air between heated and unheated samples during port changes in between heat steps.

To investigate these optimization of bisulfate conversion in a 50 μL tube using single and double heating steps was investigated. This experiment was performed as follows:

Pull 75-80 μL of bisulfate-DNA; heat 95° C.-10 s, 65° C.-300 s×8;

Pull rest+5-10 μL; pressurize; heat 95° C.-480 s, 65° C.-1800 s×1.

Figure 22:
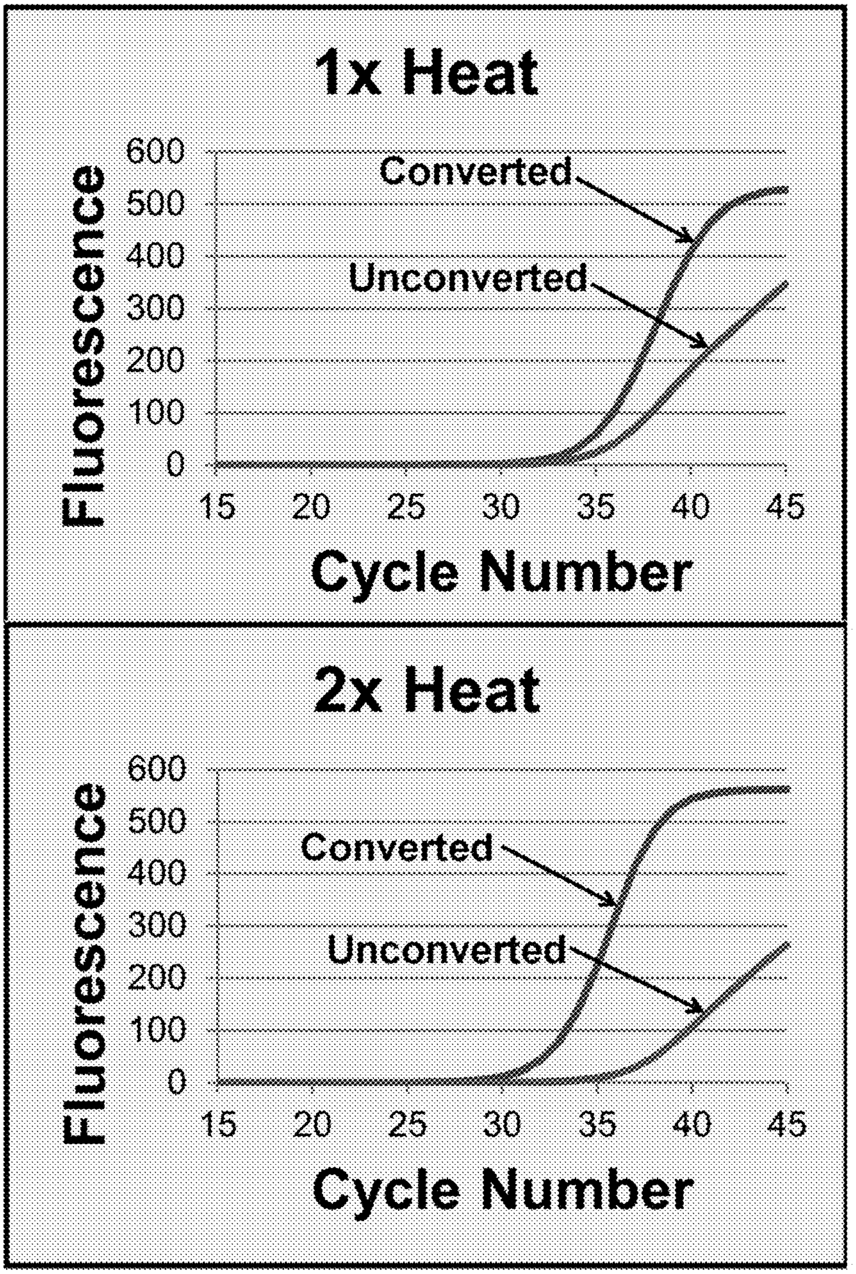
FIG. 22 illustrates the results of bisulfate conversion using multiple heating steps (bottom panel) compared to a single heating step (top panel).

The results for 0.5 mL of serum are shown in FIG. 22 where the top panel is 1× Heat (converted 33.0, unconverted 34.4) N=4, and the bottom panel is 2× Heat (converted 31.9, unconverted 36.1) N=4.

There is a gain of about 1 Ct in the converted ACTB signal when going from 1× heat to 2× heat. This suggests almost all of the DNA is converted. This is supported by the fact that there is also a loss of about 2 Ct's in the unconverted HMBS signal. A 1 Ct increase is logical since we went from heating 50/100 μL to 100/100 μL of DNA-bisulfite sample.

Example 8

Comparison of a DNA Methylation Cartridge with Tube-Based Commercial Kits

Figure 23A:
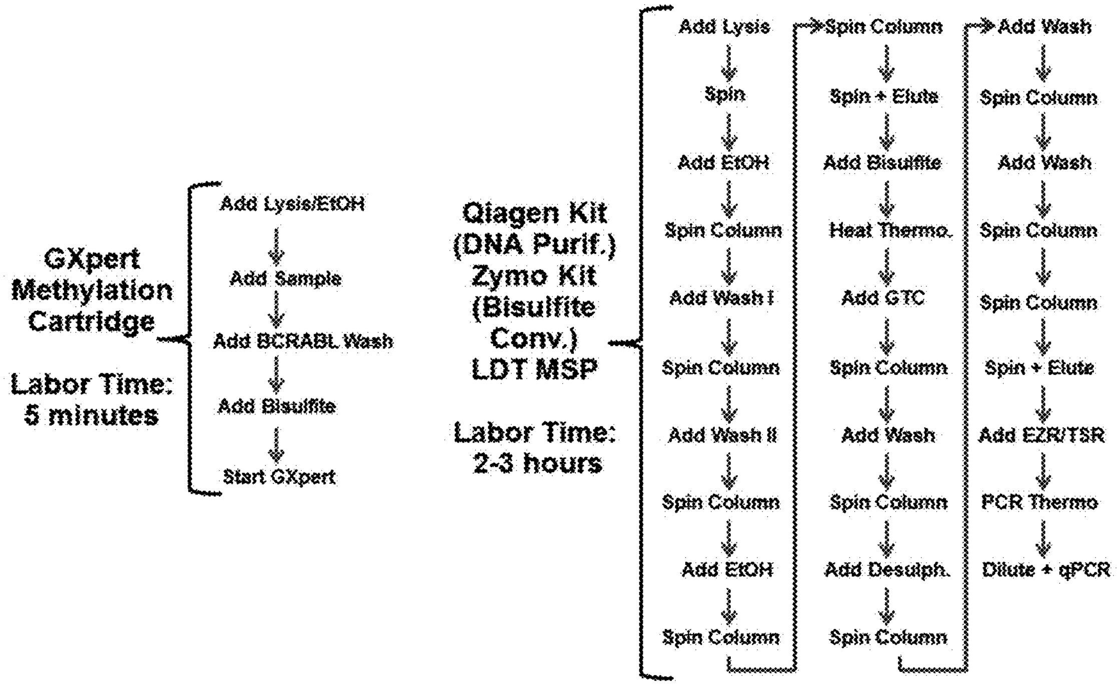
FIG. 23A illustrates the steps and labor time for a methylation analysis using a standard Qiagen DNA purification kit combined with a Zymo DNA methylation kit (right) compared to a methylation analysis using a Methylation analysis cartridge described herein.

FIG. 23A shows a comparison of the user steps required when performing a methylation analysis using cartridge as described herein (left) as compared to the steps required when using commercial kits (QIAamp MinElute Virus Spin Kit (Qiagen, Inc.), and EZ DNA Methylation-Lightning™ Kit (Zymo Research, Inc.)) to perform the same analysis. As can readily be seen the cartridge-based methylation analysis requires far few user steps with a labor time of about 5 minutes as compared to the 2-3 hour labor time required using the kits.

Figure 23B:
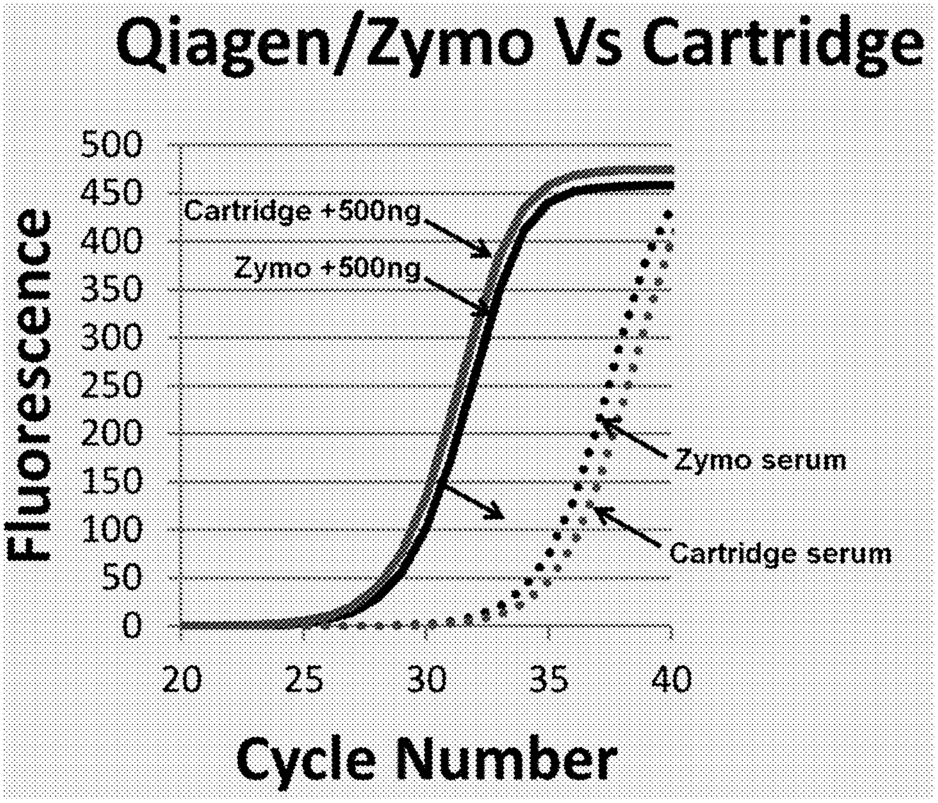
FIG. 23B shows a comparison of the results obtained using the two different protocols.

To compare the results produced by the different methods, 200 μL of serum was purified using the Qiagen kit. The DNA was converted using the Zymo kit, purified with a second spin column and eluted with 10 μL. Ran all 10 μL using converted unmethylated ACTB primers and probes (TSR). In comparison, 200 μL of serum were run in the methylation cartridge as described herein. Results are shown in FIG. 23B. As is readily evident, the cartridge method produced results extremely comparable to those obtained using the commercial kits. However, this was accomplished with far less labor and time.

Example 9

Use of DABSO for DNA Conversion

It was initially attempted to dissolve 5 g DABSO in 5 mL H2O. Ultimately a few mLs of 10M KOH and a mL of water were added and heated to solubilize the DABSO and to raise the pH up to between about pH 5 and pH 5.5 at an estimated final DABSO concentration of ~2.5M.

Figure 24:
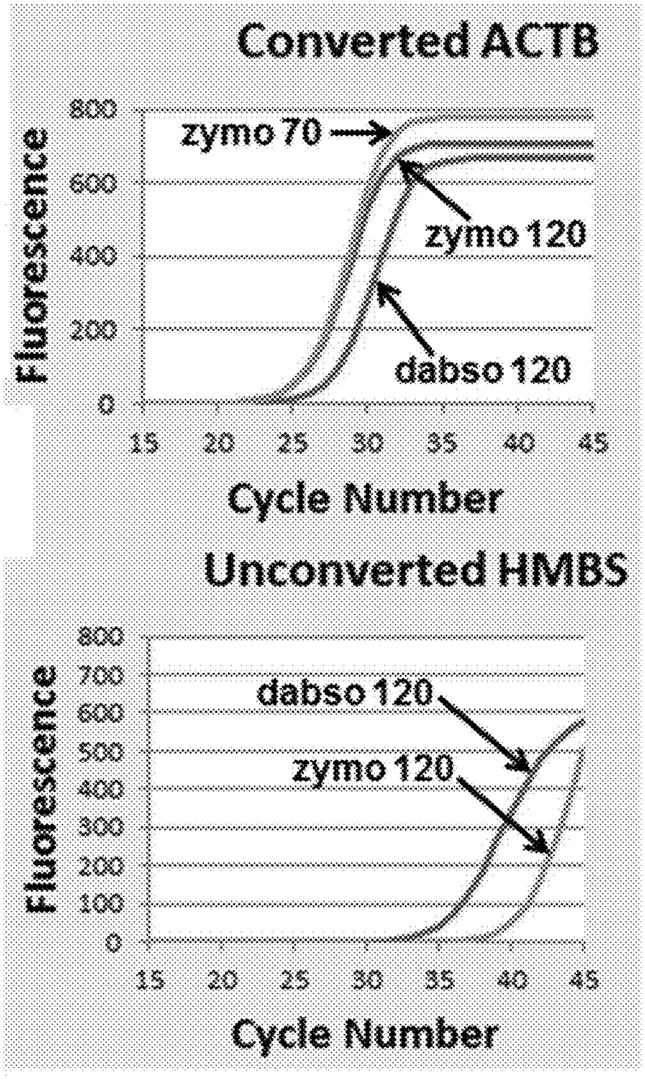
FIG. 24 shows a comparison of DNA conversion using DABSO as the conversion reagent compared to DNA conversion using the Zymo bisulfite conversion reagent.

FIG. 24 shows graphs of tubefills of 750 ng of DNA converted using DABSO or the Zymo conversion reagent. The materials were offboard heated (1 μg) in a thermocycler and purified with spin columns and run as tubefills. The 3 different experiments were:

1) 120 uL DABSO/30 uL DNA;
2) 120 uL Zymo/30 uL DNA; and
3) 70 uL Zymo/30 uL DNA (ratio currently in the cartridge).

As shown in FIG. 24, DABSO provided good conversions almost comparable to those obtained using the Zymo reagent.

Example 10

Sensitivity of Detection of Methylated DNA

To evaluate the sensitivity of detection of DNA methylation, converted ACTB gene promoter was detected as a function of copy number using a cartridge as described herein. The goal was to detect less than 25 copies of converted, unmethylated DNA. As previously shown, fallouts were observed at about 10-50 copies (1 fallout each). Similar sensitivity was observed for methylated DNA targets in a serum background.

Figure 25:
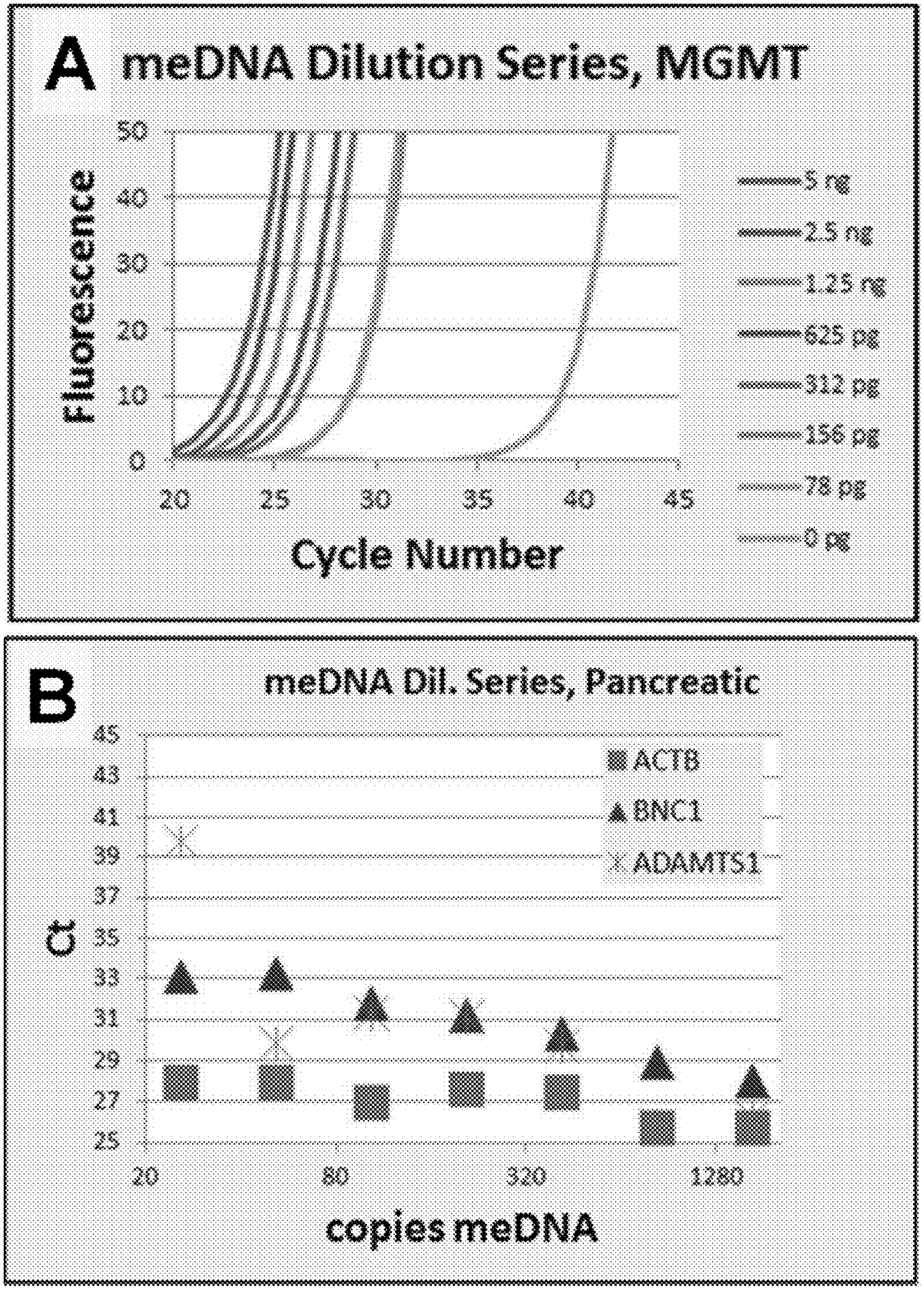
FIG. 25, panels A and B, illustrates sensitivity of detection of methylated DNA. Panel A shows a dilution series of methylated DNA (MGMT) (the curves run from the highest concentrations on the left to the lowest concentration on the right. Panel B illustrates the sensitivity of detection of methylated pancreatic cancer markers.

FIG. 25, panel A, illustrates the detection of methylated DNA in a dilution series (MGMT (O-6-Methylguanine-DNA Methyltransferase gene)). As shown therein MGMT was detected down to a level of 78 pg.

The detection of methylated breast cancer markers RASSF1A and AKR1B1 in MBA-453 cells is shown in FIG. 25, panel B. As shown therein, breast cancer markers were detected down to 100 cells.

The detection of methylated pancreatic cancer markers ACTB, BNC1, and ADAMTS1 in a dilution series is shown in FIG. 25, panel C. As shown therein, pancreatic markers were detected down to 25 copies.

Table 15 shows the hit rate of pancreatic cancer markers BNC1 and ADAMTS1 as a function of concentration. As shown therein these markers could be detected below 120 pg. Note a positive "hit rate" is an amplification in either gene for a replicate.

TABLE 15 illustrates the hit rate for pancreatic marker detection as a function of concentration.

| Concentration | Hit rate (#/replicates) |
|---|---|
| 0 pg | 0/3 |
| 16 pg | 6/8 |
| 30 pg | 5/8 |
| 60 pg | 4/8 |
| 120 pg | 4/4 |

Example 11

Reverse Complement Multiplex Assay for Both Strands

FIG. 26 illustrates the results for a reverse complement multiplex assay for both DNA strands. Following bisulfite conversion, both strands lose their complementarity. Thus, primer and probe sets have to be designed for one strand or the other, and result in unique amplicons. In addition to providing "more opportunities", this approach might potentially help with sensitivity (at LOD, if only one strand or the other ends up in the tube, this approach would ensure the signal gets picked up).

The multiplex assay allows the multiplex to detect different CpGs at the same promoter site. The reverse component multiplex provides more queries on target and the possibility to pick up heterogamous methylation.

Example 12

Detection of DNA Methylation and Mutation in a Single Cartridge

Figure 27A:
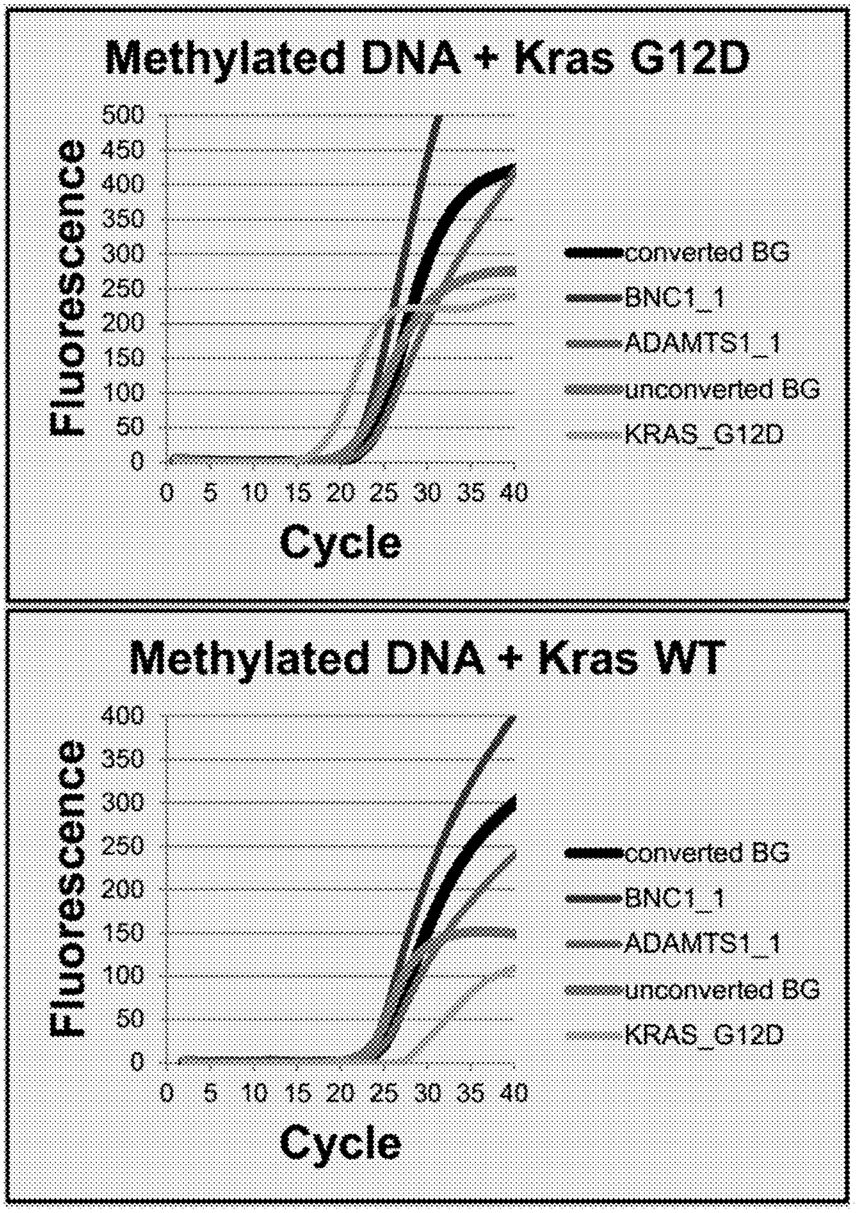
FIG. 27A illustrates the detection of both methylated DNA and mutations in the same cartridge. Top panel illustrates detection of methylated DNA and a Kras G12D mutation in one cartridge, while bottom panel illustrates detection of methylated DNA and wildtype Kras in one cartridge.

In certain embodiments the multiplex PCR reactions can contain primers and probes that permit the detection of mutations in addition to methylation in the same cartridge. FIG. 27A illustrates the detection of methylated BNC1 and ADAMTS1 along with the KRAS G12D mutation along with control BG (Top Panel) and the detection of methylated BNC1 and ADAMTS1 along with the KRAS wildtype along with control BG (Bottom Panel).

Figure 27B:
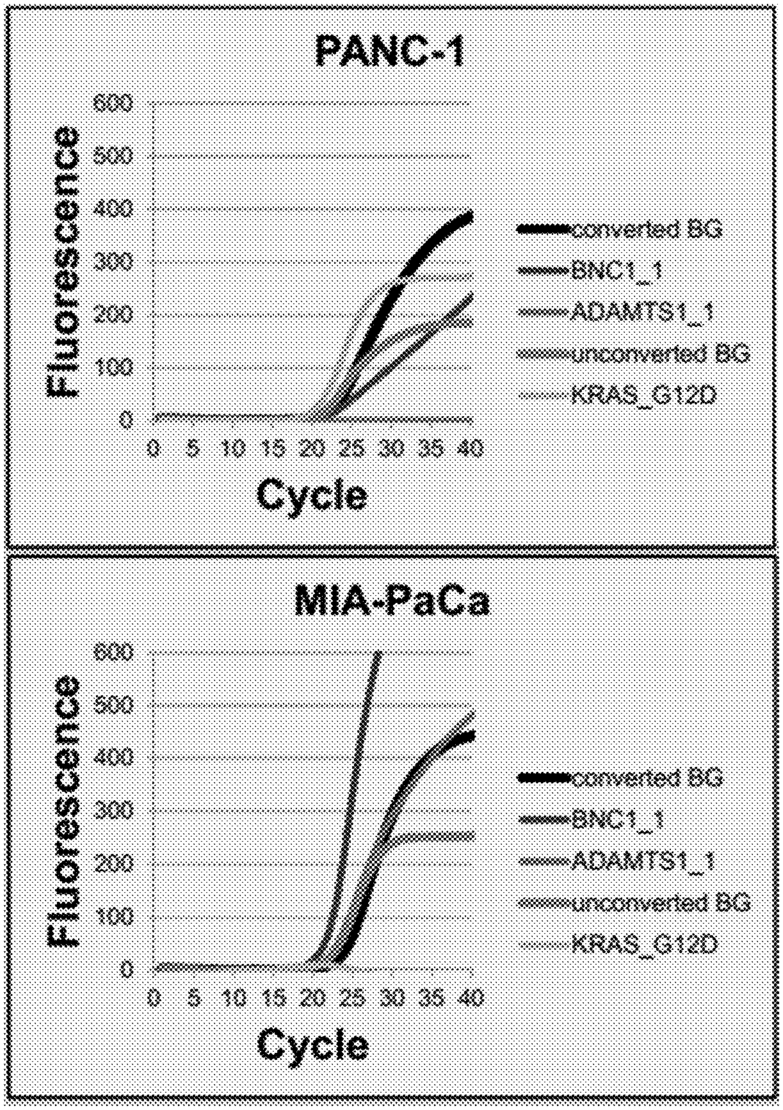
FIG. 27B illustrates detection of methylated DNA and mutations I the same cartridge in two pancreatic cancer cell lines: PANC-1 cells (top panel) and MIA-PaCa cells (bottom panel).

FIG. 27B illustrates the simultaneous detection of BNC1 and ADAMTS1 methylation in PANC-1 cells (top panel) and MIA-PaCa cells (bottom panel) along with the KRAS G12D mutation.

Example 13

Multiplex Optimization of Pancreatic Cancer

Figure 28:
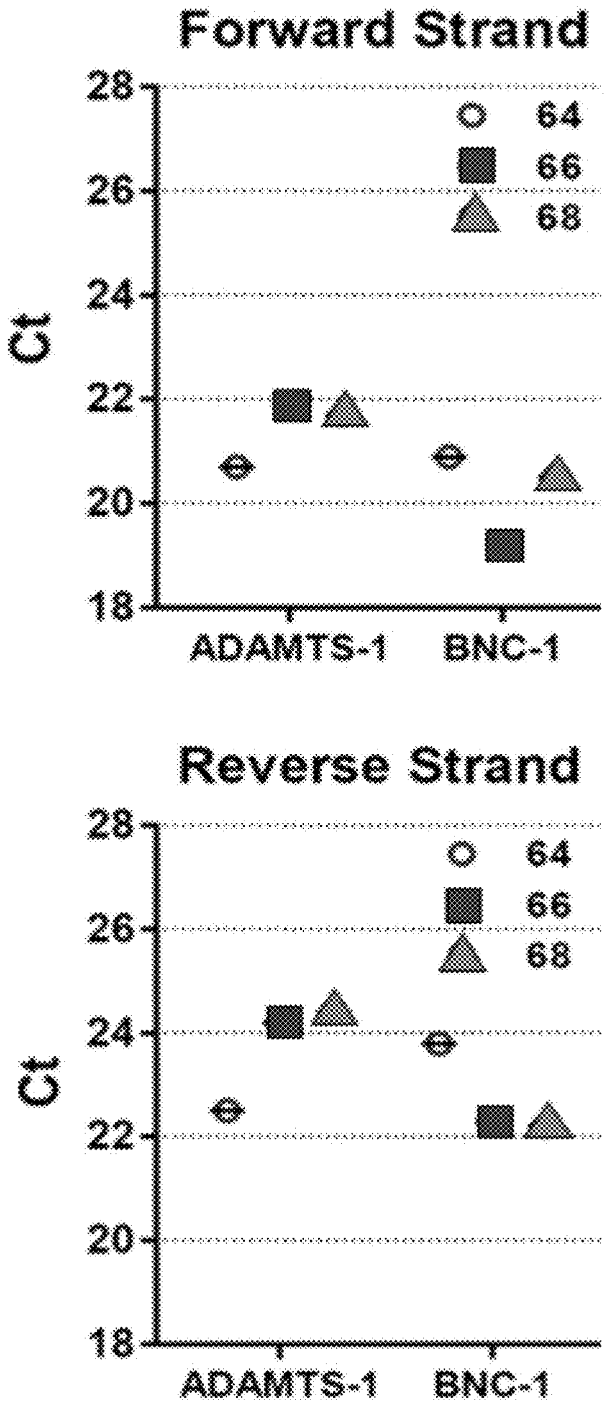
FIG. 28 illustrates temperature optimization for multiplex methylation analysis of ADAMTS1, and BNC1 of a forward strand (top) and a reverse strand (bottom) of bisulfite-converted DNA.

It was determined that methylation analysis of ADAMTS1, BNC1, (and certain other genes) permits detection and/or staging of pancreatic cancer. Accordingly, the initial multiplex assay for BNC1 and ADAMTS1 was optimized to facilitate incorporation of probes for other genes. To optimize this assay temperature gradients were run on external and internal PCRs for forward/reverse bisulfite converted strands. Single-plexes (fwd/rev for each gene) were run at external temperatures of 56° C., 58° C., and 60° C. and internal temperatures of 64° C., 66° C., and 68° C. (see, e.g., FIG. 28). In certain embodiments the assays were developed as two 4-plexes for BNC1 and ADAMTS1 and two other genes, one 4-plex for methylation analysis of a forward strand and one 4-plex for methylation analysis of a reverse strand.

Figure 29:
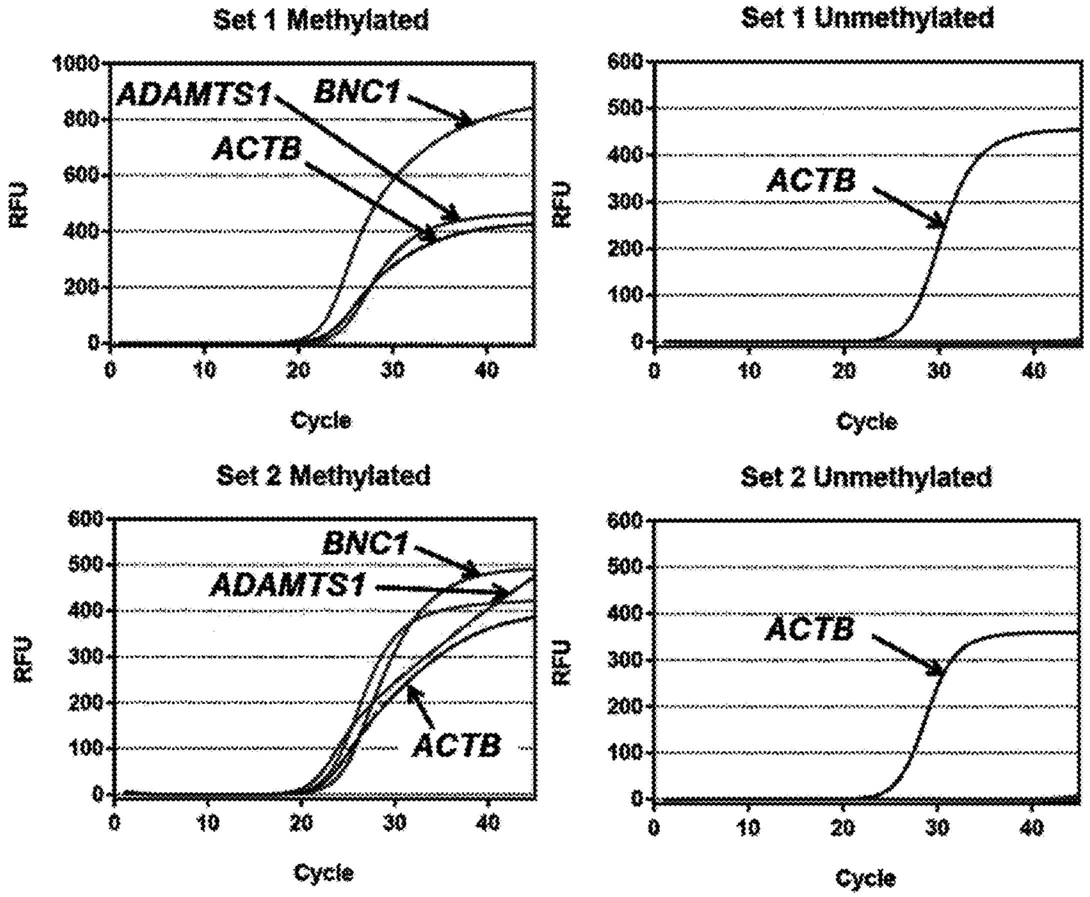
FIG. 29 illustrates the ability to multiplex the MSP primer and probe sets for BNC1, ADAMTS1, and a control gene ACTB. Probes were combined into two sets based on preferred conditions.

The probes were combined into two sets (see, FIG. 29) based on preferred reaction conditions (salt conditions 40 mM (LS), 60 mM (MS), 80 mM (HS) KCl. 15 mM $NH_4SO_4$) and optimized for specificity. The final optimized salt condition for multiplex 1 was 80 mM KCl, 5 mM $MgCl_2$, 20 mM Tris pH 8.5, and 10 mM $NH_4$ and for multiplex 2 was 62 mM KCl, 4 mM $MgCl_2$, 20 mM Tris pH 8.5, and 10 mM $NH_4$.

Example 14

Detection of MGMT Methylation

The O(6)-methylguanine-DNA methyltransferase (MGMT) gene encodes a DNA repair enzyme that can abrogate the effects of alkylating chemotherapy such as temozolamide. If the MGMT gene is active, the damage is rapidly repaired. It is believed that malignant gliomas may have the MGMT gene inactivated due to methylation of its promoter region. Methylated MGMT gene is a predictive inicator for BETTER response to chemotherapy (as the tumor has no means to repair the DNA damage induced by the alkylating agent).

Figure 30:
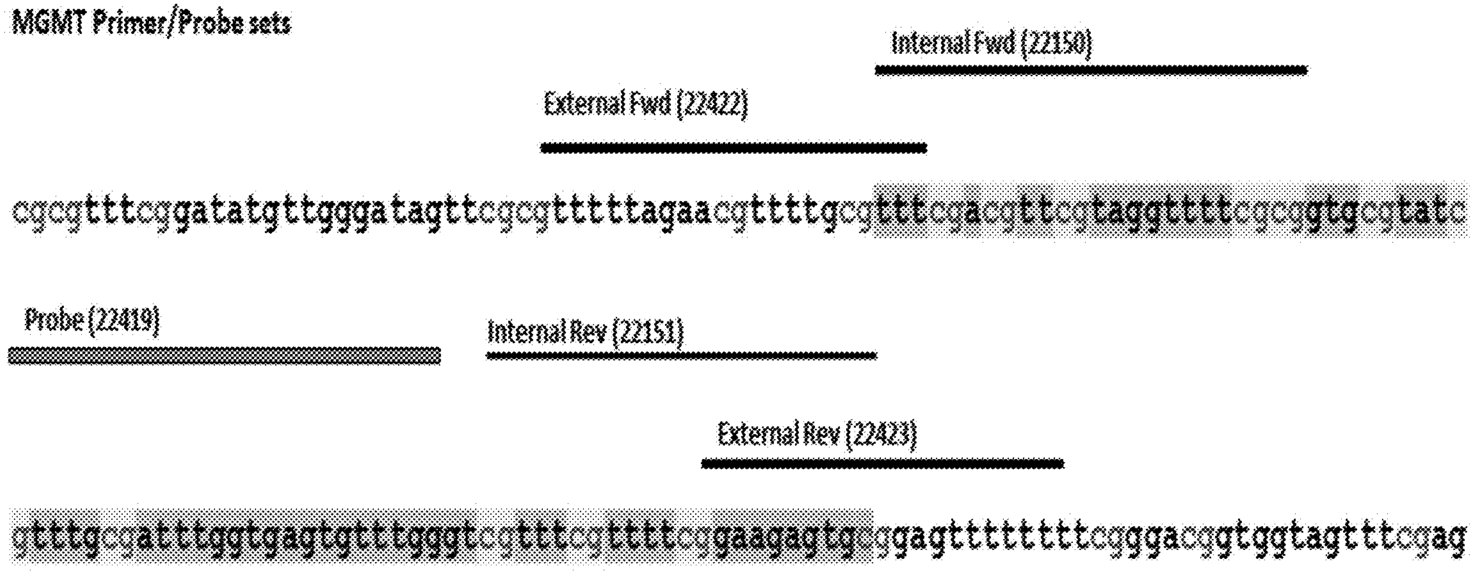
FIG. 30 illustrates one set of primers and probes used for detection of MGMT methylation. Internal fwd 22150 (SEQ ID NO: 266); External fwd 22422 (SEQ ID NO: 263); Probe 22419 (SEQ ID NO: 268), Internal rev 22151 (SEQ ID NO: 267); external rev 22423 (SEQ ID NO: 265); template (SEQ ID NO: 1).

Primers and probes were developed for the detection of MGMT methylation as illustrated in FIG. 30 and summarized below in Table 16. In particular, FIG. 30 illustrates the converted template with CPGs (as determined from pyrosequencing) shown in grey. As illustrated after bisulfite conversion the forward and reverse strand are no longer complementary permitting separate analysis of each strand.

TABLE 16

Illustrative primer/probe set for detection of MGMT methylation (see, e.g., FIG. 30).

| Probe | | Probe Type | Sequence | SEQ ID NO |
|---|---|---|---|---|
| External | 22422 | MGMT Fwd-4 | GTTTT(T*)AGAAYG(T*) TTTGYGTTT | 263 |
| | 22423 | MGMT Rev-4 | AAAAAAC(T*)CCRCACTC TTCC | 265 |
| Internal | 22150 | MGMT Fwd-2 | TTTCGACGTTCGTAGGTTT TCGC | 266 |
| | 22151 | MGMT Rev-2 | GCACTCTTCCGAAAACGAA ACG | 267 |
| | 22419 | MGMT TaqMan-2 | Fluor- CCAAACAC(T*)CACCAAA TC(N*)CAAAC | 268 |

To evaluate detection sensitivity a MGMT dilution series (5 ng to 78 pg MGMT DNA in a background of 20 ng of HS DNA)) was evaluated using ACTB as a control. In an illustrative experiment, 78 pg of methylated MGMT DNA was only about 10 cycles off the Ct of only unmethylated HS DNA.

Figure 31:
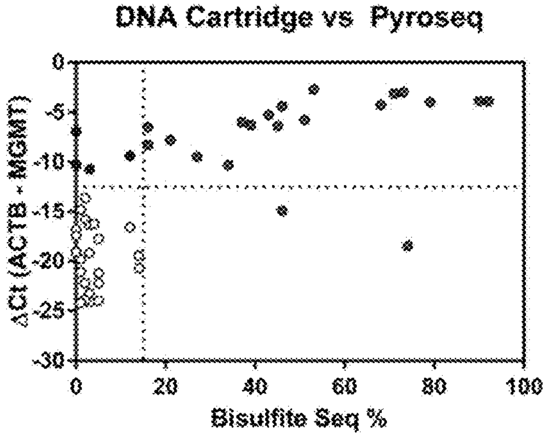
FIG. 31 shows the results of a comparison between bisulfite pyrsequencing and a MGMT methylation cartridge for extracted DNA (top) and for an FFPET sample (bottom).
Figure 31:
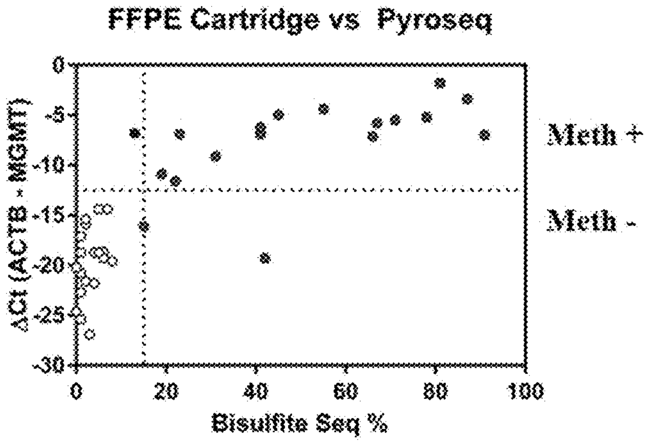

As shown in FIG. 31 results produced using the methylation cartridge described herein for the detection of MGMT methylation was compared to the results produced by pyrosequencing for extracted DNA (FIG. 31, top) and for a FFPE sample (FIG. 31, bottom). Pyrosequencing typically uses a cutoff between 10-15% to determine patient stratification. We used an arbitrary cutoff of 12.5 (between ACTB and MGMT) to match pyrosequencing results as closely as possible. Accordingly, in this example a cutoff was set at delta Ct=12.5 and calculated concordance with >15% methylation. The cartridge analysis of the extracted DNA show a sensitivity of 90% and a specificity at 86% while the cartridge analysis of the FFPE sample showed a sensitivity of 88% and a specificity of 95%.

It is noted that specificity can be improved in two ways: 1) the annealing temperature can be increased as the 62° C. annealing temperature was rather low. Additionally methylation probes that cover 3 (or more) CpGs can be utilized.

Example 15

Detection of BRCA1 Methylation

BRCA1 is a caretaker gene responsible for repairing DNA. It is believe that BRCA1 is involved in homologous, recombination, non-homologous end joining, and nucleotide excision repair. Women with an abnormal BRCA1 gene have an 80% chance of developing breast cancer.

Without being bound to a particular theory, it is believed that BRCA1 methylation is a potential predictive marker of response to chemotherapy in triple negative BC patients. Study of NSCLC patient's treated with cisplatin showed those with low BRCA1 expression had improved survival rates. High levels reduced the effectiveness of chemotherapy by repairing the damage caused to cancer cells.

Figure 32:
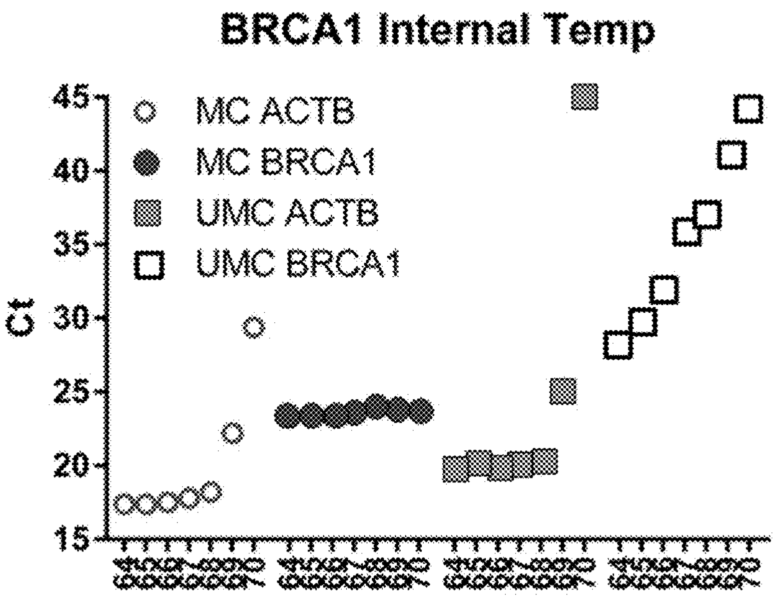
FIG. 32 illustrates BRCA1 primer and probe set optimization of ΔCt between methylated converted and unmethylated converted DNA.

In view of these, and other, observations cartridges and methods of use were developed for detection of BRCA1 methylation. In particular, the PCR condition were optimized as follows: 1) External temperature was evaluated between 56-62° C. and we settled on a 3 step 56° C. annealing PCR protocol; 2) Internal temperature was evaluated between 64° C.-70° C. and we settled on a two-step 68° C. annealing PCR protocol. Results are shown in FIG. 32.

Figure 33:
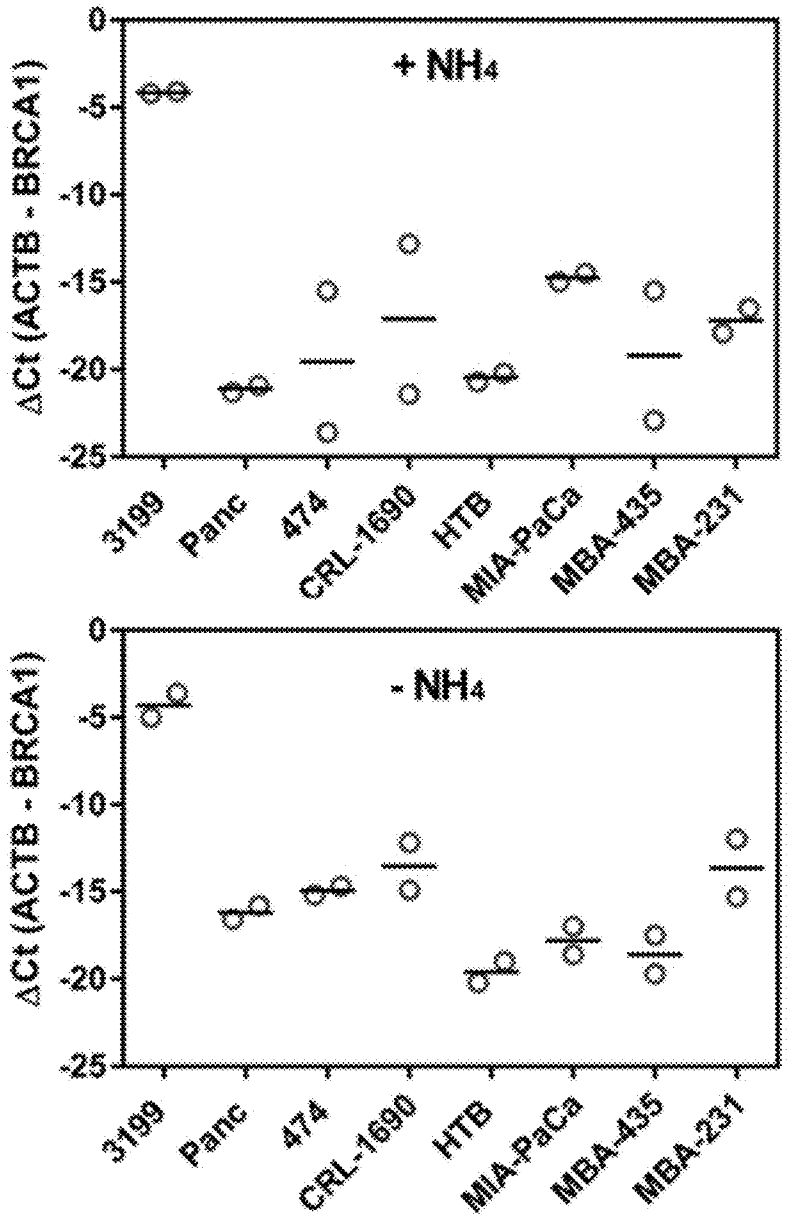
FIG. 33 illustrates a one target assay for BRCA1 methylation tested with the ACTB control gene. As shown, eight different cell lines were tested and the effect of adding $NH_4$ was compared.

For BRCA1, a one target assay was tested with the ACTB control gene. Eight different cell lines were tested and the effect of adding $NH_4$ was compared (see, FIG. 33). BRCA1 methylation was expected to be observed in the 3199 cell line.

Example 16

Detection of Gene Methylation Associated with Lung Cancer

Figure 34:
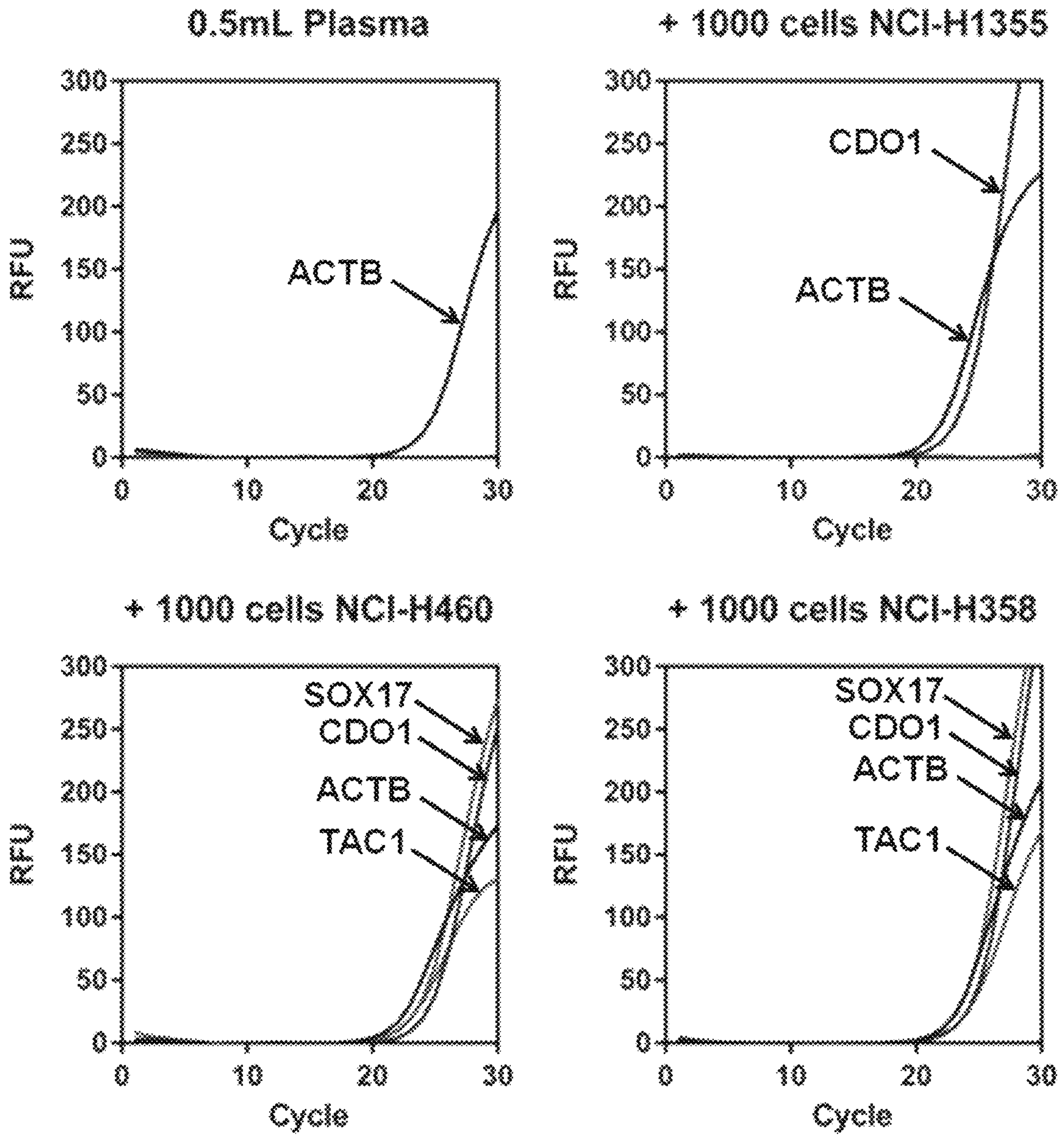
FIG. 34 illustrates the results of a three target methylation assay for genes whose methylation is associated with lung cancer (SOX17, CD01, TAC1) in a background of normal plasma and in in three different lung cancer cell lines.

A three target methylation assay for genes whose methylation is associated with lung cancer (SOX17, CD01, TAC1) was tested along with the ACTB control gene. The data shown in FIG. 34 indicate that, as expected, the 3 targets do not come up in a background of normal plasma but are present to some degree in three different lung cancer cell lines.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cartridge for determining a methylation state of a nucleic acid, said cartridge comprising:

(i) a first column comprising a first matrix material, (ii) a sample receiving chamber, (iii) a reaction channel or chamber that can be temperature controlled, (iv) a plurality of chambers for containing reagents and/or buffers, wherein:

at least one of said chambers is configured to contain a bisulfite reagent, and at least one of said chambers is configured to contain a desulphonation/elution buffer, wherein said cartridge optionally comprises a second column comprising a second matrix material, wherein said sample receiving chamber, said first and optional second column(s), said plurality of chambers, and said temperature-controlled heating channel or chamber, are selectively in fluid communication by microfluidic channels and valves, and wherein:

said sample receiving chamber, said first and optional second column(s), said plurality of chambers, and said reaction channel or chamber or a port into said reaction channel or chamber, are disposed around a central valve and selectively in fluid communication with a channel in said central valve, wherein said central valve is configured to accommodate a plunger that is capable of drawing fluid into or out of a chamber in fluid communication with said central valve, and/or said cartridge is configured to perform bisulfite conversion in the reaction channel or chamber, which can be subjected to thermocycling and later used for amplification of converted nucleic acid by polymerase chain reaction (PCR).

2. The cartridge of claim 1, wherein said sample receiving chamber, said first and optional second column(s), said plurality of chambers, and said reaction channel or chamber or a port into said reaction channel or chamber, are disposed around a central valve and selectively in fluid communication with a channel in said central valve, wherein said central valve is configured to accommodate a plunger that is capable of drawing fluid into or out of a chamber in fluid communication with said central valve.

3. The cartridge of claim 1, wherein said cartridge is configured to perform bisulfite conversion in the reaction channel or chamber, which can be subjected to thermocycling and later used for amplification of converted nucleic acid by polymerase chain reaction (PCR).

4. The cartridge of claim 1, wherein:

said sample receiving chamber, said first and optional second column(s), said plurality of chambers, and said reaction channel or chamber or a port into said reaction channel or chamber, being disposed around a central valve and selectively in fluid communication with a channel in said central valve, wherein said central valve is configured to accommodate a plunger that is capable of drawing fluid into or out of a chamber in fluid communication with said central valve, and said cartridge is configured to perform bisulfite conversion in the temperature controlled channel or chamber, which can be subjected to thermocycling and later used for amplification of converted nucleic acid by polymerase chain reaction (PCR).

5. The cartridge of claim 1, wherein said cartridge comprises a chamber configured to contain a reagent comprising guanidinium thiocyanate ethanol (GTC-EtOH).

6. The cartridge of claim 1, wherein said second column is absent.

7. The cartridge of claim 1, wherein said reaction channel or chamber is a channel or chamber that can be subjected to thermocycling.

8. The cartridge of claim 1 wherein said bisulfite reagent comprises a compound selected from the group consisting of ammonium bisulfite sodium, metabisulfite, potassium bisulfite, cesium bisulfite, and 1,4-diazoniabicyclo[2.2.2]octane-1,4-disulfinate (DABSO).

9. The cartridge of claim 1, wherein said cartridge comprises one, two, or more chambers containing one or more reagents selected from the group consisting of methylation specific PCR primers, methylation specific PCR probes, PCR enzyme(s), and PCR reaction buffer.

10. The cartridge of claim 1, wherein:

said cartridge contains at least one chamber containing primers and probes for detection of methylation of a forward strand of a converted DNA; and/or said cartridge contains at least one chamber containing primers and probes for detection of methylation of a reverse strand of a converted DNA.

11. The cartridge of claim 9, wherein said PCR primers, and/or said probes, and/or enzymes are provided as beads.

12. The cartridge of claim 1, wherein said cartridge is configured to comprise:

a first chamber containing a sample, that optionally comprises a GTC-EtOH-Tween extraction/precipitation reagent;

a second chamber containing a guanidinium thiosulfate-ethanol (GTC-EtOH) solution;

a third chamber containing a bisulfite reagent;

a fourth chamber containing a buffer;

a fifth chamber containing a rinse solution; and a sixth chamber containing an elution/desulphonation reagent.

13. The cartridge of claim 1, wherein:

the cartridge is configured for the bisulfite reagent to be added to the cartridge by the user; and/or the cartridge is configured for addition of said GTC-ETOH-Tween buffer by the user.

14. The cartridge of claim 1, wherein:

the bisulfite reagent is provided as a component of the cartridge; and/or the GTC-ETOH-Tween buffer is provided as a component of the cartridge.

15. The cartridge of claim 12, wherein said cartridge comprises a seventh chamber containing PCR primers and/or probes and/or PCR enzymes.

16. The cartridge of claim 1, wherein:

said cartridge comprises one or more chambers containing primers specific for bisulfite converted methylated and/or unmethylated sequences; and/or said cartridge comprises one or more chambers containing reagents for TaqMan PCR reactions; and/or said cartridge comprises one or more chambers containing one or more fluorescent probes that are markers for amplified methylated sequences and/or one or more fluorescent probes that are markers for amplified unmethylated sequences.

17. The cartridge of claim 16, wherein:

(a) said probes comprise a fluorescent reporter dye and a quencher dye, where the probes provide a signal upon cleavage by the 5' to 3' nuclease activity of Taq DNA polymerase; and/or (b) said cartridge comprises a plurality of probes each specific to a different methylated region in an amplified region of interest; or said cartridge comprises a plurality of probes each specific to the same methylated region in an amplified region of interest; or said cartridge comprises a single probe specific to a methylated region in an amplified region of interest; and/or (c) said cartridge contains primers and/or probes to determine methylation of a promoter region of a gene selected from the group consisting of MGMT, RASSF1A, ADAMTS1, BNC1, HIST1H3C, HOXB4, RASGRF2, TM6SF1, and AKR1B1; and/or said cartridge contains one or more primers shown in Tables 5, 9, or 10, and/or one or more probes shown in Tables 5, 9, or 10; and/or (d) the cartridge is configured for determination of the expression level of RNA for a methyltransferase.

18. The cartridge of claim 16, wherein said probes comprise a fluorescent reporter dye and a quencher dye, where the probes provide a signal upon cleavage by the 5' to 3' nuclease activity of Taq DNA polymerase.

19. The cartridge of claim 16, wherein said cartridge comprises a plurality of probes each specific to a different methylated region in an amplified region of interest; or said cartridge comprises a plurality of probes each specific to the same methylated region in an amplified region of interest; or said cartridge comprises a single probe specific to a methylated region in an amplified region of interest.

20. The cartridge of claim 16, wherein said cartridge contains primers and/or probes to determine methylation of a promoter region of a gene selected from the group consisting of MGMT, RASSF1A, ADAMTS1, BNC1, HIST1H3C, HOXB4, RASGRF2, TM6SF1, and AKR1B1; and/or said cartridge contains one or more primers shown in Tables 5, 9, or 10, and/or one or more probes shown in Tables 5, 9, or 10.

* * * * *